US011819027B2

(12) United States Patent
Djonovic et al.

(10) Patent No.: US 11,819,027 B2
(45) Date of Patent: *Nov. 21, 2023

(54) STREPTOMYCES ENDOPHYTE COMPOSITIONS AND METHODS FOR IMPROVED AGRONOMIC TRAITS IN PLANTS

(71) Applicant: INDIGO AG, INC., Boston, MA (US)

(72) Inventors: Slavica Djonovic, Malden, MA (US); Elizabeth Alexa McKenzie, Milton, MA (US); Gerardo Toledo, Hopkinton, MA (US); Craig Sadowski, Somerville, MA (US); Geoffrey Von Maltzahn, Boston, MA (US); Karen V. Ambrose, Cambridge, MA (US); Xuecheng Zhang, Newton, MA (US); David Morris Johnston, Cambridge, MA (US); Trudi A. Gulick, Topsfield, MA (US)

(73) Assignee: Indigo Ag, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/930,020

(22) Filed: Jul. 15, 2020

(65) Prior Publication Data

US 2021/0204505 A1 Jul. 8, 2021

Related U.S. Application Data

(62) Division of application No. 15/580,616, filed as application No. PCT/US2016/036504 on Jun. 8, 2016, now Pat. No. 10,750,711.

(60) Provisional application No. 62/316,386, filed on Mar. 31, 2016, provisional application No. 62/172,755, filed on Jun. 8, 2015, provisional application No. 62/172,750, filed on Jun. 8, 2015, provisional application No. 62/172,748, filed on Jun. 8, 2015.

(51) Int. Cl.

| | | |
|---|---|---|
| A01N 63/28 | (2020.01) | |
| A01C 1/06 | (2006.01) | |
| A01H 17/00 | (2006.01) | |
| A01N 63/30 | (2020.01) | |
| A01N 63/00 | (2020.01) | |
| A01G 7/00 | (2006.01) | |
| A01G 22/40 | (2018.01) | |
| A01G 22/20 | (2018.01) | |

(52) U.S. Cl.
CPC .............. *A01N 63/28* (2020.01); *A01C 1/06* (2013.01); *A01G 7/00* (2013.01); *A01H 17/00* (2013.01); *A01N 63/00* (2013.01); *A01N 63/30* (2020.01); *A01G 22/20* (2018.02); *A01G 22/40* (2018.02)

(58) Field of Classification Search
None
See application file for complete search history.

(56) References Cited

U.S. PATENT DOCUMENTS

| | | |
|---|---|---|
| 2,200,532 A | 5/1940 | Bond |
| 4,642,131 A | 2/1987 | Hoitink |
| 4,940,834 A | 7/1990 | Hurley et al. |
| 5,041,290 A | 8/1991 | Gindrat et al. |
| 5,113,619 A | 5/1992 | Leps et al. |
| 5,229,291 A | 7/1993 | Nielsen et al. |
| 5,292,507 A | 3/1994 | Charley |
| 5,300,127 A | 4/1994 | Williams |
| 5,415,672 A | 5/1995 | Fahey et al. |
| 5,730,973 A | 3/1998 | Morales et al. |
| 5,919,447 A | 7/1999 | Marrone et al. |
| 5,989,543 A | 11/1999 | Davide et al. |
| 5,994,117 A | 11/1999 | Bacon et al. |
| 6,072,107 A | 6/2000 | Latch et al. |
| 6,077,505 A | 6/2000 | Parke et al. |
| 6,337,431 B1 | 1/2002 | Tricoli et al. |
| 6,495,133 B1 | 12/2002 | Xue |
| 6,602,500 B1 | 8/2003 | Kharbanda et al. |
| 6,681,186 B1 | 1/2004 | Denisov et al. |
| 6,689,880 B2 | 2/2004 | Chen et al. |
| 6,823,623 B2 | 11/2004 | Minato et al. |
| 7,037,879 B2 | 5/2006 | Imada et al. |
| 7,080,034 B1 | 7/2006 | Reams |
| 7,084,331 B2 | 8/2006 | Isawa et al. |
| 7,335,816 B2 | 2/2008 | Kraus et al. |

(Continued)

FOREIGN PATENT DOCUMENTS

| | | |
|---|---|---|
| AU | 2015201322 | 4/2015 |
| CA | 1041788 A | 11/1978 |

(Continued)

OTHER PUBLICATIONS

Lee et al. *Streptomyces koyangensis* sp. nov., a novel actinomycete that produces 4-phenyl-3-butenoic acid. Int J Syst Evol Microbiol. Jan. 2005;55(Pt 1):257-62. (Year: 2005).*
Bently et al. Complete genome sequence of the model actinomycete *Streptomyces coelicolor* A3(2). Nature. May 9, 2002;417(6885):141-7. (Year: 2002).*
Ikeda et al. Complete genome sequence and comparative analysis of the industrial microorganism *Streptomyces avermitilis*. Nat Biotechnol. May 2003;21(5):526-31. Epub Apr. 14, 2003. (Year: 2003).*
NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA000016325.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.

(Continued)

*Primary Examiner* — Cynthia E Collins
(74) *Attorney, Agent, or Firm* — Goodwin Procter LLP

(57) ABSTRACT

This invention relates to methods and compositions for providing a benefit to a plant by associating the plant with a beneficial endophyte of the genus *Streptomyces*, including benefits to a plant derived from a seed or other plant element treated with said endophyte. For example, this invention provides purified endophytes, synthetic combinations comprising endophytes, and methods of making and using the same. In particular, this invention relates to compositions and methods of improving soybean and maize plants.

26 Claims, 7 Drawing Sheets

Specification includes a Sequence Listing.

(56) References Cited

U.S. PATENT DOCUMENTS

| | | |
|---|---|---|
| 7,341,868 B2 | 3/2008 | Chopade et al. |
| 7,435,411 B2 | 10/2008 | Park et al. |
| 7,485,451 B2 | 2/2009 | VanderGheynst et al. |
| 7,555,990 B2 | 7/2009 | Beaujot |
| 7,632,985 B2 | 12/2009 | Malven et al. |
| 7,763,420 B2 | 7/2010 | Stritzker et al. |
| 7,906,313 B2 | 3/2011 | Henson et al. |
| 7,977,550 B2 | 7/2011 | West et al. |
| 8,019,694 B2 | 9/2011 | Fell et al. |
| 8,143,045 B2 | 3/2012 | Miasnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |
| 9,113,636 B2 | 8/2015 | von Maltzahn et al. |
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 | 8/2018 | von Maltzahn et al. |
| 10,076,120 B2 | 9/2018 | von Maltzahn et al. |
| 10,104,862 B2 * | 10/2018 | Vujanovic ............... A01H 17/00 |
| 10,136,646 B2 | 11/2018 | Von Maltzahn et al. |
| 10,212,912 B2 | 2/2019 | Vujanovic et al. |
| 10,306,890 B2 | 6/2019 | Mitter et al. |
| 10,362,787 B2 | 7/2019 | Mitter et al. |
| 10,499,652 B2 | 12/2019 | von Maltzahn et al. |
| 10,499,653 B2 | 12/2019 | von Maltzahn et al. |
| 10,499,654 B2 | 12/2019 | von Maltzahn et al. |
| 10,640,783 B2 | 5/2020 | Riley |
| 10,645,938 B2 | 5/2020 | Riley |
| 10,667,523 B2 | 6/2020 | Ambrose et al. |
| 10,750,711 B2 * | 8/2020 | Djonovic ................. A01C 1/06 |
| 10,932,469 B2 | 3/2021 | Mitter et al. |
| 11,119,086 B2 | 9/2021 | Mitter et al. |
| 11,151,379 B2 | 10/2021 | Freitag et al. |
| 2001/0032162 A1 | 10/2001 | Alsberg et al. |
| 2002/0059091 A1 | 5/2002 | Hay et al. |
| 2002/0120555 A1 | 8/2002 | Lerner |
| 2002/0142917 A1 | 10/2002 | Triplett et al. |
| 2002/0147670 A1 | 10/2002 | Lange |
| 2003/0050901 A1 | 3/2003 | Jester et al. |
| 2003/0195822 A1 | 10/2003 | Tatge et al. |
| 2003/0236738 A1 | 12/2003 | Lange et al. |
| 2005/0008619 A1 | 1/2005 | Park et al. |
| 2005/0070435 A1 | 3/2005 | Chopade et al. |
| 2005/0072047 A1 | 4/2005 | Conkling et al. |
| 2006/0046246 A1 | 3/2006 | Zeng et al. |
| 2006/0178269 A1 | 8/2006 | Medina-Vega |
| 2006/0185207 A1 | 8/2006 | Mitcheltree |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2009/0300781 A1 | 12/2009 | Bancroft et al. |
| 2010/0064392 A1 | 3/2010 | Yang et al. |
| 2010/0095396 A1 | 4/2010 | Voeste et al. |
| 2010/0114753 A1 | 5/2010 | Osmanski et al. |
| 2010/0130365 A1 | 5/2010 | Notten et al. |
| 2010/0205690 A1 | 8/2010 | Blasing et al. |
| 2010/0227357 A1 | 9/2010 | Redman et al. |
| 2011/0033436 A1 | 2/2011 | Chen et al. |
| 2011/0182862 A1 | 7/2011 | Green et al. |
| 2011/0195406 A1 | 8/2011 | Sorenson et al. |
| 2012/0108431 A1 | 5/2012 | Williams et al. |
| 2012/0116943 A1 | 5/2012 | Abramson |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0134629 A1 | 5/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0218568 A1 | 8/2015 | Jones et al. |
| 2015/0230478 A1 | 8/2015 | Vujanovic et al. |
| 2015/0242970 A1 | 8/2015 | Avey et al. |
| 2015/0282490 A1 | 10/2015 | Wachendorff-Neumann et al. |
| 2015/0289518 A1 | 10/2015 | Andersch et al. |
| 2015/0296802 A1 | 10/2015 | Wachendorff-Neumann et al. |
| 2015/0296803 A1 | 10/2015 | Andersch et al. |
| 2015/0296804 A1 | 10/2015 | Andersch et al. |
| 2015/0305348 A1 | 10/2015 | Andersch et al. |
| 2015/0320050 A1 | 11/2015 | von Maltzahn et al. |
| 2015/0320051 A1 | 11/2015 | Wachendorff-Neumann et al. |
| 2015/0335029 A1 | 11/2015 | Mitter et al. |
| 2015/0342199 A1 | 12/2015 | Carrion Villanovo et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0000091 A1 | 1/2016 | Andersch et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0350855 A1 | 12/2016 | Lerner |
| 2016/0366892 A1 | 12/2016 | Ambrose et al. |
| 2017/0020138 A1 | 1/2017 | Von Maltzahn et al. |
| 2017/0161560 A1 | 6/2017 | Itzhaky et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0060771 A1 | 3/2018 | Mangin |
| 2018/0092365 A1 | 4/2018 | Sword |
| 2018/0153174 A1 | 6/2018 | Riley et al. |
| 2018/0177196 A1 | 6/2018 | Sword |
| 2018/0189564 A1 | 7/2018 | Freitag et al. |
| 2018/0213800 A1 | 8/2018 | Djonovic et al. |
| 2018/0249716 A1 | 9/2018 | Riley |
| 2018/0251776 A1 | 9/2018 | Riley |
| 2018/0322426 A1 | 11/2018 | Schmaltz et al. |

(56) References Cited

U.S. PATENT DOCUMENTS

| | | | |
|---|---|---|---|
| 2019/0130999 | A1 | 5/2019 | Oppenheim et al. |
| 2021/0372997 | A1 | 12/2021 | Von Maltzahn et al. |

FOREIGN PATENT DOCUMENTS

| | | | |
|---|---|---|---|
| CA | 1229497 | A | 11/1987 |
| CA | 2562175 | A1 | 4/2008 |
| CA | 2916678 | A1 | 12/2014 |
| CA | 2960032 | A1 | 3/2015 |
| CA | 2935218 | A1 | 7/2015 |
| CA | 2953466 | A1 | 12/2015 |
| CA | 2953697 | A1 | 12/2015 |
| CN | 1604732 | A | 4/2005 |
| CN | 101311262 | A | 11/2008 |
| CN | 101423810 | A | 5/2009 |
| CN | 101570738 | A | 11/2009 |
| CN | 101693881 | A | 4/2010 |
| CN | 102010835 | A | 4/2011 |
| CN | 102123596 | A | 7/2011 |
| CN | 102168022 | A | 8/2011 |
| CN | 102352327 | A | 2/2012 |
| CN | 102533601 | A | 7/2012 |
| CN | 103642725 | A | 3/2014 |
| CN | 103865837 | | 6/2014 |
| CN | 104250616 | A | 12/2014 |
| CN | 104388356 | A | 3/2015 |
| CN | 104560742 | A | 4/2015 |
| CN | 105886428 | | 8/2016 |
| CN | 106434493 | | 2/2017 |
| EP | 0192342 | A2 | 8/1986 |
| EP | 0223662 | A1 | 5/1987 |
| EP | 0378000 | A2 | 7/1990 |
| EP | 0494802 | A1 | 7/1992 |
| EP | 0818135 | A1 | 1/1998 |
| EP | 1389767 | | 2/2004 |
| EP | 1621632 | A1 | 2/2006 |
| EP | 1935245 | A1 | 6/2008 |
| EP | 1967057 | | 9/2008 |
| EP | 2114118 | | 9/2012 |
| EP | 2676536 | A1 | 12/2013 |
| EP | 2959779 | | 12/2015 |
| EP | 3041338 | | 7/2016 |
| EP | 3659414 | | 6/2020 |
| IN | 1948459 | A | 4/2007 |
| JP | 2003300804 | A | 10/2003 |
| JP | 2009/072168 | A | 4/2009 |
| KR | 20050039979 | | 5/2005 |
| KR | 20100114806 | A | 10/2010 |
| KR | 101066283 | | 9/2011 |
| KR | 101091151 | B1 | 12/2011 |
| KR | 20120004958 | | 1/2012 |
| KR | 20130023491 | A | 3/2013 |
| RU | 2043028 | C1 | 9/1995 |
| WO | 1988/009114 | | 1/1988 |
| WO | 1994/016076 | | 7/1994 |
| WO | 98/35017 | | 8/1998 |
| WO | 99/59412 | | 11/1999 |
| WO | 2000/029607 | A1 | 5/2000 |
| WO | 2001/046774 | | 12/2000 |
| WO | 2001/083697 | A2 | 11/2001 |
| WO | 2001/083818 | A2 | 11/2001 |
| WO | 2002/065836 | A2 | 8/2002 |
| WO | 2003/038066 | | 5/2003 |
| WO | 2004/046357 | A1 | 6/2004 |
| WO | 2005/003328 | A1 | 1/2005 |
| WO | 2007/021200 | A1 | 2/2007 |
| WO | 2007/107000 | A1 | 9/2007 |
| WO | 2008/103422 | A2 | 8/2008 |
| WO | 2008/107097 | | 9/2008 |
| WO | 2009/012480 | A2 | 1/2009 |
| WO | 2009/078710 | A1 | 6/2009 |
| WO | 2009/126473 | A1 | 10/2009 |
| WO | 2010/109436 | A1 | 9/2010 |
| WO | 2010/115156 | A2 | 10/2010 |
| WO | 2011/001127 | A1 | 1/2011 |
| WO | 2011/011627 | A1 | 1/2011 |
| WO | 2011/082455 | A1 | 7/2011 |
| WO | 2011/112781 | A2 | 9/2011 |
| WO | 2011/117351 | A1 | 9/2011 |
| WO | 2012/016140 | | 2/2012 |
| WO | 2012/034996 | A1 | 3/2012 |
| WO | 2013/016361 | A2 | 1/2013 |
| WO | 2013/029112 | A1 | 3/2013 |
| WO | 2013/054272 | | 4/2013 |
| WO | 2013/090628 | A1 | 6/2013 |
| WO | 2013/122473 | A1 | 8/2013 |
| WO | 2013/148290 | | 10/2013 |
| WO | 2013/177615 | A1 | 12/2013 |
| WO | 2013/190082 | A1 | 12/2013 |
| WO | 2014/046553 | A1 | 3/2014 |
| WO | 2014/079728 | | 5/2014 |
| WO | 2014/082950 | A1 | 6/2014 |
| WO | 2014/086747 | | 6/2014 |
| WO | 2014/086749 | | 6/2014 |
| WO | 2014/086750 | | 6/2014 |
| WO | 2014/086752 | | 6/2014 |
| WO | 2014/086753 | | 6/2014 |
| WO | 2014/086756 | | 6/2014 |
| WO | 2014/086758 | | 6/2014 |
| WO | 2014/086759 | | 6/2014 |
| WO | 2014/086764 | | 6/2014 |
| WO | 2014/086776 | | 6/2014 |
| WO | 2014/121366 | A1 | 8/2014 |
| WO | 2014/206953 | A1 | 12/2014 |
| WO | 2014/210372 | A1 | 12/2014 |
| WO | 2015/035099 | A1 | 3/2015 |
| WO | 2015/069938 | A1 | 5/2015 |
| WO | 2015/100431 | A2 | 7/2015 |
| WO | 2015/100432 | A2 | 7/2015 |
| WO | 2015/114552 | | 8/2015 |
| WO | 2015/116838 | | 8/2015 |
| WO | 2015/192172 | A1 | 12/2015 |
| WO | 2015/200852 | A2 | 12/2015 |
| WO | 2015/200902 | A2 | 12/2015 |
| WO | 2016020371 | | 2/2016 |
| WO | 2016/050726 | | 4/2016 |
| WO | 2016/057991 | A1 | 4/2016 |
| WO | 2016/090212 | A1 | 6/2016 |
| WO | 2016/109758 | A2 | 7/2016 |
| WO | 2016/179046 | A1 | 11/2016 |
| WO | 2016/179047 | A1 | 11/2016 |
| WO | 2016/200987 | A1 | 12/2016 |
| WO | 2018094027 | | 5/2018 |
| WO | 2018/119419 | | 6/2018 |
| WO | 2018102733 | A1 | 6/2018 |
| WO | 2018160244 | A1 | 9/2018 |
| WO | 2018160245 | A1 | 9/2018 |
| WO | 2019/046909 | | 3/2019 |
| WO | 2019084380 | | 5/2019 |
| WO | 2019113468 | | 6/2019 |

OTHER PUBLICATIONS

NCBI GenBank: Accession No. JX880250.1, "Enterobacteriaceae bacterium Clero1 16S ribosomal RNA gene, partial sequence," NIH, Jun. 24, 2015, 2 Pages, can be retrieved at <URL:https://www.ncbi.nlm.nih.gov/nucleotidelJX880250.1?report=genbank&log$=nuclalign&blast_rank=80 &RID=KWUPBV08015>.
GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.
NCBI, GenBankAccession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Goudjal, Y., et al., "Biocontrol of Rhizoctonia solani damping-off and promotion of tomato plant growth by endophytic actinomycetes

(56) References Cited

OTHER PUBLICATIONS isolated from native plants of Algerian Sahara", Microbiological Research, 2014, vol. 169, No. 1, pp. 59-65.
Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.
Grondona, I., et al., "Tusal®, a commercial biocontrol formulation based on Trichoderma," Bulletin OILB/SROP, 2004, pp. 285-288, vol. 27, No. 8.
Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.
Hain, T., et al., "Chitinolytic transgenes from Streptomyces albidoflavus as phytochemicals defences against; herbivorous insects, use in transgenic plants and effect in plant development", International Journal of Systematic Bacteriology, Jan. 1997, vol. 47, No. 1, pp. 202-206.
Hanshew, A., et al., "Characterization of Actinobacteria Associated with Three Ant-Plant Mutualisms", Microbiol Ecology, Aug. 6, 2014, vol. 69, No. 1, pp. 192-203.
Hardoim, P.R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Hung, P.Q., et al., "Isolation and Characterization of Endophytic Bacteria in Soybean (*Glycine* Sp.)," Omonrice, 2004, pp. 92-101, vol. 12.
Iverson, C., et al, "The taxonomy of Enterobacter sakazakii: proposal of a new genus *Cronobacter* gen. nov. and descriptions of Cronobacter sakazakii comb. nov. *Cronobacter sakazakii* subsp. *sakazakii*, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter genomospecies* I", BMC Evolutionary Biology 2007, Apr. 17, 2017, 14 pages.
Joe, M.M. et al., "Development of alginate-based aggregate inoculants of *Methylobacterium* sp. And *Azospirillum prasilense* tested under in vitro conditions to promote plant growth," Journal of Applied Microbiology 2013, 116(2):408-423, XP055225426, Nov. 22, 2013.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Kruger, M., et al., "DNA-Based Species Level Detection of Glomeromycota: One PCR Primer Set for All Arbuscular Mycorrhizal Fungi," New Phytol., 2009, pp. 212-223, vol. 183.
Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Leonard, C. A., et al., "Random Mutagenesis of the Aspergillus oryzae Genome Results in Fungal Antibacterial Activity," Int J Microbiol., 2013, vol. 2013, Article ID 901697, 6 Pages.
Li, M., et al., "ATP Modulates the Growth of Specific Microbial Strains", Current Microbiology, May 30, 2010, vol. 62, No. 1, pp. 84-89.
Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.
Liu, Y., et al., "Phylogenetic relationships among ascomycetes: evidence from an RNA polymerase II subunit," Mol. Biol. Evol. 1999. vol. 16, No. 12, pp. 1799-1808.
Liu, Y., et al., "Study on Diversity of Endophytic Bacterial Communities in Seeds of Hybrid Maize and their Parental Lines," Arch Microbiol., 2012, pp. 1001-1012, vol. 194.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lugtenberg, B., et al., "Plant-Growth-Promoting Rhizobacteria," Ann. Rev. Microbiol., 2009, pp. 541-556, vol. 63.
Manoharan, M. J. et al., "Survival of flocculated cells in alginate and its inoculatin effect on growth and yield of maize under water deficit conditions," EP J of Soil Biology, Gauthier-Villars, Montrouge, FR, vol. 50, Mar. 7, 2012, pp. 198-206, XP028421147.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mateos, P.F., et al., "Cell-Associated Pectinolytic and Cellulolytic Enzymes in Rhizobium leguminosarum biovartrifolii," Appl Environ Microbiol., 1992, pp. 816-1822, vol. 58, No. 6.
Medina, P., et al., "Rapid Identification of Gelatin and Casein Hydrolysis Using TCA," J Microbiol Methods, 2007, pp. 391-393, vol. 69.
Miyoshi-Akiyama, T., et al., "Multilocus Sequence Typing (MLST) for Characterization of Enterobacter cloacae," PLoS ONE, 2013, vol. 8, No. 6, 10 Pages, e66358.
Moe, L. A., "Amino Acids in the Rhizosphere: From Plants to Microbes," American Journal of Botany, 2013, pp. 1692-1705, vol. 100, No. 9.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.
Murali, Gopal, et al., "Microbiome Selection Could Spur Next-Generation Plant Breeding Strategies," Frontiers in Microbiology, vol. 7, Dec. 7, 2016, XP055531064.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Ogbo, F., et al., "Some Characteristics of a Plant Growth Promoting; i*Enterobacter*/isp. Isolated from the Roots of Maize", Advances in Microbiology, Jan. 1, 2012, vol. 02, No. 03, pp. 368-374.
Orakçi GE et al, "Selection of antagonistic actinomycete isolates as biocontrol agents against root-rot fungi", Fresenius Environmental Bulletin, 2010, 19: 417-424 & GenBank Accession No. GQ475299, Oct. 5, 2009.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
Pedraza, R.O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Miranda, S., et al., "O-CAS, A Fast and Universal Method for Siderophore Detection," J Microbiol Methods, 2007, pp. 127-131, vol. 70.
Philippot, L., et al., "Going Back to the Roots: The Microbial Ecology of the Rhizosphere," Nat Rev Microbiol., Nov. 2013, pp. 789-799, vol. 11.
Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.
Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.
Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.

(56) References Cited

OTHER PUBLICATIONS

Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.

Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.

Sardi, P, et al., "Isolation of Endophytic Streptomyces Strains from Surface Sterilized Roots," Applied and Environmental Microbiology, 1992, pp. 2691-2693, vol. 58, No. 8.

"Sequence Alignment of JQ047949 with Instant Seq ID No. 2," Search conducted on Jan. 2, 2019, 2 pages.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Sharma et al., "Detection and identification of bacteria intimately associated with fungi of the order Sebacinales", Cellular Microbiology, Aug. 5, 2008, pp. 2235-2246, vol. 10, No. 11.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by Rhizobium tropici," Arch Microbiol., 2012, pp. 197-206, vol. 194.

Sturz, A. V., et al., "Weeds as a Source of Plant Growth Promoting Rhizobacteria in Agricultural Soils," Can J Microbiol., 2001, pp. 1013-1024, vol. 47, No. 11.

Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.

Valencia, C. U., et al., "Endophytic Establishment as an Unintended Consequence of Biocontrol with Fungal Entomopathogens," Power Point Presentation dated Jan. 7, 2013, 10 Pages.

Wang, L. et al. Application of Bioorganic Fertilizer Significantly Increased Apple Yields and Shaped Bacterial Community Structure in Orchard Soil.

Weaver, P.F., et al., "Characterization of Rhodopseudomonas capsulata," Arch Microbiol., 1975, pp. 207-216, vol. 105.

Whelehan, et al., "Microencapsulation using vibrating technology," Journal of Microencapsulation 2011, vol. 28(8), pp. 669-688.

Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings" World J Microbiol Biotechnol., 2014, pp. 835-845, vol. 30.

Yashiro et al., "Effect of Streptomycin Treatment on Bacterial Community Structure in the Apple Phyllosphere," PLOS ONE, May 21, 2012, vol. 7, No. 5, 10 pages.

Zhang, J., et al. "Isolation and Characterization of Plant Growth-Promoting Rhizobacteria from Wheat Roots by Wheat Germ Agglutinin Labeled with Fluorescein Isothiocyanate", The Journal Of Microbiology, Apr. 27, 2012, vol. 50, No. 2, pp. 191-198, GenBank Accession No. JN210900.

Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.

Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.

PCT International Search Report and Written Opinion for PCT/US2018/051467, dated Feb. 4, 2019, 22 pages.

Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.

Bashan, Yoav E., et al., "Alginate Beads as Synthetic Inoculant Carriers for Slow Release of Bacteria that Affect Plant Growth," Applied and Environmental Microbiology, pp. 1089-1098, May 1986.

Bragantia, et al, "Identificaqao e Avaliaqao de Rizobacterias Isoladas de Raizes de Milho," Jan. 1, 2010, pp. 905-911, Retrieved from the Internet: URL:http://www.scielo.br/pdf/brag/v69n4/v69n4a17.pdf (With English Abstract).

De Medeiros, L., et al., "Evaluation of Herbicidal Potential of Depsides from *Cladosporium uredinicola* an Endophytic Fungus found in Guava Fruit," J. Braz. Chem. Soc., 2012, vol. 23, No. 8, p. 1551-1557.

Azcon, R., et al., "Selective interactions between different species of mycorrhizal fungi and Rhizobium meliloti strains, and their effects on growth, N2-fixation (15N) and nutrition of Medicago sativa L.," New Phytol., 1991, vol. 117, pp. 399-404.

NCBI, GenBankAccession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at<URL:https://www.ncbi.nlm.nih.gov/nuccore/KX641980>.

Chaves, J., et al., "Identification and Phylogeny of Streptomyces Based on Gene Sequences", Research Journal of Microbiology, vol. 13, No. 1, Dec. 15, 2017, pp. 13-20, XP055675917.

Girard, G., et al., "A novel taxonomic marker that discriminates between morphologically complex actinomycetes", Open Biology, vol. 3, No. 10, Oct. 2013, p. 130073,XP055675916.

Guo, Y., et al. "A multi locus phylogeny of the Streptomyces griseus 16S rRNA gene clade: use of multilocus sequence analysis for streptomycete systematics", International Journal of Systematic and Evolutionary Microbiology, vol. 58, No. 1, 2008, pp. 149-159, XP055675936.

PCT International Search Report and Written Opinion for PCT/AU2018/050387, dated Jul. 12, 2018, 8 pages.

PCT International Search Report and Written Opinionfor PCT/US2018/051467, dated Mar. 25, 2019 26 pages.

PCT International Search Report and Written Opinion, Application No. PCT/AU2015/000360, dated Aug. 5, 2015, 12 Pages.

Djordjevic, D., et al., "Microtiter Plate Assay for Assessment of Listeria monocytogenes Biofilm Formation," Annl Environ Microbiol., 2002, pp. 2950-2958, vol. 68, No. 6.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 2 Pages.

Jalgaonwala, R., et al., "A Review on Microbiol Endophytes from Plants: A Treasure Search for Biologically Active Metabolites," Global Journal of Research on Medicinal Plants & Indigenous Medicine, 2014, pp. 263-277, vol. 3, No. 6.

Phalip, V., et al., "A Method for Screening Diacetyl and Acetoin-Producing Bacteria on Agar Plates," J Basic Microbiol., 1994, pp. 277-280, vol. 34.

Sword, G., et al., "Manipulating Fungal Endophytes for the Protection of Cotton in the Field," Power Point Presentation dated Jan. 7, 2013.

Theis, K. R., et al., "Uncultured Bacterium Clone GM2GI8201A64RC 16S Ribosomal RNA Gene, Partial Sequence," NCBI GenBank Accession No. JX051943, Submitted May 14, 2012, 1 Page.

Wiegand, I., et al., "Agar and Broth Dilution Methods to Determine the Minimal Inhibitory Concentration (MIC) of AntiMicrobiol Substances," Nature Protocols, 2008, pp. 163-175, vol. 3, No. 2.

Langille, M.G.I. et al., "Predictive functional profiling of microbial communities using 16S rRNA marker; gene sequences," Nature Biotechnology, 2013, vol. 31, No. 9, pp. 814-821.

Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.

R Core Team, "R: A Language and Environment for Statistical Computing," R Foundation for Statistical Computing, Vienna, Aus-

(56) References Cited

OTHER PUBLICATIONS tria, May 2013, ISBN: 3-900051-07-0. Available online at http://www.R-25project.org/, 3604 Pages.
Redman, R. S., et al., "Thermotolerance Generated by Plant/Fungal Symbiosis," Science, Nov. 2002, vol. 298, 1 Page (with 4 pages of supplemental material).
You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).
Invitation to Pay Additional Fees, PCT Application No. PCT/CA2013/000091, dated Mar. 27, 2013, 2 Pages.
International Search Report and Written Opinion for PCT/EP2013/062976, dated Dec. 22, 2014, 9 Pages.
International Search Report and Written Opinion, Application No. PCT/US2014/054160, dated Dec. 9, 2014, 21 Pages.
Invitation to Pay Additional Fees, PCT Application No. PCT/US2014/064411, dated Feb. 5, 2015, 2 Pages.
International Search Report and Written Opinion, International Application No. PCT/US2014/064411, dated Mar. 27, 2015, 15 Pages.
International Search Report and Written Opinion, International Application No. PCT/US2014/072399, dated Jun. 26, 2015, 22 Pages.
Antony-Badu, S., et al., "Multiple *Streptomyces* species with distinct secondary metabolomes have identical 16S rRNA gene sequences." Scientific Reports 7.1, Sep. 2017, No. 7, 11089, pp. 1-8.
Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession; No. AY016368 sequence.
Hubbard, M., et al., 2011. "Agricultural Potential of Fungal Endophytes of Grasses, Cereals and Wheat," In: Wheat: Genetics, Crops and Food Production. Nova Science Publishers Hauppauge, pp. 333-345.
Impullitti, A.E., et al., "Fungal endophyte diversity in soybean", Journal of Applied Microbiolog, vol. 114, No. 5, May 1, 2013, pp. 1500-1506.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Nassar, A., et al., "Promotion of plant growth by an auxin-producing isolate of the yeast *Williopsis saturnus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 5, 2012, pp. 69-78.
Sarkar, S., et al., "New report of additional enterobacterial species causing wilt in West Bengal, India," Canadian Journal of Microbiology, 2015, vol. 61, No. 7, pp. 477-486.
Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.
Vujanovic, V., et al., "A comparative study of endophytic mycobiota in leaves of Acer saccharum in eastern North America," Mycological Progress, May 2002, pp. 147-154, vol. 1, Issue 2.
Vujanovic, V., et al., "Orchid seed viability testing by fungal bioassays and molecular phylogeny," Floriculture, ornamental and plant biotechnology, 2006, vol. 63, pp. 563-569.
Vujanovic, V., et al., "19th International Conference on *Arabidopsis*. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.
Zhang, Y., et al., "BcGsl, a glycoprotein from Botrytis cinerea, elicits defence response and improves disease resistance in host plants. Biochemical and biophysical research communications," Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien de Botan, National Research Council, Ottawa, CA, vol. 75, Jan. 1, 1997, pp. 685-692.
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT International Search Report and Written Opinion for PCT/US2017/064361, dated May 11, 2018, 22 Pages.

(56) References Cited

OTHER PUBLICATIONS

PCT International Search Report and Written Opinion, PCT Application No. PCT/US2017/064292, dated May 11, 2018, 20 Pages.
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., et al., "Fungal Endophytes Improve Wheat Seed Germination Under Heat and Drought Stress," Botany, 2012, pp. 137-149, vol. 90.
Humann, J., et al., "Complete genome of the onion pathogen Enterobacter cloacae EcWSU1," Standard in Genomic Sciences, Dec. 31, 2011, vol. 5, No. 3, pp. 279-286.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of The Calcium/Calmodulin-Dependent Protein Kinase Gene (CCaMK) Determines Bacterial Community Diversity in Rice Roots Under Paddy And Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Janda, J.M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Johnston-Monje, D., et al., "Conservation and Diversity of Seed Associated Endophytes in Zea Across Boundaries of Evolution, Ethnography and Ecology," PLoS ONE, 2011, vol. 6, No. 6, 22 Pages.
Johnston-Monje, D., et al., "Plant and Endophyte Relationships: Nutrient Management," Comprehensive Biotechnol., 2011, pp. 713-727, vol. 4.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013, 17 Pages.
Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.
Kasana, R. C., et al., "A Rapid and Easy Method for the Detection of Microbial Cellulases on Agar Plates Using Gram's Iodine," Curr Microbiol., 2008, pp. 503-507, vol. 57.

Khan, A.L., et al., "Salinity Stress Resistance Offered by Endophytic Fungal Interaction Between Penicillium minioluteum LHL09 and Glycine max. L," J. Microbiol. Biotechnol., 2011, pp. 893-902, vol. 21, No. 9.
Kim, M., et al., "Towards a taxonomic coherence between average nucleotide identity and 16S rRNA gene sequence similarity for species demarcation of prokaryotes", Int J Systematic Evolutionary Microbiol., 2014, vol. 64, pp. 346-351.
Klaubauf, S., et al., "Molecular diversity of fungal communities in agricultural soils from Lower Austria," Fungal Diversity, Aug. 13, 2010, pp. 65-75, vol. 44, No. 1.
Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.
Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.
Kuklinsky-Sobral, J., et al., "Isolation and characterization of soybean-associated bacteria and their potential for plant growth promotion," Environmental Microbiology, 2004, pp. 1244-1251, vol. 6, No. 12.
Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.
Kusari, S., et al. "Chemical ecology of endophytic fungi: origins of secondary metabolites," Cell Press, Chem & Biol, vol. 19, pp. 792-798, 2012.
Labeda, D.P., et al., "Phylogenetic study of the species within the family Streptomycetaceae," Antonie van Leeuwenhoek, 2012, vol. 101, pp. 73-104, Springer.
Lanver, D., et al., "Sho1 and Msb2-Related Proteins Regulate Appressorium Development in the Smut Fungus *Ustilago aydis*," Plant Cell, 2010, pp. 2085-2101, vol. 22.
Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Lehman, S.G., "Treat Cotton Seed," Review of Applied Mycology, 1945, 24, 369, 16 Pages.
Lehman, S.G., "Treat Cotton Seed," Research and Farming III, Progr. Rept., 1945, 3, 5, 16 Pages.
Li, H. M., et al., "Expression of a Novel Chitinase by the Fungal Endophyte in Poa ampla," Mycologia, 2004, pp. 526-536, vol. 96, No. 3.
Li, H., et al., "Endophytes and their role in phytoremediation," Fungal Diversity, 2012, pp. 11-18, vol. 54.
Liu, M., et al., "A Novel Screening Method for Isolating Exopolysaccharide-Deficient Mutants," Appl Environ Microbiol., 1998, pp. 4600-4602, vol. 64, No. 11.
Liu, D., et al., "Osmotin Overexpression in Potato Delays Development of Disease Symptoms," Proc Natl Acad Sci USA, 1994, pp. 1888-1892, vol. 91.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lorck, H., "Production of Hydrocyanic Acid by Bacteria," Physiol Plant, 1948, pp. 142-146, vol. 1.
Lundberg, D.S., et al., "Defining the Core *Arabidopsis thaliana* Root Microbiome," Nature, 2012, pp. 86-90, vol. 488, No. 7409.
Lundberg, D.S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.

(56) References Cited

OTHER PUBLICATIONS

Mandyam, K., et al., "Mutualism-parasitism paradigm synthesized from results of root-endophyte models", Frontiers in Microbiology, vol. 5, Jan. 12, 2015, pp. 1-14.
Mannisto, M.K., et al., "Characterization of Psychrotolerant Heterotrophic Bacteria From Finnish Lapland," Syst Appl Microbiol., 2006, pp. 229-243, vol. 29.
Mano, H., et al., "Culturable Surface and Endophytic Bacterial Flora of the Maturing Seeds of Rice Plants (*Oryza saliva*) Cultivated in a Paddy Field," Microbes Environ., 2006, vol. 21, No. 2.
Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.
Marasco, R., et al., "A Drought Resistance-Promoting Microbiome is Selected by Root System Under Desert Farming," PLoS ONE, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mcdonald, D., et al., "An Improved Greengenes Taxonomy with Explicit Ranks for Ecological and Evolutionary Analyses of Bacteria and Archaea," ISME J., 2012, pp. 610-618, vol. 6.
Mcguire, K.L., et al., "Digging the New York City Skyline: Soil Fungal Communities in Green Roofs and City Parks," PloS One, 2013, vol. 8, No. 3, 13 Pages.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
De Souza, J. J., et al., "Terpenoids from Endophytic Fungi," Molecules, 2011, pp. 10604-10618, vol. 16, No. 12.
Dennis, C., et al., "Antagonistic Properties of Species Groups of Trichoderma," Trans Brit Mycol Soc, 1971, pp. 25-39, vol. 57, No. 1.
Desiro, A., et al., "Detection of a novel intracellular microbiome hosted in *Arbuscular mycorrhizal* fungi," ISME Journal, 2014, pp. 257-270, vol. 8.
Edgar, R. C., "Search and Clustering Orders of Magnitude Faster than BLAST," Bioinformatics, 2010, pp. 2460-2461, vol. 26, No. 19.
Edgar, R. C., "UPARSE: Highly Accurate OTU Sequences From Microbial Amplicon Reads," Nat. Methods, 2013, pp. 996-998, vol. 10, No. 10.
Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.
Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.
Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.
El-Shanshoury, A. R., "Growth Promotion of Wheat Seedlings by Streptomyces atroolivaceus," Journal of Agronomy and Crop Science, 1989, pp. 109-114, vol. 163.
Emerson, D., et al., "Identifying and Characterizing Bacteria in an Era of Genomics and Proteomics," BioScience, 2008, pp. 925-936, vol. 58, No. 10.
Endre, G., et al., "A Receptor Kinase Gene Regulating Symbiotic Nodule Development," Nature, 2002, pp. 962-966, vol. 417.
Faria, D. C., et al., "Endophytic Bacteria Isolated from Orchid and Their Potential to Promote Plant Growth," World J Microbiol Biotechnol., 2013, pp. 217-221, vol. 29.

Fierer, N., et al., "Cross-Biome Metagenomic Analyses of Soil Microbiol Communities and Their Functional Attributes," Proc Natl Acad Sci USA, 2012, pp. 21390-21395, vol. 109, No. 52.
Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.
Fisher, P. J., et al., "Fungal saprobes and pathogens as endophytes of rice (*Oryza sativa* L.), " New Phytol., 1992, pp. 137-143, vol. 120.
Fisher, P.R., et al., "Isolation and Characterization of the Pesticide-Degrading Plasmid pJP1 from Alcaligenes paradoxus," J Bacteriol., 1978, pp. 798-804, vol. 135, No. 3.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007, 1 Page.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: NP_001237541.1, "aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001237541.1 >.
NCBI GenBank: EBI accession No. EM STD:JQ759988, "*Dothideomycetes* sp. genotype 226 isolate FL0175 internal transcribed spacer 1, partial sequence; 5.8S ribosomal RNA gene and internal transcribed spacer 2, complete sequence; and 28S ribosomal RNA gene, partial sequence," May 17, 2012, 2 Pages.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl database, GenEmbl Record No. EU 977189, Jan. 21, 2009, 4 pages, Smith, S.A., et al., "Bioactive endophytes warrant intensified exploration and conservation," PloS ONE 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, Seq ID 1." Aug. 15, 2013, 1 Page.
Giraldo, A., et al., "Phylogeny of Sarocladium (Hypocreales)," Persoonia, 2015, pp. 10-24, vol. 34.
Gitaitis, R., et al., "The Epidemiology and Management of Seedborne Bacterial Diseases," Annu Rev Phytopathol., 2007, pp. 371-397, vol. 45.

(56) References Cited

OTHER PUBLICATIONS

Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hamayun, M., et al., "Cladosporium sphaerospermum as a new plant growth-promoting endophyte from the roots of Glycine max (L.) Merr," World Journal of Microbiology and Biotechnology, Kluwer Academic Publishers, DO, vol. 25, No. 4, Feb. 15, 2009 (Feb. 15, 2009), pp. 627-632.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, LE., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P.R., et al., "Dynamics of Seed-Borne Rice Endophytes on Early Plant Growth Stages," PLoS ONE, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hiatt, E.E., et al., "Tall Fescue Endophyte Detection: Commerical Immunoblot Test Kit Compared with Microscopic Analysis," Crop Science, 1999, pp. 796-799, vol. 39.
Hibbett, D.S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Li, J., et al., "Antitumour and antimicrobial activities of endophytic stretomycetes from pharmaceutical plants in rainforest", Lett Appl Microbiol. Dec. 2008; 47(6): 574-80. (Year: 2008).
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report for European Patent Application No. 15810847.2, dated Feb. 28, 2018, 19 Pages.
European Patent Office, Supplementary European Search Report, European Patent Application No. EP 15812324.0, dated Nov. 2, 2017, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
European Patent Office, Extended European Search Report, European Patent Application No. EP 15876324.3, dated Jun. 12, 2018, 9 Pages.
Abarenkov, K., et al., "The UNITE Database for Molecular Identification of Fungi—Recent Updates and Future Perspectives," New Phvtol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.
Abdou, R., et al., "Botryorhodines A-D, antifungal and cytotoxic depsidones from Botryosphaeria rhodina, an endophyte of the medicinal plant *Bidens pilosa*," Phytochemistry, 2010, vol. 71, pp. 110-116.
Abou-Shanab, R.A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Adhikari, M., et al., "A New Record of Pseudeurotium bakeri from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promotinq Activities," Microbiol Res., 2008, pp. 173-181, vol. 163.
Amann, R., et al., "The Identification of Microorganisms by Fluorescence in Situ Hybridisation," Curr Opin Biotechnol., 2001, pp. 231-236, vol. 12.
Amatuzzi, R.F., et al., "Potential of endophytic fungi as biocontrol agents of Duponchelia fovealis (Zeller) (Lepidoptera:Crambidae," Brazilian Journal of Biology, Nov. 9, 2017, 7 Pages.
Apel, K., et al., "Reactive Oxygen Species: Metabolism, Oxidative Stress, and Signal Transduction," Annu Rev Plant Biol., 2004, pp. 373-399, vol. 55.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Aveskamp, M., et al., "DNA phylogeny reveals polyphyly of Phoma section Peyronellaea and multiple taxonomic novelties," Mycologia, 2009, vol. 101, No. 3, pp. 363-382.
Bacon, C. W, et al., "Isolation, In Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev. Phytopathol., 1966, pp. 311-334, vol. 4.
Baltruschat, H., et al., "Salt tolerance of barley induced by the root endophyte Piriformospora indica is associated with a strong increase in antioxidants," New Phytologist., 2008, pp. 501-510, vol. 180.
Bensch, K., et al., "Species and ecological diversity within the Cladosporium cladosporioides complex (Davidiellaceae, Capnodiales)," Studies in Mycology, 2010, pp. 1-94, vol. 67.
Bethlenfalvay, G., et al., "Mycorrhizal fungi effects on nutrient composition and yield of soybean seeds", Journal of Plant Nutrition, vol. 20, pp. 4-5, Apr. 1, 1997, pp. 581-591.
Block, C. C., et al., "Seed Transmission of Pantoea stewartii in Field and Sweet Corn," Plant Disease, 1998, pp. 775-780, vol. 82.
Brodie, E.L., et al., "Uncultured Bacterium Clone BANW722 16S Ribosomal RNA Gene, Partial Sequence," NCBI GenBank Accession No. DQ264636, Submitted Oct. 25, 2005, 1 Page.

(56) References Cited

OTHER PUBLICATIONS

Bulgarelli, D., et al., "Structure and Functions of the Bacterial Microbiota of Plants," Annu Rev Plant Biol., 2013, pp. 807-838, vol. 64.
Castillo, D., et al., "Fungal Entomopathogenic Endophytes: Negative Effects on Cotton Aphid Reproduction in Greenhouse and Field Conditions," Power Point Presentation dated Mar. 23, 2013, 21 Pages.
Castillo, D., et al., "Fungal Endophytes: Plant Protective Agents Against Herbivores," Power Point Presentation dated Aug. 4, 2013.
Cavalier-Smith, T., "A Revised Six-Kingdom System of Life," Biol Rev Camb Philos Soc., 1998, pp. 203-266, vol. 73.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chagas, F., et al., "A Mixed Culture of Endophytic Fungi Increases Production of Antifungal Polyketides," J. Chem Ecol., Oct. 2013, pp. 1335-1342, vol. 39.
Clark, E. M., et al., "Improved Histochemical Techniques for the Detection of Acremonium coenophilum in Tall Fescue and Methods of in vitro Culture of the Fungus," J Microbiol Methods, 1983, pp. 149-155, vol. 1.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Clay, K., "Effects of fungal endophytes on the seed and seedling biology of Lolium perenne and Festuca arundinacea," Oecologia, 1987, pp. 358-362, vol. 73.
Clough, S. J., et al., "Floral Dip: A Simplified Method for Agrobacterium-mediated Transformation of *Arabidopsis thaliana*," Plant J., 1998, pp. 735-743, vol. 16, No. 6.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.
Cottyn, B., et al., "Phenotypic and genetic diversity of rice seed-associated bacteria and their role in pathogenicity and biological control," Journal of Applied Microbiology, 2009, pp. 885-897, vol. 107.
Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.
Daniels, R., et al., "Quorum Signal Molecules as Biosurfactants Affecting Swarming in Rhizobium etli," PNAS, 2006, pp. 14965-14970, vol. 103, No. 40.
Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Environmental Microbiology, 2008, pp. 2669-2678, vol. 74, No. 9.
De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.
De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.
Andreolli, M., et al., "Endophytic Burkholderia fungorum DBT1 can improve phytoremediation efficiency of polycyclic aromatic hyrocarbons", Chemosphere, Pergamon Press, Oxford, GB, vol. 92, No. 6, May 21, 2013, pp. 688-694.
Extended European Search Report for EP 20202875.9, 16 pages.
Douglas, G., et al., "PICRUSt2 for prediction of metagenome functions", Nature Biotechnology, vol. 38, No. 6, Jun. 1, 2020, pp. 685-688.
Kemp, N., et al., "Sarocladium zeae is a systemic endophyte of wheat and an effective biocontrol agent against Fusarium head blight", Biological Control, vol. 149, Publication No. 104329, 10 pages (2020).
Wicklow, D., et al., "A protective endophyte of maize: Acremonium zeae antibiotics inhibitory to Aspergillus flavus and Fasarium verticillioides", Mycol. Res. 109 (5):610-618 (May 2005).
Pan, J., et al., "Effects of host plant environment and Ustilago maydis infection on the fungal endophyte community of maize (*Zea mays*)", New Phytologist, vol. 178, pp. 147-156 (2008).
Wicklow, D., et al., "Occurrence of pyrrocidine and dihydroresorcylide production among Acremonium zeae populations from maize grown in different regions", Canadian Journal of Plant Pathology, vol. 30, pp. 425-433 (2008).
European Patent Office, Partial European Search Report, European Patent Application No. 18791606.9, dated Jul. 26, 2021, 16 Pages.
Abaid-Ullah, M., et al., "Plant Growth Promoting Rhizobacteria: An Alternate Way to Improve Yield and Quality of Wheat (*Triticum aestivum*)", International Journal of Agriculture and Biology, vol. 17, No. 1, Jan. 1, 2015, pp. 51-60.
Colla, G., et al., "Coating seeds with endophytic fungi enhances growth, nutrient uptake, yield and grain quality of winter wheat", International Journal of Plant Production, vol. 9, No. 2, Apr. 1, 2015, pp. 171-190.
Larran, S., et al., "Endophytes from wheat as biocontrol agents against tan spot disease", Biological Control, vol. 92, Sep. 11, 2015, pp. 17-23.
European Patent Office, Search Report, European Patent Application No. 17825317.5, dated Oct. 12, 2021, 9 Pages.
Yuan, J., et al., "Roots from distinct plant developmental stages are capable of rapidly selecting their own microbiome without the influence of environmental and soil edaphic factors", Soil Biology and Biochemistry 89 (2015): 206-209.
Bing, L., et al., "Suppression of Ostrinia nubilalis (Hübner) (Lepidoptera: Pyralidae) by Endophytic Beauveria bassiana (Balsamo) Vuillemin, Environ. Entomol. 20(4): 1207-1211 (1991).
Frichot, E., et al., "Testing for Associations between loci and environmental gradients using latent factor mixed models", Mol. Biol. Evol. 30:7 1687-1699 (Year: 2013).
Bicego, M., et al., "Investigating Topic Models' Capabilities in Expression Microarray Data Classification", IEEE/transactions on computational biology and bioinformatics, 9:8 1831-1836 (Year: 2012).
Gerber, G., et al., "Inferring Dynamic Signatures of Microbes in Complex Host Ecosystems", PLOS Computational Biology 8:8 e1002624, 14 pages (Year: 2012).
Holmes, I., et al., "Dirichlet Multinomial Mixtures: Generative Models for Microbial Metagenomics", PLoSONE 7:2, e30126, 15 pages (Year: 2012).
Kim, Y., et al., "Deciphering the human microbiome using next-generation sequencing data and bioinformatics approaches", Methods 79-80, p. 52-59 (Year: 2015).
Anesi, A., et al., "Towards a scientific interpretation of the terrior concept: platicisity of the grape berry metabolome", BMP plant biology 15:191, 17 pages (Year: 2015).
Hill, S.T., The pursuit of hoppiness: propelling hop into the genomic era. Thesis, Oregon State University, 80 pages (Year: 2016).
Li, M., et al., "Persistent homology and the branching topologies of plants", American Journal of Botany, 104:3, 349-353 (Year: 2017).
Mei, C., et al., "The Use of Beneficial Microbial Endophytes for Plant Biomass and Stress Tolerance Improvement," Recent Patents on Biotechnology, 2010, pp. 81-95, vol. 4.

(56) References Cited

OTHER PUBLICATIONS

Michel, B. E., et al., "The Osmotic Potential of Polyethylene Glycol 6000," Plant Physiol., 1973, pp. 914-916, vol. 51.
Misk, A., et al., "Biocontrol of chickpea root rot using endophytic actinobacteria", Biocontrol, vol. 56, No. 5, Mar. 12, 2011, pp. 811-822, XP036215297.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato," Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin max*) wtth Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Orole, O. O., et al., "Bacterial and fungal endophytes associated with grains and roots of maize," Journal of Ecology and the Natural Environment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.
Pearson, W.R., et al., "Rapid and Sensitive Sequence Comparison With FASTP and FASTA," Methods Enzymol., 2011, pp. 63-98, vol. 183.
Perez-Fernandez, M.A., et al., "Simulation of Germination of Pioneer Species Along an Experimental Drought Gradient," J Environ Biol., 2006, pp. 669-685, vol. 27, No. 4.
Petti, C. A., "Detection and Identification of Microorganisms by Gene Amplification and Sequencing," Clinical Infectious Diseases, 2007, pp. 1108-1114, vol. 44.
Philrice Batac, Philippine Rice R&D Highlights, 2012, Area-Based R&D Projects, [online][Retrieved Aug. 11, 2016] Retrieved from the Internet URL:http://www.philrice.gov.ph/2012-rd-highlights/, 52 Pages.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval Helicoverpa zea (Lepidoptera: Noctuidae)," J. Entomol. Sci., 2009, pp. 391-396, vol. 44, No. 4.
Quadt-Hallmann, A, et al., "Bacterial Endophytes in Cotton: Mechanisms of Entering the Plant," Can J Microbiol., 1997, pp. 577-582, vol. 43.
Rae, R., et al., "A subset of naturally isolated Bacillus strains show extreme virulence to the free-living nematodes *Caenorhabditis elegans* and *Pristionchus pacificus*", Environmental Microbiology, vol. 12, No. 11, 2010, pp. 3007-3021.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Riess, K., et al., "High genetic diversity at the regional scale and possible speciation in Sebacina epigaea and S. incrustans," BMC Evolutionary Biology, 2013, vol. 13, No. 102, 17 Pages.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001, pp. 11-29, vol. 13.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Samways, M.J., et al., "Assessment of the Fungus *Cladosporium oxysporum* (Berk. And Curt.) As a Potential BioControl Agent Against Certain Homoptera," Elsevier Science Publishers B.V., Jan. 1, 1986, pp. 231-239.
Sarwar, M., et al., "Tryptophan Dependent Biosynthesis of Auxins in Soil," Plant Soil, 1992, pp. 207-215, vol. 147.
Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74, No. 1.
Schmieder, R., et al., "Quality Control and Preprocessing of Metagenomic Datasets," Bioinformatics, 2011, pp. 863-864, vol. 27, No. 6.
Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B et al., "Universal Chemical Assay for the Detection and Determination of Siderophores," Analytical Biochemistry, 1987, pp. 47-56, vol. 160.
Senthilkumar, M., et al., "Biocontrol Potential of Soybean Bacterial Endophytes Against Charcoal Rot Fungus, Rhizoctonia batatiola," Current Microbiology, 2009, vol. 58, pp. 288-293.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Shankar, M., et al., "Root colonization of a rice growth promoting strain of Enterobacter cloacae," Journal of Basic Microbiology, 2011, pp. 523-530, vol. 51.
Shiraishi, A., et al., "Nodulation in black locust by the ammaproteobacteria *Pseudomonas* sp. and the Betaproteobacteria *Burkholderia* sp", Systematic and Applied Microbiology, vol. 33, No. 5, Aug. 2010, pp. 269-274.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.

(56) References Cited

OTHER PUBLICATIONS

Singh, A K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011, 1 page.

Soares, M. M. C. N., et al., "Screening of Bacterial Strains for Pectinolytic Activity: Characterization of the Polygalacturonase Produced by Bacillus SP," Revista de Microbiolgia, 1999, pp. 299-303, vol. 30.

Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.

Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Genmination of Hordeum brevisubulatum under Temperature and Water Stress Conditions," Acta Agrestia Sinica, 2010, pp. 834-837, vol. 18, No. 6. (English Abstract).

Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.

Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.

Strobel, G. A., "Endophytes as Sources of Bioactive Products," Microbes and Infection, 2003, pp. 535-544, vol. 5.

Surette, M.A., et al. "Bacterial Endophytes in Processing Carrots (*Daucus carota* L. var. sativus): Their Localization, Population Density, Biodiversity and Their Effects on Plant Growth," Plant and Soil, 2003, pp. 381-390, vol. 253, No. 2.

Suto, M., et al., "Endophytes as Producers of Xylanase," J Biosci Bioeng., 2002, pp. 88-90, vol. 93, No. 1.

Sword, G., "Manipulating Fungal Endophytes to Protect Plants from Insects and Nematodes," Power Point Presentation dated Aug. 7, 2013, 48 Pages.

Sword, G., et al., "Field Trials of Potentially Beneficial Fungal Endophytes in Cotton," Power Point Presentation dated Jan. 7, 2013, 17 Pages.

Sword, G., "Fungal Endophytes to Protect Cotton from Insects and Nematodes," Power Point Presentation dated Dec. 7, 2012, 20 Pages.

Sword, G., "Natural Enemies—The Forgotten Basis of IPM?," Power Point Presentation dated Sep. 6, 2013, 33 Pages.

Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.

Taghavi, S., et al., "Genome Sequence of the Plant Growth promoting Endophytic Bacterium *Enterobacter* sp. 638", PLoS Genet., May 2010, vol. 6, Issue 5, e1000943, pp. 1-15.

Tamura, K., et al., "Estimation of the number of nucleotide substitutions in the control region of mitochondrial DNA in humans and chimpanzees," Molecular Biology and Evolution, 1993, vol. 10, No. 3, pp. 512-526.

Taylor, A.G., et al., "Concepts and Technologies of Selected Seed Treatments," Annu. Rev. Phytopathol., 1990, pp. 321-339, vol. 28.

Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.

Thakur, A., et al., "Enhanced Resistance to Spodoptera litura in Endophyte Infected Cauliflower Plants," Environmental Entomology, Apr. 1, 2013, pp. 240-246, vol. 42, No. 2.

Thakur, A., et al., "Suppression of Cellular Immune Response in Spodoptera litura (Lepidoptera: Noctuidae) Larvae by Endophytic Fungi *Nigrospora oryzae* and *Cladosporium uredinicola*,", Annals of the Entomological Society of America, May 1, 2014, pp. 674-679, vol. 107, No. 3.

Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.

Thomashow, M. F., "So What's New in the Field of Plant Cold Acclimation? Lots!," Plant Physiol., 2001, pp. 89-93, vol. 125.

Tokala, R. T., et al., "Novel Plant-Microbe Rhizosphere Interaction Involving Streptomyces Lydicus WYEC108 and the Pea Plant (*Pisum sativum*)," Applied and Environmental Microbiology, May 2002, pp. 2161-2171, vol. 68, No. 5.

Trichoderma definition, 2016, 6 Pages, [online] [Retrieved on Sep. 16, 2016,] Retrieved from the Internet <URL: https://en.wikipedia.org/wiki/Trichoderma>.

Trotel-Aziz, P., et al., "Characterization of New Bacterial Biocontrol Agents Acinetobacter, Bacillus, Pantoea and *Pseudomonas* spp. Mediating Grapevine Resistance Against Botrytis cinerea," Environmental and Experimental Botany, 2008, pp. 21-32, vol. 64.

Truyens, S., et al., "Changes in the Population of Seed Bacteria of Transgenerationally Cd-Exposed *Arabidopsis thaliana*," Plant Biol., 2013, pp. 971-981, vol. 15.

U'ren, J.M., et al., "Host and geographic structure of endophytic and endolichenic fungi at the continental scale," American Journal of Botany, May 1, 2012, pp. 898-914, vol. 99, No. 5.

Usadel, B., et al., "The Plant Transcriptome—From Integrating Observations to Models," Front Plant Sci., 2013, pp. 1-3, vol. 4., Article 48, 3 Pages.

Vacheron, J., et al., "Plant Growth-Promoting Rhizobacteria and Root System Functioning," Frontiers Plant Sci., 2013, vol. 4, Article 356, 19 Pages.

Valencia, E., et al., "Mini-review: Brazilian fungi diversity for biomass degradation," Fungal Genetics and Biology, 2013, pp. 9-18, vol. 60.

Van Der Lelie, D., et al., "Poplar and its Bacterial Endophytes: Coexistence and Harmony," Critical Rev Plant Sci., 2009, pp. 346-358, vol. 28.

Verkley, G., et al., "Paraconiothyrium, a new genus to accommodate the mycoparasite *Coniothyrium minitans*, anamorphs of Paraphaeosphaeria, and four new species," Studies in Mycology, 2004,; pp. 323-335, vol. 50.

Vining, K., et al., "Methylome Reorganization During in vitro Dedifferentiation and Regeneration of Populus trichocarpa," BMC Plant Biol., 2013, vol. 13, No. 92, 15 Pages.

Viruel, E., et al., "Pseudomonas thiveralensis Strain IEHa 16S Ribosomal RNA Gene, Partial Sequence," NCBI GenBankAccession No. GQ169380.1, Submitted May 15, 2009, 1 Page.

Visagie, C.M., et al., "Identification and nomenclature of the genus *Penicillium*," Studies in Mycology, Jun. 2014, pp. 343-371, vol. 78.

Vujanovic, V., et al., "Viability Testing of Orchid Seed and the Promotion of Colouration and Germination," Annals of Botany, Mar. 17, 2000, pp. 79-86, vol. 86.

Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.

Vujanovic, V., et al., "Mycovitality—a new concept of plant biotechnology," Canadian Journal Plant Pathol. 2007, vol. 29, p. 451.

Vujanovic, V., et al., "Seed endosymbiosis: a vital relationship in providing prenatal care to plants," Can. J. Plant Sci., NRC Research Press, Feb. 6, 2017, pp. 972-981, vol. 97.

Waller, F., et al., "The Endophytic Fungus *Piriformospora indica* Reprograms Barley to Salt-Stress Tolerance, Disease Resistance, and Higher Yield," PNAS, 2005, pp. 13386-13391, vol. 102, No. 38.

Wang, B., et al., "Fungal endophytes of native *Gossypium* species in Australia," Mycological Research, 2007, pp. 347-354, vol. 111, No. 3.

Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.

(56) References Cited

OTHER PUBLICATIONS

Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weindling, R., "Relation of dosage to control of cotton seedling diseases by seed treatment," Plant Disease Reporter, 1943, 27, pp. 68-70.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.
Yezerski, A., et al., "The Effects of the Presence of Stored Product Pests on the Microfauna of a Flour Community," Journal of Applied Microbiology, 2005, pp. 507-515, vol. 98.
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhou, W., et al., "Effects of the Fungal Endophyte *Paecilomyces* sp. in Cotton on the Roo-Knot Nematode Meloidogyne incognita," poster dated Jan. 7, 2013.
Zhu et al., "*Helminthosporium velutinum* and *H. aquaticum* sp. nov. from aquatic habitats in Yunnan Province, China." Phytotaxa, 2016, vol. 253, No. 3, pp. 179-190.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
United States Patent Office, Non-Final Office Action, U.S. Appl. No. 14/766,065, dated Oct. 27, 2017, 11 Pages.
United States Patent Office, Non-Final Office Action, U.S. Appl. No. 14/964,429, dated Aug. 9, 2016, 6 Pages.
United States Patent Office, Final Office Action, U.S. Appl. No. 14/964,429, dated May 31, 2017, 9 Pages.
United States Patent Office, Non-Final Office Action, U.S. Appl. No. 15/212,038, dated Sep. 21, 2016, 10 Pages.
United States Patent Office, Non-Final Office Action, U.S. Appl. No. 15/063,350, dated Nov. 10, 2016, 18 Pages.
United States Patent Office, Final Office Action, U.S. Appl. No. 14/614,193, dated Dec. 22, 2016, 13 Pages.
United States Patent Office, Final Office Action, U.S. Appl. No. 14/614,193, dated Jul. 18, 2017, 14 Pages.
United States Patent Office, Final Office Action, U.S. Appl. No. 14/614,193, dated May 3, 2018, 10 Pages.
United States Patent Office, Non-Final Office Action, U.S. Appl. No. 15/107,973, dated Apr. 10, 2017, 39 Pages.
United States Patent Office, Final Office Action, U.S. Appl. No. 15/107,973, dated Jan. 26, 2018, 20 Pages.
United States Patent Office, Final Office Action, U.S. Appl. No. 14/410,537, dated May 5, 2017, 9 Pages.
United States Patent Office, Non-Final Office Action, U.S. Appl. No. 15/034,862, dated May 19, 2017, 8 Pages.
United States Patent Office, Final Office Action, U.S. Appl. No. 15/034,862, dated Jan. 12, 2018, 14 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/143,398, dated Sep. 22, 2017, 17 Pages.
United States Patent Office, Non-Final Office Action, U.S. Appl. No. 15/143,394, dated Sep. 25, 2017, 15 Pages.
United States Patent Office, Non-Final Office Action, dated U.S. Appl. No. 15/107,965, dated Jun. 21, 2018, 27 Pages.
Abello, J., et al., "Agrobacterium-mediated transformation of the endophytic fungus *Acremonium implicatum* associated with Brachiaria grasses", Mycological Research, pp. 407-413, vol. 112, Pt 3.
Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.
Amatuzzi, R.F., et al., "Universidade Federal do Parana," Jan. 1, 2014, 52 Pages. (With English Abstract).
Ardakani, M.R. et al., "Absorption of N, P, K thorugh triple inoculation of wheat (*Triticum aestivum* L.) by Azospirillum brasilense, *Streptomyces* sp., Glomus intraradices and manure application," Physiol Mol Biol Plants, 2011, vol. 17, No. 2, pp. 181-192.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Bandara, WM.M.S., et al., "Interactions among endophytic bacteria and fungi: effects and potentials" Journal of Biosciences, Dec. 2006, vol. 31, No. 5, pp. 645-650.
Barnett, S., et al., "Selection of microbes for control of Rhizoctonia root rot on wheat using a high throughput pathosystem", Biological Control, Jul. 6, 2017, 113: 45-57.
Bing, LA, et al., "Suppression of Ostrinia nubilalis (Hübner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Büttner, D., et al., "Regulation and secretion of Xanthomonas virulence factors," FEMS Microbiology Reviews, 2010, pp. 107-133, vol. 34, No. 2.
Caporaso, J.G., et al., "Ultra-High-Throughput Microbiol Community Analysis on the Illumina HiSeq and MiSeq Platforms," ISME J., 2012, pp. 1621-1624, vol. 6.
Chenhua Li , et al., "Change in deep soil microbial communities due to long-term fertilization," Soil Biology and Biochemistry, vol. 75, Mar. 5, 2014, pp. 264-272, XP055530941.
Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.
Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.
Compant, S., et al., "Endophytic colonization of Vitis vinfera L. by Burkholderia phytofirmans strain PsJN: from the rhizosphere to inflorescence tissues," FEMS Microbiol Ecol, 2008, pp. 84-93, vol. 63.
Danhorn, T., et al., "Biofilm Formation by Plant-Associated Bacteria," Annu Rev Microbiol., 2007, pp. 401-422, vol. 61.
Dbget, "Orthology: K14454," 2005, 2 pages, can be retrieved at <URL:http://www.genome.jp/dbget-bin/wwwbget?ko:K14454>.

(56) References Cited

OTHER PUBLICATIONS

De Santi, M. et al., "A combined morphologic and molecular approach for characterizing fungal microflora from a traditional Italian cheese (Fossa cheese)," Inter. Dairy J., 2010, vol. 10, No. 7, pp. 465-471.
Don, R.H., et al., "Properties of Six Pesticide Degradation Plasmids Isolated From Alcaligenes Paradoxus and Alcaligenes eutrophus," J Bacteriol., 1981, pp. 681-686, vol. 145, No. 2.
Eberhard, A., et al., "Structural Identification of Autoinducer of Photobacterium fischeri Luciferase," Biochem., 1981, pp. 2444-2449, vol. 20.
Fatima Z et al, "Antifungal activity of plant growth-promoting rhizobacteria isolates against Rhizoctonia solani in wheat", African Journal of Biotechnology, 2009, 8: 219-225.
Ferrando, L., et al., "Molecular and Culture-Dependent Analyses Revealed Similarities in the Endophytic Bacterial Community Composition of Leaves from Three Rice (Oryza sativa) Varieties," FEMS Microbiol Ecol., 2012, pp. 696-708, vol. 80.
Fiehn, O., et al., "Metabolite Profiling for Plant Functional Genomics," Nature Biotechnol., 2000, pp. 1157-1161, vol. 8.
Fox, G., et al., "How close is close: 16S rRNA sequence identity may not be sufficient to guarantee species identity." International Journal of Systematic and Evolutionary Microbiology 42.1, 1992, pp. 166-170.
Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
GenBank: AF034210.1 "Glycine max aspartate aminotransferase glyoxysomal isozyme AAT1 precursor and aspartate aminotransferase cytosolic isozyme AAT2 (AAT) mRNA, complete eds," NCBI, May 26, 1998, 2 Pages, can be retrieved at <URL:https://www.ncbi.nlm.nih.gov/nuccore/AF034210>.
GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
NCBI GenBank: CP000653.1 "*Enterobacter* sp. 638, complete genome" Jan. 28, 2014, 5 Pages, Can be retrieved at<URL:https://www.ncbi.nlm.nih.gov/nuccore/CP000653.1>.
Hamayun, M., et al., "Gibberellin production and plant growth promotion from pure cultures of *Cladosporium* sp. MH-6 isolated from cucumber (*Cucumis sativus* L.)", Mycologia, 102 (5), 2010, pp. 989-995.
Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.
Kim, S., et al., "Physiological and proteomic analyses of Korean F1 maize (*Zea mays* L.) hybrids under water-deficit stress during flowering", Appl. Biol. Chem. (2019) 62:32.
Halligan, B., et al., "Cloning of the murine cDNA encoding VDJP, a protein homologous to the large subunit of replication factor C and bacterial DNA ligases", Gene (1995) 217-222.
Arend, J., et al., "Hydroquinone: O-glucosytransferase from cultivated Rauvolfia cells: enrichment and partial amino acid sequences", Phytochemistry (2000) 53:187-193.
Enchev, R., et al., "Protein neddylation: beyond cullin-RING ligases", (Nature Reviews: Molecular Cell Biology (2015) 16:30-44.
Bais, H., et al., "The Role of Root Exudates in Rhizosphere Interactions with Plants and Other Organisms", Annual Review. Plant Biol. (2006) 57:233-266.
Goepfert, S., et al., "Molecular Identification and Characterization of the *Arabidopsis* D3,5, D2,4-Dienoyl-Coenzyme A Isomerase, a Peroxisomal Enzyme Participating in the b-Oxidation Cycle of Unsaturated Fatty Acids1", Plant Physiology (2005) 138:1947-1956.
Thomas, P., et al: "Endophytic Bacteria Associated with Growing Shoot Tips of Banana (*Musa* sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007 /S00248-009-9559-Z.
Database Geneseq [Online] Sep. 30, 2010 (Sep. 30, 2010), "Cellulomonas fermentans 16s rRNA gene Seq ID:39.", retrieved from EBI accession No. GSN:AWL84299 Database accession No. AWL84299; & JP 2009 072168 A (Univ of Occupational & Environ) Apr. 9, 2009 (Apr. 9, 2009).
European Patent Office, Partial European Search Report, European Patent Application No. 20171870.7, dated Nov. 20, 2020, 18 Pages.
European Patent Office, European Search Report, European Patent Application No. 20171870.7, dated Mar. 1, 2021, 15 Pages.
GenBank Accession NR_041978, dated Aug. 8, 2011. (Year: 2011).
GenBank Accession AF394537, dated Jul. 2, 2002. (Year: 2002).
Invitation to Pay Additional Fees, PCT Application No. PCT/US2014/072400, dated Apr. 16, 2015, 6 Pages.
International Search Report and Written Opinion, Application No. PCT/US2014/072400, dated Jul. 8, 2015, 38 Pages.
Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.
Li, Q., "Agrobacterium tumefaciens Strain TA-AT-10 16S Ribosomal RNA Gene, Partial Sequence: GenBank: KF673157.1," Submitted Dec. 16, 2013.
Invitation to Pay Additional Fees, PCT Application No. PCT/US2015/038110, dated Sep. 22, 2015, 8 Pages.
NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https://www.ncbi.nlm.nih.gov/nuccore/J Q765415.1/.
NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/K C355340.
NCBI GenBank: Accession No. XP55670279, "Uncultured bacterium clone bb2s4 16S ribosomal RNA gene, partial seque—Nucleotide", May 6, 2005, 1 Page, can be retreived at URL:https://www.ncbi.nlm.nih.gov/nuccore/D Q068880.
European Patent Office, Communication Pursuant to Article 94(3) EPC for European Patent Application No. EP 14777213.1, dated Jun. 18, 2018, 4 Pages.
De Melo Pereira, G. V., et al. "A Multiphasic Approach for the Identification of Endophytic Bacterial in Strawberry Fruit and their Potential for Plant Growth Promotion," Microb. Ecology, 2012, pp. 405-417, vol. 63, No. 2.
Result 11 from a search in the GenEmbl database, GenEmbl Record No. EU 977189, Smith et al., "Bioactive endophytes warrant intensified exploration and conservation," PLoS ONE 3(8):E3052, 2008.
Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.
PCT Invitation to Pay Additional Fees, PCT Application No. PCT/US2017/064292, dated Mar. 6, 2018, 15 Pages.
PCT International Search Report and Written Opinion, PCT Application No. PCT/US2017/068255, dated Mar. 19, 2018, 14 Pages.
PCT International Search Report and Written Opinion PCT/AU2018/050387, dated Jul. 12, 2018 (Filing date is Apr. 27, 2018).
PCT International Search Report and Written Opinion for PCT/US2017/064292, dated May 11, 2018, 20 Pages.
Bentley, S.D., et al., Complete genome sequence of the model actinomycete Streptomyces coelicolor A3(2), Nature. May 9, 2002;417(6885):141-7. (Year: 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of *Streptomyces* spp. In sorghum and rice", SpringerPlus, 2/1/574, pp. 1-8, http://www.springerplus.com/content/2/1/574, 2013.
Groppe, K., et al., "Interaction between the endophytic fungus *Epichloë bromicola* and the grass *Bromus erectus*: effects of endophyte

(56) References Cited

OTHER PUBLICATIONS infection, fungal concentration and environment on grass growth and flowering," Mol Ecol., 8:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year: 2003).
Lee, J., et al., "*Streptomyces koyangensis* sp. nov., a novel actinomycete that produces 4-phenyl-3-butenoic acid," Int J Syst Evol Microbial. Jan. 2005;55(Pt 1):257-62. (Year: 2005).
Lind, A., et al., "Drivers of genetic diversity in secondary metabolic gene clusters within a fungal species", PLOS Biology, Nov. 17, 2017, 26 pages.
Pacovsky, R., "Carbohydrate, protein and amino acid status of Glycine-Glomus-Bradyrhizobium symbioses," Physiologia Pantarium; 75:346-354, 1989).
Sha, T. et al., "Genetic diversity of the endemic gourmet mushroom *Thelephora ganbajun* from southwestern China", Microbiology (2008), 154, 3460-3468.
Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.
Wiebold, M., et al., "Agriculture Experiment Station, College of Agriculture, Food & Natural Resources, University of Missouri, Special Report 589, pp. 1-124)."
Le, X.H., et al., "Effects of endophytic Streptomyces on the lucerne (Medicago sativa L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
European Patent Office, Supplementary European Search Report, European Patent Application No. 13874703.5, dated Jun. 21, 2016, 3 Pages.
Invitation to Pay Additional Fees, PCT Application No. PCT/US2015/038187, dated Oct. 14, 2015, 5 Pages.
Coombs, J. T., et al., "Isolation and Identification of Actinobacteria from Surface-Sterilized Wheat Roots," Applied and Environmental Microbiology, 2003, pp. 5603-5608, vol. 69, No. 9.
Laus, M. C., et al., "Role of Cellulose Fibrils and Exopolysaccharides of Rhizobium leguminosarum in Attachment to and Infection of Vicia sativa Root Hairs," Mol Plant Microbe Internet., 2005, pp. 533-538, vol. 16, No. 6.
PCT International Search Report and Wlitten Opinion, PCT Application No. PCT/US2015/068206, dated Jun. 27, 2016, 20 Pages.
PCT International Search Report and Wlitten Opinion, PCT Application No. PCT/US2016/036504, dated Nov. 4, 2016, 18 Pages.
GenEmbl Database, GenEmbl Record No. JN872548.1, 2 Pages.
Soe, K.M, et al., "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).
Ngom, A et al., "A novel symbiotic nitrogen-fixing member of the Ochrobactrum clade isolated from root nodues of Acacia mangium". J. Gen. Appl. Microbiol. (2004) 50: 17-27.
Trujillo, M.E et al., "Nodulation of Lupinus albus by strins of *Ochrobactrum lupini* sp. nov." Appl. Environ Microbiol Mar. 2005; 71(3): 1318-1327.
Bal, H.B et al., "Isolation of ACC deaminase producting PGPR from rice rhizosphere and evaluating their plant growth promoting activity under salt stress". Plant Soil (2013) 366: 93-105 doi: 10/1007/s11104-012-1402-5.

Chakraborty et al., "Evaluation of Ochrobactrum anthropi TRS-2 and its talcbased formulation for enhancement of growth of tea plants and management of brown root rot disease." Journal of Applied Microbiology, 2009, 107(2):625-634 DOI: 10.1111/j.1365-2672.2009.04242.x <https://doi.org/10.1111/j.1365-2672.2009.04242.x.
Sulistiyani, et al., "Population and Diversity of Endophytic Bacteria Associated with Medicinal Plan Curumma zedoaria", Microbiology Indonesia 8.2 (2014):4.
Bevivino, A., et al., "Characerization of free-living maize rhizosphere populatin of Burkholderia cepacia: effect of seed treatment on disease suppresssion and growth promotion of maize", FEMS Microbiology Ecology 27 (1998) 225-237.
Ciccillo, F., et al., Effects of two different application methods of Burkholderia ambifaria MCI 7 on plant growth and rhizospheric bacterial diversity.
Estrada, P., et al., "A N2-fixing endophytic *Burkholderia* sp. associated with maize plants culitvated in Mexico", Canadian Journal of Microbiology (2002), vol. 48(4), pp. 528-536.
Sharma, V.K., et al., "Enhancement of verticillium wilt resistance in tomato transplants by in vitro co-culture of seedlings with a plant growth promoting rhizobacterium (*Pseudomonas* sp. strain PsJN)", Canadian Journal of Microbiology (1998), vol. 44(6), pp. 285-294.
Grady, E., et al., "Current knowledge and perspectives of Paenibacillus: a review" Microb Cell Fact (2016) 15:203.
Schuerger, A., "Microbial Ecology of a Crewed Rover Traverse in the Arctic: Low Microbial Dispersal and Implications for Planetary Protection on Human Mars Missions", Astrobiology, vol. 15, No. 6, 2015, pp. 478-491.
Timmusk, S., "Paenibacillus polymyxa antagonizes oomycete plant pathogens Phytophthora palmivora and Pythium aphanidermatum", Journal of Applied Microbiology, GB, vol. 105, No. 5, Jan. 5, 2009, pp. 1473-1481.
Fatima, Z., "Antifungal activity of plant growth-promoting rhizobacteria isolates against Rhizoctonia solani in wheat", African Journal of Biotechnology, vol. 8(2), pp. 219-225, Jan. 19, 2009, pp. 219-225.
Database accession No. JQ759107, European Nucleotide Archive [Online] EMBL's European Bioinformatics Institute; Mar. 7, 2012, U'ren J M et al: "*Sordariomycetes* sp.genotype 60 isolate AK0688 internal transcribed spacer."
Database accession No. MG917011, European Nucleotide Archive [Online] EMBL's European Bioinformatics Institute; Feb. 21, 2019, Lagarde A. et al: "*Coniochaeta* sp.isolate Gir_07 internal transcribed spacer 1, partial sequence."
Database accession Nos. MZ267873, MZ267979, MZ267926, MZ267820; European Nucleotide Archive [Online] EMBL's European Bioinformatics Institute; Sep. 11, 2021, Arnold A E: "Coniochaeta nivea isolate LG0013 various submissions."
Database accession Nos. MZ267874, MZ267980, MZ267927, MZ267821; European Nucleotide Archive [Online] EMBL's European Bioinformatics Institute; Sep. 11, 2021, Arnold A E: "Coniochaeta nivea isolate LG0023."
Arnold, A. Elizabeth et al; "*Coniochaeta elegans* sp. nov., *Coniochaeta montana* sp. nov. and *Coniochaeta nivea* sp. nov., three new species of endophytes with distinctive morphology and functional traits", Int J Syst Evolu Microb vol. 71 No. 11, p. 5003.
Kokaew, J. et al; "Coniochaeta ligniaria an endophytic fungus from Baeckea frutescens and its antagonistic effects against plant pathogenic fungi", Thai Journal of Agricultural Science, vol. 44, Jun. 1, 2011, pp. 123-131.
Lagarde A. et al: "Antiproliferative and antibiofilm potentials of endolichenic fungi associated with the lichen *Nephroma laevigatum*", Journal of Applied Microbiology, vol. 126, No. 4, Jan. 30, 2019, pp. 1044-1058.
Nilsson et al; "Correspondence: Intraspecific ITS Variability in the Kingdom Fungi as Expressed in the International Sequence Databases and Its Implications for Molecular Species Identification", Evolutionary Bioinformatics, Jan. 1, 2008, pp. 193-201.
Trifonova, R. et al; "Interactions of plant-beneficial bacteria with the ascomycete Coniochaeta ligniaria", Journal of Applied Microbiology, vol. 106, No. 6, Jun. 1, 2009, pp. 1859-1866.

(56) References Cited

OTHER PUBLICATIONS

U'ren, Jana M., et al; "Community Analysis Reveals Close Affinities Between Endophytic and Endolichenic Fungi in Mosses and Lichens", Microbial Ecology, vol. 60, No. 2, Jul. 13, 2010, pp. 340-353.

Shah, S., et al: "Colonization with non-mycorrhizal culturable endophytic fungi enhances orchid growth and indole acetic acid production", BMC Microbiology, vol. 22, No. 1, Jan. 1, 2022, pp. 1-13.

Aerts A et al: "NCBI Reference Sequence: XP_024757499.1: glycoside hydrolase family 18 protein [Trichoderma asperellum CBS 433. 97]", Apr. 26, 2018 (Apr. 26, 2018), pp. 1-2, XP055973177.

Database Genbank [Online] NIH; Jul. 25, 2016 (Jul. 25, 2016), Steyaert J M et al: "Trichoderma hamatum endochitinase (chit42) gene, partial eds", XP055973252, Database accession No. AY258898 abstract.

Database Genbank [Online] NIH; Sep. 25, 1998 (Sep. 25, 1998), Giczey G et al: "endochitinase [Trichoderma hamatum]", XP055973364, Database accession No. AAC60385 abstract.

Database Genbank [Online] NIH; Sep. 25, 1998 (Sep. 25, 1998), Giczey G et al: "Trichoderma hamatum endochitinase gene, complete eds", XP055973251, Database accession No. U88560 abstract.

Liu, H.J., et al., "Bacillus subtilis strain A2-9 16S ribosomal RNA gene, partial sequence", Accession No. JF496331, deposited Aug. 2011.

Li, C., et al., "Bacillus subtilis strain B2-1 16S ribosomal RNA gene, partial sequence", Accession No. JN256114, deposited Sep. 2011.

Jiang, L., "Bacillus subtilis strain jllsy 16S ribosomal RNA gene, partial sequence", Accession No. FJ793201, deposited Apr. 2009.

Choi, N.S., et al., "Bacillus licheniformis strain DJ-2 16S ribosomal RNA gene, partial sequence", Accession No. FJ435676, deposited Jan. 2009.

Peng, S., et al., "Bacillus subtilis strain CCM9 16S ribosomal RNA gene, partial sequence", Accession No. HQ536000, deposited Dec. 2010.

Jee, H., et al., "Bacillus subtilis strain R2-1 16S ribosomal RNA gene, partial sequence", Accession No. EU852929, deposited Jul. 2009.

Zhao, Y., et al., "Bacillus amyloliquefaciens strain BGP14 16S ribosomal RNA gene, partial sequence", Accession No. JQ734536, deposited May 2012.

Allard, G. et al., "SPINGO: a rapid species-classifier for microbial amplicon sequences," BMC Bioinformatics, 2015, vol. 16, No. 324, 8 pages.

Anders, S. et al., "Differential expression analysis for sequence count data," Genome Biology, 2010, vol. 11, No. 11, pp. R106.

Ansari, M.A.; Brownbridge, M.; Shah, F.A.; Butt, T.M. Efficacy of entomopathogenic fungi against soil-dwelling life stages of western flower thrips, Frankliniella occidentalis, in plant-growing media. Entomol. Exp. Appl. 2008, 127, 80-87.

Asaff, A.; Cerda-Garcia-Rojas, C.; De la Torre, M. Isolation of dipicolinic acid as an insecticidal toxin from Paecilomyces fumosoroseus. Appl. Microbiol. Biotechnol. 2005, 68, 542-547.

BB-CBI, "*Beauveria bassiana* (white muscardine fungus)," Invasive Species Compendium, 2021, pp. 1-68.

Beris, E.I.; Papachristos, D.P.; Fytrou, A.; Antonatos, S.A.; Kontodimas, D.C. Pathogenicity of three entomopathogenic fungi on pupae and adults of the Mediterranean fruit fly, *Ceratitis capitata* (Diptera: Tephritidae). J. Pest Sci. 2013, 86, 275-284.

Chen, F. et al., "Assessing Performance of Orthology Detection Strategies Applied to Eukaryotic Genomes," PLoS ONE, Apr. 2007, No. 4, pp. e383.

Cole, J.R. et al., "Ribosomal Database Project: data and tools for high throughput rRNA analysis," Nucleic Acids Research, 2014, vol. 42, pp. D633-D642.

Deshpande, V. et al., "Fungal identification using a Bayesian classifier and the Warcup training set of internal transcribed spacer sequences," Mycologia, 2016, vol. 108, No. 1, pp. 1-5.

Djian, C. et al., Acetic acid: A selective nematicidal metabolite from culture filtrates of Paecilomyces lilacinus (Thom) Samson and Trichoderma longibrachiatum Rifai. Nematologica 1991, 37, 101-112.

Doster, M.A. et al., "Biocontrol of Aflatoxins in Figs," Proceedings of the Third International Symposium on Fig, 798, 2008, pp. 223-226.

Eberhardt, C. et al., "Proteomic Analysis of Kveim Reagent Identifies Targets of Cellular Immunity in Sarcoidosis," PLOS One, Jan. 23, 2017, vol. 12, No. 1, pp. 1-16.

Edgar, R.C., "UNOISE2: Improved Error-Correction For Illumina 16S and ITS Amplicon Sequncing," BioRxiv, 2016, No. 081257, 21 pages.

Ehteshamul-Haque, S. et al., "Biological control of root rot diseases of okra, sunflower, soybean and mungbean," Pakistan Journal of Botany, vol. 22, No. 2, Jun. 1990, pp. 121-124.

Enright, A.J. et al., "An efficient algorithm for large-scale detection of protein families," Nucleic Acids Research, 2002, vol. 30, No. 7, pp. 1575-1584.

Enright, A.J. et al., "Protein families and TRIBES in genome sequence space," Nucleic Acids Research, 2003, vol. 31, No. 15, pp. 4632-4638.

Faria, M.; Wraight, S.P. Biological control of Bemisia tabaci with fungi. Crop Prot. 2001, 20, 767-778.

Friedman, J. et al., "Regularization Path for Generalized Linear Models via Coordinate Descent," Journal of Statistical Software, 2010, vol. 33, No. 1, pp. 1-22.

Hoy, M.A.; Singh, R.; Rogers, M.E. Evaluations of a novel isolate of Isaria fumosorosea for control of the Asian citrus psyllid, *Diaphorina citri* (Hemiptera: Psyllidae). Fla. Entomol. 2010, 93, 24-32.

Kepenekci, I. et al., "Pathogenicity of the Entomopathogenic Fungus, Purpureocillium Lilacinum TR1 Against the Black Cherry Aphid, *Myzus cerasi* Fabricus (Hemiptera: Aphididae)," Mun. Ent. Zool., vol. 10, No. 1, Jan. 2015, pp. 53-60.

Koljalg. U. et al., "Towards a unified paradigm for sequence-based identification of fungi," Molecular Ecology, 2013, vol. 22, pp. 5271-5277.

Kozich, J.J. et al., "Development of a Dual-Index Sequencing Strategy and Curation Pipeline for Analyzing Amplicon Sequence Data on the MiSeq Illumina Sequencing Platform," Applied and Environmental Microbiology, Sep. 2013, vol. 79, No. 17, pp. 5112-5120.

Li, W. et al., "Ultrafast clustering algorithms for metagenomic sequence analysis," Briefings in Bioinformatics, Nov. 1, 2012, vol. 13, No. 6., pp. 656-668.

McMurdie, P.J. et al., "Waste Not, Want Not: Why Rarefying Microbiome Data Is Inadmissible," PLOS Computational Biology, 2014, vol. 10, No. 4, pp. e1003531.

Mezeal, I.A.; Mizil, S.N.; Hussin, M.S. Researching biocontrol of Trichoderma viride, Paecilomyces lilacinus in contradiction of effectiveness of fungi insulated as of selected therapeutic herbals. Plant Arch. 2018, 18, 1631-1637.

NCBI, "Purpureocillium lilacinum," Taxonomy ID: 33203, 2021, three pages, [Online] [Retrieved on Feb. 27, 2021] Retrieved from the Internet <URL: https://www.ncbi.nlm.nih.gov/Taxonomy/Browser/wwwtax.cgi?id=33203>.

Needleman, S.B. et al., "A General Method Applicable to the Search for Similarities in the Amino Acid Sequence of Two Proteins," Journal Of Molecular Biology, 1970, vol. 28, No. 3, pp. 443-453.

O'Callaghan, M., "Microbial inoculation of seed for improved crop performance: issues and opportunities," Applied Microbiology and Biotechnology, vol. 100, May 2016, pp. 5729-5746.

Pandey, R. K. et al., "Effect of different bioformulations of Paecilomyces lilacinus against root-knot nematode (*Meloidogyne incognita*) infecting tomato (*Solanum esculentum*)," Indian Journal of Agricultural Sciences, vol. 81, No. 3, Mar. 2011, pp. 261-267.

Panyasiri, C.; Attathom, T.; Poehling, H.M. Pathogenicity of entomopathogenic fungi-potential candidates to control insect pests on tomato under protected cultivation in Thailand. J. Plant Dis. Prot. 2007, 114, 278-287.

(56) References Cited

OTHER PUBLICATIONS

Paul, N.C.; Deng, J.X.; Lee, J.H.; Yu, S.H. New records of endophytic Paecilomyces inflatus and Bionectria ochroleuca from chili pepper plants in Korea. Mycobiology 2013, 41, 18-24.
Perveen, Z.; Shahzad, S.A. Comparative study of the efficacy of Paecilomyces species against root-knot nematode Meloidogyne incognita. Pak. J. Nematol. 2013, 31, 125-131.
Piatkowski, J.; Krzyzewska, U.; Nawrot, U. Antifungal activity of enthomopathogenic species of the genus Paecilomyces. Mikol. Lek. 2003, 10, 93-99 (with copy of abstract).
Quast, C. et al., "The SILVA ribosomal RNA gene database project: improved data processing and web-based tools," Nucleic Acids Research, 2013, vol. 41, pp. D590-D596.
Raafat, I et al., "Nezara viridula (Hemiptera: Pentatomidae) Cuticle as a Barrier for Beauveria bassiana and Paecilomyces sp. Infection," African Entomology, vol. 23, Iss. 1, Mar. 2015, pp. 75-87.
Rajinikanth, R. et al., "Management of nematode induced disease complex in seedlings of cauliflower (Brsassica pleraceae var. botrytis) using bio-pesticides," Pest Management in Horticultural Ecosystems, vol. 19, No. 2, Dec. 2013, pp. 203-210.
Ratnalikar, K.K. et al., "Biological management of root-rot of cotton caused by Rhizoctonia bataticola," Indian Phytopathol. 44-45, Suppl., XV, 1993, pp. 1-2.
Rideout, J.R. et al., "Subsampled open-reference clustering creates consistent, comprehensive OTU definitions and scales to billions of sequences," PeerJ, 2014, 2:e545.
Roth, A.C.J. et al., "Algorithm of OMA for large-scale orthology inference," BMC Bioinformatics, 2008, vol. 9, pp. 518.
Shenoy, B.D. et al., "Impact of DNA sequence-data on the taxonomy of anamorphic fungi," Fungal Diversity, 2007, vol. 26, No. 10, pp. 1-54.
Shibuya, H. et al., "Transformation of Cinchona Alkaloids into 1-N-Oxide Derivatives by Endophytic Xylaria sp. Isolated from Chinchona pubescens," Chem Pharm Bull, 2003, vol. 41, No. 1, pp. 71-74.
Singh, S. et al., "Bio-control activity of Purpureocillium lilacinum strains in managing root-knot disease of tomato caused by Meloidogyne incognita," Biocontrol Science and Technology, vol. 23, No. 12, Sep. 2013, pp. 1469-1489.
Sivakumar, T.; Eswaran, A.; Balabaskar, P. Bioefficacy of antagonists against for the management of Fusarium oxysporum f. sp. lycopersici and Meloidogyne incognita disease complex of tomato under field condition. Plant Arch. 2008, 8, 373-377 (with copy of abstract).
Smith, T.F. et al., "Identification of Common Molecular Subsequences," Journal of Molecular Biology, 1981, vol. 147, pp. 195-197.
Spurgeon, D.W., "Efficacy of Beauveria bassiana Against Lygus hesperus (Hemiptera: Miridae) at Low Temperatures," Journal of Entomological Science, vol. 45, Iss. 3, Jul. 2010, pp. 211-219.
Sword, G. A. et al., "Endophytic fungi alter sucking bug responses to cotton reproductive structures," Insect Science, vol. 24, Mar. 22, 2017, pp. 1003-1014.
Yeo, H.; Pell, J.K.; Alderson, P.G.; Clark, S.J.; Pye, B.J. Laboratory evaluation of temperature effects on the germination and growth of entomopathogenic fungi and on their pathogenicity to two aphid species. Pest Manag. Sci. 2003, 59, 156-165.
Zhang, X-Y. et al., "Diversity and Antimicrobial Activity of Culturable Fungi Isolated from Six Species of the South China Sea Gorgonians," Microbial Ecology, vol. 64, Apr. 2012, pp. 617-627.
Zhou, W. et al., "A fungal endophyte defensive symbiosis affects plant-nematode interactions in cotton," Plant Soil, vol. 422, Dec. 21, 2016, pp. 251-266.
Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.
Gaussian process model definition from towarddatascience.com downloaded May 15, 2023 (Year: 2023).
Gaussian process model definition from wikipedia.com, downloaded May 15, 2023 (Year: 2023).
Ghahramani, Z. (2013) Bayesian non-parametrics and the probabilistic approach to modeling. Philosophical transactions of the royal society A, vol. 371, 20110553, 20 pages.
Donahue, J. et al. Adversarial feature learning. arXiv: 1605.09782V7, Apr. 3, 2017.
Buee, et al. ("The rhizosphere zoo: an overview of plant-associated communities of microorganisms, including phages, bacteria, archaea, and fungi, and of some of their structuring factors." (2009): 189-212). (Year: 2009).
Hanapi, et al. ("Biofertilizer: Ingredients for Sustainable Agriculture." Biotechnology Development in Agriculture, Industry and Health: Current Industrial Application and Future Trends 1 (2012): 359-385). (Year: 2012).
Singh ("Screening and characterization of plant growth promoting rhizobacteria (PGPR): An overview." Bulletin of Environmental and Scientific Research 4.1-2 (2015): 1-2). (Year: 2016).
Sato, I., et al., "Suppressive Potential of Paenibacillus Strains Isolated from the Tomato Phyllosphere against Fusarium Crown and Root Rot of Tomato", Microbes Environ, vol. 29, No. 2, 168-177, 2014.
Combined printouts of term definitions from world wide web, performed by mkz Oct. 19, 2022 (Year. 2022).
Sarangi, S., et al., "Agricultural Activity Recognition with Smartshirt and Crop Protocol", IEEE global humanitarian technology conference, p. 298-305 (Year: 2015).
Gibbs, A., et al., "Chemical Diversity: Definition and Quantification", IN Exploiting chemical diversity for drug discovery, Bartlett et al EDS. elBSN 978-1-84755-255-6 p. 137-160.
Peiffer, J., et al., "The Genetic Architecture of Maize Height", Genetics, vol. 196, p. 1337-1356 (Year: 2015).
Kazemian, M., et al., "Improved accuracy of supervised CRM discovery with interpolated Markov models and cross-specieis comparison", Nucleic Acids Research, 2011, vol. 39, No. 22, 9463-9472.
Yeh, J.H., "Protein Remote Homology Detection Based on Latent Topic Vector Model", International conference on Networking and information technology, p. 456-460, (Year: 2010).
Heydari, A., "A Review on Biological Control of Fungal Plant Pathogens Using Microbial Antagonists", Journal of Biological Sciences, vol. 10 (4) 273-290 (Year: 2010).
Sessitsch, A., et al., "Functional Characteristics of an Endophyte Community Colonizing Rice Roots as Revealed by Metagenomic Analysis", MPMP vol. 25, No. 1, 2012, pp. 28-36.
Muhammad, N., et al., "Endophytes in biotechnology and agriculture", E-COST FA1103 Working Group Meeting in Trento/S. Michele, Italy Nov. 2012. (poster).
Hurek, T., et al., "Azoarcus sp. strain BH72 as a model for nitrogen-fixing grass endophytes", Journal of Biotechnology 106 (2003) 169-178.
Engelhard, M., et al., "Preferential occurrence of diazotrophic endophytes, Azoarcus spp., in wild rice species and and races of Oryza sativa in comparison with moder races", Environmental Microbiology (2000) 2(2), 131-141.
Sessitsch, A., et al., "Endophytic bacterial communities of field-grown potato plants and their plant-growth-promoting and antagonistic abilities", Can. J. Microbiol. 50: 239-249 (2004).
Sessitsch, A., et al., "Cultivation-independent poplulation analysis of bacterial endophytes in three potato varieties based on eubacterial and Actinomycetes-specific PCR of 16S rRNA genes", FEMS Microbiology Ecology 39 (2002) 23-32.
Minamisawa K., et al., "Anaerobic Nitrogen-Fixing Consortia Consisting of Clostridia Isolated from Gramineous Plants", Applied and Environmental Microbiology, May 2004, p. 3096-3102, vol. 70, No. 5.
Seghers, D., et al., "Impact of Agricultural Practices on the Zea mays L. Endophytic Community", Applied and Environmental Microbiology, Mar. 2004, p. 1475-1482, vol. 70, No. 3.
Bulgari, D., et al., "Endophytic Bacterial Diversity in Grapevine (Vitis vinifera L.) Leaves Described by 16S rRNA Gene Sequence Analysis and Length Beterogeneity-PCR", The Journal of Microbiology, Aug. 2009, p. 393-401, vol. 47, No. 4.

(56) References Cited

OTHER PUBLICATIONS

Amann, R., et al., "Single-cell identification in microbial communities by improved fluorescence in situ hybridization techniques", Nature Reviews Microbiology, 6: 339-348 (2008).
Chelius, M.K., et al., "The Diversity of Archaea and Bacteria in Association with the Roots of Zea mays L.", Microb Ecol (2001) 41:252-263.
Edwards, U., et al., "Isolation and direct complete nucleotide determination of entire genes. Characterization of a gene coding for 16S ribosomal RNA", Nucleic Acids Research 17: 7843-7853 (1989).
Prischl, M., et al., "Genetically modified Bt maize lines containing cry3Bb1, cry1A105 or cry1Ab2 do not affect the structure and functioning of root-associated endophyte communities", Applied Soil Ecology 54 (2012) 39-48.
Naveed, M., et al., "The endophyte *Enterobacter* sp. FD17: a maize growth enhancer selected based on rigorous testing of plant beneficial traits and colonization characteristics", Biol Fertil Soils (2014) 50:249-262.
Rashid, M., et al., "Inorganic polyphosphate is needed for swimming, swarming, and twitching motilities of Pseudomonas aeruginosa", PNAS vol. 97, No. 9, Apr. 25, 2000, pp. 4885-4890.
Mehta, S., et al., "An Efficient Method for Qualitative Screening of Phosphate-Solubilizing Bacteria", Current Microbiology vol. 43 (2001), pp. 51-56.
Dunn,R., et al., "Home Life: Factors Structuring the Bacterial Diversity Found within and between Homes", PLoS One, vol. 8, Issue 5, May 2013.
Massol-Deya, A., et al., "Bacterial community fingerprinting of amplified 16S and 16-23S ribosomal DNA gene sequences and restriction endonuclease analysis (ARDRA)", Molecular Microbial Ecology Manual 3.3.2: 1-8, 1995.
Extended European Search Report for Application No. 22190659,7, dated Feb. 10, 2023, 8 pages.
GenBank Accession No. AY148074 published Nov. 30, 2002.
GenBank Accession No. FM998026 published Feb. 10, 2011.
GenBank Accession No. KJ494315 published May 3, 2014.
International Search Report and Written Opinion for PCT/US2022/026051, 38 pages.
Langner Dos Santos Miriam et al: "Benefits Associated with the Interaction of Endophytic Bacteria and Plants", Brazilian Archives of Biology and Technology, vol. 61, No. 0, Jan. 1, 2018 (Jan. 1, 2018), pp. 18160431-2018.
Database GenBank [Online] NIH; Jan. 29, 2016 (Jan. 29, 2016), Wu JR: "Chitinophaga pinensis strain CSB3-50 16S ribosomal RNA gene", XP055948434, accession No. KU305719 Database accession No. KU305719.1 abstract.
Database GenBank [Online] NIH; Mar. 10, 2017 (Mar. 10, 2017), Shaffer JP et al: "Uncultured bacterium clone EHB-PS0362 16S ribosomal RNA gene", XP055948435, accession No. KU978322 Database accession No. KU978322.1 abstract.
Database GenBank [Online] NIH; Jan. 15, 2019 (Jan. 15, 2019), Hu C. J. et al: "*Chitinophaga* sp. strain N15203 16S ribosomal RNA gene", XP055948438, accession No. MK389338 Database accession No. MK389338.1 abstract.
Database GenBank [Online] NIH; Nov. 26, 2014 (Nov. 26, 2014), Han J. H. et al: "*Chitinophaga* sp. NR 1-07 16S ribosomal RNA gene", XP055948440, accession No. KM253104 Database accession No. KM253104.1 abstract.
Database GenBank [Online] NIH; Sep. 2, 2017 (Sep. 2, 2017), Jiayu T. J.: "*Chitinophaga* sp. strain PRd7 16S ribosomal RNA gene", XP055948441, accession No. KY203972 Database accession No. KY203972.1 abstract.
Database GenBank [Online] NIH; Oct. 1, 2010 (Oct. 1, 2010), Aslam Z. et al: "Chitinophaga sp. Z2-YC6856 16S ribosomal RNA gene", XP055948442, accession No. GQ369124 Database accession No. GQ369124.1 abstract.
Database GenBank [Online] NIH; Jun. 10, 2014 (Jun. 10, 2014), Zhang B. G.: "Chitinophaga oryziterrae strain ZBGKL4 16S ribosomal RNA gene", XP055948443, accession No. KJ734873 Database accession No. KJ734873.1 abstract.
Chung, E., et al: *Chitinophaga oryziterrae* sp. nov., isolated from the rhizosphere soil of rice (*Oryza sativa* L.) II, International Journal of Systematic and Evolutionary Microbiology, vol. 62, No. Pt_12, Dec. 1, 2012 (Dec. 1, 2012), pp. 3030-3035.
Proença Diogo Neves et al: "*Chitinophaga costaii* sp. nov., an endophyte of Pinus pinaster, and emended description of Chitinophaga niabensis", International Journal of Systematic and Evolutionary Microbiology, vol. 64, No. Pt_4, Apr. 1, 2014 (Apr. 1, 2014), pp. 1237-1243.
Elad, Y., et al: "Control of Rhizoctonia solani in cotton by seed-coating with *Trichoderma* spp. spores", Plant and Soil, vol. 66, No. 2, Jun. 1, 1982 (Jun. 1, 1982), pp. 279-281.
Harman, G.E., et al: "Trichoderma hamatum effects on seed and seedling disease induced in radish and pea by *Pythium* spp. or Rhizoctonia solani", Phytopathology, Dec. 1, 1980 (Dec. 1, 1980), pp. 1167-1172.
Harman, G.E., et al: "Factors affecting Trichoderma hamatum applied to seeds as a biocontrol agent", Phytopathology, Jun. 1, 1981 (Jun. 1, 1981), pp. 569-572.
Giczey, G., et al: "Homologous transformation of Trichoderma hamatum with an endochitinase encoding gene, resulting in increased levels of chitinase activity", FEMS Microbiology Letters, Jan. 1, 1998 (Jan. 1, 1998), pp. 247-252.
Freitas, R., et al: "Cloning and characterization of a protein elicitor Sml gene from Trichoderma harzianum", Biotechnology Letters, vol. 36, No. 4, Dec. 10, 2013 (Dec. 10, 2013), pp. 783-788.
Database Genbank [Online] NIH; Jan. 1, 2008 (Jan. 1, 2008), Hanada RE et al: "Trichoderma hamatum strain DIS 65G 18S ribosomal RNA gene, partial sequence; internal transcribed spacer 1", XP055973221, Database accession No. EU264000 abstract.
Database Genbank [Online] NIH; Sep. 6, 2013 (Sep. 6, 2013), Samuels G J et al: "Trichoderma hamatum strain Dis 240j actin (act) gene, partial cds", XP055973271, Database accession No. EU856256 abstract.
Database Genbank [Online] NIH; May 23, 2005 (May 23, 2005), Steyaert J M et al: "Trichoderma hamatum alkaline proteinase (prb1) gene, complete cds", XP055973243, Database accession No. AY258899 abstract.
Database Genbank [Online] NIH; Apr. 11, 2019 (Apr. 11, 2019), Chaverri P et al: "Trichoderma hamatum strain GJS 04-207 calmodulin (CAL) gene, partial cds", XP055973272, Database accession No. FJ442285 abstract.

\* cited by examiner

FIG. 1: Culture plate of Strain A
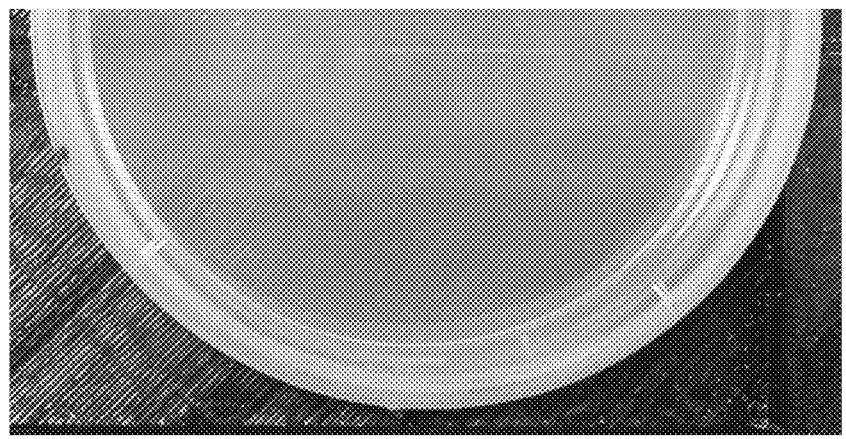
FIG. 2: Culture plate of Strain B
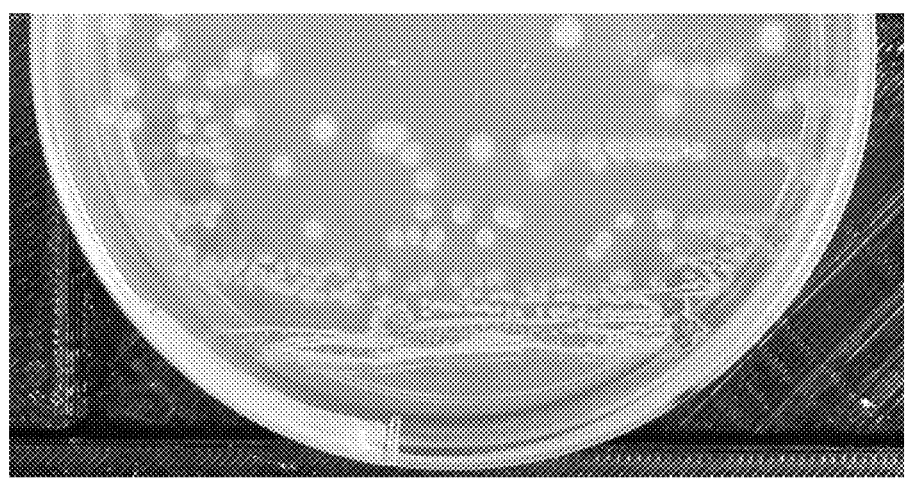
FIG. 3: Culture plate of Strain C
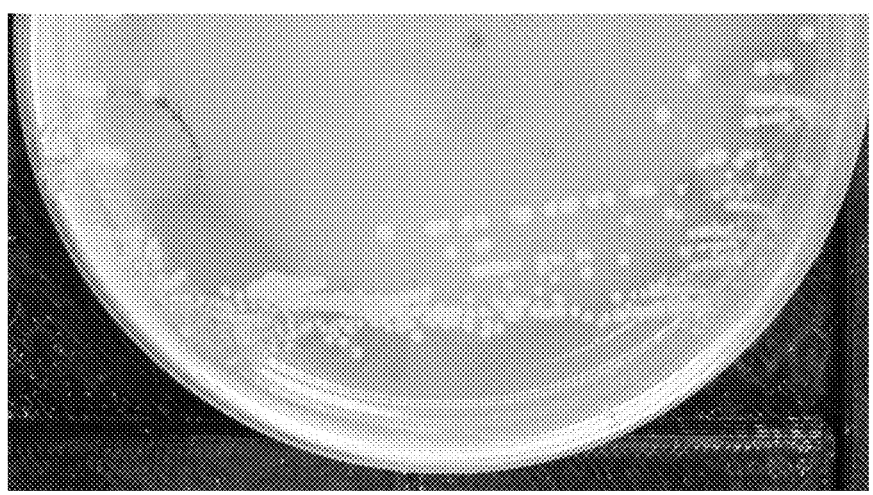

FIG. 4: Greenhouse phenotypes of Strain C-treated plants under normal watering conditions
FIG. 5: Greenhouse phenotypes of Strain C-treated plants under water-limited conditions
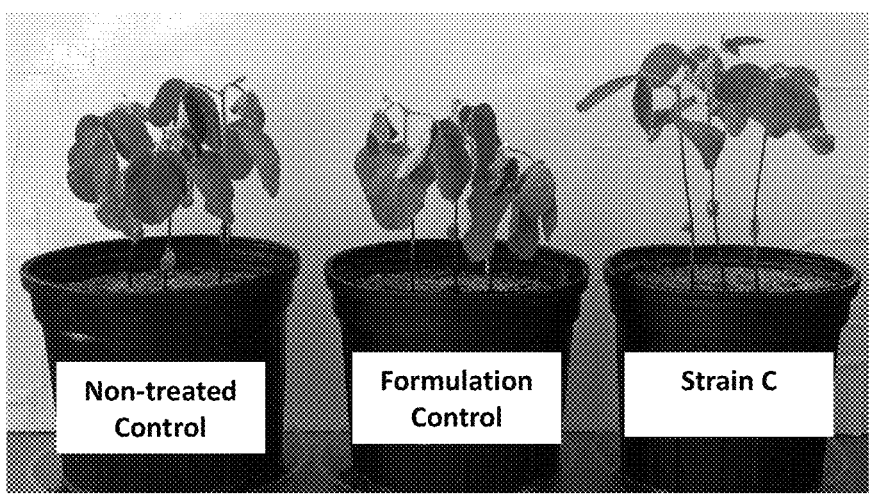

FIG. 6: Greenhouse phenotypes of plants grown from seeds treated with *Streptomyces* strains
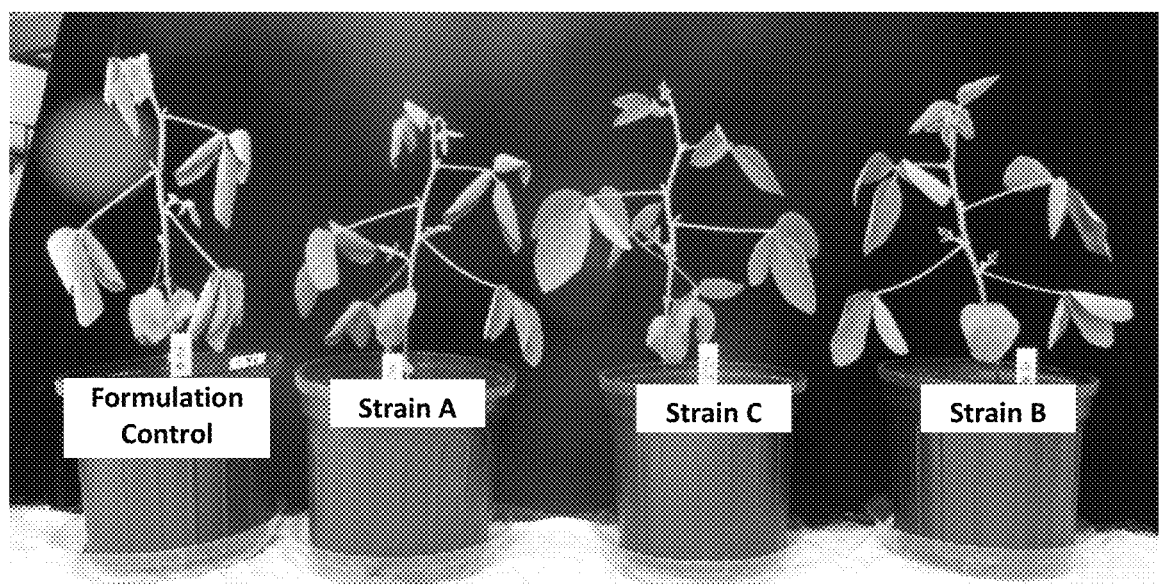

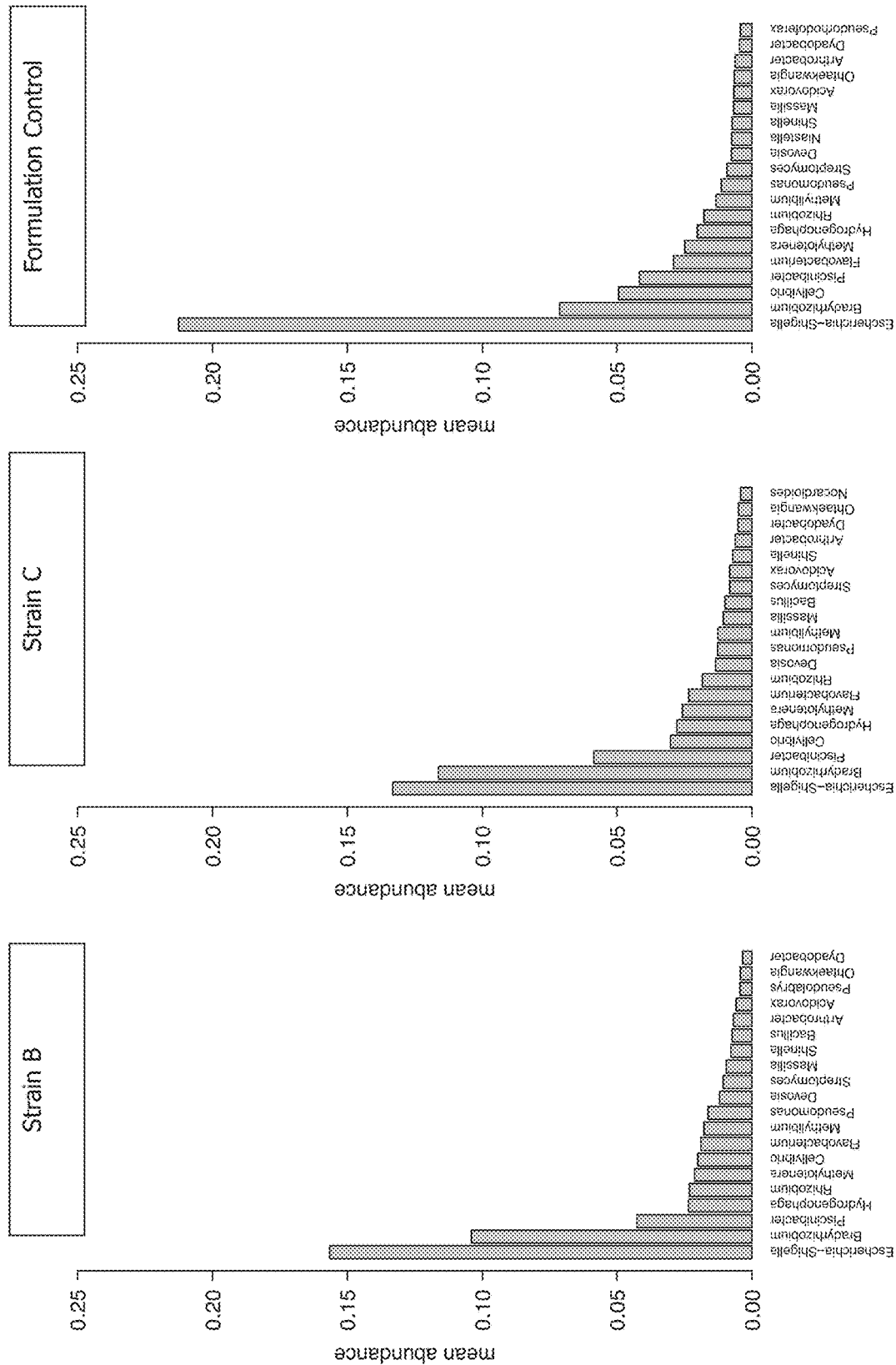
FIG. 7: Community Sequencing

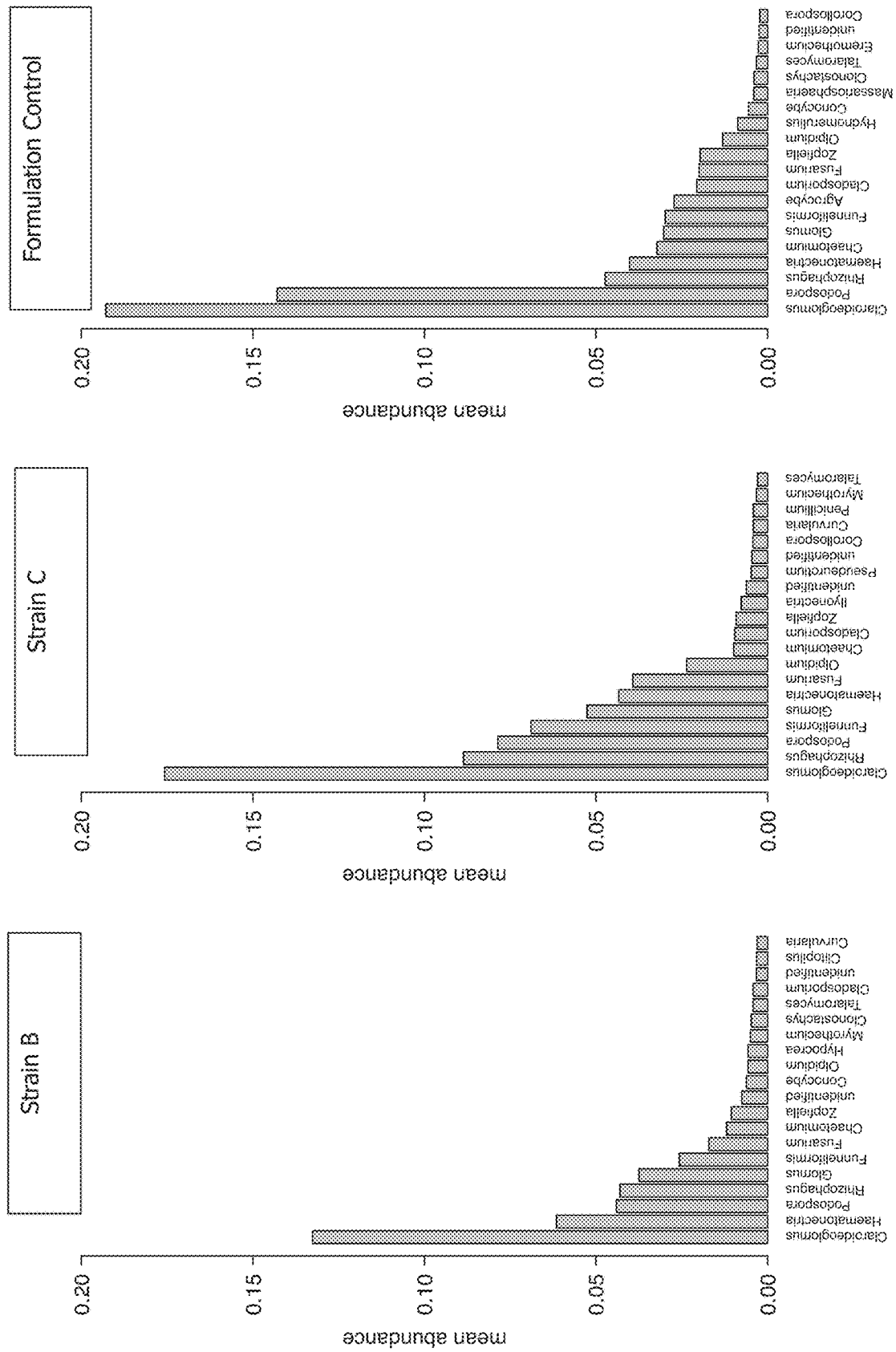
FIG. 8: Community Sequencing

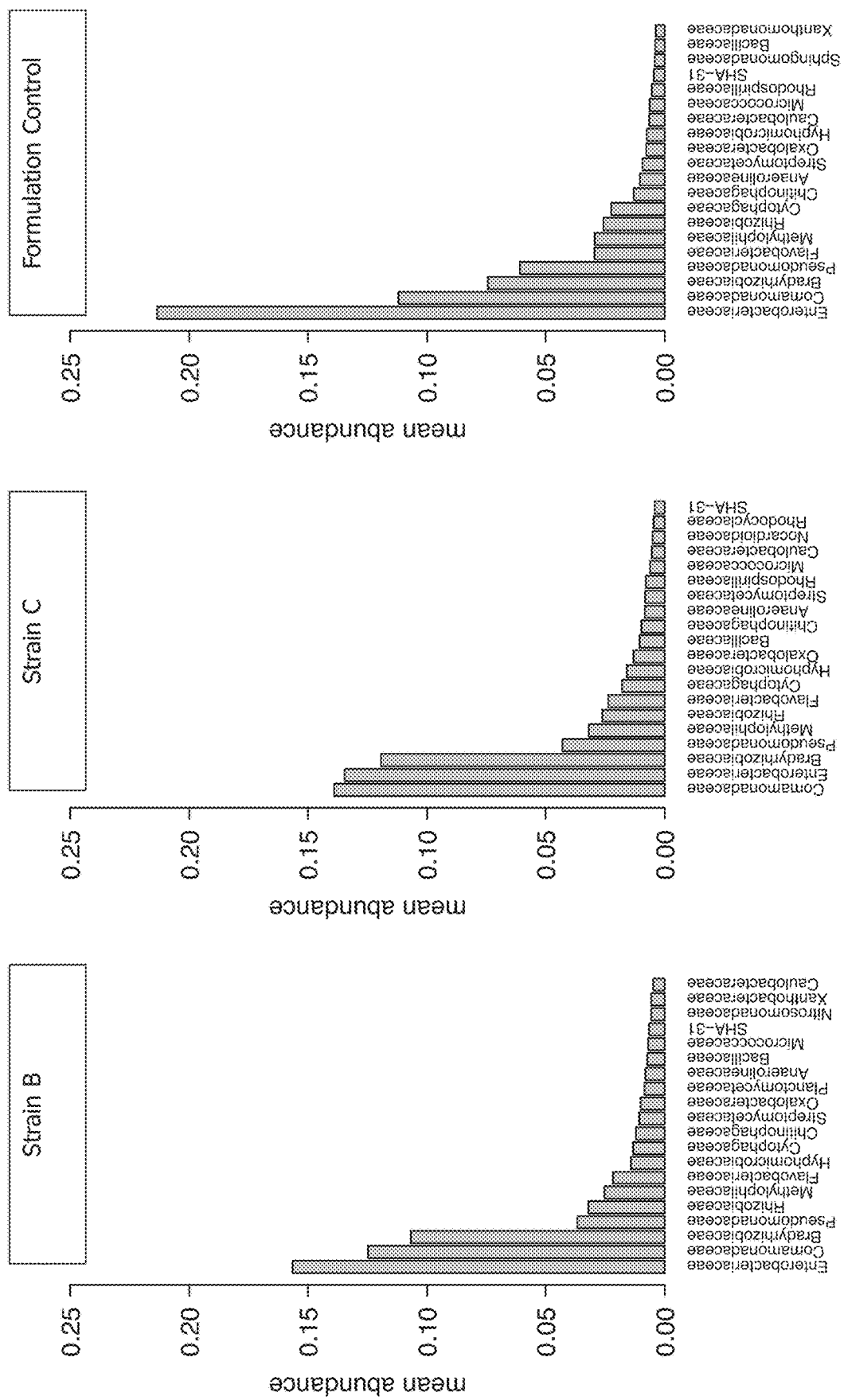

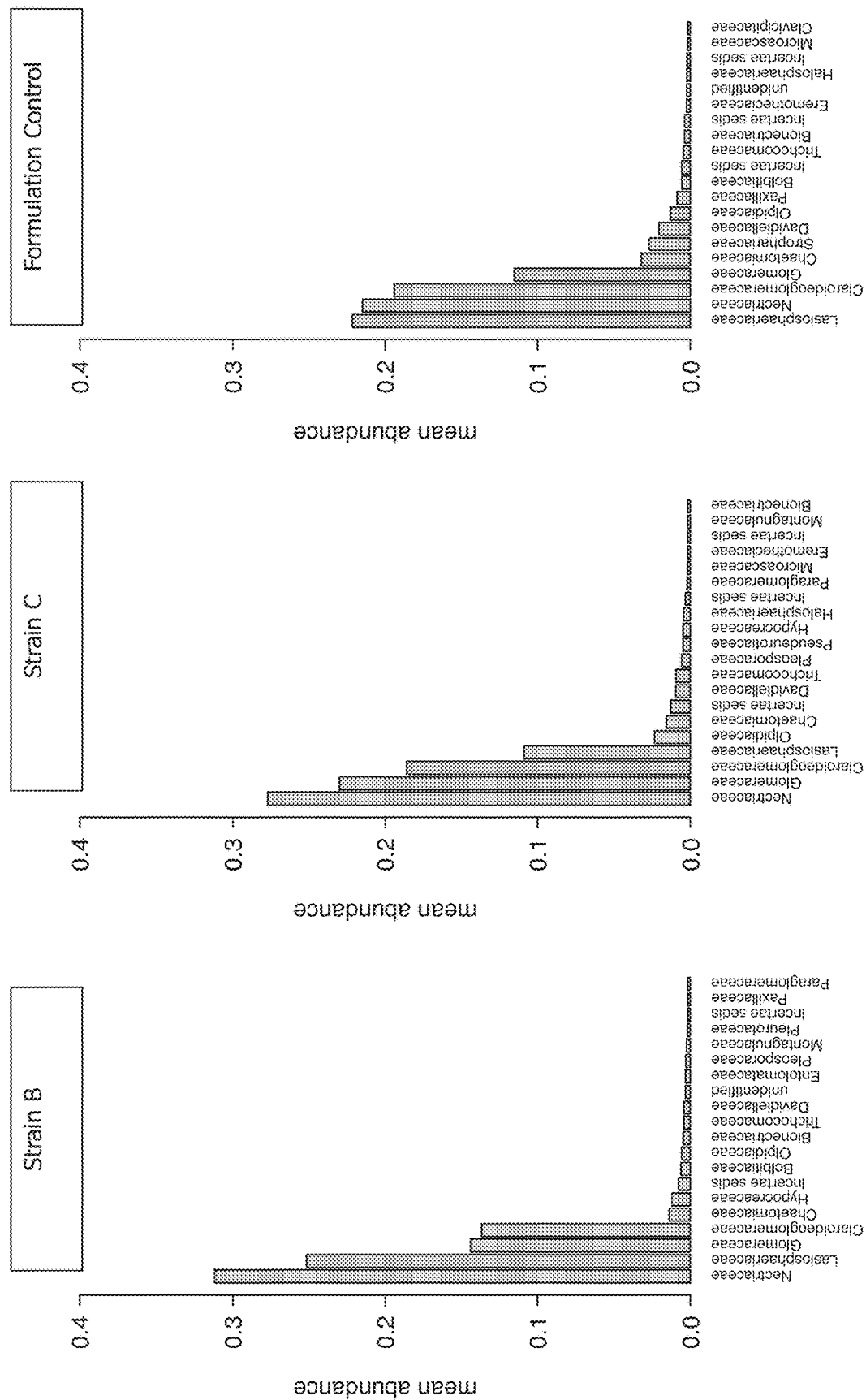

STREPTOMYCES ENDOPHYTE COMPOSITIONS AND METHODS FOR IMPROVED AGRONOMIC TRAITS IN PLANTS

CROSS REFERENCE TO RELATED APPLICATIONS

This application is a divisional of U.S. application Ser. No. 15/580,616, which is the National Stage of International Application No. PCT/US2016/036504, filed 8 Jun. 2016, which claims the benefit of and priority to U.S. Provisional Application No. 62/172,748 filed 8 Jun. 2015, and of U.S. Provisional No. 62/172,750 filed on 8 Jun. 2015, and of U.S. Provisional Application No. 62/172,755 filed on 8 Jun. 2015, and of U.S. Provisional Application No. 62/316,386 filed on 31 Mar. 2016, all of which are hereby incorporated by reference in their entireties.

SEQUENCE LISTING

The instant application includes a Sequence Listing with 4779 sequences which has been submitted via EFS-Web and is hereby incorporated by reference in its entirety. Said ASCII copy, created on Jul. 15, 2020, is named IAI044WOUSD1_sequencelisting.txt, and is 8.83 MB in size.

FIELD OF THE INVENTION

This invention relates to compositions and methods for improving the cultivation of plants, particularly agricultural plants, such as soybeans and maize. For example, this invention describes bacteria, such as strains of the genus *Streptomyces*, that are capable of living in or otherwise associated with a plant, which may be used to impart improved agronomic traits to plants. The disclosed invention also describes methods of improving plant characteristics by introducing bacteria to those plants. Further, this invention also provides methods of treating seeds and other plant elements with *Streptomyces* bacteria that are capable of living within or otherwise associated with a plant, to impart improved agronomic characteristics to plants, particularly agricultural plants, for example soybeans or maize.

BACKGROUND OF THE INVENTION

According the United Nations Food and Agricultural Organization (UN FAO), the world's population will exceed 9.6 billion people by the year 2050, which will require significant improvements in agricultural to meet growing food demands. At the same time, conservation of resources (such as water, land), reduction of inputs (such as fertilizer, pesticides, herbicides), environmental sustainability, and climate change are increasingly important factors in how food is grown. There is a need for improved agricultural plants and farming practices that will enable the need for a nearly doubled food production with fewer resources, more environmentally sustainable inputs, and with plants with improved responses to various biotic and abiotic stresses (such as pests, drought, disease).

Today, crop performance is optimized primarily via technologies directed towards the interplay between crop genotype (e.g., plant breeding, genetically-modified (GM) crops) and its surrounding environment (e.g., fertilizer, synthetic herbicides, pesticides). While these paradigms have assisted in doubling global food production in the past fifty years, yield growth rates have stalled in many major crops and shifts in the climate have been linked to production instability and declines in important crops, driving an urgent need for novel solutions to crop yield improvement. In addition to their long development and regulatory timelines, public fears of GM-crops and synthetic chemicals have challenged their use in many key crops and countries, resulting in a lack of acceptance for many GM traits and the exclusion of GM crops and many synthetic chemistries from some global markets. Thus, there is a significant need for innovative, effective, environmentally-sustainable, and publically-acceptable approaches to improving the yield and resilience of crops to stresses.

Improvement of crop resilience to biotic and abiotic stresses has proven challenging for conventional genetic and chemical paradigms for crop improvement. This challenge is in part due to the complex, network-level changes that arise during exposure to these stresses.

Like humans, who utilize a complement of beneficial microbial symbionts, plants have been purported to derive a benefit from the vast array of bacteria and fungi that live both within and around their tissues in order to support the plant's health and growth. Endophytes are symbiotic organisms (typically bacteria or fungi) that live within plants, and inhabit various plant tissues, often colonizing the intercellular spaces of host leaves, stems, flowers, fruits, seeds, or roots. To date, a small number of symbiotic endophyte-host relationships have been analyzed in limited studies to provide fitness benefits to model host plants within controlled laboratory settings, such as enhancement of biomass production (i.e., yield) and nutrition, increased tolerance to stress such as drought and pests. There is still a need to develop better plant-endophyte systems to confer benefits to a variety of agriculturally-important plants such as soybean and maize, for example to provide improved yield and tolerance to the environmental stresses present in many agricultural situations for such agricultural plants.

Thus, there is a need for compositions and methods of providing agricultural plants with improved yield and tolerance to various biotic and abiotic stresses. Provided herein are novel compositions including bacteria that are capable of living within a plant, formulations comprising these compositions for treatment of plants and plant elements, and methods of use for the same, created based on the analysis of the key properties that enhance the utility and commercialization of an endophyte composition.

SUMMARY OF THE INVENTION

In an aspect, the invention provides a method for preparing a plant reproductive element composition, comprising contacting the surface of a plant reproductive element of a plant with a formulation comprising a purified microbial population that comprises a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO:18. In another aspect, the invention provides a method for preparing a plant reproductive element composition, comprising contacting the surface of a plant reproductive element of a plant with a formulation comprising a purified microbial population that comprises a *Streptomyces* endophyte that is heterologous to the plant reproductive element and comprises a strain deposit IDAC Deposit ID 081111-06. In yet another aspect, the invention provides a method for preparing a plant reproductive element composition, comprising contacting the surface of a plant reproductive element of a plant with a formulation comprising a purified microbial population that comprises a *Streptomyces* endophyte that is heterologous to the plant reproductive element and comprises a *Streptomyces* species selected from the group consisting of: *albidoflavus*, *albus*, *aureofaciens*, *ginsengisoli*, *griseus*, *lydicus*, *mutabilis*, *neyagawaensis*, *praecox*, and SMCD2215; wherein in any of the preceding methods the endophyte is present in the formulation in an amount capable of modulating at least one of: trait of agronomic importance, transcription of a gene, level of a transcript, the expression of a protein, level of a hormone, level of a metabolite, and population of endogenous microbes; in plants grown from the plant reproductive elements, as compared to isoline plants grown from plant reproductive elements not contacted with the formulation.

In certain aspects the invention provides for any of the preceding methods, wherein the *Streptomyces* endophyte is optionally present in the plant reproductive element in an amount capable of providing a benefit to a plant derived from the plant reproductive element, as compared to a plant derived from a plant reproductive element not treated with said *Streptomyces* endophyte.

An embodiment of the invention is a plant derived from the composition of any of the preceding methods, wherein the plant comprises in at least one of its plant elements said *Streptomyces* endophyte. Another embodiment of the invention comprises the progeny of the plant derived from the composition of any of the preceding methods, wherein the progeny comprises in at least one of its plant elements the *Streptomyces* endophyte.

Another embodiment of the invention is a plurality of plant reproductive element compositions prepared according to any of the proceeding methods, wherein the compositions are confined within an object selected from the group consisting of: bottle, jar, ampule, package, vessel, bag, box, bin, envelope, carton, container, silo, shipping container, truck bed, and case.

In an aspect, the invention provides a method of modulating a trait of agronomic importance in a plant derived from a plant reproductive element, comprising treating the plant reproductive element with a formulation comprising a *Streptomyces* endophyte that comprises at least 2× higher acetoin production as compared to the strain represented by SEQ ID NO: 1. In an aspect, the invention provides a method of modulating a trait of agronomic importance in a plant derived from a plant reproductive element, comprising treating the plant reproductive element with a formulation comprising a *Streptomyces* endophyte that comprises at least 1.5× higher siderophore production as compared to the strain represented by SEQ ID NO: 1. In an aspect, the invention provides a method of modulating a trait of agronomic importance in a plant derived from a plant reproductive element, comprising treating the plant reproductive element with a formulation comprising a *Streptomyces* endophyte that comprises greater utilization of a primary carbon source selected from the group consisting of: D-Galactose, Glycerol, alpha-D-Glucose, Sucrose, beta-methyl-D-glucoside, D-cellobiose, L-alanine, L-alanyl-glycine, mono methyl succinate, glycyl-L-proline, L-lyxose, as compared to the strain represented by SEQ ID NO: 1. In an aspect, the invention provides a method of modulating a trait of agronomic importance in a plant derived from a plant reproductive element, comprising treating the plant reproductive element with a formulation comprising a *Streptomyces* endophyte that secretes at least one protein listed in Table 5C with at least a 0.4× higher rate, as compared to the strain represented by SEQ ID NO: 2. In an aspect, the invention provides a method of modulating a trait of agronomic importance in a plant derived from a plant reproductive element, comprising treating the plant reproductive element with a formulation comprising a *Streptomyces* endophyte that secretes at least one protein selected listed in Table 5D with at least a 0.7× lower rate, as compared to the strain represented by SEQ ID NO: 2. In an aspect, the invention provides a method of modulating a trait of agronomic importance in a plant derived from a plant reproductive element, comprising treating the plant reproductive element with a formulation comprising a *Streptomyces* endophyte that comprises at least 3 arabinose transporter genes in its genome. In another aspect, the invention provides a method of modulating a trait of agronomic importance in a plant derived from a plant reproductive element, comprising treating the plant reproductive element with a formulation comprising a *Streptomyces* endophyte that secretes at least one protein selected from Table 5A. In yet another aspect, the invention provides a method of modulating a trait of agronomic importance in a plant derived from a plant reproductive element, comprising treating the plant reproductive element with a formulation comprising a *Streptomyces* endophyte that does not secrete a protein selected from the proteins listed in Table 5B.

In an aspect, the invention also provides a method of using a beneficial *Streptomyces* endophyte that confers a trait of agronomic importance to a plant, wherein the endophyte comprises at least 97% identity to at least 600 nucleotides of SEQ ID NO: 3. In another aspect, the invention also provides a method of using a beneficial *Streptomyces* endophyte that confers a trait of agronomic importance to a plant, wherein said endophyte comprises at least 2× higher acetoin production as compared to the strain represented by SEQ ID NO: 1. In an aspect, the invention provides a method of using a beneficial *Streptomyces* endophyte that confers a trait of agronomic importance to a plant, wherein the endophyte comprises at least 1.5× higher siderophore production as compared to the strain represented by SEQ ID NO: 1. In another aspect, the invention provides a method of using a beneficial *Streptomyces* endophyte that confers a trait of agronomic importance to a plant, wherein the endophyte comprises greater utilization of a primary carbon source selected from the group consisting of: D-Galactose, Glycerol, alpha-D-Glucose, Sucrose, beta-methyl-D-glucoside, D-cellobiose, L-alanine, L-alanyl-glycine, mono methyl succinate, glycyl-L-proline, L-lyxose, as compared to the strain represented by SEQ ID NO: 1. In an aspect, the invention provides a method of using a beneficial *Streptomyces* endophyte that confers a trait of agronomic importance to a plant, wherein the endophyte secretes at least one protein listed in Table 5C with at least a 0.4× higher rate, as compared to the strain represented by SEQ ID NO: 2. In an aspect, the invention provides a method of using a beneficial *Streptomyces* endophyte that confers a trait of agronomic importance to a plant, wherein the endophyte secretes at least one protein listed in Table 5D with at least a 0.7× lower rate, as compared to the strain represented by SEQ ID NO: 2. In an aspect, the invention provides a method of using a beneficial *Streptomyces* endophyte that confers a trait of agronomic importance to a plant, wherein the endophyte comprises at least 3 arabinose transporter genes in its genome. In another aspect, the invention provides a method of using a beneficial *Streptomyces* endophyte that confers a trait of agronomic importance to a plant, wherein the endophyte secretes at least one protein selected from Table 5A. In yet another aspect, the invention provides a method of using a beneficial *Streptomyces* endophyte that confers a trait of agronomic importance to a plant, wherein the endophyte does not secrete a protein selected from the proteins listed in Table 5B.

In a certain aspect, the invention provides a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO:18, and modulating at least one characteristic of said plant as compared to an isoline plant not grown from reproductive elements treated with said *Streptomyces* endophyte, wherein the characteristic comprises modulation of transcription of at least one gene involved in a pathway selected from the group consisting of: symbiosis enhancement, resistance to biotic stress, resistance to abiotic stress, growth promotion, cell wall composition, and developmental regulation. In an aspect, the invention provides a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO:18, and modulating at least one characteristic of said plant as compared to an isoline plant not grown from reproductive elements treated with said *Streptomyces* endophyte, wherein the characteristic comprises modulation of at least one hormone involved in a pathway selected from the group consisting of: developmental regulation, seed maturation, dormancy, response to environmental stresses, stomatal closure, expression of stress-related genes, drought tolerance, defense responses, infection response, pathogen response, disease resistance, systemic acquired resistance, transcriptional reprogramming, mechanical support, protection against biotic stress, protection against abiotic stress, signaling, nodulation inhibition, endophyte colonization, fatty acid deoxygenation, wound healing, antimicrobial substance production, metabolite catabolism, cell proliferation, and abscission. In another aspect, the invention provides a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO:18, and modulating at least one characteristic of said plant as compared to an isoline plant not grown from reproductive elements treated with said *Streptomyces* endophyte, wherein the characteristic comprises modulation of least one metabolite in at least one of the following plant metabolic pathways: alkaloid metabolism, phenylpropanoid metabolism, flavonoid biosynthesis, isoflavonoid biosynthesis, lipid metabolism, nitrogen metabolism, and carbohydrate metabolism. In yet another aspect, the invention provides a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO:18, and modulating at least one characteristic of said plant as compared to an isoline plant not grown from reproductive elements treated with said *Streptomyces* endophyte, wherein the characteristic comprises modulation of at least one transcript involved in at least one of the following pathways: symbiosis enhancement, resistance to biotic stress, resistance to abiotic stress, growth promotion, cell wall composition, and developmental regulation.

In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises upregulation of at least one gene in root tissue, selected from the upregulated genes listed in Table 8A. In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises upregulation of at least one gene in leaf tissue, selected from the upregulated genes listed in Table 8A. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises upregulation of at least one gene in stem tissue, selected from the upregulated genes listed in Table 8A. In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises downregulation of at least one gene in root tissue, selected from the downregulated genes listed in Table 8A. In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises downregulation of at least one gene in leaf tissue, selected from the downregulated genes listed in Table 8A. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises downregulation of at least one gene in stem tissue, selected from the downregulated genes listed in Table 8A. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an increase in hormone level in root tissue, selected from the group consisting of: abscisic acid, salicylic acid, cinnaminic acid, traumatic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises a decrease in hormone level in root tissue, selected from the group consisting of: jasmonic acid, jasmonic acid-isoleucine, 12-oxo-phytodienoic acid, 10-oxo-11 phytoenoic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an increase in hormone level in stem tissue, selected from the group consisting of: jasmonic acid, jasmonic acid-isoleucine, traumatic acid, 12-oxo-phytodienoic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises a decrease in hormone level in stem tissue, selected from the group consisting of: abscisic acid, salicylic acid, cinnaminic acid, 10-oxo-11 phytoenoic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an increase in hormone level in leaf tissue, selected from the group consisting of: abscisic acid, salicylic acid, cinnaminic acid, jasmonic acid, jasmonic acid-isoleucine, traumatic acid. In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises a decrease in hormone level in leaf tissue, selected from the group consisting of: 12-oxo-phytodienoic acid, 10-oxo-11 phytoenoic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an increase in metabolite level in root tissue, selected from the group consisting of: pipecolic acid, octadecanoic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises a decrease in metabolite level in root tissue, selected from the group consisting of: aspartic acid, glutamic acid, histidine, serine, D-glucopyranose, galactose, galacturonic acid. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an increase in metabolite level in stem tissue, selected from the group consisting of: galactose, tryptophan, caffeic acid, daidzein, allantoin, glutamine, isoleucine, leucine, proline, tryptophan, trehalose. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises a decrease in metabolite level in stem tissue, selected from the group consisting of: ethanolaminephosphate, hexadecanoic acid, asparagine. In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an increase in metabolite level in leaf tissue, selected from the group consisting of: ethanolaminephosphate, hexadecanoic acid, asparagine, galactose, tryptophan, daidzein, allantoin, glutamine, isoleucine, leucine, proline, tryptophan, trehalose, histidine, D-glucopyranose, octadecanoic acid, phenylalanine, tyrosine, benzoic acid, nicotinic acid, phenylalanine, shikimic acid, quinic acid, sinapic acid, quinic acid, shikimic acid, hesperetin, ethanolamine, sphingosine, glycerol, octadecadienoic acid, dodecanol, campesterol, alanine, phenylalanine, threonine, tyrosine, valine, lyxose, threose, xylose, salicylic acid, vanillic acid, beta tocopherol. In an embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises a decrease in metabolite level in leaf tissue, selected from the group consisting of: sucrose, pyrogallol, lumichrome. In another embodiment, the invention provides for a method of modulating a trait of agronomic importance in a plant derived from a plant reproductive element under normal watering conditions, comprising treating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from reproductive elements treated with said *Streptomyces* endophyte, wherein the characteristic comprises an enrichment of at least one gene described in Table 15A, 15B, 15C, or 15D.

In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO: 18, and modulating at least one characteristic of said plant as compared to an isoline plant not grown from a reproductive element treated with said *Streptomyces* endophyte, wherein the characteristic comprises modulation of transcription of at least one gene involved in at least one of the following pathways: symbiosis enhancement, resistance to biotic stress, resistance to abiotic stress, growth promotion, cell wall composition, and developmental regulation. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises modulation of transcription of at least one transcript involved in at least one of the following pathways: symbiosis enhancement, resistance to biotic stress, resistance to abiotic stress, growth promotion, cell wall composition, and developmental regulation. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises modulation of levels of at least one hormone involved in a pathway selected from the group consisting of: developmental regulation, seed maturation, dormancy, response to environmental stresses, stomatal closure, expression of stress-related genes, drought tolerance, defense responses, infection response, pathogen response, disease resistance, systemic acquired resistance, transcriptional reprogramming, mechanical support, protection against biotic stress, protection against abiotic stress, signaling, nodulation inhibition, endophyte colonization, fatty acid deoxygenation, wound healing, antimicrobial substance production, metabolite catabolism, cell proliferation, and abscission. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises modulation of at least one metabolite in at least one of the following plant metabolic pathways: alkaloid metabolism, phenylpropanoid metabolism, flavonoid biosynthesis, isoflavonoid biosynthesis, lipid metabolism, nitrogen metabolism, and carbohydrate metabolism. In yet another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises modulation of microbiome community profile.

In a certain aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises upregulation of at least one gene in root tissue, selected from the upregulated genes listed in Tables 8A, 8B, 8C, 8D, and 8E. In certain other aspects, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO: 2 through SEQ ID NO: 18, and modulating at least one characteristic of said plant as compared to an isoline plant not grown from a reproductive element treated with said *Streptomyces* endophyte, wherein the characteristic comprises upregulation of at least one gene in leaf tissue, selected from the upregulated genes listed in Tables 8A, 8B, 8C, 8D, and 8E. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises upregulation of at least one gene in stem tissue, selected from the upregulated genes listed in Tables 8A, 8B, 8C, 8D, and 8E. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises downregulation of at least one gene in root tissue, selected from the downregulated genes listed in Tables 8A, 8B, 8C, 8D, and 8E. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises downregulation of at least one gene in leaf tissue, selected from the downregulated genes listed in Tables 8A, 8B, 8C, 8D, and 8E. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises downregulation of at least one gene in stem tissue, selected from the downregulated genes listed in Tables 8A, 8B, 8C, 8D, and 8E. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises expression of at least one sugar transporter gene selected from Table 9. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises upregulation of at least one transcript in root tissue, selected from the upregulated transcripts listed in Table 8F. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises upregulation of at least one transcript in leaf tissue, selected from the upregulated transcripts listed in Table 8F. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises upregulation of at least one transcript in stem tissue, selected from the upregulated transcripts listed in Table 8F. In another aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises downregulation of at least one transcript in root tissue, selected from the downregulated transcripts listed in Table 8F. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises downregulation of at least one transcript in leaf tissue, selected from the downregulated transcripts listed in Table 8F. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises downregulation of at least one transcript in stem tissue, selected from the downregulated transcripts listed in Table 8F. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises upregulation of a sugar transporter transcript in leaf tissue or root tissue. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a decrease in hormone level in root tissue, selected from the group consisting of: abscisic acid, salicylic acid, cinnaminic acid jasmonic acid, jasmonic acid-isoleucine, traumatic acid, 12-oxo-phytodienoic acid, 10-oxo-11 phytoenoic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in hormone level in stem tissue, selected from the group consisting of: 12-oxo-phytodienoic acid, 10-oxo-11 phytoenoic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a decrease in hormone level in stem tissue, selected from the group consisting of: abscisic acid, salicylic acid, cinnaminic acid jasmonic acid, jasmonic acid-isoleucine, traumatic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in hormone level in leaf tissue, selected from the group consisting of: salicylic acid, cinnaminic acid, 12-oxo-phytodienoic acid, 10-oxo-11 phytoenoic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a decrease in hormone level in leaf tissue, selected from the group consisting of: abscisic acid, jasmonic acid, jasmonic acid-isoleucine, traumatic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in metabolite level in root tissue, selected from the group consisting of: pipecolic acid, hexadecanoic acid, octadecanoic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a decrease in metabolite level in root tissue, selected from the group consisting of: tryptophan, tyrosine, benzoic acid, nicotinic acid, tyrosine, quinic acid, sinapic acid, ferulic acid, caffeic acid, quinic acid, daidzein, dodecanol, alanine, allantoin, asparagine, aspartic acid, glutamic acid, glutamine, histidine, leucine, methionine, proline, threonine, tryptophan, tyrosine, valine, D-glucopyranose, salicylic acid, pyrogallol, beta tocopherol, galacturonic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in metabolite level in stem tissue, selected from the group consisting of: tryptophan, ferulic acid, allantoin, glutamine, histidine, leucine, tryptophan, valine, D-glucopyranose, salicylic acid, hexadecanoic acid, octadecanoic acid, hesperetin, ethanolamine, glycerol, vanillic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a decrease in metabolite level in stem tissue, selected from the group consisting of: sphingosine. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in metabolite level in leaf tissue, selected from the group consisting of: lumichrome. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a decrease in metabolite level in leaf tissue, selected from the group consisting of: sphingosine, tryptophan, ferulic acid, allantoin, glutamine, histidine, leucine, tryptophan, valine, salicylic acid, octadecanoic acid, hesperetin, ethanolamine, vanillic acid, tyrosine, benzoic acid, nicotinic acid, tyrosine, quinic acid, sinapic acid, caffeic acid, quinic acid, daidzein, dodecanol, alanine, glutamic acid, methionine, proline, threonine, tyrosine, phenylalanine, tryptamine, phenylalanine, shikimic acid, shikimic acid, ethanolaminephosphate, octadecadienoic acid, campesterol, β-alanine, isoleucine, phenylalanine, serine, galactose, lyxose, threose, trehalose, gallic acid. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a reduced abundance of organisms of the *Escherica-Shigella* genera in the plant's leaf microbiome community. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in abundance of organisms of the *Rhizophagus* genera in the plant's root microbiome community. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in abundance of organisms of the *Glomus* genera in the plant's root microbiome community. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises a reduced abundance of organisms of the Enterobacteriaceae family in the plant's leaf microbiome community. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in abundance of organisms of the Nectriaceae family in the plant's root microbiome community. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in abundance of organisms of the Glomeraceae family in the plant's root microbiome community. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises the presence of at least one OTU described in Table 13A or Table 13B. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an increase in the presence of at least one OTU selected from Table 13C. In an aspect, the invention provides a method of modulating a trait of agronomic importance in a plant derived from a plant reproductive element under water-limited conditions, comprising associating said plant reproductive element with a formulation comprising a *Streptomyces* endophyte that is heterologous to the plant reproductive element and comprises a 16S nucleic acid sequence that is at least 95% identical, at least 96% identical, at least 97% identical, at least 98% identical, or at least 99% identical over at least 600 nucleotides to a nucleic acid sequence selected from SEQ ID NO:2 through SEQ ID NO:18, and modulating at least one characteristic of said plant as compared to an isoline plant not grown from a reproductive element treated with said *Streptomyces* endophyte, wherein the characteristic comprises an enrichment of at least gene described in Table 15A, 15B, 15C, or 15D.

In certain embodiments, the invention provides for methods of altering the native microbiome community of a plant, comprising deriving the plant from a plant reproductive element treated with a formulation comprising a beneficial *Streptomyces* endophyte. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises a reduction in abundance of organisms of the *Escherica-Shigella* genera in the plant's leaf microbiome community. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises an increase in abundance of organisms of the *Rhizophagus* genera in the plant's root microbiome community. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises an increase in abundance of organisms of the *Glomus* genera in the plant's root microbiome community. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises a reduction in abundance of organisms of the Enterobacteriaceae family in the plant's leaf microbiome community. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises an increase in abundance of organisms of the Nectriaceae family in the plant's root microbiome community. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises an increase in abundance of organisms of the Glomeraceae family in the plant's root microbiome community. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises a presence of at least one OTU described in Table 13A or Table 13B. In an aspect, the invention provides for methods of altering the native microbiome community of a plant, comprising deriving said plant from a plant reproductive element treated with a formulation comprising a beneficial *Streptomyces* endophyte, wherein the microbiome community alteration comprises an increase in presence of at least one OTU selected from Table 13C.

The invention also provides any of the preceding methods; wherein the plant is optionally soybean or maize; wherein the formulation of any of the preceding methods optionally comprises a purified population of the *Streptomyces* endophyte at a concentration of at least about $10^2$ CFU/ml in a liquid formulation or about $10^2$ CFU/gm in a non-liquid formulation; wherein the *Streptomyces* endophyte is optionally capable auxin production, nitrogen fixation, production of an antimicrobial compound, mineral phosphate solubilization, siderophore production, cellulase production, chitinase production, xylanase production, or acetoin production; wherein the trait of agronomic importance is optionally selected from the group consisting of: disease resistance, drought tolerance, heat tolerance, cold tolerance, salinity tolerance, metal tolerance, herbicide tolerance, chemical tolerance, improved water use efficiency, improved nitrogen utilization, improved nitrogen fixation, pest resistance, herbivore resistance, pathogen resistance, increase in yield, increase in yield under water-limited conditions, health enhancement, vigor improvement, growth improvement, photosynthetic capability improvement, nutrition enhancement, altered protein content, altered oil content, increase in biomass, increase in shoot length, increase in root length, improved root architecture, increase in seed weight, altered seed carbohydrate composition, altered seed oil composition, increase in radical length, number of pods, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, increase in number of pods per plant, increase in length of pods per plant, reduced number of wilted leaves per plant, reduced number of severely wilted leaves per plant, increase in number of non-wilted leaves per plant, improved plant visual appearance; wherein the *Streptomyces* endophyte is optionally capable of localizing in a plant element of said plant, said plant element selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud; wherein the plant reproductive element is optionally a seed or a transgenic seed; wherein the plant reproductive element is optionally placed into a substrate that promotes plant growth and/or wherein the substrate promotes plant growth in soil; wherein the formulation optionally further comprises one or more of the following: a stabilizer, or a preservative, or a carrier, or a surfactant, or an anticomplex agent, or any combination thereof; and wherein the formulation optionally further comprises at least one additional bacterial endophyte.

Certain embodiments of the invention are any of the preceding methods; wherein the *Streptomyces* endophyte is optionally capable of localizing in a plant element of the plant, the plant element selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud; and wherein the plant element is optionally a seed; wherein the *Streptomyces* endophyte is optionally present in at least two compartments of the seed, selected from the group consisting of: embryo, seed coat, endosperm, cotyledon, hypocotyl, and radicle.

In certain aspects, the invention provides a synthetic composition comprising a plant reproductive element treated with a formulation comprising a purified *Streptomyces* endophyte population, wherein said *Streptomyces* endophyte is heterologous to the plant reproductive element, and comprises at least 600 nucleotides at least 95% identical to a nucleic acid sequence selected from the group consisting of: SEQ ID NO:2 through SEQ ID NO:18, wherein the endophyte is present in the synthetic combination in an amount capable of modulating at least one of: a trait of agronomic importance, the expression of a gene, the level of a transcript, the expression of a protein, the level of a hormone, the level of a metabolite, the population of endogenous microbes in plants grown from said plant reproductive element, as compared to an isoline plant grown from a plant reproductive element not contacted with the bacterial endophyte. In certain other aspects, the invention provides a synthetic composition comprising a plant reproductive element treated with a formulation comprising a purified *Streptomyces* endophyte population, wherein said *Streptomyces* endophyte is heterologous to the plant reproductive element, and comprises a strain deposit IDAC Deposit ID 081111-06, wherein the endophyte is present in the synthetic combination in an amount capable of modulating at least one of: a trait of agronomic importance, the expression of a gene, the level of a transcript, the expression of a protein, the level of a hormone, the level of a metabolite, the population of endogenous microbes in plants grown from said plant reproductive element, as compared to an isoline plant grown from a plant reproductive element not contacted with the bacterial endophyte. In certain aspects, the invention provides a synthetic composition comprising a plant reproductive element treated with a formulation comprising a purified *Streptomyces* endophyte population, wherein said *Streptomyces* endophyte is heterologous to the plant reproductive element, and comprises a *Streptomyces* species selected from the group consisting of: *albidoflavus, albus, aureofaciens, ginsengisoli, griseus, lydicus, mutabilis, neyagawaensis, praecox*, and SMCD2215, wherein the endophyte is present in the synthetic combination in an amount capable of modulating at least one of: a trait of agronomic importance, the expression of a gene, the level of a transcript, the expression of a protein, the level of a hormone, the level of a metabolite, the population of endogenous microbes in plants grown from said plant reproductive element, as compared to an isoline plant grown from a plant reproductive element not contacted with the bacterial endophyte.

The invention also provides the synthetic composition of any of the preceding claims, wherein the plant is optionally soybean or maize; wherein the formulation optionally comprises a purified population of the *Streptomyces* endophyte at a concentration of at least about $10^2$ CFU/ml in a liquid formulation or about $10^2$ CFU/gm in a non-liquid formulation; wherein the *Streptomyces* endophyte is optionally capable of auxin production, nitrogen fixation, production of an antimicrobial compound, mineral phosphate solubilization, siderophore production, cellulase production, chitinase production, xylanase production, or acetoin production; wherein the trait of agronomic importance is selected from the group consisting of: disease resistance, drought tolerance, heat tolerance, cold tolerance, salinity tolerance, metal tolerance, herbicide tolerance, chemical tolerance, improved water use efficiency, improved nitrogen utilization, improved nitrogen fixation, pest resistance, herbivore resistance, pathogen resistance, increase in yield, increase in yield under water-limited conditions, health enhancement, vigor improvement, growth improvement, photosynthetic capability improvement, nutrition enhancement, altered protein content, altered oil content, increase in biomass, increase in shoot length, increase in root length, improved root architecture, increase in seed weight, altered seed carbohydrate composition, altered seed oil composition, increase in radical length, number of pods, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, increase in number of pods per plant, increase in length of pods per plant, reduced number of wilted leaves per plant, reduced number of severely wilted leaves per plant, increase in number of non-wilted leaves per plant, improved plant visual appearance; wherein the *Streptomyces* endophyte is optionally capable of localizing in a plant element of a plant grown from said seed, said plant element selected from the group consisting of: whole plant, seedling, meristematic tissue, ground tissue, vascular tissue, dermal tissue, seed, leaf, root, shoot, stem, flower, fruit, stolon, bulb, tuber, corm, keikis, and bud; wherein the plant reproductive element is optionally a seed or a transgenic seed; wherein the plant reproductive element is optionally placed into a substrate that promotes plant growth; wherein the substrate that promotes plant growth is optionally soil; and wherein the substrate that promotes plant growth is soil and wherein a plurality of the plant reproductive elements are optionally placed in the soil in rows, with substantially equal spacing between each seed within each row.

The invention also provides the synthetic composition of any of the preceding claims, wherein the formulation optionally further comprises one or more of the following: a stabilizer, or a preservative, or a carrier, or a surfactant, or an anticomplex agent, or any combination thereof; wherein the formulation optionally further comprises one or more of the following: fungicide, nematicide, bactericide, insecticide, and herbicide; and wherein the formulation optionally further comprises at least one additional bacterial endophyte; wherein the plant reproductive element is optionally a seed or a transgenic seed.

An embodiment of the invention is a plant derived from the synthetic composition of any of the preceding claims, wherein the plant optionally comprises in at least one of its plant elements the bacterial endophyte; and wherein the progeny of the plant optionally comprises in at least one of its plant elements bacterial endophyte.

Another embodiment of the invention is a plurality of synthetic compositions of any of the preceding claims, wherein the compositions are optionally confined within an object selected from the group consisting of: bottle, jar, ampule, package, vessel, bag, box, bin, envelope, carton, container, silo, shipping container, truck bed, and case.

In certain other aspects, the invention provides the synthetic compositions of any of the preceding claims, wherein the *Streptomyces* endophyte is optionally present in the plant reproductive element in an amount capable of providing a benefit to the plant reproductive element or to a plant derived therefrom;

wherein the bacterial endophyte is optionally present in at least two compartments of the seed, selected from the group consisting of: embryo, seed coat, endosperm, cotyledon, hypocotyl, and radicle.

Included with the invention, is a plurality of synthetic combinations of any of the synthetic compositions of the preceding claims, wherein the synthetic combinations are shelf-stable.

An aspect of the invention provides a plant grown from the synthetic combination of any of the synthetic compositions of the preceding claims, wherein the plant comprises modulation of the transcription of at least one gene involved in at least one of the following pathways: symbiosis enhancement, resistance to biotic stress, resistance to abiotic stress, growth promotion, cell wall composition, and developmental regulation. Another aspect of the invention provides a plant grown from the synthetic combination of any of the synthetic compositions of the preceding claims, wherein the plant comprises modulation of the transcription of at least one transcript involved in at least one of the following pathways: symbiosis enhancement, resistance to biotic stress, resistance to abiotic stress, growth promotion, cell wall composition, and developmental regulation. Another aspect of the invention provides a plant grown from the synthetic combination of any of the synthetic compositions of the preceding claims, wherein the plant comprises modulating the level of at least one hormone involved in a pathway selected from the group consisting of: developmental regulation, seed maturation, dormancy, response to environmental stresses, stomatal closure, expression of stress-related genes, drought tolerance, defense responses, infection response, pathogen response, disease resistance, systemic acquired resistance, transcriptional reprogramming, mechanical support, protection against biotic stress, protection against abiotic stress, signaling, nodulation inhibition, endophyte colonization, fatty acid deoxygenation, wound healing, antimicrobial substance production, metabolite catabolism, cell proliferation, and abscission. Yet another aspect of the invention provides a plant grown from the synthetic combination of any of the synthetic compositions of the preceding claims, wherein the plant comprises modulating at least one metabolite in at least one of the following plant metabolic pathways: alkaloid metabolism, phenylpropanoid metabolism, flavonoid biosynthesis, isoflavonoid biosynthesis, lipid metabolism, nitrogen metabolism, and carbohydrate metabolism.

An embodiment of the invention is a plant grown from the synthetic combination of any of the preceding synthetic compositions, wherein the plant comprises at most 18% total microbes from the *Escherica-Shigella* genera in the total microbiome of the plant's root microbiome community. An embodiment of the invention is a plant grown from the synthetic combination of any of the preceding synthetic compositions, wherein the plant comprises at least 5% total microbes from the *Glomus* genera in the total microbiome of the plant's root microbiome community. An embodiment of the invention is a plant grown from the synthetic combination of any of the preceding synthetic compositions, wherein the plant comprises at least 8% total microbes from the *Rhixophagus* genera in the total microbiome of the plant's root microbiome community. An embodiment of the invention is a plant grown from the synthetic combination of any of the preceding synthetic compositions, wherein the plant comprises at most 18% total microbes from the Enterobacteriaceae family of the total microbiome in the plant's leaf microbiome community. An embodiment of the invention is a plant grown from the synthetic combination of any of the preceding synthetic compositions, wherein the plant comprises at least 25% total microbes from the Nectriaceae family in the total microbiome of the plant's root microbiome community. An embodiment of the invention is a plant grown from the synthetic combination of any of the preceding synthetic compositions, wherein the plant comprises at least 5% total microbes from the Glomeraceae family in the total microbiome of the plant's root microbiome community. An embodiment of the invention is a plant grown from the synthetic combination of any of the preceding synthetic compositions, wherein the plant comprises a bacterial or fungal OTU selected from Table 13A. An embodiment of the invention is a plant grown from the synthetic combination of any of the preceding synthetic compositions, wherein the plant comprises a bacterial or fungal OTU selected from Table 13B. An embodiment of the invention is a plant grown from the synthetic combination of any of the preceding synthetic compositions, wherein the plant comprises upregulation of at least one gene in root tissue, selected from the upregulated genes listed in Tables 8A, 8B, 8C, 8D, and 8E. An embodiment of the invention is a plant grown from the synthetic combination of any of the preceding synthetic compositions, wherein the plant comprises upregulation of at least one gene in leaf tissue, selected from the upregulated genes listed in Tables 8A, 8B, 8C, 8D, and 8E. An embodiment of the invention is a plant grown from the synthetic combination of any of the preceding synthetic compositions, wherein the plant comprises upregulation of at least one gene in stem tissue, selected from the upregulated genes listed in Tables 8A, 8B, 8C, 8D, and 8E. An embodiment of the invention is a plant grown from the synthetic combination of any of the preceding synthetic compositions, wherein the plant comprises downregulation of at least one gene in root tissue, selected from the downregulated genes listed in Tables 8A, 8B, 8C, 8D, and 8E. An embodiment of the invention is a plant grown from the synthetic combination of any of the preceding synthetic compositions, wherein the plant comprises downregulation of at least one gene in leaf tissue, selected from the downregulated genes listed in Tables 8A, 8B, 8C, 8D, and 8E. An embodiment of the invention is a plant grown from the synthetic combination of any of the preceding synthetic compositions, wherein the plant comprises downregulation of at least one gene in stem tissue, selected from the downregulated genes listed in Tables 8A, 8B, 8C, 8D, and 8E. An embodiment of the invention is a plant grown from the synthetic combination of any of the preceding synthetic compositions, wherein the plant comprises expression of at least one sugar transporter gene selected from Table 9. An embodiment of the invention is a plant grown from the synthetic combination of any of the preceding synthetic compositions, wherein the plant comprises upregulation of at least one transcript in root tissue, selected from the upregulated transcripts listed in Table 8F. An embodiment of the invention is a plant grown from the synthetic combination of any of the preceding synthetic compositions, wherein the plant comprises upregulation of at least one transcript in leaf tissue, selected from the upregulated transcripts listed in Table 8F. An embodiment of the invention is a plant grown from the synthetic combination of any of the preceding synthetic compositions, wherein the plant comprises upregulation of at least one transcript in stem tissue, selected from the upregulated transcripts listed in Table 8F. An embodiment of the invention is a plant grown from the synthetic combination of any of the preceding synthetic compositions, wherein the plant comprises downregulation of at least one transcript in root tissue, selected from the downregulated transcripts listed in Table 8F. An embodiment of the invention is a plant grown from the synthetic combination of any of the preceding synthetic compositions, wherein the plant comprises downregulation of at least one transcript in leaf tissue, selected from the downregulated transcripts listed in Table 8F. An embodiment of the invention is a plant grown from the synthetic combination of any of the preceding synthetic compositions, wherein the plant comprises downregulation of at least one transcript in stem tissue, selected from the downregulated transcripts listed in Table 8F. An embodiment of the invention is a plant grown from the synthetic combination of any of the preceding synthetic compositions, wherein the plant comprises upregulation of a sugar transporter transcript in leaf tissue or root tissue. An embodiment of the invention is a plant grown from the synthetic combination of any of the preceding synthetic compositions, wherein the plant comprises decrease in hormone level in root tissue, selected from the group consisting of: abscisic acid, salicylic acid, cinnaminic acid jasmonic acid, jasmonic acid-isoleucine, traumatic acid, 12-oxo-phytodienoic acid, 10-oxo-11 phytoenoic acid. An embodiment of the invention is a plant grown from the synthetic combination of any of the preceding synthetic compositions, wherein the plant comprises an increase in hormone level in stem tissue, selected from the group consisting of: 12-oxo-phytodienoic acid, 10-oxo-11 phytoenoic acid. An embodiment of the invention is a plant grown from the synthetic combination of any of the preceding synthetic compositions, wherein the plant comprises a decrease in hormone level in stem tissue, selected from the group consisting of: abscisic acid, salicylic acid, cinnaminic acid jasmonic acid, jasmonic acid-isoleucine, traumatic acid. An embodiment of the invention is a plant grown from the synthetic combination of any of the preceding synthetic compositions, wherein the plant comprises an increase in hormone level in leaf tissue, selected from the group consisting of: salicylic acid, cinnaminic acid, 12-oxo-phytodienoic acid, 10-oxo-11 phytoenoic acid. An embodiment of the invention is a plant grown from the synthetic combination of any of the preceding synthetic compositions, wherein the plant comprises a decrease in hormone level in leaf tissue, selected from the group consisting of: abscisic acid, jasmonic acid, jasmonic acid-isoleucine, traumatic acid. An embodiment of the invention is a plant grown from the synthetic combination of any of the preceding synthetic compositions, wherein the plant comprises an increase in metabolite level in root tissue, selected from the group consisting of: pipecolic acid, hexadecanoic acid, octadecanoic acid. An embodiment of the invention is a plant grown from the synthetic combination of any of the preceding synthetic compositions, wherein the plant comprises a decrease in metabolite level in root tissue, selected from the group consisting of: tryptophan, tyrosine, benzoic acid, nicotinic acid, tyrosine, quinic acid, sinapic acid, ferulic acid, caffeic acid, quinic acid, daidzein, dodecanol, alanine, allantoin, asparagine, aspartic acid, glutamic acid, glutamine, histidine, leucine, methionine, proline, threonine, tryptophan, tyrosine, valine, D-glucopyranose, salicylic acid, pyrogallol, beta tocopherol, galacturonic acid. An embodiment of the invention is a plant grown from the synthetic combination of any of the preceding synthetic compositions, wherein the plant comprises an increase in metabolite level in stem tissue, selected from the group consisting of: tryptophan, ferulic acid, allantoin, glutamine, histidine, leucine, tryptophan, valine, D-glucopyranose, salicylic acid, hexadecanoic acid, octadecanoic acid, hesperetin, ethanolamine, glycerol, vanillic acid. An embodiment of the invention is a plant grown from the synthetic combination of any of the preceding synthetic compositions, wherein the plant comprises a decrease in metabolite level in stem tissue, selected from the group consisting of: sphingosine. An embodiment of the invention is a plant grown from the synthetic combination of any of the preceding synthetic compositions, wherein the plant comprises an increase in metabolite level in leaf tissue, selected from the group consisting of: lumichrome. An embodiment of the invention is a plant grown from the synthetic combination of any of the preceding synthetic compositions, wherein the plant comprises a decrease in metabolite level in leaf tissue, selected from the group consisting of: sphingosine, tryptophan, ferulic acid, allantoin, glutamine, histidine, leucine, tryptophan, valine, salicylic acid, octadecanoic acid, hesperetin, ethanolamine, vanillic acid, tyrosine, benzoic acid, nicotinic acid, tyrosine, quinic acid, sinapic acid, caffeic acid, quinic acid, daidzein, dodecanol, alanine, glutamic acid, methionine, proline, threonine, tyrosine, phenylalanine, tryptamine, phenylalanine, shikimic acid, shikimic acid, ethanolamine-phosphate, octadecadienoic acid, campesterol, β-alanine, isoleucine, phenylalanine, serine, galactose, lyxose, threose, trehalose, gallic acid. An embodiment of the invention is a plant grown from the synthetic combination of any of the preceding synthetic compositions, wherein the plant comprises a reduced abundance of organisms of the *Escherica-Shigella* genera in the plant's leaf microbiome community. An embodiment of the invention is a plant grown from the synthetic combination of any of the preceding synthetic compositions, wherein the plant comprises an increase in abundance of organisms of the *Rhizophagus* genera in the plant's root microbiome community. An embodiment of the invention is a plant grown from the synthetic combination of any of the preceding synthetic compositions, wherein the plant comprises an increase in abundance of organisms of the *Glomus* genera in the plant's root microbiome community. An embodiment of the invention is a plant grown from the synthetic combination of any of the preceding synthetic compositions, wherein the plant comprises a reduced abundance of organisms of the Enterobacteriaceae family in the plant's leaf microbiome community. An embodiment of the invention is a plant grown from the synthetic combination of any of the preceding synthetic compositions, wherein the plant comprises an increase in abundance of organisms of the Nectriaceae family in the plant's root microbiome community. An embodiment of the invention is a plant grown from the synthetic combination of any of the preceding synthetic compositions, wherein the plant comprises an increase in abundance of organisms of the Glomeraceae family in the plant's root microbiome community. An embodiment of the invention is a plant grown from the synthetic combination of any of the preceding synthetic compositions, wherein the plant comprises the presence of at least one OTU described in Table 13A or Table 13B. An embodiment of the invention is a plant grown from the synthetic combination of any of the preceding synthetic compositions, wherein the plant comprises an increase in presence of at least one OTU selected from Table 13C. An embodiment of the invention is a plant grown from the synthetic combination of any of the preceding synthetic compositions, wherein the plant comprises an enrichment of at least one gene described in Table 15A, 15B, 15C, or 15D.

Included with the invention is a plant grown from any of the preceding synthetic combinations, wherein the plant optionally exhibits a trait of agronomic interest, selected from the group consisting of: disease resistance, drought tolerance, heat tolerance, cold tolerance, salinity tolerance, metal tolerance, herbicide tolerance, chemical tolerance, improved water use efficiency, improved nitrogen utilization, improved nitrogen fixation, pest resistance, herbivore resistance, pathogen resistance, increase in yield, increase in yield under water-limited conditions, health enhancement, vigor improvement, growth improvement, photosynthetic capability improvement, nutrition enhancement, altered protein content, altered oil content, increase in biomass, increase in shoot length, increase in root length, improved root architecture, increase in seed weight, altered seed carbohydrate composition, altered seed oil composition, increase in radical length, number of pods, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, increase in number of pods per plant, increase in length of pods per plant, reduced number of wilted leaves per plant, reduced number of severely wilted leaves per plant, increase in number of non-wilted leaves per plant, improved plant visual appearance; wherein the plant is optionally soybean or maize; and wherein the plant or progeny of the plant, optionally comprises in at least one of its plant elements the *Streptomyces* endophyte.

BRIEF DESCRIPTION OF THE FIGURES

These and other features, aspects, and advantages of the present invention will become better understood with regard to the following description, and accompanying figure, where:

FIG. 1: Culture plate of Strain A
FIG. 2: Culture plate of Strain B
FIG. 3: Culture plate of Strain C
FIG. 4: Greenhouse phenotypes of plants grown from seeds treated with Strain C, under normal watering conditions. Soybean plants grown from Strain C-treated seeds confer improved phenotypes, including a 3.2% increase in seed count, a 0.8% increase in fresh seed weight, a 1.0% increase in dry seed weight, a 9.5% increase in pod conts (>1 cm), and a 51.4% reduction in small pods (<1 cm) count.

FIG. 5: Greenhouse phenotypes of plants grown from seeds treated with Strain C, under water-limited conditions. Soybean plants grown from Strain C-treated seeds exhibit increased tolerance to extreme drought (1st drought cycle: 18 days post watering). NT=plant grown from non-Strain C treated/non-formulation treated seed, Formulation Control=plant grown from seed treated with formulation without Strain C, Strain C treated plant=treated with Strain C microbial endophyte in formulation.

FIG. 6: Greenhouse phenotypes of plants grown from seeds treated with different *Streptomyces* strains, under water-limited conditions. Soybean plants grown from seeds treated with any *Streptomyces* strain demonstrate improved visual phenotype tolerance to water-limited growth conditions, and those treated with Strain C exhibit the most improvement.

FIG. 7: Community sequencing graphs showing average abundance of bacterial genera, as a proportion of the community, in leaf tissue of water stressed soybean plants grown from seeds treated with Strain B (left), Strain C (middle), and untreated controls (right). The average abundance of organisms in the *Escherichia-Shigella* genera are reduced from approximately 21% of the bacterial community of untreated soybean leaves to approximately 13% of the bacterial community in Strain C treated soybean leaves and 16% of the bacterial community in Strain B treated leaves. Treatment with Strain C reduces the abundance of bacteria in the *Escherichia-Shigella* genera on soybean leaves by 37% relative to untreated controls.

FIG. 8: Community sequencing graphs showing the average abundance of fungal genera, as a proportion of the community, in root tissue of water stressed soybean plants grown from seeds treated with Strain B (left), Strain C (middle), and untreated controls (right). The average abundance of fungi in the *Rhizophagus* genera are increased from approximately 4.7% of the fungal community of untreated soybean roots and 4.3% of the fungal community in Strain B treated soybean roots to approximately 8.9% of the fungal community of Strain C treated soybean roots. Treatment with Strain C resulted in a 87.7% increase in the abundance of fungi in the *Rhizophagus* genera in soybean roots relative to untreated controls. Fungi of the genus *Glomus* are also increased in the roots of soybeans treated with Strain C and Strain B treatments relative to untreated controls.

FIG. 9: Community sequencing graphs showing the average abundance of bacterial families, as a proportion of the community, in leaf tissue of water stressed soybean plants grown from seeds treated with Strain B (left), Strain C (middle), and untreated controls (right).

FIG. 10: Community sequencing graphs showing the average abundance of bacterial families, as a proportion of the community, in root tissue of water stressed soybean plants grown from seeds treated with Strain B (left), Strain C (middle), and untreated controls (right).

DEFINITIONS

Terms used in the claims and specification are defined as set forth below unless otherwise specified.

It must be noted that, as used in the specification and the appended claims, the singular forms "a," "an" and "the" include plural referents unless the context clearly dictates otherwise.

An "endophyte" is an organism capable of living within a plant or otherwise associated therewith, and does not cause disease or harm the plant otherwise. Endophytes can occupy the intracellular or extracellular spaces of plant tissue, including the leaves, stems, flowers, fruits, seeds, or roots. An endophyte can be for example a bacterial or fungal organism, and can confer a beneficial property to the host plant such as an increase in yield, biomass, resistance, or fitness. An endophyte can be a fungus or a bacterium.

A "plurality of endophytes" means two or more types of endophyte entities, e.g., of simple bacteria or simple fungi, complex fungi, or combinations thereof: In some embodiments, the two or more types of endophyte entities are two or more strains of endophytes. In other embodiments, the two or more types of endophyte entities are two or more species of endophytes. In yet other embodiments, the two or more types of endophyte entities are two or more genera of endophytes. In yet other embodiments, the two or more types of endophyte entities are two or more families of endophytes. In yet other embodiments, the two or more types of endophyte entities are two or more orders of endophytes.

As used herein, the term "microbe" or "microorganism" refers to any species or taxon of microorganism, including, but not limited to, archaea, bacteria, microalgae, fungi (including mold and yeast species), mycoplasmas, microspores, nanobacteria, oomycetes, and protozoa. In some embodiments, a microbe or microorganism is an endophyte. In some embodiments, a microbe is an endophyte, for example a bacterial or fungal endophyte, which is capable of living within a plant. In some embodiments, a microbe or microorganism encompasses individual cells (e.g., unicellular microorganisms) or more than one cell (e.g., multi-cellular microorganism). A "population of microorganisms" may thus refer to a multiple cells of a single microorganism, in which the cells share common genetic derivation.

As used herein, the term "bacterium" or "bacteria" refers in general to any prokaryotic organism, and may reference an organism from either Kingdom Eubacteria (Bacteria), Kingdom Archaebacteria (Archae), or both. In some cases, bacterial genera or other taxonomic classifications have been reassigned due to various reasons (such as but not limited to the evolving field of whole genome sequencing), and it is understood that such nomenclature reassignments are within the scope of any claimed taxonomy. For example, certain species of the genus *Erwinia* have been described in the literature as belonging to genus *Pantoea* (Zhang and Qiu, 2015).

The term 16S refers to the DNA sequence of the 16S ribosomal RNA (rRNA) sequence of a bacterium. 16S rRNA gene sequencing is a well-established method for studying phylogeny and taxonomy of bacteria.

As used herein, the term "fungus" or "fungi" refers in general to any organism from Kingdom Fungi. Historical taxonomic classification of fungi has been according to morphological presentation. Beginning in the mid-1800's, it was became recognized that some fungi have a pleomorphic life cycle, and that different nomenclature designations were being used for different forms of the same fungus. In 1981, the Sydney Congress of the International Mycological Association laid out rules for the naming of fungi according to their status as anamorph, teleomorph, or holomorph (Taylor, 2011). With the development of genomic sequencing, it became evident that taxonomic classification based on molecular phylogenetics did not align with morphological-based nomenclature (Shenoy, 2007). As a result, in 2011 the International Botanical Congress adopted a resolution approving the International Code of Nomenclature for Algae, Fungi, and Plants (Melbourne Code) (2012), with the stated outcome of designating "One Fungus=One Name" (Hawksworth, 2012). However, systematics experts have not aligned on common nomenclature for all fungi, nor are all existing databases and information resources inclusive of updated taxonomies. As such, many fungi referenced herein may be described by their anamorph form but it is understood that based on identical genomic sequencing, any pleomorphic state of that fungus may be considered to be the same organism. For example, the genus *Alternaria* is the anamorph form of the teleomorph genus Lewia (Kwasna 2003), ergo both would be understood to be the same organism with the same DNA sequence. For example, it is understood that the genus *Acremonium* is also reported in the literature as genus *Sarocladium* as well as genus *Tilachilidium* (Summerbell, 2011). For example, the genus *Cladosporium* is an anamorph of the teleomorph genus *Davidiella* (Bensch, 2012), and is understood to describe the same organism. In some cases, fungal genera have been reassigned due to various reasons, and it is understood that such nomenclature reassignments are within the scope of any claimed genus. For example, certain species of the genus *Microdiplodia* have been described in the literature as belonging to genus *Paraconiothyrium* (Crous and Groenveld, 2006).

"Internal Transcribed Spacer" (ITS) refers to the spacer DNA (non-coding DNA) situated between the small-subunit ribosomal RNA (rRNA) and large-subunit (LSU) rRNA genes in the chromosome or the corresponding transcribed region in the polycistronic rRNA precursor transcript. ITS gene sequencing is a well-established method for studying phylogeny and taxonomy of fungi. In some cases, the "Large SubUnit" (LSU) sequence is used to identify fungi. LSU gene sequencing is a well-established method for studying phylogeny and taxonomy of fungi. Some fungal endophytes of the present invention may be described by an ITS sequence and some may be described by an LSU sequence. Both are understood to be equally descriptive and accurate for determining taxonomy.

As used herein with respect to fungi and bacteria, the term "marker gene" refers to an organism's 16S (for bacteria) or ITS (for fungi) polynucleotide sequence, by which a microbe may be specifically identified and assigned taxonomic nomenclature.

The terms "pathogen" and "pathogenic" in reference to a bacterium or fungus includes any such organism that is capable of causing or affecting a disease, disorder or condition of a host comprising the organism.

A "spore" or a population of "spores" refers to bacteria or fungi that are generally viable, more resistant to environmental influences such as heat and bactericidal or fungicidal agents than other forms of the same bacteria or fungi, and typically capable of germination and out-growth. Bacteria and fungi that are "capable of forming spores" are those bacteria and fungi comprising the genes and other necessary abilities to produce spores under suitable environmental conditions.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

The term "isolated" is intended to specifically reference an organism, cell, tissue, polynucleotide, or polypeptide that is removed from its original source and purified from additional components with which it was originally associated. For example, an endophyte may be considered isolated from a seed if it is removed from that seed source and purified so that it is isolated from any additional components with which it was originally associated. Similarly, an endophyte may be removed and purified from a plant or plant element so that it is isolated and no longer associated with its source plant or plant element.

As used herein, an isolated strain of a microbe is a strain that has been removed from its natural milieu. "Pure cultures" or "isolated cultures" are cultures in which the organisms present are only of one strain of a particular genus and species. This is in contrast to "mixed cultures," which are cultures in which more than one genus and/or species of microorganism are present. As such, the term "isolated" does not necessarily reflect the extent to which the microbe has been purified. A "substantially pure culture" of the strain of microbe refers to a culture which contains substantially no other microbes than the desired strain or strains of microbe. In other words, a substantially pure culture of a strain of microbe is substantially free of other contaminants, which can include microbial contaminants. Further, as used herein, a "biologically pure" strain is intended to mean the strain separated from materials with which it is normally associated in nature. A strain associated with other strains, or with compounds or materials that it is not normally found with in nature, is still defined as "biologically pure." A monoculture of a particular strain is, of course, "biologically pure." As used herein, the term "enriched culture" of an isolated microbial strain refers to a microbial culture that contains more that 50%, 60%, 70%, 80%, 90%, or 95% of the isolated strain.

A "host plant" includes any plant, particularly a plant of agronomic importance, which an endophytic entity such as an endophyte can colonize. As used herein, an endophyte is said to "colonize" a plant or plant element when it can be stably detected within the plant or plant element over a period time, such as one or more days, weeks, months or years, in other words, a colonizing entity is not transiently associated with the plant or plant element. Such host plants are preferably plants of agronomic importance.

A "non-host target" means an organism or chemical compound that is altered in some way after contacting a host plant that comprises an endophyte, as a result of a property conferred to the host plant by the endophyte.

As used herein, a nucleic acid has "homology" or is "homologous" to a second nucleic acid if the nucleic acid sequence has a similar sequence to the second nucleic acid sequence. The terms "identity," "percent sequence identity" or "identical" in the context of nucleic acid sequences refer to the residues in the two sequences that are the same when aligned for maximum correspondence. There are a number of different algorithms known in the art that can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). In some embodiments, sequences can be compared using Geneious (Biomatters, Ltd., Auckland, New Zealand). In other embodiments, polynucleotide sequences can be compared using the multiple sequence alignment algorithm MUSCLE (Edgar R C, 2004).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% 99%, 99.5% or 100% of the nucleotide bases, as measured by any well-known algorithm of sequence identity, such as FASTA, BLAST, Gap, MUSCLE, or any other method known in the art.

As used herein, the terms "operational taxonomic unit," "OTU," "taxon," "hierarchical cluster," and "cluster" are used interchangeably. An operational taxon unit (OTU) refers to a group of one or more organisms that comprises a node in a clustering tree. The level of a cluster is determined by its hierarchical order. In one embodiment, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, or a species. In some embodiments, OTUs can represent one or more organisms from the kingdoms eubacteria, protista, or fungi at any level of a hierarchal order. In some embodiments, an OTU represents a prokaryotic or fungal order.

In some embodiments, the present invention contemplates the synthetic compositions comprising the combination of a plant element, seedling, or whole plants and an endophyte population, in which the endophyte population is "heterologously disposed." In some embodiments, "heterologously disposed" means that the native plant element, seedling, or plant does not contain detectable levels of the microbe in that same plant element, seedling, or plant. For example if said plant element or seedling or plant does not naturally have the endophyte associated with it and the endophyte is applied, the endophyte would be considered to be heterologously disposed. In some embodiments, "heterologously disposed" means that the endophyte is being applied to a different plant element than that with which the endophyte is naturally associated. For example, if said plant element or seedling or plant has the endophyte normally found in the root tissue but not in the leaf tissue, and the endophyte is applied to the leaf, the endophyte would be considered to be heterologously disposed. In some embodiments, "heterologously disposed" means that the endophyte being applied to a different tissue or cell layer of the plant element than that in which the microbe is naturally found. For example, if endophyte is naturally found in the mesophyll layer of leaf tissue but is being applied to the epithelial layer, the endophyte would be considered to be heterologously disposed. In some embodiments, "heterologously disposed" means that the endophyte being applied is at a greater concentration, number, or amount of the plant element, seedling, or plant, than that which is naturally found in said plant element, seedling, or plant. For example, an endophyte concentration that is being applied is at least 1.5 times greater, between 1.5 and 2 times greater, 2 times greater, between 2 and 3 times greater, 3 times greater, between 3 and 5 times greater, 5 times greater, between 5 and 7 times greater, 7 times greater, between 7 and 10 times greater, 10 times greater, or even greater than 10 times higher number, amount, or concentration than that which is naturally present, the endophyte would be considered to be heterologously disposed. In some embodiments, "heterologously disposed" means that the endophyte is applied to a developmental stage of the plant element, seedling, or plant in which said endophyte is not naturally associated, but may be associated at other stages. For example, if an endophyte is normally found at the flowering stage of a plant and no other stage, an endophyte applied at the seedling stage may be considered to be heterologously disposed. For example, an endophyte that is normally associated with leaf tissue of a cupressaceous tree sample would be considered heterologous to leaf tissue of a maize plant. In another example, an endophyte that is normally associated with leaf tissue of a maize plant is considered heterologous to a leaf tissue of another maize plant that naturally lacks said endophyte. In another example, an endophyte that is normally associated at low levels in a plant is considered heterologous to that plant if a higher concentration of that endophyte is introduced into the plant. In yet another example, an endophyte that is associated with a tropical grass species would be considered heterologous to a wheat plant.

The term "isoline" is a comparative term, and references organisms that are genetically identical, but may differ in treatment. In one example, two genetically identical maize plant embryos may be separated into two different groups, one receiving a treatment (such as transformation with a heterologous polynucleotide, to create a genetically modified plant) and one control that does not receive such treatment. Any phenotypic differences between the two groups may thus be attributed solely to the treatment and not to any inherency of the plant's genetic makeup. In another example, two genetically identical soybean seeds may be treated with a formulation that introduces an endophyte composition. Any phenotypic differences between the plants derived from (e.g., grown from or obtained from) those seeds may be attributed to the treatment, thus forming an isoline comparison.

Similarly, by the term "reference agricultural plant," it is meant an agricultural plant of the same species, strain, or cultivar to which a treatment, formulation, composition or endophyte preparation as described herein is not administered/contacted. A reference agricultural plant, therefore, is identical to the treated plant with the exception of the presence of the endophyte and can serve as a control for detecting the effects of the endophyte that is conferred to the plant.

A "reference environment" refers to the environment, treatment or condition of the plant in which a measurement is made. For example, production of a compound in a plant associated with an endophyte can be measured in a reference environment of drought stress, and compared with the levels of the compound in a reference agricultural plant under the same conditions of drought stress. Alternatively, the levels of a compound in plant associated with an endophyte and reference agricultural plant can be measured under identical conditions of no stress.

A "plant element" is intended to generically reference either a whole plant or a plant component, including but not limited to plant tissues, parts, and cell types. A plant element is preferably one of the following: whole plant, seedling, meristematic tissue, ground tissue, vascular tissue, dermal tissue, seed, leaf, root, shoot, stem, flower, fruit, stolon, bulb, tuber, corm, kelkis, shoot, bud. As used herein, a "plant element" is synonymous to a "portion" of a plant, and refers to any part of the plant, and can include distinct tissues and/or organs, and may be used interchangeably with the term "tissue" throughout.

Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keikis, or bud.

A "population" of plants refers to more than one plant, that are of the same taxonomic category, typically be of the same species, and will also typically share a common genetic derivation.

As used herein, an "agricultural seed" is a seed used to grow a plant typically used in agriculture (an "agricultural plant"). The seed may be of a monocot or dicot plant, and may be planted for the production of an agricultural product, for example feed, food, fiber, fuel, industrial uses, etc. As used herein, an agricultural seed is a seed that is prepared for planting, for example, in farms for growing.

"Agricultural plants," or "plants of agronomic importance," include plants that are cultivated by humans for food, feed, fiber, fuel, and/or industrial purposes. Agricultural plants include monocotyledonous species such as: maize (*Zea mays*), common wheat (*Triticum aestivum*), spelt (*Triticum spelta*), einkorn wheat (*Triticum monococcum*), emmer wheat (*Triticum dicoccum*), durum wheat (*Triticum durum*), Asian rice (*Oryza sativa*), African rice (*Oryza glabaerrima*), wild rice (*Zizania aquatica, Zizania latifolia, Zizania palustris, Zizania texana*), barley (*Hordeum vulgare*), Sorghum (*Sorghum bicolor*), Finger millet (*Eleusine coracana*), Proso millet (*Panicum miliaceum*), Pearl millet (*Pennisetum glaucum*), Foxtail millet (*Setaria italica*), Oat (*Avena sativa*), Triticale (*Triticosecale*), rye (*Secale cereal*), Russian wild rye (*Psathyrostachys juncea*), bamboo (*Bambuseae*), or sugarcane (e.g., *Saccharum arundinaceum, Saccharum barberi, Saccharum bengalense, Saccharum edule, Saccharum munja, Saccharum officinarum, Saccharum procerum, Saccharum ravennae, Saccharum robustum, Saccharum sinense,* or *Saccharum spontaneum*); as well as dicotyledonous species such as: soybean (*Glycine max*), canola and rapeseed cultivars (*Brassica napus*), cotton (genus *Gossypium*), alfalfa (*Medicago sativa*), cassava (genus *Manihot*), potato (*Solanum tuberosum*), tomato (*Solanum lycopersicum*), pea (*Pisum sativum*), chick pea (*Cicer arietinum*), lentil (*Lens culinaris*), flax (*Linum usitatissimum*) and many varieties of vegetables.

The term "synthetic composition" means one or more plant elements associated by human endeavor with an isolated, purified endophyte composition, said association which is not found in nature. In some embodiments of the present invention, "synthetic composition" is used to refer to a treatment formulation comprising an isolated, purified population of endophytes associated with a plant element. In some embodiments of the present invention, "synthetic composition" refers to a purified population of endophytes in a treatment formulation comprising additional compositions with which said endophytes are not found associated in nature.

A "treatment formulation" refers to a mixture of chemicals that facilitate the stability, storage, and/or application of the endophyte composition(s). Treatment formulations may comprise any one or more agents such as: surfactant, a buffer, a tackifier, a microbial stabilizer, a fungicide, an anticomplex agent, an herbicide, a nematicide, an insecticide, a plant growth regulator, a rodenticide, a desiccant, a nutrient, an excipient, a wetting agent, a salt.

In some embodiments, an "agriculturally compatible carrier" can be used to formulate an agricultural formulation or other composition that includes a purified endophyte preparation. As used herein an "agriculturally compatible carrier" refers to any material, other than water, that can be added to a plant element without causing or having an adverse effect on the plant element (e.g., reducing seed germination) or the plant that grows from the plant element, or the like.

The compositions and methods herein may provide for an improved "agronomic trait" or "trait of agronomic importance" to a host plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, compared to an isoline plant derived from a seed without said seed treatment formulation.

As used herein, the terms "water-limited condition" and "drought condition," or "water-limited" and "drought," may be used interchangeably. For example, a method or composition for improving a plant's ability to grow under drought conditions means the same as the ability to grow under water-limited conditions. In such cases, the plant can be further said to display improved tolerance to drought stress.

As used herein, the terms "normal watering" and "well-watered" are used interchangeably, to describe a plant grown under typical growth conditions with no water restriction.

Additionally, "altered metabolic function" or "altered enzymatic function" may include, but not be limited to, the following: altered production of an auxin, altered nitrogen fixation, altered production of an antimicrobial compound, altered production of a siderophore, altered mineral phosphate solubilization, altered production of a cellulase, altered production of a chitinase, altered production of a xylanase, altered production of acetoin, altered utilization of a carbon source.

An "increased yield" can refer to any increase in biomass or seed or fruit weight, seed size, seed number per plant, seed number per unit area, bushels per acre, tons per acre, kilo per hectare, or carbohydrate yield. Typically, the particular characteristic is designated when referring to increased yield, e.g., increased grain yield or increased seed size.

"Nutrient" or "seed nutrient" refers to any composition of the associated plant element, most particularly compositions providing benefit to other organisms that consume or utilize said plant element.

"Agronomic trait potential" is intended to mean a capability of a plant element for exhibiting a phenotype, preferably an improved agronomic trait, at some point during its life cycle, or conveying said phenotype to another plant element with which it is associated in the same plant. For example, a plant element may comprise an endophyte that will provide benefit to leaf tissue of a plant from which the plant element is grown; in such case, the plant element comprising such endophyte has the agronomic trait potential for a particular phenotype (for example, increased biomass in the plant) even if the plant element itself does not display said phenotype.

In some cases, the present invention contemplates the use of compositions that are "compatible" with agricultural chemicals, including but not limited to, a fungicide, an anti-complex compound, a bactericide, a virucide, an herbicide, a nematicide, a parasiticide, a pesticide, or any other agent widely used in agricultural which has the effect of killing or otherwise interfering with optimal growth of another organism. As used herein, a composition is "compatible" with an agricultural chemical when the organism is modified, such as by genetic modification, e.g., contains a transgene that confers resistance to an herbicide, or is adapted to grow in, or otherwise survive, the concentration of the agricultural chemical used in agriculture. For example, an endophyte disposed on the surface of a plant element is compatible with the fungicide metalaxyl if it is able to survive the concentrations that are applied on the plant element surface.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

The terms "decreased," "fewer," "slower" and "increased" "faster" "enhanced" "greater" as used herein refers to a decrease or increase in a characteristic of the endophyte treated plant element or resulting plant compared to an untreated plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than the untreated control.

DETAILED DESCRIPTION OF THE INVENTION

As demonstrated herein, agricultural plants may be associated with symbiotic microorganisms, termed endophytes, particularly bacteria and fungi, which may contribute to plant survival, performance, and characteristics. However, modern agricultural processes may have perturbed this relationship, resulting in increased crop losses, diminished stress resilience, biodiversity losses, and increasing dependence on external chemicals, fertilizers, and other unsustainable agricultural practices. There is a need for novel compositions and methods for generating plants with novel microbiome properties that can sustainably increase yield, improve stress resilience, and decrease fertilizer and chemical use.

Currently, the generally accepted view of plant endophytic communities focuses on their homologous derivation, predominantly from the soil communities in which the plants are grown (Hallman, et al., (1997) Canadian Journal of Microbiology. 43(10): 895-914). Upon observing taxonomic overlap between the endophytic and soil microbiota in *A. thaliana*, it was stated, "Our rigorous definition of an endophytic compartment microbiome should facilitate controlled dissection of plant-microbe interactions derived from complex soil communities" (Lundberg et al., (2012) Nature. 488, 86-90). There is strong support in the art for soil representing the repository from which plant endophytes are derived. New Phytologist (2010) 185: 554-567. Notable plant-microbe interactions such as mycorrhyzal fungi and complex *rhizobia* fit the paradigm of soil-based colonization of plant hosts and appear to primarily establish themselves independently of seed. As a result of focusing attention on the derivation of endophytes from the soil in which the target agricultural plant is currently growing, there has been an inability to achieve commercially significant improvements in plant yields and other plant characteristics such as increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to insect and nematode stresses, increased resistance to a fungal pathogen, increased resistance to a complex pathogen, increased resistance to a viral pathogen, a detectable modulation in the level of a metabolite, and a detectable modulation in the proteome relative to a reference plant.

The inventors herein have conceived of using endophytes that are capable of living within or otherwise associated with plants to improve plant characteristics, as well as methods of using endophytes that are capable of being associated with plants, to impart novel characteristics to a host plant, as well as to distinct plant elements of the host plant. In an embodiment of this invention, endophyte compositions are isolated and purified from plant or fungal sources, and synthetically combined with a plant element, to impart improved agronomic potential and/or improved agronomic traits to the host plant. In another embodiment of the invention, endophytes that are capable of living within plants are isolated and purified from their native source(s) and synthetically combined with a plant element, to impart improved agronomic potential and/or improved agronomic traits to the host plant or the host plant's elements. Such endophytes that are capable of living within plants may be further manipulated or combined with additional elements prior to combining with the plant element(s).

As described herein, beneficial organisms can be robustly obtained from heterologous, homologous, or engineered sources, optionally cultured, administered heterologously to plant elements, and, as a result of the administration, confer multiple beneficial properties. This is surprising given the variability observed in the art in endophytic microbe isolation and the previous observations of inefficient plant element pathogen colonization of plant host's tissues.

In part, the present invention provides preparations of endophytes that are capable of living within plants, and the creation of synthetic compositions of plant elements and/or seedlings with heterologous endophytes, and formulations comprising the synthetic compositions, as well as the recognition that such synthetic compositions display a diversity of beneficial properties present in the agricultural plants and the associated endophyte populations newly created by the present inventors. Such beneficial properties include metabolism, transcript expression, proteome alterations, morphology, and the resilience to a variety of environmental stresses, and any combination of such properties. The present invention also provides methods of using such endophytes to benefit the host plant with which it is associated.

Endophyte Compositions and Methods of Isolation

The endophytes of the present invention provide several unexpected and significant advantages over other plant-associated microbes. Different environments can comprise significantly different populations of endophytes and thus may provide reservoirs for desired endophytes. Once a choice environment is selected, plant elements of choice plants to be sampled can be identified by their healthy and/or robust growth, or other desired phenotypic characteristics.

In some embodiments of the present invention, endophytes may be bacteria identified from a plant source. In some embodiments of the present invention, endophytes are bacteria identified from a non-plant source, yet be capable of living within a plant, to create a new endophyte entity.

Endophyte Selection: Sourcing

In some embodiments of the present invention, endophytes may be isolated from plants or plant elements. In an embodiment of the present invention, endophytes described herein can also be isolated from plants, plant elements, or endophytic fungi of plants or plant elements adapted to a particular environment, including, but not limited to, an environment with water deficiency, salinity, acute and/or chronic heat stress, acute and/or chronic cold stress, nutrient deprived soils including, but not limited to, micronutrient deprived soils, macronutrient (e.g., potassium, phosphate, nitrogen) deprived soils, pathogen stress, including fungal, nematode, insect, viral, and complex pathogen stress.

In one embodiment, a plant is harvested from a soil type different than that in which the plant is normally grown. In another embodiment, the plant is harvested from an ecosystem where the agricultural plant is not normally found. In another embodiment, the plant is harvested from a soil with an average pH range that is different from the optimal soil pH range of the agricultural plant. In one embodiment, the plant is harvested from an environment with average air temperatures lower than the normal growing temperature of the agricultural plant. In one embodiment, the plant is harvested from an environment with average air temperatures higher than the normal growing temperature of the agricultural plant. In another embodiment, the plant is harvested from an environment with average rainfall lower than the optimal average rainfall received by the agricultural plant. In one embodiment, the plant is harvested from an environment with average rainfall higher than the optimal average rainfall of the agricultural plant. In another embodiment, the plant is harvested from a soil type with different soil moisture classification than the normal soil type that the agricultural plant is grown on. In one embodiment, the plant is harvested from an environment with average rainfall lower than the optimal average rainfall of the agricultural plant. In one embodiment, the plant is harvested from an environment with average rainfall higher than the optimal average rainfall of the agricultural plant. In another embodiment, the plant is harvested from an agricultural environment with a yield lower than the average yield expected from the agricultural plant grown under average cultivation practices on normal agricultural land. In another embodiment, the plant is harvested from an agricultural environment with a yield lower than the average yield expected from the agricultural plant grown under average cultivation practices on normal agricultural land. In another embodiment, the plant is harvested from an environment with average yield higher than the optimal average yield of the agricultural plant. In another embodiment, the plant is harvested from an environment with average yield higher than the optimal average yield of the agricultural plant. In another embodiment, the plant is harvested from an environment where soil contains lower total nitrogen than the optimum levels recommended in order to achieve average yields for a plant grown under average cultivation practices on normal agricultural land. In another embodiment, the plant is harvested from an environment where soil contains higher total nitrogen than the optimum levels recommended in order to achieve average yields for a plant grown under average cultivation practices on normal agricultural land. In another embodiment, the plant is harvested from an environment where soil contains lower total phosphorus than the optimum levels recommended in order to achieve average yields for a plant grown under average cultivation practices on normal agricultural land. In another embodiment, the plant is harvested from an environment where soil contains higher total phosphorus than the optimum levels recommended in order to achieve average yields for a plant grown under average cultivation practices on normal agricultural land. In another embodiment, the plant is harvested from an environment where soil contains lower total potassium than the optimum levels recommended in order to achieve average yields for a plant grown under average cultivation practices on normal agricultural land. In another embodiment, the plant is harvested from an environment where soil contains higher total potassium than the optimum levels recommended in order to achieve average yields for a plant grown under average cultivation practices on normal agricultural land. In another embodiment, the plant is harvested from an environment where soil contains lower total sulfur than the optimum levels recommended in order to achieve average yields for a plant grown under average cultivation practices on normal agricultural land. In another embodiment, the plant is harvested from an environment where soil contains higher total sulfur than the optimum levels recommended in order to achieve average yields for a plant grown under average cultivation practices on normal agricultural land. In another embodiment, the plant is harvested from an environment where soil contains lower total calcium than the optimum levels recommended in order to achieve average yields for a plant grown under average cultivation practices on normal agricultural land. In another embodiment, the plant is harvested from an environment where soil contains lower total magnesium than the optimum levels recommended in order to achieve average yields for a plant grown under average cultivation practices on normal agricultural land. In another embodiment, the plant is harvested from an environment where soil contains higher total sodium chloride (salt) than the optimum levels recommended in order to achieve average yields for a plant grown under average cultivation practices on normal agricultural land.

Endophytes can be obtained from a host plant or a plant element of many distinct plants. In an embodiment, the endophyte can be obtained a plant element of the same or different crop, and can be from the same or different cultivar or variety as the plant element to which the composition is heterologously associated.

In another embodiment, endophytes used in a composition or used to make a synthetic composition can be obtained from the same cultivar or species of agricultural plant to which the composition is intended for heterologous association, or can be obtained from a different cultivar or species of agricultural plant. For example, endophytes from a particular corn variety can be isolated and coated onto the surface of a corn plant element of the same variety.

In another embodiment, endophytes used in a composition or used to make a synthetic composition can be obtained from a plant element of a plant that is related to the plant element to which the composition is intended to be association. For example, an endophyte isolated from *Triticum monococcum* (einkorn wheat) can be coated onto the surface of a *T. aestivum* (common wheat) plant element; or, an endophyte from *Hordeum vulgare* (barley) can be isolated and coated onto the plant element of a member of the Triticeae family, for example, plant elements of the rye plant, *Secale cereale*).

In still another embodiment, endophytes used in a composition or used to make a synthetic composition can be obtained from a plant element of a plant that is distantly related to the plant element onto which the endophyte is to be coated. For example, a tomato-derived endophyte can be isolated and coated onto a soybean plant element.

In some embodiments, a purified endophytes population is used that includes two or more (e.g., 3, 4, 5, 6, 7, 8, 9, 10, 15, 20, 25 or greater than 25) different endophytes, e.g., obtained from different families of plant or fungus, or different genera of plant or fungus, or from the same genera but different species of plant or fungus.

In yet another embodiment, endophytes used in a composition or used to make a synthetic composition can be obtained from different individual plants of the same variety, each of which has been subjected to different growth conditions. For example, an endophyte obtained from a drought-affected plant of one variety can be isolated and coated onto the plant element that was derived from a plant of the same variety not subjected to drought. In such cases, the endophyte is considered to be heterologously associated with the plant element onto which it is applied.

The heterologous relationship between the endophyte and the host plant element may result from an endophyte obtained from any different plant or plant element than that which with it becomes associated. In some cases, the endophyte is obtained from a different cultivar of the same species. In some cases, the endophyte is obtained from a different plant species. In some cases, the endophyte is obtained from the same plant species but from two different plants, each exposed to some different environmental condition (for example, differences in heat units or water stress). In some cases, the endophyte is obtained from the same plant individual but from different plant elements or tissues (for example, a root endophyte applied to a leaf).

In some embodiments, compositions described herein comprise a purified endophyte population is used that includes at least two or more, at least 3, at least 4, at least 5, at least 6, at least 7, at least 8, at least 9, at least 10, at least 15, at least 20, at least 25, or more (e.g., 3, 4, 5, 6, 7, 8, 9, 10, 15, 20, 25 or greater than 25) different endophytes, e.g., obtained from different families of plants, or different genera of plant or fungus, or from the same genera but different species of plants.

The different endophytes can be obtained from the same cultivar of agricultural plant (e.g., the same maize, wheat, rice, or barley plant), different cultivars of the same agricultural plant (e.g., two or more cultivars of maize, two or more cultivars of wheat, two or more cultivars of rice, or two or more cultivars of barley), or different species of the same type of agricultural plant (e.g., two or more different species of maize, two or more different species of wheat, two or more different species of rice, or two or more different species of barley). In embodiments in which two or more endophytes are used, each of the endophytes can have different properties or activities, e.g., produce different metabolites, produce different enzymes such as different hydrolytic enzymes, confer different beneficial traits, or colonize different elements of a plant (e.g., leaves, stems, flowers, fruits, seeds, or roots). For example, one endophyte can colonize a first and a second endophyte can colonize a tissue that differs from the first tissue. Combinations of endophytes are disclosed in detail below.

In an embodiment, the endophyte is an endophytic microbe isolated from a different plant than the inoculated plant. For example, in an embodiment, the endophyte is an endophyte isolated from a different plant of the same species as the inoculated plant. In some cases, the endophyte is isolated from a species related to the inoculated plant.

Endophyte Selection: Compatibility with Agrichemicals

In certain embodiments, the endophyte is selected on the basis of its compatibility with commonly used agrichemicals. As mentioned earlier, plants, particularly agricultural plants, can be treated with a vast array of agrichemicals, including fungicides, biocides (anti-complex agents), herbicides, insecticides, nematicides, rodenticides, bactericides, virucides, fertilizers, and other agents.

In some embodiments, the endophytes of the present invention display tolerance to an agrichemical selected from the group consisting of: Aeris®, Avicta® DuoCot 202, Cruiser®, Syntenta CCB® (A), Clariva®, Albaugh, Dynasty®, Apron®, Maxim®, Gaucho®, Provoke® ST, Syngenta CCB®, Trilex®, WG Purple, WG Silver, Azoxystrobin, Carboxin, Difenoconazole, Fludioxonil, fluxapyroxad, Ipconazole, Mefenoxam, Metalaxyl, Myclobutanil, Penflufen, pyraclostrobin, Sedaxane, TCMTB, Tebuconazole, Thiram, Triadimenol (Baytan®), Trifloxystrobin, Triticonazole, Tolclofos-methyl, PCNB, Abamectin, Chlorpyrifos, Clothianidin, Imidacloprid, Thiamethoxam, Thiodicarb.

In some cases, it can be important for the endophyte to be compatible with agrichemicals, particularly those with anticomplex properties, in order to persist in the plant although, as mentioned earlier, there are many such anticomplex agents that do not penetrate the plant, at least at a concentration sufficient to interfere with the endophyte. Therefore, where a systemic anticomplex agent is used in the plant, compatibility of the endophyte to be inoculated with such agents will be an important criterion.

In an embodiment, natural isolates of endophytes that are compatible with agrichemicals can be used to inoculate the plants according to the methods described herein. For example, endophytes that are compatible with agriculturally employed anticomplex agents can be isolated by plating a culture of endophytes on a petri dish comprising an effective concentration of the anticomplex agent, and isolating colonies of endophytes that are compatible with the anticomplex agent. In another embodiment, an endophyte that is compatible with an anticomplex agent is used for the methods described herein.

Bactericide-compatible endophyte can also be isolated by selection on liquid medium. The culture of endophytes can be plated on petri dishes without any forms of mutagenesis; alternatively, endophytes can be mutagenized using any means known in the art. For example, endophyte cultures can be exposed to UV light, gamma-irradiation, or chemical mutagens such as ethylmethanesulfonate (EMS), ethidium bromide (EtBr) dichlovos (DDVP, methyl methane sulphonale (MMS), triethylphosphate (TEP), trimethylphosphate (TMP), nitrous acid, or DNA base analogs, prior to selection on fungicide comprising media. Finally, where the mechanism of action of a particular bactericide is known, the target gene can be specifically mutated (either by gene deletion, gene replacement, site-directed mutagenesis, etc.) to generate an endophyte that is resilient against that particular chemical. It is noted that the above-described methods can be used to isolate endophytes that are compatible with both bacteriostatic and bactericidal compounds.

It will also be appreciated by one skilled in the art that a plant may be exposed to multiple types of anticomplex compounds, either simultaneously or in succession, for example at different stages of plant growth. Where the target plant is likely to be exposed to multiple anticomplex agents, an endophyte that is compatible with many or all of these agrichemicals can be used to inoculate the plant. An endophyte that is compatible with several agents can be isolated, for example, by serial selection. An endophyte that is compatible with the first agent can be isolated as described above (with or without prior mutagenesis). A culture of the resulting endophyte can then be selected for the ability to grow on liquid or solid media comprising the second agent (again, with or without prior mutagenesis). Colonies isolated from the second selection are then tested to confirm its compatibility to both agents.

Likewise, endophytes that are compatible to biocides (including herbicides such as glyphosate or anticomplex compounds, whether bacteriostatic or bactericidal) that are agriculturally employed can be isolated using methods similar to those described for isolating compatible endophytes. In one embodiment, mutagenesis of the endophyte population can be performed prior to selection with an anticomplex agent. In another embodiment, selection is performed on the endophyte population without prior mutagenesis. In still another embodiment, serial selection is performed on an endophyte: the endophyte is first selected for compatibility to a first anticomplex agent. The isolated compatible endophyte is then cultured and selected for compatibility to the second anticomplex agent. Any colony thus isolated is tested for compatibility to each, or both anticomplex agents to confirm compatibility with these two agents.

Compatibility with an antimicrobial agent can be determined by a number of means known in the art, including the comparison of the minimal inhibitory concentration (MIC) of the unmodified and modified endophytes. Therefore, in one embodiment, the present invention discloses an isolated modified endophyte, wherein the endophyte is modified such that it exhibits at least 3 fold greater, for example, at least 5 fold greater, between 5 and 10 fold greater, at least 10 fold greater, between 10 and 20 fold greater, at least 20 fold greater, between 20 and 30 fold greater, at least 30 fold greater or more MIC to an antimicrobial agent when compared with the unmodified endophyte.

In one embodiment, disclosed herein are endophytes with enhanced compatibility to the herbicide glyphosate. In one embodiment, the endophyte has a doubling time in growth medium comprising at least 1 mM glyphosate, for example, between 1 mM and 2 mM glyphosate, at least 2 mM glyphosate, between 2 mM and 5 mM glyphosate, at least 5 mM glyphosate, between 5 mM and 10 mM glyphosate, at least 10 mM glyphosate, between 10 mM and 15 mM glyphosate, at least 15 mM glyphosate or more, that is no more than 250%, between 250% and 100%, for example, no more than 200%, between 200% and 175%, no more than 175%, between 175% and 150%, no more than 150%, between 150% and 125%, or no more than 125%, of the doubling time of the endophyte in the same growth medium comprising no glyphosate. In one particular embodiment, the endophyte has a doubling time in growth medium comprising 5 mM glyphosate that is no more than 150% the doubling time of the endophyte in the same growth medium comprising no glyphosate.

In another embodiment, the endophyte has a doubling time in a plant tissue comprising at least 10 ppm glyphosate, between 10 and 15 ppm, for example, at least 15 ppm glyphosate, between 15 and 10 ppm, at least 20 ppm glyphosate, between 20 and 30 ppm, at least 30 ppm glyphosate, between 30 and 40 ppm, at least 40 ppm glyphosate or more, that is no more than 250%, between 250% and 200%, for example, no more than 200%, between 200% and 175%, no more than 175%, between 175% and 150%, no more than 150%, between 150% and 125%, or no more than 125%, of the doubling time of the endophyte in a reference plant tissue comprising no glyphosate. In one particular embodiment, the endophyte has a doubling time in a plant tissue comprising 40 ppm glyphosate that is no more than 150% the doubling time of the endophyte in a reference plant tissue comprising no glyphosate.

The selection process described above can be repeated to identify isolates of endophytes that are compatible with a multitude of agents.

Candidate isolates can be tested to ensure that the selection for agrichemical compatibility did not result in loss of a desired bioactivity. Isolates of endophytes that are compatible with commonly employed agents can be selected as described above. The resulting compatible endophyte can be compared with the parental endophyte on plants in its ability to promote germination.

The agrichemical compatible endophytes generated as described above can be detected in samples. For example, where a transgene was introduced to render the endophyte compatible with the agrichemical(s), the transgene can be used as a target gene for amplification and detection by PCR. In addition, where point mutations or deletions to a portion of a specific gene or a number of genes results in compatibility with the agrichemical(s), the unique point mutations can likewise be detected by PCR or other means known in the art. Such methods allow the detection of the endophyte even if it is no longer viable. Thus, commodity plant products produced using the agrichemical compatible endophytes described herein can readily be identified by employing these and related methods of nucleic acid detection.

Endophyte Selection: Combinations

Combinations of endophytes can be selected by any one or more of several criteria. In one embodiment, compatible endophytes are selected. As used herein, "compatibility" refers to endophyte populations that do not significantly interfere with the growth, propagation, and/or production of beneficial substances of the other. Incompatible endophyte populations can arise, for example, where one of the populations produces or secrets a compound that is toxic or deleterious to the growth of the other population(s). Incompatibility arising from production of deleterious compounds/agents can be detected using methods known in the art, and as described herein elsewhere. Similarly, the distinct populations can compete for limited resources in a way that makes co-existence difficult.

In another embodiment, combinations are selected on the basis of compounds produced by each population of endophytes. For example, the first population is capable of producing siderophores, and another population is capable of producing anti-fungal compounds. In an embodiment, the first population of endophytes or endophytic components is capable of a function selected from the group consisting of auxin production, nitrogen fixation, and production of an antimicrobial compound, siderophore production, mineral phosphate solubilization, cellulase production, chitinase production, xylanase production, and acetoin production, carbon source utilization, and combinations thereof: In another embodiment, the second population of endophytes or endophytic component is capable of a function selected from the group consisting of auxin production, nitrogen fixation, production of an antimicrobial compound, siderophore production, mineral phosphate solubilization, cellulase production, chitinase production, xylanase production, and acetoin production, and combinations thereof: In still another embodiment, the first and second populations are capable of at least one different function.

In still another embodiment, the combinations of endophytes are selected for their distinct localization in the plant after colonization. For example, the first population of endophytes or endophytic components can colonize, and in some cases preferentially colonize, the root tissue, while a second population can be selected on the basis of its preferential colonization of the aerial parts of the agricultural plant. Therefore, in an embodiment, the first population is capable of colonizing one or more of the tissues selected from the group consisting of a root, shoot, leaf, flower, and seed. In another embodiment, the second population is capable of colonizing one or more tissues selected from the group consisting of root, shoot, leaf, flower, and seed. In still another embodiment, the first and second populations are capable of colonizing a different tissue within the agricultural plant.

In some embodiments, combinations of endophytes are selected for their ability to confer a benefit to the host plant at different points in the life cycle of said host plant. In one example, one endophyte can be selected to impart improved seedling vigor, and a second endophyte can be selected to improve soil nutrient acquisition by roots of the mature plant.

In still another embodiment, combinations of endophytes are selected for their ability to confer one or more distinct fitness traits on the inoculated agricultural plant, either individually or in synergistic association with other endophytes. In another embodiment, one endophyte may induce the colonization of a second endophyte. Alternatively, two or more endophytes may induce the colonization of a third endophyte. For example, the first population of endophytes or endophytic components is selected on the basis that it confers significant increase in biomass, while the second population promotes increased drought tolerance on the inoculated agricultural plant. Therefore, in one embodiment, the first population is capable of conferring at least one trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof: In another embodiment, the second population is capable of conferring a trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, and enhanced soil water retention. In still another embodiment, each of the first and second population is capable of conferring a different trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, and enhanced soil water retention.

The combinations of endophytes can also be selected based on combinations of the above criteria. For example, the first population of endophytes can be selected on the basis of the compound it produces (e.g., its ability to fix nitrogen, thus providing a potential nitrogen source to the plant), while the second population can be selected on the basis of its ability to confer increased resistance of the plant to a pathogen (e.g., a fungal pathogen).

In some embodiments of the present invention, it is contemplated that combinations of endophytes can provide an increased benefit to the host plant, as compared to that conferred by a single endophyte, by virtue of additive effects. For example, one endophyte strain that induces a benefit in the host plant may induce such benefit equally well in a plant that is also colonized with a different endophyte strain that also induces the same benefit in the host plant. The host plant thus exhibits the same total benefit from the combination of different endophyte strains as the additive benefit to individual plants colonized with each individual endophyte of the combination. In one example, a plant is colonized with two different endophyte strains: one provides a 1× increase in biomass when associated with the plant, and the other provides a 2× increase in biomass when associated with a different plant. When both endophyte strains are associated with the same plant, that plant would experience a 3× (additive of 1×+2× single effects) increase in auxin biomass. Additive effects are a surprising embodiment of the present invention, as non-compatibility of endophytes may result in a cancelation of the beneficial effects of both endophytes.

In some embodiments of the present invention, it is contemplated that a combination of endophytes can provide an increased benefit to the host plant, as compared to that conferred by a single endophyte, by virtue of synergistic effects. For example, one endophyte strain that induces a benefit in the host plant may induce such benefit beyond additive effects in a plant that is also colonized with a different endophyte strain that also induces that benefit in the host plant. The host plant thus exhibits the greater total benefit from the combination of different endophyte strains than could be seen from the additive benefit of individual plants colonized with each individual endophyte of the combination. In one example, a plant is colonized with two different endophyte strains: one provides a 1× increase in biomass when associated with a plant, and the other provides a 2× increase in biomass when associated with a different plant. When both endophyte strains are associated with the same plant, that plant would experience a 5× (greater than an additive of 1×+2× single effects) increase in biomass. Synergistic effects are a surprising embodiment of the present invention.

Endophyte Selection: Compositions of the Invention

In some embodiments, the endophyte is selected from the genus *Streptomyces*. In some embodiments, the endophyte comprises a nucleotide sequence that is at least 97% identical to SEQ ID NO: 1. In some embodiments, the endophyte comprises a nucleotide sequence that is at least 97% identical to SEQ ID NO: 2. In some embodiments, the endophyte comprises a nucleotide sequence that is at least 97% identical to SEQ ID NO: 3. In some embodiments, the endophyte comprises a nucleotide sequence that is at least 97% identical to SEQ ID NO: 4. In some embodiments, the endophyte comprises a nucleotide sequence that is at least 97% identical to SEQ ID NO: 5. In some embodiments, the endophyte comprises a nucleotide sequence that is at least 97% identical to SEQ ID NO: 6. In some embodiments, the endophyte comprises a nucleotide sequence that is at least 97% identical to SEQ ID NO: 7. In some embodiments, the endophyte comprises a nucleotide sequence that is at least 97% identical to SEQ ID NO: 8. In some embodiments, the endophyte comprises a nucleotide sequence that is at least 97% identical to SEQ ID NO: 9. In some embodiments, the endophyte comprises a nucleotide sequence that is at least 97% identical to SEQ ID NO: 10. In some embodiments, the endophyte comprises a nucleotide sequence that is at least 97% identical to SEQ ID NO: 11. In some embodiments, the endophyte comprises a nucleotide sequence that is at least 97% identical to SEQ ID NO: 12. In some embodiments, the endophyte comprises a nucleotide sequence that is at least 97% identical to SEQ ID NO: 13. In some embodiments, the endophyte comprises a nucleotide sequence that is at least 97% identical to SEQ ID NO: 14. In some embodiments, the endophyte comprises a nucleotide sequence that is at least 97% identical to SEQ ID NO: 15. In some embodiments, the endophyte comprises a nucleotide sequence that is at least 97% identical to SEQ ID NO: 16. In some embodiments, the endophyte comprises a nucleotide sequence that is at least 97% identical to SEQ ID NO: 17. In some embodiments, the endophyte comprises a nucleotide sequence that is at least 97% identical to SEQ ID NO: 18.

In some embodiments, the endophyte is at least 97% identical to a sequence selected from the group consisting of SEQ ID NO: 1-SEQ ID NO:18. In some embodiments, the endophyte is between 97% and 98% identical, at least 98% identical, between 98% identical and 99% identical, or at least 99% identical to a sequence selected from the group consisting of SEQ ID NO: 1-SEQ ID NO:18.

In some cases, the endophyte, or one or more components thereof, is of monoclonal origin, providing high genetic uniformity of the endophyte population in an agricultural formulation or within a synthetic plant element or plant combination with the endophyte.

In some embodiments, the endophyte can be cultured on a culture medium or can be adapted to culture on a culture medium.

The compositions provided herein are preferably stable. The endophyte may be shelf-stable, where at least 0.01%, of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf-stable formulation is in a dry formulation, a powder formulation, or a lyophilized formulation. In some embodiments, the formulation is formulated to provide stability for the population of endophytes. In an embodiment, the formulation is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

Endophytes and Synthetic Compositions with Plants and Plant Elements

It is contemplated that the methods and compositions of the present invention may be used to improve any characteristic of any agricultural plant. The methods described herein can also be used with transgenic plants comprising one or more exogenous transgenes, for example, to yield additional trait benefits conferred by the newly introduced endophytic microbes. Therefore, in one embodiment, a plant element of a transgenic soybean plant is contacted with an endophytic microbe. In one embodiment, a plant element of a transgenic maize plant is contacted with an endophytic microbe.

For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In one embodiment, it is contemplated that the plant of the present invention is soybean (*Glycine max*).

The primary uses for harvested soybean crops include: soybean oil, soybean meal, livestock feed, and uses for human consumption. All parts of a soy plant are utilized, including the starch, flours, oils, and proteins.

The primary uses for harvested maize crops include: livestock feed, food for human consumption, biofuels, high fructose corn syrup, sweeteners, dry distiller grains, plastics, cosmetics, and textiles. All parts of a corn plant are utilized, including the starch, fiber, proteins, and oils.

The endophyte compositions and methods of the present invention are capable of providing improvements of agronomic interest agricultural plants, for example soybeans and maize.

In some embodiments, the present invention contemplates the use of endophytes that can confer a beneficial agronomic trait upon the plant element or resulting plant with which it is associated.

In some cases, the endophytes described herein are capable of moving from one tissue type to another. For example, the present invention's detection and isolation of endophytes within the mature tissues of plants after coating on the exterior of a plant element demonstrates their ability to move from the plant element into the vegetative tissues of a maturing plant. Therefore, in one embodiment, the population of endophytes is capable of moving from the plant element exterior into the vegetative tissues of a plant. In one embodiment, the endophyte that is coated onto the plant element of a plant is capable, upon germination of the plant element into a vegetative state, of localizing to a different tissue of the plant. For example, endophytes can be capable of localizing to any one of the tissues in the plant, including: the root, adventitious root, seminal root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In an embodiment, the endophyte is capable of localizing to the root and/or the root hair of the plant. In another embodiment, the endophyte is capable of localizing to the photosynthetic tissues, for example, leaves and shoots of the plant. In other cases, the endophyte is localized to the vascular tissues of the plant, for example, in the xylem and phloem. In still another embodiment, the endophyte is capable of localizing to the reproductive tissues (flower, pollen, pistil, ovaries, stamen, fruit) of the plant. In another embodiment, the endophyte is capable of localizing to the root, shoots, leaves and reproductive tissues of the plant. In still another embodiment, the endophyte colonizes a fruit or plant element tissue of the plant. In still another embodiment, the endophyte is able to colonize the plant such that it is present in the surface of the plant (i.e., its presence is detectably present on the plant exterior, or the episphere of the plant). In still other embodiments, the endophyte is capable of localizing to substantially all, or all, tissues of the plant. In certain embodiments, the endophyte is not localized to the root of a plant. In other cases, the endophyte is not localized to the photosynthetic tissues of the plant.

In some cases, endophytes are capable of replicating within the host plant and colonizing the plant.

As shown in the Examples section below, the endophyte populations described herein are capable of colonizing a host plant. Successful colonization can be confirmed by detecting the presence of the endophyte population within the plant. For example, after applying the fungi to the plant elements, high titers of the fungi can be detected in the roots and shoots of the plants that germinate from the plant elements. Detecting the presence of the endophyte inside the plant can be accomplished by measuring the viability of the endophyte after surface sterilization of the plant element or the plant: endophyte colonization results in an internal localization of the endophyte, rendering it resistant to conditions of surface sterilization. The presence and quantity of endophyte can also be established using other means known in the art, for example, immunofluorescence microscopy using microbe-specific antibodies, or fluorescence in situ hybridization (see, for example, Amann et al. (2001) Current Opinion in Biotechnology 12:231-236, incorporated herein by reference in its entirety). Alternatively, specific nucleic acid probes recognizing conserved sequences from an endophyte can be employed to amplify a region, for example by quantitative PCR, and correlated to CFUs by means of a standard curve.

In some cases, plants are inoculated with endophytes that are isolated from the same species of plant as the plant element of the inoculated plant. For example, an endophyte that is normally found in one variety of a plant is associated with a plant element of a plant of another variety of that plant that in its natural state lacks said endophyte. For example, an endophyte that is normally found in one variety of *Glycine max* (soybean) is associated with a plant element of a plant of another variety of *Glycine max* that in its natural state lacks said endophyte. In an embodiment, the endophyte is obtained from a plant of a related species of plant as the plant element of the inoculated plant. For example, an endophyte that is normally found in one species of a plant is applied to another species of the same genus, or vice versa. In some cases, plants are inoculated with endophytes that are heterologous to the plant element of the inoculated plant. In an embodiment, the endophyte is obtained from a plant of another species. For example, an endophyte that is normally found in dicots is applied to a monocot plant, or vice versa. In other cases, the endophyte to be inoculated onto a plant is obtained from a related species of the plant that is being inoculated. In one embodiment, the endophyte is obtained from a related taxon, for example, from a related species. The plant of another species can be an agricultural plant. In another embodiment, the endophyte is part of a designed composition inoculated into any host plant element.

In another embodiment, the endophyte is disposed, for example, on the surface of a reproductive element of an agricultural plant, in an amount effective to be detectable in the mature agricultural plant. In one embodiment, the endophyte is disposed in an amount effective to be detectable in an amount of at least about 100 CFU between 100 and 200 CFU, at least about 200 CFU, between 200 and 300 CFU, at least about 300 CFU, between 300 and 400 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 and 30,000 CFU, at least about 30,000 CFU, between 30,000 and 100,000 CFU, at least about 100,000 CFU or more in the mature agricultural plant.

In some cases, the endophyte is capable of colonizing particular plant elements or tissue types of the plant. In an embodiment, the endophyte is disposed on the plant element or seedling in an amount effective to be detectable within a target tissue of the mature agricultural plant selected from a fruit, a seed, a leaf, or a root, or portion thereof: For example, the endophyte can be detected in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, in the target tissue of the mature agricultural plant.

Beneficial Attributes of Synthetic Compositions of Plant Elements and Endophytes Improved Attributes Conferred by Endophytes The present invention contemplates the establishment of a relationship between a symbiont and a plant element. In one embodiment, endophyte association results in a detectable change to the plant element, or the whole plant. The detectable change can be an improvement in a number of agronomic traits (e.g., improved general health, increased response to biotic or abiotic stresses, or enhanced properties of the plant or a plant element, including fruits and grains). Alternatively, the detectable change can be a physiological or biological change that can be measured by methods known in the art. The detectable changes are described in more detail in the sections below. As used herein, an endophyte is considered to have conferred an improved agricultural trait whether or not the improved trait arose from the plant, the endophyte, or the concerted action between the plant and endophyte. Therefore, for example, whether a beneficial hormone or chemical is produced by the plant or the endophyte, for purposes of the present invention, the endophyte will be considered to have conferred an improved agronomic trait upon the host plant, as compared to an isoline plant that has not been associated with said endophyte.

In some embodiments, provided herein, are methods for producing a plant element of a plant with a heritably altered trait. The trait of the plant can be altered without known genetic modification of the plant genome, and comprises the following steps. First, a preparation of an isolated endophyte that is heterologous to the plant element of the plant is provided, and optionally processed to produce an endophyte formulation. The endophyte formulation is then contacted with the plant. The plants are then allowed to go to seed, and the seeds are collected.

Improved General Health

Also described herein are plants, and fields of plants, that are associated with beneficial endophytes, such that the overall fitness, productivity or health of the plant or a portion thereof, is maintained, increased and/or improved over a period of time. Improvement in overall plant health can be assessed using numerous physiological parameters including, but not limited to, height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof: Improved plant health, or improved field health, can also be demonstrated through improved resistance or response to a given stress, either biotic or abiotic stress, or a combination of one or more abiotic stresses, as provided herein.

Other Abiotic Stresses

Disclosed herein are endophyte-associated plants with increased resistance to an abiotic stress. Exemplary abiotic stresses include, but are not limited to: drought, heat, salt content, metal content, low nutrient conditions, cold, excess water conditions.

Drought and heat tolerance. In some cases, a plant resulting from seeds or other plant elements treated with an endophyte can exhibit a physiological change, such as a compensation of the stress-induced reduction in photosynthetic activity. Fv/Fm tests whether or not plant stress affects photosystem II in a dark adapted state. Fv/Fm is one of the most commonly used chlorophyll fluorescence measuring parameter. The Fv/Fm test is designed to allow the maximum amount of the light energy to take the fluorescence pathway. It compares the dark-adapted leaf pre-photosynthetic fluorescent state, called minimum fluorescence, or Fo, to maximum fluorescence called Fm. In maximum fluorescence, the maximum number of reaction centers have been reduced or closed by a saturating light source. In general, the greater the plant stress, the fewer open reaction centers available, and the Fv/Fm ratio is lowered. Fv/Fm is a measuring protocol that works for many types of plant stress. For example, there would be a difference in the Fv/Fm after exposure of an endophyte treated plant that had been subjected to heat shock or drought conditions, as compared to a corresponding control, a genetically identical plant that does not contain the endophytes grown in the same conditions. In some cases, the endophyte-associated plant as disclosed herein can exhibit an increased change in photosynthetic activity ΔFv(ΔFv/Fm) after heat-shock or drought stress treatment, for example 1, 2, 3, 4, 5, 6, 7 days or more after the heat-shock or drought stress treatment, or until photosynthesis ceases, as compared with corresponding control plant of similar developmental stage but not comprising endophytes. For example, a plant having an endophyte able to confer heat and/or drought-tolerance can exhibit a ΔFv/Fm of from about 0.1 to about 0.8 after exposure to heat-shock or drought stress or a ΔFv/Fm range of from about 0.03 to about 0.8 under one day, or 1, 2, 3, 4, 5, 6, 7, or over 7 days post heat-shock or drought stress treatment, or until photosynthesis ceases. In some embodiments, stress-induced reductions in photosynthetic activity can be compensated by at least about 0.25% (for example, at least about 0.5%, between 0.5% and 1%, at least about 1%, between 1% and 2%, at least about 2%, between 2% and 3%, at least about 3%, between 3% and 5%, at least about 5%, between 5% and 10%, at least about 8%, at least about 10%, between 10% and 15%, at least about 15%, between 15% and 20%, at least about 20%, between 20$ and 25%, at least about 25%, between 25% and 30%, at least about 30%, between 30% and 40%, at least about 40%, between 40% and 50%, at least about 50%, between 50% and 60%, at least about 60%, between 60% and 75%, at least about 75%, between 75% and 80%, at least about 80%, between 80% and 85%, at least about 85%, between 85% and 90%, at least about 90%, between 90% and 95%, at least about 95%, between 95% and 99%, at least about 99% or at least 100%) as compared to the photosynthetic activity decrease in a corresponding reference agricultural plant following heat shock conditions. Significance of the difference between endophyte-associated and reference agricultural plants can be established upon demonstrating statistical significance, for example at p<0.05 with an appropriate parametric or non-parametric statistic, e.g., Chi-square test, Student's t-test, Mann-Whitney test, or F-test based on the assumption or known facts that the endophyte-associated plant and reference agricultural plant have identical or near identical genomes (isoline comparison).

In some embodiments, the plants comprise endophytes able to increase heat and/or drought-tolerance in sufficient quantity, such that increased growth or improved recovery from wilting under conditions of heat or drought stress is observed. For example, an endophyte population described herein can be present in sufficient quantity in a plant, resulting in increased growth as compared to a plant that does not contain endophytes, when grown under drought conditions or heat shock conditions, or following such conditions. Increased heat and/or drought tolerance can be assessed with physiological parameters including, but not limited to, increased height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, wilt recovery, turgor pressure, or any combination thereof, as compared to a reference agricultural plant grown under similar conditions. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In various embodiments, endophytes introduced into the plant can confer in the resulting plant thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased protein content, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. A difference between the endophyte-associated plant and a reference agricultural plant can also be measured using other methods known in the art.

Salt Stress. In other embodiments, endophytes able to confer increased tolerance to salinity stress can be introduced into plants. The resulting plants comprising endophytes can exhibit increased resistance to salt stress, whether measured in terms of survival under saline conditions, or overall growth during, or following salt stress. The physiological parameters of plant health recited above, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., isogenic plants without the endophytes) grown under identical conditions. For example, the endophyte may provide an improved benefit or tolerance to a plant that is of at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions. In other instances, endophyte-associated plants and reference agricultural plants can be grown in soil or growth media comprising different concentration of sodium to establish the inhibitory concentration of sodium (expressed, for example, as the concentration in which growth of the plant is inhibited by 50% when compared with plants grown under no sodium stress). Therefore, in another embodiment, a plant resulting from plant elements comprising an endophyte able to confer salt tolerance described herein exhibits an increase in the inhibitory sodium concentration by at least 10 mM, between 10 mM and 15 mM, for example at least 15 mM, between 15 mM and 20 mM, at least 20 mM, between 20 mM and 30 mM, at least 30 mM, between 30 mM and 40 mM, at least 40 mM, between 40 mM and 50 mM, at least 50 mM, between 50 mM and 60 mM, at least 60 mM, between 60 mM and 70 mM, at least 70 mM, between 70 mM and 80 mM, at least 80 mM, between 80 mM and 90 mM, at least 90 mM, between 90 mM and 100 mM, at least 100 mM or more, when compared with the reference agricultural plants.

High Metal Content. Plants are sessile organisms and therefore must contend with the environment in which they are placed. Plants have adapted many mechanisms to deal with chemicals and substances that may be deleterious to their health. Heavy metals in particular represent a class of toxins that are highly relevant for plant growth and agriculture, because many of them are associated with fertilizers and sewage sludge used to amend soils and can accumulate to toxic levels in agricultural fields. Therefore, for agricultural purposes, it is important to have plants that are able to tolerate soils comprising elevated levels of toxic heavy metals. Plants cope with toxic levels of heavy metals (for example, nickel, cadmium, lead, mercury, arsenic, or aluminum) in the soil by excretion and internal sequestration. Endophytes that are able to confer increased heavy metal tolerance may do so by enhancing sequestration of the metal in certain compartments away from the seed or fruit and/or by supplementing other nutrients necessary to remediate the stress. Use of such endophytes in a plant would allow the development of novel plant-endophyte combinations for purposes of environmental remediation (also known as phytoremediation). Therefore, in one embodiment, the plant comprising endophytes shows increased metal tolerance as compared to a reference agricultural plant grown under the same heavy metal concentration in the soil.

Alternatively, the inhibitory concentration of the heavy metal can be determined for endophyte-associated plant and compared with a reference agricultural plant under the same conditions. Therefore, in one embodiment, the plants resulting from plant elements comprising an endophyte able to confer heavy metal tolerance described herein exhibit an increase in the inhibitory metal concentration by at least 0.1 mM, between 0.1 mM and 0.3 mM, for example at least 0.3 mM, between 0.3 mM and 0.5 mM, at least 0.5 mM, between 0.5 mM and 1 mM, at least 1 mM, between 1 mM and 2 mM, at least 2 mM, between 2 mM and 5 mM, at least 5 mM, between 5 mM and 10 mM, at least 10 mM, between 10 mM and 15 mM, at least 15 mM, between 15 mM and 20 mM, at least 20 mM, between 20 mM and 30 mM, at least 30 mM, between 30 mM and 50 mM, at least 50 mM or more, when compared with the reference agricultural plants.

Finally, plants inoculated with endophytes that are able to confer increased metal tolerance exhibit an increase in overall metal excretion by at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Low Nutrient Stress. Endophytes described herein may also confer to the plant an increased ability to grow in nutrient limiting conditions, for example by solubilizing or otherwise making available to the plants macronutrients or micronutrients that are complexed, insoluble, or otherwise in an unavailable form. In one embodiment, a plant is inoculated with an endophyte that confers increased ability to liberate and/or otherwise provide to the plant with nutrients selected from the group consisting of phosphate, nitrogen, potassium, iron, manganese, calcium, molybdenum, vitamins, or other micronutrients. Such a plant can exhibit increased growth in soil comprising limiting amounts of such nutrients when compared with reference agricultural plant. Differences between the endophyte-associated plant and reference agricultural plant can be measured by comparing the biomass of the two plant types grown under limiting conditions, or by measuring the physical parameters described above. Therefore, in one embodiment, the plant comprising endophyte shows increased tolerance to nutrient limiting conditions as compared to a reference agricultural plant grown under the same nutrient limited concentration in the soil, as measured for example by increased biomass or seed yield of at least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Cold Stress. In some cases, endophytes can confer to the plant the ability to tolerate cold stress. As used herein, cold stress refers to both the stress induced by chilling (0° C.-15° C.) and freezing (<0° C.). Some cultivars of agricultural plants can be particularly sensitive to cold stress, but cold tolerance traits may be multigenic, making the breeding process difficult. Endophytes able to confer cold tolerance can reduce the damage suffered by farmers on an annual basis. Improved response to cold stress can be measured by survival of plants, production of protectant substances such as anthocyanin, the amount of necrosis of parts of the plant, or a change in crop yield loss, as well as the physiological parameters used in other examples. Therefore, in an embodiment, the plant comprising endophytes shows increased cold tolerance exhibits as compared to a reference agricultural plant grown under the same conditions of cold stress. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Biotic Stress. In other embodiments, the endophyte protects the plant from a biotic stress, for example, insect infestation, nematode infestation, complex infection, fungal infection, bacterial infection, oomycete infection, protozoal infection, viral infection, and herbivore grazing, or a combination thereof. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Insect herbivory. There are an abundance of insect pest species that can infect or infest a wide variety of plants. Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as cotton, soybean, wheat, barley, and corn (maize).

In some cases, endophytes described herein may confer upon the host plant the ability to repel insect herbivores. In other cases, endophytes may produce, or induce the production in the plant of, compounds which are insecticidal or insect repellant. The insect may be any one of the common pathogenic insects affecting plants, particularly agricultural plants.

The endophyte-associated plant can be tested for its ability to resist, or otherwise repel, pathogenic insects by measuring, for example, insect load, overall plant biomass, biomass of the fruit or grain, percentage of intact leaves, or other physiological parameters described herein, and comparing with a reference agricultural plant. In an embodiment, the endophyte-associated plant exhibits increased biomass as compared to a reference agricultural plant grown under the same conditions (e.g., grown side-by-side, or adjacent to, endophyte-associated plants). In other embodiments, the endophyte-associated plant exhibits increased fruit or grain yield as compared to a reference agricultural plant grown under the same conditions (e.g., grown side-by-side, or adjacent to, endophyte-associated plants).

Nematodes. Nematodes are microscopic roundworms that feed on the roots, fluids, leaves and stems of more than 2,000 row crops, vegetables, fruits, and ornamental plants, causing an estimated $100 billion crop loss worldwide and accounting for 13% of global crop losses due to disease. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore parasitic on a large number of crop species. The cyst- and lesion-forming nematode species have a more limited host range, but still cause considerable losses in susceptible crops.

Signs of nematode damage include stunting and yellowing of leaves, and wilting of the plants during hot periods. Nematode infestation, however, can cause significant yield losses without any obvious above-ground disease symptoms. The primary causes of yield reduction are due to underground root damage. Roots infected by SCN are dwarfed or stunted. Nematode infestation also can decrease the number of nitrogen-fixing nodules on the roots, and may make the roots more susceptible to attacks by other soil-borne plant nematodes.

In an embodiment, the endophyte-associated plant has an increased resistance to a nematode when compared with a reference agricultural plant. As before with insect herbivores, biomass of the plant or a portion of the plant, or any of the other physiological parameters mentioned elsewhere, can be compared with the reference agricultural plant grown under the same conditions. Particularly useful measurements include overall plant biomass, biomass and/or size of the fruit or grain, and root biomass. In one embodiment, the endophyte-associated plant exhibits increased biomass as compared to a reference agricultural plant grown under the same conditions (e.g., grown side-by-side, or adjacent to, the endophyte-associated plants, under conditions of nematode challenge). In another embodiment, the endophyte-associated plant exhibits increased root biomass as compared to a reference agricultural plant grown under the same conditions (e.g., grown side-by-side, or adjacent to, the endophyte-associated plants, under conditions of nematode challenge). In still another embodiment, the endophyte-associated plant exhibits increased fruit or grain yield as compared to a reference agricultural plant grown under the same conditions (e.g., grown side-by-side, or adjacent to, the endophyte-associated plants, under conditions of nematode challenge).

Fungal Pathogens. Fungal diseases are responsible for yearly losses of over $10 Billion on agricultural crops in the US, represent 42% of global crop losses due to disease, and are caused by a large variety of biologically diverse pathogens. Different strategies have traditionally been used to control them. Resistance traits have been bred into agriculturally important varieties, thus providing various levels of resistance against either a narrow range of pathogen isolates or races, or against a broader range. However, this involves the long and labor intensive process of introducing desirable traits into commercial lines by genetic crosses and, due to the risk of pests evolving to overcome natural plant resistance, a constant effort to breed new resistance traits into commercial lines is required. Alternatively, fungal diseases have been controlled by the application of chemical fungicides. This strategy usually results in efficient control, but is also associated with the possible development of resistant pathogens and can be associated with a negative impact on the environment. Moreover, in certain crops, such as barley and wheat, the control of fungal pathogens by chemical fungicides is difficult or impractical.

The present invention contemplates the use of endophytes that are able to confer resistance to fungal pathogens to the host plant. Increased resistance to fungal inoculation can be measured, for example, using any of the physiological parameters presented above, by comparing with reference agricultural plants. In an embodiment, the endophyte-associated plant exhibits increased biomass and/or less pronounced disease symptoms as compared to a reference agricultural plant grown under the same conditions (e.g., grown side-by-side, or adjacent to, the endophyte-associated plants, infected with the fungal pathogen). In still another embodiment, the endophyte-associated plant exhibits increased fruit or grain yield as compared to a reference agricultural plant grown under the same conditions (e.g., grown side-by-side, or adjacent to, the endophyte-associated plants, infected with the fungal pathogen). In another embodiment, the endophyte-associated plant exhibits decreased hyphal growth as compared to a reference agricultural plant grown under the same conditions (e.g., grown side-by-side, or adjacent to, the endophyte-associated plants, infected with the fungal pathogen). For example, the endophyte may provide an improved benefit to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

Viral Pathogens. Plant viruses are estimated to account for 18% of global crop losses due to disease. There are numerous examples of viral pathogens affecting agricultural productivity. In an embodiment, the endophyte provides protection against viral pathogens such that the plant has increased biomass as compared to a reference agricultural plant grown under the same conditions. In still another embodiment, the endophyte-associated plant exhibits greater fruit or grain yield, when challenged with a virus, as compared to a reference agricultural plant grown under the same conditions. In yet another embodiment, the endophyte-associated plant exhibits lower viral titer, when challenged with a virus, as compared to a reference agricultural plant grown under the same conditions.

Complex Pathogens. Likewise, bacterial pathogens are a significant problem negatively affecting agricultural productivity and accounting for 27% of global crop losses due to plant disease. In an embodiment, the endophyte described herein provides protection against bacterial pathogens such that the plant has greater biomass as compared to a reference agricultural plant grown under the same conditions. In still another embodiment, the endophyte-associated plant exhibits greater fruit or grain yield, when challenged with a complex pathogen, as compared to a reference agricultural plant grown under the same conditions. In yet another embodiment, the endophyte-associated plant exhibits lower complex count, when challenged with a bacterium, as compared to a reference agricultural plant grown under the same conditions.

Improvement of Other Traits

In other embodiments, the endophyte can confer other beneficial traits to the plant. Improved traits can include an improved nutritional content of the plant or plant element used for human consumption. In one embodiment, the endophyte-associated plant is able to produce a detectable change in the content of at least one nutrient. Examples of such nutrients include amino acid, protein, oil (including any one of Oleic acid, Linoleic acid, Alpha-linoleic acid, Saturated fatty acids, Palmitic acid, Stearic acid and Trans fats), carbohydrate (including sugars such as sucrose, glucose and fructose, starch, or dietary fiber), Vitamin A, Thiamine (vit. B1), Riboflavin (vit. B2), Niacin (vit. B3), Pantothenic acid (B5), Vitamin B6, Folate (vit. B9), Choline, Vitamin C, Vitamin E, Vitamin K, Calcium, Iron, Magnesium, Manganese, Phosphorus, Potassium, Sodium, Zinc. In an embodiment, the endophyte-associated plant or part thereof contains at least one increased nutrient when compared with reference agricultural plants.

In other cases, the improved trait can include reduced content of a harmful or undesirable substance when compared with reference agricultural plants. Such compounds include those which are harmful when ingested in large quantities or are bitter tasting (for example, oxalic acid, amygdalin, certain alkaloids such as solanine, caffeine, nicotine, quinine and morphine, tannins, cyanide). As such, in one embodiment, the endophyte-associated plant or part thereof contains less of the undesirable substance when compared with reference agricultural plant. In a related embodiment, the improved trait can include improved taste of the plant or a part of the plant, including the fruit or plant reproductive element. In a related embodiment, the improved trait can include reduction of undesirable compounds produced by other endophytes in plants, such as degradation of *Fusarium*-produced deoxynivalenol (also known as vomitoxin and a virulence factor involved in *Fusarium* head blight of maize and wheat) in a part of the plant, including the fruit or plant reproductive element.

In other cases, the improved trait can be an increase in overall biomass of the plant or a part of the plant, including its fruit or plant reproductive element.

The endophyte-associated plant can also have an altered hormone status or altered levels of hormone production when compared with a reference agricultural plant. An alteration in hormonal status may affect many physiological parameters, including flowering time, water efficiency, apical dominance and/or lateral shoot branching, increase in root hair, and alteration in fruit ripening.

The association between the endophyte and the plant can also be detected using other methods known in the art. For example, the biochemical, metabolomics, proteomic, genomic, epigenomic and/or transcriptomic profiles of endophyte-associated plants can be compared with reference agricultural plants under the same conditions.

Methods of Using Endophytes and Synthetic Compositions Comprising Endophytes

As described herein, purified endophyte populations and compositions comprising the same (e.g., formulations) can be used to confer beneficial traits to the host plant including, for example, one or more of the following: increased root biomass, increased root length, increased height, increased shoot length, increased leaf number, improved water use efficiency (drought tolerance), increased overall biomass, increase grain yield, increased photosynthesis rate, increased tolerance to drought, increased heat tolerance, increased salt tolerance, increased resistance to nematode stress, increased resistance to a fungal pathogen, increased resistance to a complex pathogen, increased resistance to a viral pathogen, a detectable modulation in the level of a metabolite, and a detectable modulation in the proteome relative to a reference plant. For example, in some embodiments, a purified endophyte population can improve two or more such beneficial traits, e.g., water use efficiency and increased tolerance to drought.

In some cases, the endophyte may produce one or more compounds and/or have one or more activities, e.g., one or more of the following: production of a metabolite, production of a phytohormone such as auxin, production of acetoin, production of an antimicrobial compound, production of a siderophore, production of a cellulase, production of a pectinase, production of a chitinase, production of a xylanase, nitrogen fixation, or mineral phosphate solubilization. For example, an endophyte can produce a phytohormone selected from the group consisting of an auxin, a cytokinin, a gibberellin, ethylene, a brassinosteroid, and abscisic acid. In one particular embodiment, the endophyte produces auxin (e.g., indole-3-acetic acid (IAA)). Production of auxin can be assayed as described herein. Many of the microbes described herein are capable of producing the plant hormone auxin indole-3-acetic acid (IAA) when grown in culture. Auxin plays a key role in altering the physiology of the plant, including the extent of root growth. Therefore, in another embodiment, the endophytic population is disposed on the surface or within a tissue of the seed or seedling in an amount effective to detectably increase production of auxin in the agricultural plant when compared with a reference agricultural plant. In one embodiment, the increased auxin production can be detected in a tissue type selected from the group consisting of the root, shoot, leaves, and flowers.

In some embodiments, the endophyte can produce a compound with antimicrobial properties. For example, the compound can have antibacterial properties, as determined by the growth assays provided herein. In one embodiment, the compound with antibacterial properties shows bacteriostatic or bactericidal activity against *E. coli* and/or *Bacillus* sp. In another embodiment, the endophyte produces a compound with antifungal properties, for example, fungicidal or fungistatic activity against *S. cerevisiae* and/or *Rhizoctonia*.

In some embodiments, the endophyte is a bacterium capable of nitrogen fixation, and is thus capable of producing ammonium from atmospheric nitrogen. The ability of a bacterium to fix nitrogen can be confirmed by testing for growth of the bacterium in nitrogen-free growth media, for example, LGI media, as described herein.

In some embodiments, the endophyte can produce a compound that increases the solubility of mineral phosphate in the medium, i.e., mineral phosphate solubilization, for example, using the growth assays described herein. In one embodiment, the endophyte produces a compound that allows the bacterium to grow in growth media comprising $Ca_3HPO_4$ as the sole phosphate source.

In some embodiments, the endophyte can produce a siderophore. Siderophores are small high-affinity iron chelating agents secreted by microorganisms that increase the bioavailability of iron. Siderophore production by the endophyte can be detected, for example, using any known method in the art.

In some embodiments, the endophyte can produce a hydrolytic enzyme. For example, in one embodiment, an endophyte can produce a hydrolytic enzyme selected from the group consisting of a cellulase, a pectinase, a chitinase and a xylanase. Hydrolytic enzymes can be detected using the methods known in the art.

In some embodiments, metabolites in plants can be modulated by making synthetic compositions of purified endophytic populations. For example, an endophyte described herein can cause a detectable modulation (e.g., an increase or decrease) in the level of various metabolites, e.g., indole-3-carboxylic acid, trans-zeatin, abscisic acid, phaseic acid, indole-3-acetic acid, indole-3-butyric acid, indole-3-acrylic acid, jasmonic acid, jasmonic acid methyl ester, dihydrophaseic acid, gibberellin A3, salicylic acid, upon colonization of a plant.

In some embodiments, the endophyte modulates the level of the metabolite directly (e.g., the microbe itself produces the metabolite, resulting in an overall increase in the level of the metabolite found in the plant). In other cases, the agricultural plant, as a result of the association with the endophytic microbe (e.g., an endophyte), exhibits a modulated level of the metabolite (e.g., the plant reduces the expression of a biosynthetic enzyme responsible for production of the metabolite as a result of the microbe inoculation). In still other cases, the modulation in the level of the metabolite is a consequence of the activity of both the microbe and the plant (e.g., the plant produces increased amounts of the metabolite when compared with a reference agricultural plant, and the endophytic microbe also produces the metabolite). Therefore, as used herein, a modulation in the level of a metabolite can be an alteration in the metabolite level through the actions of the microbe and/or the inoculated plant.

The levels of a metabolite can be measured in an agricultural plant, and compared with the levels of the metabolite in a reference agricultural plant, and grown under the same conditions as the inoculated plant. The uninoculated plant that is used as a reference agricultural plant is a plant that has not been applied with a formulation with the endophytic microbe (e.g., a formulation comprising a population of purified endophytes). The uninoculated plant used as the reference agricultural plant is generally the same species and cultivar as, and is isogenic to, the inoculated plant.

The metabolite whose levels are modulated (e.g., increased or decreased) in the endophyte-associated plant may serve as a primary nutrient (i.e., it provides nutrition for the humans and/or animals who consume the plant, plant tissue, or the commodity plant product derived therefrom, including, but not limited to, a sugar, a starch, a carbohydrate, a protein, an oil, a fatty acid, a mineral, or a vitamin). The metabolite can be a compound that is important for plant growth, development or homeostasis (for example, a phytohormone such as an auxin, cytokinin, gibberellin, a brassinosteroid, ethylene, or abscisic acid, a signaling molecule, or an antioxidant). In other embodiments, the metabolite can have other functions. For example, in one embodiment, a metabolite can have bacteriostatic, bactericidal, fungistatic, fungicidal or antiviral properties. In other embodiments, the metabolite can have insect-repelling, insecticidal, nematode-repelling, or nematicidal properties. In still other embodiments, the metabolite can serve a role in protecting the plant from stresses, may help improve plant vigor or the general health of the plant. In yet another embodiment, the metabolite can be a useful compound for industrial production. For example, the metabolite may itself be a useful compound that is extracted for industrial use, or serve as an intermediate for the synthesis of other compounds used in industry. In a particular embodiment, the level of the metabolite is increased within the agricultural plant or a portion thereof such that it is present at a concentration of at least 0.1 ug/g dry weight, between 0.1 ug/g to 0.3 ug/g, for example, at least 0.3 ug/g dry weight, between 0.3 ug/g to 1.0 ug/g, 1.0 ug/g dry weight, between 1 ug/g and 3 ug/g, 3.0 ug/g dry weight, between 3 ug/g and 10 ug/g, 10 ug/g dry weight, between 10 ug/g and 30 ug/g, 30 ug/g dry weight, between 30 ug/g and 100 ug/g, 100 ug/g dry weight, between 100 ug/g and 300 ug/g, 300 ug/g dry weight, between 300 ug/g and 1 mg/g, 1 mg/g dry weight, between 1 mg/g and 3 mg/g, 3 mg/g dry weight, between 3 mg/g and 10 mg/g, 10 mg/g dry weight, between 10 mg/g and 30 mg/g, 30 mg/g dry weight, between 30 mg/g and 100 mg/g, 100 mg/g dry weight or more, of the plant or portion thereof.

Likewise, the modulation can be a decrease in the level of a metabolite. The reduction can be in a metabolite affecting the taste of a plant or a commodity plant product derived from a plant (for example, a bitter tasting compound), or in a metabolite which makes a plant or the resulting commodity plant product otherwise less valuable (for example, reduction of oxalate content in certain plants, or compounds which are deleterious to human and/or animal health). The metabolite whose level is to be reduced can be a compound that affects quality of a commodity plant product (e.g., reduction of lignin levels).

In some embodiments, the endophyte is capable of generating a complex network in the plant or surrounding environment of the plant, which network is capable of causing a detectable modulation in the level of a metabolite in the host plant.

In a particular embodiment, the metabolite can serve as a signaling or regulatory molecule. The signaling pathway can be associated with a response to a stress, for example, one of the stress conditions selected from the group consisting of drought stress, salt stress, heat stress, cold stress, low nutrient stress, nematode stress, insect herbivory stress, fungal pathogen stress, complex pathogen stress, and viral pathogen stress.

The inoculated agricultural plant is grown under conditions such that the level of one or more metabolites is modulated in the plant, wherein the modulation is indicative of increased resistance to a stress selected from the group consisting of drought stress, salt stress, heat stress, cold stress, low nutrient stress, nematode stress, insect herbivory stress, fungal pathogen stress, complex pathogen stress, and viral pathogen stress. The increased resistance can be measured at about 10 minutes after applying the stress, between 10 minutes and 20 minutes, for example about 20 minutes, between 20 and 30 minutes, 30 minutes, between 30 and 45 minutes, about 45 minutes, between 45 minutes and 1 hour, about 1 hour, between 1 and 2 hours, about 2 hours, between 2 and 4 hours, about 4 hours, between 4 and 8 hours, about 8 hours, between 8 and 12 hours, about 12 hours, between 12 and 16 hours, about 16 hours, between 16 and 20 hours, about 20 hours, between 20 and 24 hours, about 24 hours, between 24 and 36 hours, about 36 hours, between 36 and 48 hours, about 48 hours, between 48 and 72 hours, about 72 hours, between 72 and 96 hours, about 96 hours, between 96 and 120 hours, about 120 hours, between 120 hours and one week, or about a week after applying the stress.

The metabolites or other compounds described herein can be detected using any suitable method including, but not limited to gel electrophoresis, liquid and gas phase chromatography, either alone or coupled to mass spectrometry, NMR, immunoassays (radioimmunoassays (RIA) or enzyme-linked immunosorbent assays (ELISA)), chemical assays, spectroscopy and the like. In some embodiments, commercial systems for chromatography and NMR analysis are utilized.

In other embodiments, metabolites or other compounds are detected using optical imaging techniques such as magnetic resonance spectroscopy (MRS), magnetic resonance imaging (MRI), CAT scans, ultra sound, MS-based tissue imaging or X-ray detection methods (e.g., energy dispersive x-ray fluorescence detection).

Any suitable method may be used to analyze the biological sample (e.g., seed or plant tissue) in order to determine the presence, absence or level(s) of the one or more metabolites or other compounds in the sample. Suitable methods include chromatography (e.g., HPLC, gas chromatography, liquid chromatography), mass spectrometry (e.g., MS, MS-MS), LC-MS, enzyme-linked immunosorbent assay (ELISA), antibody linkage, other immunochemical techniques, biochemical or enzymatic reactions or assays, and combinations thereof: The levels of one or more of the recited metabolites or compounds may be determined in the methods of the present invention. For example, the level(s) of one metabolites or compounds, two or more metabolites, three or more metabolites, four or more metabolites, five or more metabolites, six or more metabolites, seven or more metabolites, eight or more metabolites, nine or more metabolites, ten or more metabolites, or compounds etc., including a combination of some or all of the metabolites or compounds including, but not limited to those disclosed herein may be determined and used in such methods.

In some embodiments, a synthetic composition of a plant and a formulation comprising at least one endophytic microbe will cause an increase in the level of a protein in the plant.

In some embodiments, a synthetic composition of a plant and a formulation comprising at least one endophytic microbe will cause a decrease in the level of a protein in the plant.

In some embodiments, a synthetic composition of a plant and a formulation comprising at least one endophytic microbe will cause an increase in the level of expression of a gene in the plant.

In some embodiments, a synthetic composition of a plant and a formulation comprising at least one endophytic microbe will cause a decrease in the level of expression of a gene in the plant.

In some embodiments, a synthetic composition of a plant and a formulation comprising at least one endophytic microbe will cause an increase in the level of a plant hormone.

In some embodiments, a synthetic composition of a plant and a formulation comprising at least one endophytic microbe will cause a modulation in the concentration or amount of a metabolite.

As shown in the Examples and otherwise herein, endophyte-inoculated plants display increased thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased protein content, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof.

Therefore, in an embodiment, the endophytic population is disposed on the surface or on or within a tissue of the seed or seedling in an amount effective to increase the biomass of the plant, or a part or tissue of the plant derived from the seed or seedling. The increased biomass is useful in the production of commodity products derived from the plant. Such commodity products include an animal feed, a fish fodder, a cereal product, a processed human-food product, a sugar or an alcohol. Such products may be a fermentation product or a fermentable product, one such exemplary product is a biofuel. The increase in biomass can occur in a part of the plant (e.g., the root tissue, shoots, leaves, etc.), or can be an increase in overall biomass when compared with a reference agricultural plant. Such increase in overall biomass can be under relatively stress-free conditions. In other cases, the increase in biomass can be in plants grown under any number of abiotic or biotic stresses, including drought stress, salt stress, heat stress, cold stress, low nutrient stress, nematode stress, insect herbivory stress, fungal pathogen stress, complex pathogen stress, and viral pathogen stress.

In another embodiment, the endophytic population is disposed on the surface or within a tissue of the seed or seedling in an amount effective to increase the rate of seed germination when compared with a reference agricultural plant.

In other cases, the microbe is disposed on the seed or seedling in an amount effective to increase the average biomass of the fruit or cob from the resulting plant when compared with a reference agricultural plant.

Plants inoculated with an endophytic population may also show an increase in overall plant height. Therefore, in an embodiment, the present invention provides for a seed comprising an endophytic population that is disposed on the surface or within a tissue of the seed or seedling in an amount effective to increase the height of the plant. For example, the endophytic population is disposed in an amount effective to result in an increase in height of the agricultural plant when compared with a reference agricultural plant. Such an increase in height can be under relatively stress-free conditions. In other cases, the increase in height can be in plants grown under any number of abiotic or biotic stresses, including drought stress, salt stress, heat stress, cold stress, low nutrient stress, nematode stress, insect herbivory stress, fungal pathogen stress, complex pathogen stress, or viral pathogen stress.

In another embodiment, the plant containing the endophyte is able to grown under nutrient stress conditions while exhibiting no difference in the physiological parameter compared to a plant that is grown without nutrient stress. In some embodiments, such a plant will exhibit no difference in the physiological parameter when grown with 2-5% less nitrogen than average cultivation practices on normal agricultural land, for example, at least 5-10% less nitrogen, at least 10-15% less nitrogen, at least 15-20% less nitrogen, at least 20-25% less nitrogen, at least 25-30% less nitrogen, at least 30-35% less nitrogen, at least 35-40% less nitrogen, at least 40-45% less nitrogen, at least 45-50% less nitrogen, at least 50-55% less nitrogen, at least 55-60% less nitrogen, at least 60-65% less nitrogen, at least 65-70% less nitrogen, at least 70-75% less nitrogen, at least 80-85% less nitrogen, at least 85-90% less nitrogen, at least 90-95% less nitrogen, or less, when compared with crop plants grown under normal conditions during an average growing season. In some embodiments, the microbe capable of providing nitrogen-stress tolerance to a plant is diazotrophic. In other embodiments, the microbe capable of providing nitrogen-stress tolerance to a plant is non-diazotrophic.

The host plants inoculated with the endophytic population may also show improvements in their ability to utilize water more efficiently. Water use efficiency is a parameter often correlated with drought tolerance. Water use efficiency (WUE) is a parameter often correlated with drought tolerance, and is the $CO_2$ assimilation rate per amount of water transpired by the plant. An increase in biomass at low water availability may be due to relatively improved efficiency of growth or reduced water consumption. In selecting traits for improving crops, a decrease in water use, without a change in growth would have particular merit in an irrigated agricultural system where the water input costs were high. An increase in growth without a corresponding jump in water use would have applicability to all agricultural systems. In many agricultural systems where water supply is not limiting, an increase in growth, even if it came at the expense of an increase in water use also increases yield.

When soil water is depleted or if water is not available during periods of drought, crop yields are restricted. Plant water deficit develops if transpiration from leaves exceeds the supply of water from the roots. The available water supply is related to the amount of water held in the soil and the ability of the plant to reach that water with its root system. Transpiration of water from leaves is linked to the fixation of carbon dioxide by photosynthesis through the stomata. The two processes are positively correlated so that high carbon dioxide influx through photosynthesis is closely linked to water loss by transpiration. As water transpires from the leaf, leaf water potential is reduced and the stomata tend to close in a hydraulic process limiting the amount of photosynthesis. Since crop yield is dependent on the fixation of carbon dioxide in photosynthesis, water uptake and transpiration are contributing factors to crop yield. Plants which are able to use less water to fix the same amount of carbon dioxide or which are able to function normally at a low water potential, are more efficient and thereby are able to produce more biomass and economic yield in many agricultural systems. An increased water use efficiency of the plant relates in some cases to an increased fruit/kernel size or number.

Therefore, in one embodiment, the plants described herein exhibit an increased water use efficiency (WUE) when compared with a reference agricultural plant grown under the same conditions. For example, the endophyte may provide an increase in WUE to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions. Such an increase in WUE can occur under conditions without water deficit, or under conditions of water deficit, for example, when the soil water content is less than or equal to 60% of water saturated soil, for example, less than or equal to 50%, less than or equal to 40%, less than or equal to 30%, less than or equal to 20%, less than or equal to 10% of water saturated soil on a weight basis. In some embodiments, the plants inoculated with the endophytic population show increased yield under non-irrigated conditions, as compared to reference agricultural plants grown under the same conditions.

In a related embodiment, the plant comprising endophyte can have a higher relative water content (RWC), than a reference agricultural plant grown under the same conditions.

Formulations for Agricultural Use

The endophyte populations described herein are intended to be useful in the improvement of agricultural plants, and as such, may be formulated with other compositions as part of an agriculturally compatible carrier. It is contemplated that such carriers can include applications such as, but not be limited to: seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, aeroponics. The carrier composition with the endophyte populations, may be prepared for agricultural application as a liquid, a solid, or a gas formulation. Application to the plant may be achieved, for example, as a powder for surface deposition onto plant leaves, as a spray to the whole plant or selected plant element, as part of a drip to the soil or the roots, or as a coating onto the plant element prior to planting. Such examples are meant to be illustrative and not limiting to the scope of the invention.

The formulation useful for these embodiments generally and typically include at least one member selected from the group consisting of a buffer, a tackifier, a microbial stabilizer, a fungicide, an anticomplex agent, an herbicide, a nematicide, an insecticide, a bactericide, a virucide, a plant growth regulator, a rodenticide, a desiccant, and a nutrient.

The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified population (see, for example, U.S. Pat. No. 7,485,451, which is incorporated herein by reference in its entirety). Suitable formulations that may be prepared include wettable powders, granules, gels, agar strips or pellets, thickeners, biopolymers, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof: Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

In an embodiment, the formulation can include a tackifier or adherent. Such agents are useful for combining the complex population of the invention with carriers that can contain other compounds (e.g., control agents that are not biologic), to yield a coating composition. Such compositions help create coatings around the plant or plant element to maintain contact between the endophyte and other agents with the plant or plant element. In one embodiment, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, carragennan, PGA, other biopolymers, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788, each of which is incorporated herein by reference in its entirety.

It is also contemplated that the formulation may further comprise an anti-caking agent.

The formulation can also contain a surfactant, wetting agent, emulsifier, stabilizer, or anti-foaming agent. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision), polysorbate 20, polysorbate 80, Tween 20, Tween 80, Scattics, Alktest TW20, Canarcel, Peogabsorb 80, Triton X-100, Conco NI, Dowfax 9N, Igebapl C O, Makon, Neutronyx 600, Nonipol NO, Plytergent B, Renex 600, Solar NO, Sterox, Serfonic N, T-DET-N, Tergitol NP, Triton N, IGEPAL CA-630, Nonident P-40, Pluronic. In one embodiment, the surfactant is present at a concentration of between 0.01% v/v to 10% v/v. In another embodiment, the surfactant is present at a concentration of between 0.1% v/v to 1% v/v. An example of an anti-foaming agent would be Antifoam-C.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the population used, and should promote the ability of the endophyte population to survive application on the seeds and to survive desiccation. Examples of suitable desiccants include one or more of trehalose, sucrose, glycerol, and methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%.

In some cases, it is advantageous for the formulation to contain agents such as a fungicide, an anticomplex agent, an herbicide, a nematicide, an insecticide, a plant growth regulator, a rodenticide, a bactericide, a virucide, or a nutrient. Such agents are ideally compatible with the agricultural plant element or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

In the liquid form, for example, solutions or suspensions, endophyte populations of the present invention can be mixed or suspended in water or in aqueous solutions. Suitable liquid diluents or carriers include water, aqueous solutions, petroleum distillates, or other liquid carriers.

Solid compositions can be prepared by dispersing the endophyte populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as nonionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils (such as soybean oil, maize (corn) oil, and cottonseed oil), glycerol, ethylene glycol, polyethylene glycol, propylene glycol, polypropylene glycol, etc.

In an embodiment, the formulation is ideally suited for coating of a population of endophytes onto plant elements. The endophytes populations described in the present invention are capable of conferring many fitness benefits to the host plants. The ability to confer such benefits by coating the populations on the surface of plant elements has many potential advantages, particularly when used in a commercial (agricultural) scale.

The endophyte populations herein can be combined with one or more of the agents described above to yield a formulation suitable for combining with an agricultural plant element, seedling, or other plant element. Endophyte populations can be obtained from growth in culture, for example, using a synthetic growth medium. In addition, endophytes can be cultured on solid media, for example on petri dishes, scraped off and suspended into the preparation. Endophytes at different growth phases can be used. For example, endophytes at lag phase, early-log phase, mid-log phase, late-log phase, stationary phase, early death phase, or death phase can be used. Endophytic spores may be used for the present invention, for example but not limited to: arthospores, sporangispores, conidia, chlamadospores, pycnidiospores, endospores, zoospores.

The formulations comprising endophyte populations of the present invention typically contains between about 0.1 to 95% by weight, for example, between about 1% and 90%, between about 3% and 75%, between about 5% and 60%, between about 10% and 50% in wet weight of the population of the present invention. It is preferred that the formulation contains at least about $10^3$ CFU per ml of formulation, for example, at least about $10^4$, at least about $10^5$, at least about $10^6$, at least about $10^7$ CFU, at least about $10^8$ CFU per ml of formulation. It is preferred that the formulation be applied to the plant element at about $10^2$ CFU/seed, between $10^2$ and $10^3$ CFU, at least about $10^3$ CFU, between $10^3$ and $10^4$ CFU, at least about $10^4$ CFU, between $10^4$ and $10^5$ CFU, at least about $10^5$ CFU, between $10^5$ and $10^6$ CFU, at least about $10^6$ CFU, between $10^6$ and $10^7$ CFU, at least about $10^7$ CFU, between $10^7$ and $10^8$ CFU, or even greater than $10^8$ CFU per seed.

In some embodiments, fungal endophytes may be encapsulated in a fungal host, whether its native host or a heterologous host, before incorporation into a formulation.

Populations of Plant Elements (PEs)

In another embodiment, the invention provides for a substantially uniform population of plant elements (PEs) comprising two or more PEs comprising the endophytic population, as described herein above. Substantial uniformity can be determined in many ways. In some cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the PEs in the population, contains the endophytic population in an amount effective to colonize the plant disposed on the surface of the PEs. In other cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant element s in the population, contains at least 1, between 10 and 10, 10, between 10 and 100, or 100 CFU on the plant element surface or per gram of plant element, for example, between 100 and 200 CFU, at least 200 CFU, between 200 and 300 CFU, at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU, between 100,000 and 300,000 CFU, at least 300,000 CFU, between 300,000 and 1,000,000 CFU, or at least 1,000,000 CFU per plant element or more.

In a particular embodiment, the population of plant elements is packaged in a bag or container suitable for commercial sale. Such a bag contains a unit weight or count of the plant elements comprising the endophytic population as described herein, and further comprises a label. In an embodiment, the bag or container contains at least 100 plant elements, between 100 and 1,000 plant elements, 1,000 plant elements, between 1,000 and 5,000 plant elements, for example, at least 5,000 plant elements, between 5,000 and 10,000 plant elements, at least 10,000 plant elements, between 10,000 and 20,000 plant elements, at least 20,000 plant elements, between 20,000 and 30,000 plant elements, at least 30,000 plant elements, between 30,000 and 50,000 plant elements, at least 50,000 plant elements, between 50,000 and 70,000 plant elements, at least 70,000 plant elements, between 70,000 and 80,000 plant elements, at least 80,000 plant elements, between 80,000 and 90,000, at least 90,000 plant elements or more. In another embodiment, the bag or container can comprise a discrete weight of plant elements, for example, at least 1 lb, between 1 and 2 lbs, at least 2 lbs, between 2 and 5 lbs, at least 5 lbs, between 5 and 10 lbs, at least 10 lbs, between 10 and 30 lbs, at least 30 lbs, between 30 and 50 lbs, at least 50 lbs, between 50 and 70 lmbs, at least 70 lbs or more. The bag or container comprises a label describing the plant elements and/or said endophytic population. The label can contain additional information, for example, the information selected from the group consisting of: net weight, lot number, geographic origin of the plant elements, test date, germination rate, inert matter content, and the amount of noxious weeds, if any. Suitable containers or packages include those traditionally used in plant seed commercialization. The invention also contemplates other containers with more sophisticated storage capabilities (e.g., with microbiologically tight wrappings or with gas- or water-proof containments).

In some cases, a sub-population of seeds comprising the endophytic population is further selected on the basis of increased uniformity, for example, on the basis of uniformity of microbial population. For example, individual plant elements of pools collected from individual cobs, individual plants, individual plots (representing plants inoculated on the same day) or individual fields can be tested for uniformity of microbial density, and only those pools meeting specifications (e.g., at least 80% of tested plant elements have minimum density, as determined by quantitative methods described elsewhere) are combined to provide the agricultural seed sub-population.

The methods described herein can also comprise a validating step. The validating step can entail, for example, growing some plant elements collected from the inoculated plants into mature agricultural plants, and testing those individual plants for uniformity. Such validating step can be performed on individual seeds collected from cobs, individual plants, individual plots (representing plants inoculated on the same day) or individual fields, and tested as described above to identify pools meeting the required specifications.

In some embodiments, methods described herein include planting a synthetic composition described herein. Suitable planters include an air seeder and/or fertilizer apparatus used in agricultural operations to apply particulate materials including one or more of the following, seed, fertilizer and/or inoculants, into soil during the planting operation. Seeder/fertilizer devices can include a tool bar having ground-engaging openers thereon, behind which is towed a wheeled cart that includes one or more containment tanks or bins and associated metering means to respectively contain and meter therefrom particulate materials.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating plant elements. When used to coat plant elements, the composition may be applied to the plant elements and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the endophyte populations described herein. Such methods can include introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In an embodiment, plant elements may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed.

In another embodiment, the treatment entails coating plant elements. One such process involves coating the inside wall of a round container with the composition(s) described herein, adding plant elements, then rotating the container to cause the plant elements to contact the wall and the composition(s), a process known in the art as "container coating." Plant elements can be coated by combinations of coating methods. Soaking typically entails using liquid forms of the compositions described. For example, plant elements can be soaked for about 1 minute to about 24 hours (e.g., for at least 1 min, between 1 and 5 min, 5 min, between 5 and 10 min, 10 min, between 10 and 20 min, 20 min, between 20 and 40 min, 40 min, between 40 and 80 min, 80 min, between 80 min and 3 hrs, 3 hrs, between 3 hrs and 6 hrs, 6 hr, between 6 hrs and 12 hrs, 12 hr, between 12 hrs and 24 hrs, 24 hrs).

Population of Plants and Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability is caused by a multitude of factors, including uneven environmental conditions and management practices. Another possible source of variability can, in some cases, be due to the heterogeneity of the endophyte population inhabiting the plants. By providing endophyte populations onto plant reproductive elements, the resulting plants generated by germinating the plant reproductive elements have a more consistent endophyte composition, and thus are expected to yield a more uniform population of plants.

Therefore, in another embodiment, the invention provides a substantially uniform population of plants. The population can include at least 10 plants, between 10 and 100 plants, for example, at least 100 plants, between 100 and 300 plants, at least 300 plants, between 300 and 1,000 plants, at least 1,000 plants, between 1,000 and 3,000 plants, at least 3,000 plants, between 3,000 and 10,000 plants, at least 10,000 plants, between 10,000 and 30,000 plants, at least 30,000 plants, between 30,000 and 100,000 plants, at least 100,000 plants or more. The plants are derived from plant reproductive elements comprising endophyte populations as described herein. The plants are cultivated in substantially uniform groups, for example in rows, groves, blocks, circles, or other planting layout.

The uniformity of the plants can be measured in a number of different ways. In one embodiment, there is an increased uniformity with respect to endophytes within the plant population. For example, in one embodiment, a substantial portion of the population of plants, for example at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant elements or plants in a population, contains a threshold number of an endophyte population. The threshold number can be at least 10 CFU, between 10 and 100 CFU, at least 100 CFU, between 100 and 300 CFU, for example at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU or more, in the plant or a part of the plant. Alternatively, in a substantial portion of the population of plants, for example, in at least 1%, between 1% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plants in the population, the endophyte population that is provided to the seed or seedling represents at least 0.1%, between 0.1% and 1% at least 1%, between 1% and 5%, at least 5%, between 5% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 80%, at least 80%, between 80% and 90%, at least 90%, between 90% and 95%, at least 95%, between 95% and 99%, at least 99%, between 99% and 100%, or 100% of the total endophyte population in the plant/seed.

In an embodiment, there is increased genetic uniformity of a substantial proportion or all detectable endophytes within the taxa, genus, or species of a component relative to an uninoculated control. This increased uniformity can be a result of the endophyte being of monoclonal origin or otherwise deriving from a population comprising a more uniform genome sequence and plasmid repertoire than would be present in the endophyte population a plant that derives its endophyte community largely via assimilation of diverse soil symbionts.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, between 5% and 10%, for example, at least 10%, between 15 and 15, at least 15, between 15 and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions. In other cases, there can be a reduction in the standard deviation in the flowering time of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions.

Commodity Plant Products

The present invention provides a commodity plant product, as well as methods for producing a commodity plant product, that is derived from a plant of the present invention. As used herein, a "commodity plant product" refers to any composition or product that is comprised of material derived from a plant, seed, plant cell, or plant element of the present invention. Commodity plant products may be sold to consumers and can be viable or nonviable. Nonviable commodity products include but are not limited to nonviable plant elements and grains; processed seeds, seed parts, and plant elements; dehydrated plant tissue, frozen plant tissue, and processed plant tissue; seeds and plant elements processed for animal feed for terrestrial and/or aquatic animal consumption, oil, meal, flour, flakes, bran, fiber, paper, tea, coffee, silage, crushed of whole grain, and any other food for human or animal consumption such as the fruit or other edible portion of the plant; and biomasses and fuel products; and raw material in industry.

Industrial uses of oils derived from the agricultural plants described herein include ingredients for paints, plastics, fibers, detergents, cosmetics, lubricants, and biodiesel fuel. Plant oils may be split, inter-esterified, sulfurized, epoxidized, polymerized, ethoxylated, or cleaved. Designing and producing plant oil derivatives with improved functionality and improved oliochemistry is a rapidly growing field. For example, a mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams.

Although the present invention has been described in detail with reference to examples below, it is understood that various modifications can be made without departing from the spirit of the invention. For instance, while the particular examples below may illustrate the methods and embodiments described herein using a specific plant, the principles in these examples may be applied to any agricultural crop. Therefore, it will be appreciated that the scope of this invention is encompassed by the embodiments of the inventions recited herein and the specification rather than the specific examples that are exemplified below. All cited patents and publications referred to in this application are herein incorporated by reference in their entirety.

EXAMPLES

Example 1: Isolation and Identification of *Streptomyces* Bacterial Endophytes

Isolation and cultivation of endophytic microbes from agricultural plants was performed according to methods well known in the art. Microbial taxa found in agriculturally relevant communities were identified using high-throughput marker gene sequencing across several crops and numerous varieties of seeds.

Classification of bacterial strains using 16S sequences was done by the following methodology.

To accurately characterize isolated bacterial endophytes, colonies were submitted for marker gene sequencing, and the sequences were analyzed to provide taxonomic classifications. Colonies were subjected to 16S rRNA gene PCR amplification using a 27f/1492r primer set (27f-YM primer for 16S sequencing given as SEQ ID NO: 20; 1492R primer for 16S sequencing given as SEQ ID NO: 21), and Sanger sequencing of paired ends was performed at Genewiz (South Plainfield, NJ). Raw chromatograms were converted to sequences, and corresponding quality scores were assigned using TraceTuner v3.0.6beta (U.S. Pat. No. 6,681,186, incorporated herein by reference). These sequences were quality filtered using PRINSEQ v0.20.3 [Schmieder and Edwards (2011) Bioinformatics. 2011; 27:863-864, incorporated herein by reference] with left and right trim quality score thresholds of 30 and a quality window of 20 bp. Sequences without paired reads were discarded from further processing. Paired end quality filtered sequences were merged using USEARCH v7.0 [Edgar (2010) Nature methods 10:996-8]. Taxonomic classifications were assigned to the sequences using the RDP classifier [Wang et al., (2007) Applied and environmental microbiology 73:5261-7, incorporated herein by reference] trained on the Greengenes database [McDonald et al. (2012), ISME journal 6:610-8, incorporated herein by reference].

Strain A (*Streptomyces murinus*) is given as SEQ ID NO: 1. Based on performance in experiments demonstrating modulations of plant traits, in the present invention Strain A is described as a reference *Streptomyces* strain to which Strain B and Strain C are compared.

Strain B (*Streptomyces* sp.) is given as SEQ ID NO: 2. Based on performance in experiments demonstrating modulations of plant traits, in the present invention Strain B is described as a beneficial *Streptomyces* strain compared to Strain A, and described as a reference Streptomcyes strain to Strain C.

Strain C (*Streptomyces* SMCD2215) is given as SEQ ID NO: 3. The strain-specific primer pair for Strain C is given as SEQ ID NO: 22 for the forward primer and SEQ ID NO: 23 for the reverse primer. The amplicon resulting from sequencing using those primers is given as SEQ ID NO: 18. Strain C is deposited with the International Depositary Authority of Canada (IDAC, National Microbiology Laboratory, Public Health Agency of Canada, 1015 Arlington Street, Winnipeg, Manitoba, Canada, R3E 3R2) as Deposit ID 081111-06, and with the Saskatchewan Microbial Collection and Database as SMCD2215. Based on performance in experiments demonstrating modulations of plant traits, in the present invention, Strain C is described as a beneficial *Streptomyces* strain as compared to both Strains B and Strains C.

SEQ ID NO: 4-17 represent additional *Streptomyces* endophyte strains of the present invention.

Example 2: In Vitro Testing and Characterization of *Streptomyces* Bacterial Endophytes Strains and Culture Preparations Bacterial endophyte strains Strain C and Strain A, were tested for various metabolic activities as described below.

To prepare the cultures as initial inocula for various assays, bacteria were grown in one liter of Yeast Extract Peptone Dextrose (YEPD) broth in a 2.5-liter Ultra Yield flasks (Thomson Instrument Company). The cultures were grown at 25° C. with continuous shaking at a speed of 130 revolutions per minute (rpm) for five days. The cultures were aliquoted into 50-mL Falcon tubes and were harvested by centrifugation at a speed of 3,500 rpm for 20 minutes. For each sample, one gram (g) of fresh biomass was first rinsed in 5 mL sterile water and resuspended in 15 mL of sterile water. In order to achieve homogeneity, samples were sonicated for 15 seconds continuously with probe intensity set to 3 using the Sonic Dismembrator Model 100 (Thermo Fisher Scientific, Waltham, MA). Strain purity was assessed by plating 100 microliter (uL) of bacterial strain resuspension on PDA. After sonication, the cultures were allowed to sit at room temperature for 5-10 minutes before being used in in vitro assays.

The culture of Strain A is shown in FIG. 1. The culture of Strain B is shown in FIG. 2. The culture of Strain C is shown in FIG. 3.

Auxin Biosynthesis by Endophytes

To measure auxin levels, 100 microliters of bacteria culture prepared as described above was inoculated into 1 mL of R2A broth supplemented with L-tryptophan (5 mM) in transparent flat bottom, 12-well tissue culture plates. Each culture was grown in three duplicates. The plates were sealed with a breathable membrane, wrapped in aluminum foil, and incubated at 25° C. on a shaker at a speed of 150 rpm in the dark for 3 days. After 3 days the OD600 nm and OD530 nm were measured on a plate reader to check for bacterial growth. After measuring these ODs, the culture from each well was transferred into a 1.5 mL Eppendorf tube and briefly spun for 1 minute at top speed in a conventional centrifuge. An aliquot of 250 microliters of supernatant was transferred into each well of transparent flat bottom, 48-well tissue culture plates. 50 microliters of yellowish Salkowski reagent (0.01 M FeCl3 in 35% HClO4 (perchloric acid, #311421, Sigma) were added to each well and incubated in the dark for 30 minutes before measuring the OD540 nm in a plate reader to detect pink/red color. Images were also taken for qualitative scoring of the results later.

Auxin is an important plant hormone that can promote cell enlargement and inhibit branch development (meristem activity) in above ground plant tissues, while below ground it has the opposite effect, promoting root branching and growth. Additionally, auxin signaling pathway has been shown to interact with plant defense signaling pathways. Several microbes utilize the auxin-defense crosstalk to down-regulate the defense responses, therefore allowing harmonious co-existence of the microbe and plants.

Strain C was screened for the ability to produce auxin as a possible growth-promoting agent. Strain C yielded a high absorption at OD540 nm, suggesting a high level of auxin (Table 2).

Acetoin and Diacetyl Production

The method was adapted from Phalip et al., (1994) J Basic Microbiol 34: 277-280. (incorporated herein by reference). 100 microliters of bacteria culture prepared as described above was inoculated into 1 mL of R2A broth supplemented with 5% sterile glucose in transparent flat bottom, 12-well tissue culture plates. Each culture was grown in triplicates. The plates were sealed with a breathable membrane, wrapped in aluminum foil, and incubated at 25° C. on a shaker at a speed of 150 rpm in the dark for 3 days. After 3 days the OD600 nm and OD525 nm were measured on a plate reader to check for bacterial growth. After measuring these ODs, the culture from each well was transferred into a 1.5 mL Eppendorf tube and briefly spun for 1 minute at top speed in a conventional centrifuge. An aliquot of 250 microliters of supernatant was transferred into each well of transparent flat bottom, 48-well tissue culture plates. 50 microliters per well was added of freshly blended Barritt's Reagents A and B [5 g/L creatine mixed 3:1 (v/v) with freshly prepared alpha-naphthol (75 g/L in 2.5 M sodium hydroxide)]. After 30 minutes, images were taken to score for red or pink coloration relative to a copper colored negative control and the absorption at 525 nm was measured using a plate reader to quantify the acetoin and diacetyl abundance.

Acetoin is a neutral, four-carbon molecule used as an external energy storage by a number of fermentive microbes. It is produced by the decarboxylation of alpha-acetolactate, a common precursor in the biosynthesis of branched-chain amino acids. Owing to its neutral nature, production and excretion of acetoin during exponential growth prevents overacidification of the cytoplasm and the surrounding medium that would result from accumulation of acidic metabolic products, such as acetic acid and citric acid. Once superior carbon sources are exhausted, and the culture enters stationary phase, acetoin can be used to maintain the culture density.

Qualitatively and quantitatively, Strain C, but not its closely related strain, Strain A, produced a very high level of acetoin and diacetyl compounds (Table 2).

Siderophore Production

To ensure no contaminating iron was carried over from previous experiments, all glassware was deferrated with 6 M HCl and water prior to media preparation [Cox (1994) Methods Enzymol 235: 315-329, incorporated herein by reference]. In this cleaned glassware, 1 mL of R2A broth media, which is iron limited, was aliquoted into each well of transparent flat bottom, 12-well tissue culture plates. 100 microliters of fungal and bacteria culture prepared as described above were inoculated into each well. Each culture was grown in three duplicates. The plates were sealed with a breathable membrane, wrapped in aluminum foil, and incubated at 25° C. on a shaker at a speed of 150 rpm in the dark for 3 days. After 3 days the OD600 nm and OD530 nm were measured on a plate reader to check for bacterial growth. After measuring these ODs, the culture from each well was transferred into a 1.5 mL Eppendorf tube and briefly spun for 1 minute at top speed in a conventional centrifuge. An aliquot of 250 microliters of supernatant was transferred into each well of transparent flat bottom, 48-well tissue culture plates. After incubation, 100 microliters of O-CAS preparation without gelling agent [Perez-Miranda et al. (2007), J Microbiol Methods 70: 127-131, incorporated herein by reference] was added into each well. One liter of O-CAS reagent was prepared using the cleaned glassware by mixing 60.5 mg of chrome azurol S (CAS), 72.9 mg of hexadecyltrimethyl ammonium bromide (HDTMA), 30.24 g of finely crushed Piperazine-1,4-bis-2-ethanesulfonic acid (PIPES) with 10 mL of 1 mM FeCl3.6H2O in 10 mM HCl solvent. The PIPES was finely powdered and mixed gently with stirring (not shaking) to avoid producing bubbles, until a deep blue color was achieved. 30 minutes after adding the reagent to each well, images were taken and color change was scored by looking for purple halos (catechol type siderophores) or orange colonies (hydroxamate siderophores) relative to the deep blue of the O-CAS. Absorption at 420 nm was measured using a plate reader to quantify the abundance of siderophore.

Siderophore production by bacteria on a plant surface or inside a plant may both show that a microbe is equipped to grow in a nutrient limited environment, and perhaps protect the plant environment from invasion by other, perhaps undesirable microbes.

Notably, the beneficial *Streptomyces* strain Strain C accumulated hydroxamate siderophore to a high level evidenced by the high absorption at OD420 nm (Table 2) at a higher concentration than the control *Streptomyces* strain Strain A.

Additional In Vitro Testing and Characterization of Bacterial Endophytes

Examples below are adapted from: Johnston-Monje and Raizada (2011), which is incorporated herein by reference in its entirety.

Assay for growth on nitrogen free LGI media. All glassware is cleaned with 6 M HCl before media preparation. A new 96 deep-well plate (2 mL well volume) is filled with 1 mL/well of sterile LGI broth [per L, 50 g Sucrose, 0.01 g $FeCl_3$-$6H_2O$, 0.8 g $K_3PO_4$, 0.2 g $MgSO_4$-$7H_2O$, 0.002 g $Na_2MoO_4$-$2H_2O$, pH 7.5]. Bacteria are inoculated with a flame-sterilized 96 pin replicator. The plate is sealed with a breathable membrane, incubated at 25° C. with gentle shaking for 5 days, and OD600 readings taken.

ACC deaminase activity assay. Microbes are assayed for growth with ACC as their sole source of nitrogen. Prior to media preparation all glassware is cleaned with 6 M HCl. A 2 M filter sterilized solution of ACC (#1373A, Research Organics, USA) is prepared in water. 1 μl/mL of this is added to autoclaved LGI broth (see above), and 1 mL aliquots are placed in a new 96 well plate. The plate is sealed with a breathable membrane, incubated at 25° C. with gentle shaking for 5 days, and OD600 readings taken. Only wells that are significantly more turbid than their corresponding nitrogen free LGI wells are considered to display ACC deaminase activity.

Mineral phosphate solubilization assay. Microbes are plated on tricalcium phosphate media. This is prepared as follows: 10 g/L glucose, 0.373 g/L $NH_4NO_3$, 0.41 g/L $MgSO_4$, 0.295 g/L NaCl, 0.003 $FeCl_3$, 0.7 g/L $Ca_3HPO_4$ and 20 g/L Agar, pH 6, then autoclaved and poured into 150 mm plates. After 3 days of growth at 25° C. in darkness, clear halos are measured around colonies able to solubilize the tricalcium phosphate.

RNAse activity assay. 1.5 g of torula yeast RNA (#R6625, Sigma) is dissolved in 1 mL of 0.1 M $Na_2HPO_4$ at pH 8, filter sterilized and added to 250 mL of autoclaved R2A agar media which is poured into 150 mm plates. The bacteria from a glycerol stock plate are inoculated using a flame-sterilized 96 pin replicator, and incubated at 25° C. for 3 days. On day three, plates are flooded with 70% perchloric acid (#311421, Sigma) for 15 minutes and scored for clear halo production around colonies.

Pectinase activity assay. Adapting a previous protocol 0.2% (w/v) of citrus pectin (#76280, Sigma) and 0.1% triton X-100 are added to R2A media, autoclaved and poured into 150 mm plates. Bacteria are inoculated using a 96 pin plate replicator. After 3 days of culturing in the darkness at 25° C., pectinase activity is visualized by flooding the plate with Gram's iodine. Positive colonies are surrounded by clear halos.

Cellulase activity assay. Adapting a previous protocol, 0.2% carboxymethylcellulose (CMC) sodium salt (#C5678, Sigma) and 0.1% triton X-100 are added to R2A media, autoclaved and poured into 150 mm plates. Bacteria are inoculated using a 96 pin plate replicator. After 3 days of culturing in the darkness at 25° C., cellulose activity is visualized by flooding the plate with Gram's iodine. Positive colonies are surrounded by clear halos.

Antibiosis assay. Bacteria or fungi are inoculated using a 96 pin plate replicator onto 150 mm Petri dishes containing R2A agar, then grown for 3 days at 25° C. At this time, colonies of either *E. coli* DH5α (gram negative tester), *Bacillus subtillus* ssp. *Subtilis* (gram positive tester), or yeast strain AH109 (fungal tester) are resuspended in 1 mL of 50 mM $Na_2HPO_4$ buffer to an OD600 of 0.2, and 30 μl of this is mixed with 30 mL of warm LB agar. This is quickly poured completely over a microbe array plate, allowed to solidify and incubated at 37° C. for 16 hours. Antibiosis is scored by looking for clear halos around microbial colonies.

Biolog Assay

Bacterial strains Strain C and Strain A were maintained on potato dextrose agar (PDA) in dark at 25° C. and subcultured at regular intervals to maintain viability. Bacterial plugs for each strain was used to inoculate 1 liter (L) of Yeast Extract Peptone Dextrose (YEPD) broth and grown at 25° C. for five days at 130 RPM. On day five, 50 milliliters (mL) of the culture was used as inoculum to propagate the bacterial strain in 1 L of YEPD under the same conditions. Thirty mL aliquots of seven-day-old bacterial liquid culture were harvested by centrifuging at 3,500 RPM for 20 minutes to separate the supernatant. One gram (g) of pellet biomass was first rinsed in 5 mL sterile water, resuspended in 15 mL of sterile water and sonicated for 1 minute to obtain a homogenous resuspension. Strain purity was assessed by plating 100 microliters (uL) of bacterial strain resuspension on PDA.

Sole carbon substrate assays were done using Phenotype MicroArray (PM) 1 and 2A MicroPlates (Hayward, CA). Bacterial cells grown for 5 days on PDA were inoculated into sterile Inoculation Fluid-0 (IF-0) obtained from BIOLOG. Cells were stirred in order to achieve uniformity and subsequently adjusted with IF-0 to achieve an absorbance value of approximately 0.3. For each PM assay, 2.32 mL of the bacterial suspension was added to 20 mL IF-0 and 0.24 mL 100× Dye Mix D obtained from BIOLOG and brought to a final volume of 24 mL with sterile distilled water. One hundred microliters of the solution was added per well to 96-well PM MicroPlates that contained 95 carbon sources.

MicroPlates were incubated at 25° C. in an enclosed container for 7 days and examined at regular intervals. Carbon utilization by bacterial strains was evidenced by the change from colorless to violet that indicated the reduction of terrazolium violet redox dye (Pohland and Owen, 2009). Visual scorings of dye accumulation were made at hours 12, 24, 48, 72, 96, 120, 144 and 168 hours to determine the rate and pattern of carbon substrate utilization for each strain. Results were recorded upon stable dye pattern development. Very low amounts of violet dye accumulation at day 7 were attributed to slow or stopped cell respiration and those carbon sources were scored as weak substrates. All MicroPlates contained a negative control (water only) well that remained colorless until the end of each experiment.

The ability of a strain to utilize a specific carbon substrate in the BIOLOG PM MicroPlates could be visually observed by the formation of violet dye in that particular well. When microbial strains undergo respiration (NADH production), they reduce a tetrazolium dye that is included in each well with the carbon source. The reduction of the tetrazolium dye results in the formation of a violet dye that is used to obtain metabolic fingerprint of each strain. Using the colorimetric indicator, metabolic fingerprint comparisons were performed for bacterial strains. Time-course visual examination of MicroPlates over duration of 7 days allowed substrate utilization rates to be determined. Cells undergoing respiration actively when grown on a given substrate typically produced a strong violet phenotype either at the onset of the experiment i.e. by hour 12 or steadily over the course of the entire experiment compared to substrates that were not as robustly utilized that resulted in wells that had a weak violet tint suggesting slowed or stopped cell respiration (Table 3).

The following carbon substrates were utilized by Strain C and Strain A: L-Arabinose, N-Acetyl-D-Glucosamine, L-Proline, D-Alanine, D-Trehalose, D-Sorbitol, Glycerol, D-Gluconic acid, D-Xylose, D-Mannitol, L-Glutamic acid, D-Galactonic acid-γ-lactone, D-L-Malic acid, D-Ribose, D-Fructose, α-D-Glucose, Maltose, L-Asparagine, D-Glucosaminic acid, Sucrose, L-glutamine, Adonitol, Maltotriose, Citric acid, m-Inositol, Mucic acid, Glycyl-L-Glutamic acid, L-Serine, L-Malic acid, Glycyl-L-Proline, Tyramine, Pyruvic acid, and L-Galactonic-acid-y-lactone. The following carbon sources were utilized by Strain C but not Strain A: D-Galactose, P-Methyl-D-glucoside, D-Cellobiose, L-Alanine, L-Alanyl-Glycine, Mono Methyl Succinate, and L-Lyxose.

The following carbon substrates were utilized at a higher rate by the beneficial *Streptomyces* strain Strain C as compared to the control *Streptomyces* strain Strain A: D-galactose, glycerol, beta-methyl-D-glucoside, L-alanine, L-alanyl glycine, monomethyl succinate, glycyl-L-proline, L-lyxose.

Analysis of Gene Frequencies

Identification of Arabinose Transporter Genes

Sequence identity to the arabinose transporter gene as described by SEQ ID NO: 19 was identified in sequences from *Streptomyces* genomes available in public databases, including the National Center for Biotechnology Information (NCBI) Genome and NCBI Assembly, and *Streptomyces* genomes generated by whole genome sequencing and annotation. Sequence similarity was determined using the blastp algorithm (v 2.2.30+) (Altschul, Gish, Miller, Myers, & Lipman, 1990; Camacho et al., 2009) with composition-based score adjustment conditioned on sequence properties (Yu & Altschul, 2005), the BLOSUM62 substitution matrix, and additional parameters set as follows: word size of 3, gap penalties of 11 for existence and 1 for extension, neighboring words threshold of 11, and windows for multiple hits of 40. Query sequences were not filtered with SEG.

*Streptomyces* strains that were predicted to be beneficial were found to comprise at least 3 copies of the arabinose transporter gene in the genome. Of the endophytes disclosed in the present invention, the beneficial endophyte Strain C comprised 3. The endophyte Strain B, which conferred benefit in greenhouse plant phenotypes under water-limited conditions, comprised 4. Additional *Streptomyces* strains that comprise at least 3 are shown in Table 4, and would be expected to confer at least one beneficial trait of agronomic importance to a plant grown associated with, or grown from a seed treated with, said bacterium.

Example 3: Identification of Differentially Regulated Proteins in *Streptomyces* Bacterial Culture (Proteomics)

Methods

Microbial samples preparation: Microbes were cultivated in three biological replicates for each strain. Briefly, each bacterium was initially streaked on Reasoner's 2A (R2A) agar, distinct CFUs selected and cultured in 10 mL R2A broth for 4 days. Fungal strains were streaked on potato dextrose (PD) agar and individual plugs containing spores and mycelial tissues were used to initiate growth in 10 mL PD broth for 6 days. All strains were grown with agitation at room temperature. Microbial culture filtrate was harvested by centrifuging at 4500 RPM for 20 minutes in 15 mL Falcon tubes to allow culture separation and removal of the supernatant. Five mL of culture supernatant were used for secreted proteomics analysis. All steps were performed in sterile conditions. Culture filtrates were kept in dry ice after harvest at all times to preserve protein stability. Media only samples consisting of PDB and R2A were tested independently to ensure the absence of intact proteins that may potentially interfere with the secreted microbial peptides.

Protein purification and visualization: Samples were shipped to the vendor site (MS Bioworks, Ann Arbor, MI) for peptide purification and analysis. Each sample was concentrated on a Pall 3 kD MWCO MicroSep Spin Column (VWR Cat #89132-006) and quantified at 1:10 dilution by Qubit fluorometry (Life Technologies). Twelve g of each sample was separated ~1.5 cm on a 10% Bis-Tris Novex mini-gel (Invitrogen) using the MES buffer system. The gel was stained with Coomassie and each lane was excised into ten equally sized segments. Gel pieces were processed using a robot (ProGest, DigiLab) by washing with 25 mM ammonium bicarbonate followed by acetonitrile. The samples were subsequently reduced with 10 mM dithiothreitol at 60° C. followed by alkylation with 50 mM iodoacetamide at room temperature, digested with trypsin (Promega) at 37° C. for 4 hours and quenched with formic acid. The supernatant was analyzed directly without further processing.

Mass spectrometry: The digests were analyzed by nano LC/MS/MS with a Waters NanoAcquity HPLC system interfaced to a ThermoFisher Q Exactive. Peptides were loaded on a trapping column and eluted over a 75 μm analytical column at 350 nL/min; both columns were packed with Proteo Jupiter resin (Phenomenex). A 30 min gradient was employed (5 h total). The mass spectrometer was operated in data-dependent mode, with MS and MS/MS performed in the Orbitrap at 70,000 FWHM and 17,500 FWHM resolution, respectively. The fifteen most abundant ions were selected for MS/MS.

Data acquisition and processing: Symbiota provided protein sequence data, KEGG annotations and corresponding protein mass spectrometry spectral count data to ABiL. Data were provided for Strain C and Strain B strains from the bacterial genus *Streptomyces*. All data were converted into file formats and a local database suitable for subsequent processing, analysis and parallelization.

Protein ortholog identification: Pairs/groups of orthologous proteins were identified using a modified version of the OrthoMCL pipeline (Fischer, 2011). Orthologs were identified as reciprocal best BLASTP hits, and then clusters of orthologous proteins were defined using the modified OrthoMCL pipeline. This process was done independently for the within genera and the between genera analyses. BLASTP was run in parallel on the Georgia Tech PACE HPC environment.

Protein Functional Annotation: KEGG annotations for individual proteins were provided by Symbiota. The program BLAST2GO (Conesa, 2005) was used to annotate proteins with gene ontology (GO) terms based on sequence similarity to previously annotated proteins.

Protein expression quantification and normalization: Individual protein expression levels were taken as the number of observed spectra (i.e. the spectra count) corresponding to each protein. Protein spectra counts were retrieved across three replicates for each species. Missing counts for any given ortholog or replicate were assigned values of 0. Individual protein expression levels (spectra counts) were then normalized by the total number of observed spectra for each replicate. This process was done independently for the three replicates corresponding to each member of the A-B pair of every species. Fold-change (FC) values for orthologous pairs/groups were computed as log 2 A/B spectra counts for the purpose of functional enrichment analysis (below).

Protein differential expression analysis: Differential protein expression analysis was done for a) pairs of orthologous proteins from the within genera analysis and b) groups of orthologous proteins from the between genera analysis. Differential expression was quantified by comparing the within group normalized spectra count variation to the between group normalized spectra count variation using the Students t-test. A Benjamini-Hochberg False Discover Rate threshold of 0.2 was used to identify differentially abundant orthologous proteins.

Pathway and functional enrichment analysis: Enrichment analysis was done in parallel using both KEGG and GO annotations with the hypergeometric test and via Gene Set Enrichment Analysis (GSEA) (Huang, 2009; Subramanian, 2005). For the hypergeometric test, for any given functional annotation category (i.e. KEGG pathway or GO term), the number of proteins up-regulated in the beneficial member of the orthologous pair (species A) was compared to the total number of proteins up-regulated in the complete set of orthologs. For GSEA analysis, orthologous protein pairs/groups were ranked by FC values (as defined in #3 above) and the distribution of FC values was evaluated for a shift using the clusterprofiler R package (Yu, 2012).

Results

The in-culture secretomics analysis of beneficial and control filamentous Gram-positive bacteria *Streptomyces* sp. revealed a total of 505 small secreted proteins including uncharacterized proteins. Out of the 505 total, 460 were categorized in either Gene Ontology (GO) or Kyoto Encyclopedia of Genes and Genomes (KEGG) categories.

Differential protein expression analysis of the orthologous proteins between the Strain C and Strain B revealed a total of 266 total (238 categorized either in GO or KEGG) orthologous proteins that were detected in the beneficial strain only. The proteins ranged between 10.3 to 2.7-fold difference (Differential expression was quantified by comparing the within group normalized spectra count variation to the between group normalized spectra count variation using the Students t test).

Similar differential expression analysis of the small secreted proteins showed that 68 (63 categorized either in GO or KEGG) total orthologous proteins were detected only in the Strain B. The expression levels of proteins in the beneficial strain relative to the control strain were found to range from −11.2 to −2.7 in fold difference.

In addition, 57 (54 categorized either in GO or KEGG) orthologous proteins were found to be present in higher fold changes (7.2 to 0.4) in the beneficial *Streptomyces* strain relative to the control strain, and 114 (105 categorized either in GO or KEGG) orthologous proteins were detected at a lower expression level (−5.6 to −0.7) in the beneficial strain in comparison with the control bacterial strain.

Proteins that were expressed only in the culture of the *Streptomyces* strain Strain C, and not in the culture of the Strain B, are given in Table 5A. Differential protein expression analysis of the orthologous proteins between the Strain C and Strain B strains of *Streptomyces* revealed a total of 266 total (238 categorized either in GO or KEGG) orthologous proteins that were detected in the Strain C only. The proteins ranged between 10.3 to 2.7-fold difference (differential expression was quantified by comparing the within group normalized spectra count variation to the between group normalized spectra count variation using the Students t test).

Proteins that were never expressed in the culture of *Streptomyces* strain Strain C, but that were found in the culture of Strain B, are given in Table 5B. Similar differential expression analysis of the small secreted proteins showed that 68 (63 categorized either in GO or KEGG) total orthologous proteins were detected only in Strain B. The expression levels of proteins in Strain C relative to Strain B were found to range from −11.2 to −2.7 in fold difference (differential expression was quantified by comparing the within group normalized spectra count variation to the between group normalized spectra count variation using the Students t test).

Proteins that were expressed at a higher rate in the culture of *Streptomyces* strain Strain C vs. Strain B are given in Table 5C. In addition, 57 (54 categorized either in GO or KEGG) orthologous proteins were found to be present in higher fold changes (7.2 to 0.4) in the beneficial *Streptomyces* strain relative to the control strain (differential expression was quantified by comparing the within group normalized spectra count variation to the between group normalized spectra count variation using the Students t test).

Proteins that were expressed at a lower rate in the culture *Streptomyces* strain Strain C vs. Strain B are given in Table 5C. 114 (105 categorized either in GO or KEGG) orthologous proteins were detected at a lower expression level (−5.6 to −0.7) in the beneficial strain in comparison with the control bacterial strain (differential expression was quantified by comparing the within group normalized spectra count variation to the between group normalized spectra count variation using the Students t test).

Overall, the small proteins found to be secreted in the bacterial culture could be categorized into various biological categories based on Gene Ontology (GO) clustering. Striking differential expression patterns were observed for proteins within the following gene families:

Mitochondria (i.e. small and large ribosomal subunits): Ribosome; RP-S9; MRPS9; rpsI; Ribosome; RP-S8; rpsH; Ribosome; RP-S7; MRPS7; rpsG; Ribosome; RP-S6; MRPS6; rpsF; Ribosome; RP-S5; MRPS5; rpsE; Ribosome; RP-S4; rpsD; Ribosome; RP-S3; rpsC; Ribosome; RP-S2; MRPS2; rpsB; Ribosome; RP-S19; rpsS; Ribosome; RP-S18; MRPS18; rpsR; Ribosome; RP-S17; MRPS17; rpsQ; Ribosome; RP-S16; MRPS16; rpsP; Ribosome; RP-S15; MRPS15; rpsO; Ribosome; RP-S13; rpsM; Ribosome; RP-S12; MRPS12; rpsL; Ribosome; RP-S11; MRPS11; rpsK; Ribosome; RP-S10; MRPS10; rpsJ; Ribosome; RP-S1; rpsA; Ribosome; RP-L4; MRPL4; rpD; Ribosome; RP-L22; MRPL22; rplV; Ribosome; RP-L20; MRPL20; rplT; Ribosome; RP-L2; MRPL2; rplB; Ribosome; RP-L16; MRPL16; rplP; Ribosome; RP-L13; MRPL13; rpM; Ribosome; RP-L11; MRPL11; rplK; Ribosome; RP-L10; MRPL10; rplJ; ybeB.

Bacterial stress response: Response to stress; terA; terZ; terD; terD; terD; terD; catalase activity; heme binding; hydrogen peroxide catabolic process; metal ion binding; oxidation-reduction process; response to oxidative stress.

Carbon and amino acid biosynthesis and metabolism: Amino sugar and nucleotide sugar metabolism, beta-Lactam resistance, nagZ; Carbon metabolism, Citrate cycle (TCA cycle), DLD, lpd, pdhD, Glycine, serine and threonine metabolism, Glycolysis/Gluconeogenesis, Pyruvate metabolism, Valine, leucine and isoleucine degradation; Butanoate metabolism, Carbon fixation pathways in prokaryotes, Carbon metabolism, Citrate cycle (TCA cycle), Oxidative phosphorylation, sdhB, frdB; Carbon fixation pathways in prokaryotes, Carbon metabolism, folD, One carbon pool by folate; Biosynthesis of amino acids, Carbon fixation in photosynthetic organisms, Carbon metabolism, FBA, fbaA, Fructose and mannose metabolism, Glycolysis/Gluconeogenesis, Methane metabolism, Pentose phosphate pathway; Biosynthesis of amino acids, Carbon fixation in photosynthetic organisms, Carbon metabolism, FBA, fbaA, Fructose and mannose metabolism, Glycolysis/Gluconeogenesis, Methane metabolism, Pentose phosphate pathway; 2-Oxocarboxylic acid metabolism, Biosynthesis of amino acids, C5-Branched dibasic acid metabolism, leuB, Valine, leucine and isoleucine biosynthesis; Biosynthesis of amino acids, Carbon metabolism, Cyanoamino acid metabolism, glyA, SHMT, Glycine, serine and threonine metabolism, Glyoxylate and dicarboxylate metabolism, Methane metabolism, One carbon pool by folate; ackA, Carbon fixation pathways in prokaryotes, Carbon metabolism, Methane metabolism, Propanoate metabolism, Pyruvate metabolism, Taurine and hypotaurine metabolism; Carbon fixation pathways in prokaryotes, Carbon metabolism, Glyoxylate and dicarboxylate metabolism, MCEE, epi, Propanoate metabolism, Valine, leucine and isoleucine degradation; Biosynthesis of amino acids, Carbon metabolism, E2.2.1.2, talA, talB, Pentose phosphate pathway; Amino sugar and nucleotide sugar metabolism, Carbon metabolism, Glycolysis/Gluconeogenesis, GPI, pgi, Pentose phosphate pathway, Starch and sucrose metabolism; Cyanoamino acid metabolism, ggt, Glutathione metabolism, Taurine and hypotaurine metabolism; Cyanoamino acid metabolism, ggt, Glutathione metabolism, Taurine and hypotaurine metabolism; aroE, Biosynthesis of amino acids, Phenylalanine, tyrosine and tryptophan biosynthesis; ACADM, acd, beta-Alanine metabolism, Carbon metabolism, Fatty acid degradation, Fatty acid metabolism, PPAR signaling pathway, Propanoate metabolism, Valine, leucine and isoleucine degradation; Arginine and proline metabolism, Biosynthesis of amino acids, OTC, argF, argI; Amino sugar and nucleotide sugar metabolism, Carbon metabolism, Glycolysis/Gluconeogenesis, GPI, pgi, Pentose phosphate pathway, Starch and sucrose metabolism; Aminobenzoate degradation, Folate biosynthesis, phoD, Two-component system; Biosynthesis of amino acids, Carbon metabolism, Glycine, serine and threonine metabolism, Methane metabolism, serC, PSAT1, Vitamin B6 metabolism; Benzoate degradation, Butanoate metabolism, Carbon fixation pathways in prokaryotes, Carbon metabolism, E2.3.1.9, atoB, Fatty acid degradation, Fatty acid metabolism, Glyoxylate and dicarboxylate metabolism, Lysine degradation, Propanoate metabolism, Pyruvate metabolism, Synthesis and degradation of ketone bodies, Terpenoid backbone biosynthesis, Tryptophan metabolism, Two-component system, Valine, leucine and isoleucine degradation; Biosynthesis of amino acids, Carbon metabolism, cysK, Cysteine and methionine metabolism, Sulfur metabolism; Carbon metabolism, Citrate cycle (TCA cycle), DLD, lpd, pdhD, Glycine, serine and threonine metabolism, Glycolysis/Gluconeogenesis, Pyruvate metabolism, Valine, leucine and isoleucine degradation; Alzheimer's disease, Biosynthesis of amino acids, Carbon fixation in photosynthetic organisms, Carbon metabolism, GAPDH, gapA, Glycolysis/Gluconeogenesis, HIF-1 signaling pathway; beta-Alanine metabolism, Biosynthesis of unsaturated fatty acids, Butanoate metabolism, Caprolactam degradation, Carbon metabolism, fadJ, Fatty acid degradation, Fatty acid metabolism, Geraniol degradation, Limonene and pinene degradation, Lysine degradation, Propanoate metabolism, Tryptophan metabolism, Valine, leucine and isoleucine degradation; Carbon fixation in photosynthetic organisms, Carbon fixation pathways in prokaryotes, Carbon metabolism, Citrate cycle (TCA cycle), Cysteine and methionine metabolism, Glyoxylate and dicarboxylate metabolism, mdh, Methane metabolism, Pyruvate metabolism; Benzoate degradation, Butanoate metabolism, Carbon fixation pathways in prokaryotes, Carbon metabolism, E2.3.1.9, atoB, Fatty acid degradation, Fatty acid metabolism, Glyoxylate and dicarboxylate metabolism, Lysine degradation, Propanoate metabolism, Pyruvate metabolism, Synthesis and degradation of ketone bodies, Terpenoid backbone biosynthesis, Tryptophan metabolism, Two-component system, Valine, leucine and isoleucine degradation; Carbon fixation pathways in prokaryotes, Carbon metabolism, Citrate cycle (TCA cycle), E4.2.1.2A, fumA, fumB, Pyruvate metabolism; Carbon metabolism, E2.3.3.9, aceB, glcB, Glyoxylate and dicarboxylate metabolism, Pyruvate metabolism; 2-Oxocarboxylic acid metabolism, ACO, acnA, Biosynthesis of amino acids, Carbon fixation pathways in prokaryotes, Carbon metabolism, Citrate cycle (TCA cycle), Glyoxylate and dicarboxylate metabolism; Biosynthesis of amino acids, Carbon fixation in photosynthetic organisms, Carbon metabolism, Fructose and mannose metabolism, Pentose phosphate pathway, rpiB; Carbon metabolism, GLDC, gcvP, Glycine, serine and threonine metabolism; 2-Oxocarboxylic acid metabolism, Biosynthesis of amino acids, E2.6.1.42, ilvE, Pantothenate and CoA biosynthesis, Valine, leucine and isoleucine biosynthesis, Valine, leucine and isoleucine degradation; Glutathione metabolism, pepN; 2-Oxocarboxylic acid metabolism, argC, Arginine and proline metabolism, Biosynthesis of amino acids; Alzheimer's disease, Biosynthesis of amino acids, Carbon fixation in photosynthetic organisms, Carbon metabolism, GAPDH, gapA, Glycolysis/Gluconeogenesis, HIF-1 signaling pathway; Biosynthesis of amino acids, Carbon metabolism, Cyanoamino acid metabolism, glyA, SHMT, Glycine, serine and threonine metabolism, Glyoxylate and dicarboxylate metabolism, Methane metabolism, One carbon pool by folate; Biosynthesis of amino acids, dapA, Lysine biosynthesis; Biosynthesis of amino acids, dapB, Lysine biosynthesis; Biosynthesis of amino acids, Glycine, serine and threonine metabolism, thrC, Vitamin B6 metabolism; Butanoate metabolism, Carbon fixation pathways in prokaryotes, Carbon metabolism, Citrate cycle (TCA cycle), Oxidative phosphorylation, sdhD, frdD; Butanoate metabolism, Carbon metabolism, ccrA; Carbon fixation pathways in prokaryotes, Carbon metabolism, coxS, Methane metabolism, Nitrotoluene degradation; Carbon metabolism, Citrate cycle (TCA cycle), DLD, lpd, pdhD, Glycine, serine and threonine metabolism, Glycolysis/Gluconeogenesis, Pyruvate metabolism, Valine, leucine and isoleucine degradation; Biosynthesis of amino acids, dapB, Lysine biosynthesis; pepP; Carbon metabolism, Glutathione metabolism, Pentose phosphate pathway, PGD, gnd; Biosynthesis of amino acids, Cysteine and methionine metabolism, metE, Selenocompound metabolism; 2-Oxocarboxylic acid metabolism, Biosynthesis of amino acids, Carbon fixation pathways in prokaryotes, Carbon metabolism, Citrate cycle (TCA cycle), Glutathione metabolism, IDH1, IDH2, icd, Peroxisome; 2-Oxocarboxylic acid metabolism, Biosynthesis of amino acids, Carbon metabolism, Citrate cycle (TCA cycle), CS, gltA, Glyoxylate and dicarboxylate metabolism; Biosynthesis of amino acids, Cysteine and methionine metabolism, metB, Selenocompound metabolism, Sulfur metabolism; Amino sugar and nucleotide sugar metabolism, Fructose and mannose metabolism, manB; Aminoacyl-tRNA biosynthesis, lysK; Aminoacyl-tRNA biosynthesis, RARS, argS; 2-Oxocarboxylic acid metabolism, Biosynthesis of amino acids, ilvD, Pantothenate and CoA biosynthesis, Valine, leucine and isoleucine biosynthesis; tilS, mesJ; aceE, Carbon metabolism, Citrate cycle (TCA cycle), Glycolysis/Gluconeogenesis, Pyruvate metabolism; ACSS, acs, Carbon fixation pathways in prokaryotes, Carbon metabolism, Glycolysis/Gluconeogenesis, Methane metabolism, Propanoate metabolism, Pyruvate metabolism; Aminobenzoate degradation, Bisphenol degradation, E1.14.-.-, E1.14.14.1, Fatty acid degradation, Limonene and pinene degradation, Polycyclic aromatic hydrocarbon degradation, Stilbenoid, diarylheptanoid and gingerol biosynthesis, Tryptophan metabolism; Aminoacyl-tRNA biosynthesis, DARS, aspS; Carbon metabolism, Citrate cycle (TCA cycle), DLAT, aceF, pdhC, Glycolysis/Gluconeogenesis, Pyruvate metabolism; Carbon metabolism, Central carbon metabolism in cancer, Citrate cycle (TCA cycle), Glycolysis/Gluconeogenesis, HIF-1 signaling pathway, PDHB, pdhB, Pyruvate metabolism; Carbon metabolism, Glutathione metabolism, Pentose phosphate pathway, PGD, gnd; Biosynthesis of amino acids, CTH, Cysteine and methionine metabolism, Glycine, serine and threonine metabolism, Selenocompound metabolism; Biosynthesis of amino acids, hisC, Histidine metabolism, Novobiocin biosynthesis, Phenylalanine metabolism, Phenylalanine, tyrosine and tryptophan biosynthesis, Tropane, piperidine and pyridine alkaloid biosynthesis, Tyrosine metabolism; Biosynthesis of amino acids, pheA2, Phenylalanine, tyrosine and tryptophan biosynthesis; Aminoacyl-tRNA biosynthesis, PARS, proS; Aminoacyl-tRNA biosynthesis, EARS, gltX, Porphyrin and chlorophyll metabolism; 2-Oxocarboxylic acid metabolism, Biosynthesis of amino acids, E2.6.1.42, ilvE, Pantothenate and CoA biosynthesis, Valine, leucine and isoleucine biosynthesis, Valine, leucine and isoleucine degradation; Biosynthesis of amino acids, Carbon metabolism, Glycine, serine and threonine metabolism, Methane metabolism, serA, PHGDH; 2-Oxocarboxylic acid metabolism, Biosynthesis of amino acids, Butanoate metabolism, C5-Branched dibasic acid metabolism, E2.2.1.6S, ilvH, ilvN, Pantothenate and CoA biosynthesis, Valine, leucine and isoleucine biosynthesis; Carbon metabolism, gcvT, AMT, Glycine, serine and threonine metabolism, One carbon pool by folate; Biosynthesis of amino acids, Glycine, serine and threonine metabolism, thrC, Vitamin B6 metabolism; Biosynthesis of amino acids, lysA, Lysine biosynthesis; Carbon metabolism, Citrate cycle (TCA cycle), Lysine degradation, OGDH, sucA, Tryptophan metabolism; Amino sugar and nucleotide sugar metabolism, nagB, GNPDA; Amino sugar and nucleotide sugar metabolism, nagB, GNPDA; Biosynthesis of amino acids, dapE, Lysine biosynthesis; Carbon metabolism, ME2, sfcA, maeA, Pyruvate metabolism, Two-component system; Biosynthesis of amino acids, Biosynthesis of ansamycins, Carbon fixation in photosynthetic organisms, Carbon metabolism, E2.2.1.1, tktA, tktB, Pentose phosphate pathway; K07047; AARS, alaS, Aminoacyl-tRNA biosynthesis; Aminoacyl-tRNA biosynthesis, TARS, thrS; Alanine, aspartate and glutamate metabolism, argH, ASL, Arginine and proline metabolism, Biosynthesis of amino acids; Aminoacyl-tRNA biosynthesis, FARSB, pheT; Aminoacyl-tRNA biosynthesis, FARSA, pheS; aroH, Biosynthesis of amino acids, Phenylalanine, tyrosine and tryptophan biosynthesis; Biosynthesis of amino acids, Biosynthesis of ansamycins, Carbon fixation in photosynthetic organisms, Carbon metabolism, E2.2.1.1, tktA, tktB, Pentose phosphate pathway; Biosynthesis of amino acids, Carbon fixation in photosynthetic organisms, Carbon metabolism, Fructose and mannose metabolism, Glycolysis/Gluconeogenesis, Inositol phosphate metabolism, TPI, tpiA; Biosynthesis of amino acids, Carbon fixation in photosynthetic organisms, Carbon metabolism, Glycolysis/Gluconeogenesis, PGK, pgk; Biosynthesis of amino acids, Phenylalanine, tyrosine and tryptophan biosynthesis, trpC; Biosynthesis of amino acids, hisB, Histidine metabolism; Biosynthesis of amino acids, hisD, Histidine metabolism; Aminoacyl-tRNA biosynthesis, IARS, ileS; cynT, can, Nitrogen metabolism; Biosynthesis of amino acids, Carbon metabolism, Central carbon metabolism in cancer, Glycine, serine and threonine metabolism, Glycolysis/Gluconeogenesis, Methane metabolism, PGAM, gpmA; Aminoacyl-tRNA biosynthesis, CARS, cysS; Amino sugar and nucleotide sugar metabolism, murQ; Aminobenzoate degradation, Bisphenol degradation, E1.14.-.-, Limonene and pinene degradation, Polycyclic aromatic hydrocarbon degradation, Stilbenoid, diarylheptanoid and gingerol biosynthesis; 2-Oxocarboxylic acid metabolism, Biosynthesis of amino acids, Carbon metabolism, Citrate cycle (TCA cycle), CS, gltA, Glyoxylate and dicarboxylate metabolism; Carbon fixation in photosynthetic organisms, Carbon fixation pathways in prokaryotes, Carbon metabolism, Methane metabolism, ppc, Pyruvate metabolism; Amino sugar and nucleotide sugar metabolism, glmU; Biosynthesis of amino acids, Carbon metabolism, ENO, eno, Glycolysis/Gluconeogenesis, HIF-1 signaling pathway, Methane metabolism, RNA degradation; Aminoacyl-tRNA biosynthesis, LARS, leuS; Amino sugar and nucleotide sugar metabolism, Fructose and mannose metabolism, manB; Amino sugar and nucleotide sugar metabolism, Fructose and mannose metabolism, manA, MPI; Biosynthesis of amino acids, Carbon metabolism, Glycine, serine and threonine metabolism, Glycolysis/Gluconeogenesis, gpmB, Methane metabolism; Arginine and proline metabolism, Biosynthesis of amino acids, Carbapenem biosynthesis, proA; Aminoacyl-tRNA biosynthesis, VARS, valS; Amino sugar and nucleotide sugar metabolism, Fructose and mannose metabolism, K16881; Biosynthesis of amino acids, Glycine, serine and threonine metabolism, ltaE; Amino sugar and nucleotide sugar metabolism, Butirosin and neomycin biosynthesis, Carbon metabolism, Galactose metabolism, glk, Glycolysis/Gluconeogenesis, Starch and sucrose metabolism, Streptomycin biosynthesis; Carbon metabolism, Citrate cycle (TCA cycle), DLD, lpd, pdhD, Glycine, serine and threonine metabolism, Glycolysis/Gluconeogenesis, Pyruvate metabolism, Valine, leucine and isoleucine degradation;

Energy generation, i.e. ATP binding functions and nucleotide metabolism: 4 iron, 4 sulfur cluster binding, ATP synthesis coupled electron transport, electron carrier activity, membrane, molybdenum ion binding, NADH dehydrogenase (ubiquinone) activity; 5-phosphoribose 1-diphosphate biosynthetic process, ATP binding, cytoplasm, kinase activity, magnesium ion binding, nucleotide biosynthetic process, phosphorylation, ribonucleoside monophosphate biosynthetic process, ribose phosphate diphosphokinase activity; acetate-CoA ligase activity, acetyl-CoA biosynthetic process from acetate, AMP binding, ATP binding, metal ion binding; add, ADA, Primary immunodeficiency, Purine metabolism; alanine-tRNA ligase activity, alanyl-tRNA aminoacylation, ATP binding, cytoplasm, tRNA binding, zinc ion binding; Alanine, aspartate and glutamate metabolism, purA, ADSS, Purine metabolism; alc, ALLC, Purine metabolism; allB, Purine metabolism; aminoacyl-tRNA editing activity, ATP binding, cytoplasm, isoleucine-tRNA ligase activity, isoleucyl-tRNA aminoacylation, regulation of translational fidelity, zinc ion binding; aminoacyl-tRNA editing activity, ATP binding, cytoplasm, leucine-tRNA ligase activity, leucyl-tRNA aminoacylation, regulation of translational fidelity; aminoacyl-tRNA editing activity, ATP binding, cytoplasm, proline-tRNA ligase activity, prolyl-tRNA aminoacylation, regulation of translational fidelity; aminoacyl-tRNA editing activity, ATP binding, cytoplasm, regulation of translational fidelity, valine-tRNA ligase activity, valyl-tRNA aminoacylation; aminoacyl-tRNA ligase activity, aspartate-tRNA ligase activity, ATP binding, cytoplasm, nucleic acid binding, tRNA aminoacylation for protein translation; Arginine and proline metabolism, Atrazine degradation, Epithelial cell signaling in *Helicobacter pylori* infection, Purine metabolism, ureC; Arginine and proline metabolism, Atrazine degradation, Purine metabolism, ureA; Arginine and proline metabolism, Atrazine degradation, Purine metabolism, ureB; Arginine and proline metabolism, codA, Pyrimidine metabolism; arginyl-tRNA ligase activity, arginyl-tRNA aminoacylation, ATP binding, cytoplasm; ATP binding; ATP binding; ATP binding, ATP hydrolysis coupled proton transport, plasma membrane, plasma membrane ATP synthesis coupled proton transport, proton-transporting ATP synthase activity, rotational mechanism, proton-transporting ATP synthase complex, catalytic core F(1); ATP binding, ATP hydrolysis coupled proton transport, plasma membrane, plasma membrane ATP synthesis coupled proton transport, proton-transporting ATP synthase activity, rotational mechanism, proton-transporting ATP synthase complex, catalytic core F(1), proton-transporting ATPase activity, rotational mechanism; ATP binding, ATP-binding cassette (ABC) transporter complex, inorganic phosphate transmembrane transporter activity, metabolic process, phosphate ion transmembrane transport, phosphate ion transmembrane-transporting ATPase activity; ATP binding, ATPase activity, cell division, integral component of membrane, metalloendopeptidase activity, plasma membrane, protein catabolic process, proteolysis, zinc ion binding; ATP binding, ATPase activity, metabolic process, peptide transport; ATP binding, ATPase activity, metabolic process, peptide transport; ATP binding, ATPase activity, metabolic process, peptide transport; ATP binding, biotin carboxylase activity, metabolic process, metal ion binding; ATP binding, biotin carboxylase activity, metabolic process, metal ion binding, methylcrotonoyl-CoA carboxylase activity; ATP binding, cell cycle, cell division, cell wall organization, cytoplasm, peptidoglycan biosynthetic process, regulation of cell shape, UDP-N-acetylmuramoyl-tripeptide-D-alanyl-D-alanine ligase activity, UDP-N-acetylmuramoylalanyl-D-glutamyl-2,6-diaminopimelate-D-alanyl-D-alanine ligase activity; ATP binding, chromosome, cytoplasm, DNA binding, DNA topoisomerase type II (ATP-hydrolyzing) activity, DNA topological change, DNA-dependent DNA replication; ATP binding, chromosome, cytoplasm, DNA binding, DNA topoisomerase type II (ATP-hydrolyzing) activity, DNA topological change, DNA-dependent DNA replication, magnesium ion binding; ATP binding, coenzyme A biosynthetic process, cytoplasm, pantetheine-phosphate adenylyltransferase activity; ATP binding, cysteine-glucosaminylinositol ligase activity, mycothiol biosynthetic process, zinc ion binding; ATP binding, cysteine-tRNA ligase activity, cysteinyl-tRNA aminoacylation, cytoplasm, zinc ion binding; ATP binding, cytoplasm, damaged DNA binding, DNA recombination, DNA repair, DNA-dependent ATPase activity, single-stranded DNA binding, SOS response; ATP binding, cytoplasm, damaged DNA binding, DNA recombination, DNA repair, DNA-dependent ATPase activity, single-stranded DNA binding, SOS response; ATP binding, cytoplasm, glutamate-tRNA ligase activity, glutamyl-tRNA aminoacylation, tRNA binding; ATP binding, cytoplasm, glycolytic process, phosphoglycerate kinase activity; ATP binding, cytoplasm, intracellular protein transmembrane transport, plasma membrane, protein import, protein targeting; ATP binding, cytoplasm, ligase activity, forming carbon-nitrogen bonds, tRNA modification; ATP binding, cytoplasm, lysine-tRNA ligase activity, lysyl-tRNA aminoacylation, tRNA binding; ATP binding, cytoplasm, magnesium ion binding, phenylalanine-tRNA ligase activity, phenylalanyl-tRNA aminoacylation, tRNA binding; ATP binding, cytoplasm, magnesium ion binding, phenylalanine-tRNA ligase activity, phenylalanyl-tRNA aminoacylation, tRNA binding, tRNA processing; ATP binding, cytoplasm, metal ion binding, threonine-tRNA ligase activity, threonyl-tRNA aminoacylation; ATP binding, cytoplasm, protein folding; ATP binding, cytoplasm, protein refolding, unfolded protein binding; ATP binding, DNA binding, DNA topoisomerase type II (ATP-hydrolyzing) activity, DNA topological change; ATP binding, GTP binding; ATP binding, peptidase activity, proteolysis; ATP binding, protein folding, unfolded protein binding; ATP diphosphatase activity, hydrolase activity, methylation, methyltransferase activity; Base excision repair, DNA replication, DPO1, polA, Homologous recombination, Nucleotide excision repair, Purine metabolism, Pyrimidine metabolism; beta-Alanine metabolism, DPYS, dht, hydA, Drug metabolism—other enzymes, Pantothenate and CoA biosynthesis, Pyrimidine metabolism; Biosynthesis of amino acids, Carbon metabolism, Central carbon metabolism in cancer, Glycolysis/Gluconeogenesis, PK, pyk, Purine metabolism, Pyruvate metabolism, Type II diabetes mellitus, Viral carcinogenesis; Biosynthesis of amino acids, Carbon metabolism, Pentose phosphate pathway, PRPS, prsA, Purine metabolism; dcd, Pyrimidine metabolism; dgt, Purine metabolism; DHODH, pyrD, Pyrimidine metabolism; DNA replication, DPO3B, dnaN, Homologous recombination, Mismatch repair, Purine metabolism, Pyrimidine metabolism; Drug metabolism—other enzymes, guaB, Purine metabolism; Drug metabolism—other enzymes, guaB, Purine metabolism; Drug metabolism—other enzymes, hprT, hpt, HPRT1, Purine metabolism; E1.17.4.1B, nrdB, nrdF, Purine metabolism, Pyrimidine metabolism; E2.7.1.20, ADK, Purine metabolism; folic acid-containing compound biosynthetic process, histidine biosynthetic process, methenyltetrahydrofolate cyclohydrolase activity, methionine biosynthetic process, methylenetetrahydrofolate dehydrogenase (NADP+) activity, oxidation-reduction process, purine nucleotide biosynthetic process, tetrahydrofolate interconversion; Nicotinate and nicotinamide metabolism, punA, Purine metabolism, Pyrimidine metabolism; nudF, Purine metabolism; One carbon pool by folate, Purine metabolism, purN; plasma membrane, plasma membrane ATP synthesis coupled proton transport, proton-transporting ATP synthase activity, rotational mechanism, proton-transporting ATP synthase complex, catalytic core F(1); pnp, PNPT1, Purine metabolism, Pyrimidine metabolism, RNA degradation; Purine metabolism, purL, PFAS; Purine metabolism, purM; Purine metabolism, Pyrimidine metabolism, RNA polymerase, rpoA; Purine metabolism, Pyrimidine metabolism, RNA polymerase, rpoC; Purine metabolism, rdgB; Purine metabolism, uraH, pucM, hiuH; Purine metabolism, yagR; Purine metabolism, yagS; pyrF, Pyrimidine metabolism; Pyrimidine metabolism, Selenocompound metabolism, trxB; Pyrimidine metabolism, URA4, pyrC.

Respiration: coxA, Oxidative Phosphorylation.

DNA binding and regulation of transcription: aminoacyl-tRNA editing activity, ATP binding, cytoplasm, isoleucine-tRNA ligase activity, isoleucyl-tRNA aminoacylation, regulation of translational fidelity, zinc ion binding; aminoacyl-tRNA editing activity, ATP binding, cytoplasm, leucine-tRNA ligase activity, leucyl-tRNA aminoacylation, regulation of translational fidelity; aminoacyl-tRNA editing activity, ATP binding, cytoplasm, proline-tRNA ligase activity, prolyl-tRNA aminoacylation, regulation of translational fidelity; aminoacyl-tRNA editing activity, ATP binding, cytoplasm, regulation of translational fidelity, valine-tRNA ligase activity, valyl-tRNA aminoacylation; antisigma factor binding, identical protein binding, regulation of transcription, DNA-templated; ATP binding, cell cycle, cell division, cell wall organization, cytoplasm, peptidoglycan biosynthetic process, regulation of cell shape, UDP-N-acetylmuramoyl-tripeptide-D-alanyl-D-alanine ligase activity, UDP-N-acetylmuramoylalanyl-D-glutamyl-2,6-diaminopimelate-D-alanyl-D-alanine ligase activity; bacterial-type RNA polymerase core enzyme binding, bacterial-type RNA polymerase holo enzyme binding, positive regulation of transcription, DNA-templated, response to antibiotic, zinc ion binding; cell wall organization, cytoplasm, glucosamine-1-phosphate N-acetyltransferase activity, lipid A biosynthetic process, lipopolysaccharide biosynthetic process, magnesium ion binding, peptidoglycan biosynthetic process, regulation of cell shape, UDP-N-acetylglucosamine biosynthetic process, UDP-N-acetylglucosamine diphosphorylase activity; cytoplasm, DNA binding, regulation of transcription, DNA-templated, sigma factor activity, transcription factor activity, sequence-specific DNA binding, transcription initiation from bacterial-type RNA polymerase promoter; cytoplasm, DNA catabolic process, exodeoxyribonuclease VII activity, exodeoxyribonuclease VII complex, nucleic acid binding, nucleic acid phosphodiester bond hydrolysis; cytoplasm, mature ribosome assembly, negative regulation of ribosome biogenesis, negative regulation of translation; DNA binding, DNA-directed RNA polymerase activity, protein dimerization activity, transcription, DNA-templated; DNA binding, DNA-directed RNA polymerase activity, ribonucleoside binding, transcription, DNA-templated; DNA binding, DNA-directed RNA polymerase activity, transcription, DNA-templated; DNA binding, DNA-templated transcription, initiation, intracellular, regulation of transcription, DNA-templated, sigma factor activity, transcription factor activity, sequence-specific DNA binding, transport; DNA binding, DNA-templated transcription, initiation, regulation of transcription, DNA-templated, sigma factor activity, transcription factor activity, sequence-specific DNA binding; DNA binding, DNA-templated transcription, initiation, regulation of transcription, DNA-templated, sigma factor activity, transcription factor activity, sequence-specific DNA binding; DNA binding, intracellular, phosphorelay signal transduction system, regulation of transcription, DNA-templated; DNA binding, intracellular, phosphorelay signal transduction system, regulation of transcription, DNA-templated; DNA binding, intracellular, phosphorelay signal transduction system, regulation of transcription, DNA-templated; DNA binding, intracellular, phosphorelay signal transduction system, regulation of transcription, DNA-templated; DNA binding, intracellular, phosphorelay signal transduction system, regulation of transcription, DNA-templated; DNA binding, regulation of DNA-templated transcription, elongation, RNA polymerase binding, translation elongation factor activity, translational elongation; DNA binding, regulation of transcription, DNA-templated; DNA binding, regulation of transcription, DNA-templated; DNA binding, regulation of transcription, DNA-templated; DNA binding, regulation of transcription, DNA-templated; DNA binding, regulation of transcription, DNA-templated; DNA binding, regulation of transcription, DNA-templated; DNA binding, regulation of transcription, DNA-templated, transcription factor activity, sequence-specific DNA binding; DNA binding, regulation of transcription, DNA-templated, transcription factor activity, sequence-specific DNA binding; isomerase activity, regulation of proteasomal protein catabolic process; lrp, intracellular, regulation of transcription, DNA-templated, sequence-specific DNA binding, transcription factor activity, sequence-specific DNA binding; regulation of transcription, DNA-templated; regulation of transcription, DNA-templated, transcription factor activity, sequence-specific DNA binding.

Hydrolase activity: adenosine deaminase activity, deaminase activity, hydrolase activity, menaquinone biosynthetic process, metabolic process, metal ion binding; ADP-ribose diphosphatase activity, hydrolase activity, metabolic process; alpha-glucan biosynthetic process, cation binding, hydrolase activity, hydrolyzing O-glycosyl compounds, transferase activity, transferring hexosyl groups; aminopeptidase activity, hydrolase activity, acting on carbon-nitrogen (but not peptide) bonds, metabolic process, proteolysis; ATP diphosphatase activity, hydrolase activity, methylation, methyltransferase activity; carbohydrate metabolic process, glucan endo-1,3-beta-D-glucosidase activity, hydrolase activity, hydrolyzing O-glycosyl compounds; carbohydrate metabolic process, glucosamine-6-phosphate deaminase activity, hydrolase activity, N-acetylglucosamine metabolic process; carbohydrate metabolic process, glucosamine-6-phosphate deaminase activity, hydrolase activity, N-acetylglucosamine metabolic process; carbohydrate metabolic process, hydrolase activity, hydrolyzing O-glycosyl compounds; cation binding, glycogen catabolic process, glycogen debranching enzyme activity, hydrolase activity, hydrolyzing O-glycosyl compounds; cellulose catabolic process, hydrolase activity, hydrolyzing O-glycosyl compounds; chloride peroxidase activity, hydrolase activity, oxidation-reduction process, peroxidase activity; cytoplasm, dihydropyrimidinase activity, hydrolase activity, acting on carbon-nitrogen (but not peptide) bonds, metabolic process, metal ion binding; cytoplasm, dimethylallyl diphosphate biosynthetic process, hydrolase activity, isopentenyl-diphosphate delta-isomerase activity, isoprenoid biosynthetic process, metal ion binding; dipeptidase activity, hydrolase activity, metabolic process, proteolysis; DNA binding, DNA biosynthetic process, DNA replication, DNA-directed DNA polymerase activity, hydrolase activity; folic acid-containing compound biosynthetic process, histidine biosynthetic process, methenyltetrahydrofolate cyclohydrolase activity, methionine biosynthetic process, methylenetetrahydrofolate dehydrogenase (NADP+) activity, oxidation-reduction process, purine nucleotide biosynthetic process, tetrahydrofolate interconversion; hydrolase activity, acting on carbon-nitrogen (but not peptide) bonds, in linear amidines, metabolic process, N-carbamoyl-L-amino-acid hydrolase activity, N-formylglutamate deformylase activity; hydrolase activity, acting on carbon-nitrogen (but not peptide) bonds, metabolic process; hydrolase activity, kinase activity, phosphorylation, protein phosphorylation, protein serine/threonine kinase activity; hydrolase activity, metabolic process; hydrolase activity, metabolic process; hydrolase activity, metabolic process; hydrolase activity, metabolic process; hydrolase activity, metabolic process; hydrolase activity, metabolic process; hydrolase activity, metabolic process; hydrolase activity, metabolic process; hydrolase activity, metabolic process; hydrolase activity, metabolic process, triglyceride lipase activity; hydrolase activity, mycothiol metabolic process, mycothiol-dependent detoxification, zinc ion binding; hydroxyisourate hydrolase activity, purine nucleobase metabolic process.

Proteolysis: aminopeptidase activity, cytoplasm, manganese ion binding, metalloexopeptidase activity, proteolysis; aminopeptidase activity, hydrolase activity, acting on carbon-nitrogen (but not peptide) bonds, metabolic process, proteolysis; aminopeptidase activity, manganese ion binding, proteolysis; aminopeptidase activity, manganese ion binding, proteolysis; aminopeptidase activity, metallopeptidase activity, proteolysis, zinc ion binding; aminopeptidase activity, metallopeptidase activity, proteolysis, zinc ion binding; aminopeptidase activity, metallopeptidase activity, proteolysis, zinc ion binding; aminopeptidase activity, metallopeptidase activity, proteolysis, zinc ion binding; aminopeptidase activity, proteolysis; aminopeptidase activity, proteolysis; aminopeptidase activity, proteolysis, serine-type endopeptidase activity; ATP binding, ATPase activity, cell division, integral component of membrane, metalloendopeptidase activity, plasma membrane, protein catabolic process, proteolysis, zinc ion binding; ATP binding, peptidase activity, proteolysis; cell wall, cell wall organization, dipeptidase activity, metallopeptidase activity, proteolysis, zinc ion binding; dipeptidase activity, hydrolase activity, metabolic process, proteolysis; dipeptidase activity, proteolysis; dipeptidyl-peptidase activity, proteolysis; extracellular region, proteolysis, serine-type endopeptidase activity; integral component of membrane, proteolysis, serine-type peptidase activity; metal ion binding, metalloaminopeptidase activity, protein initiator methionine removal, proteolysis; metal ion binding, metalloaminopeptidase activity, protein initiator methionine removal, proteolysis; metalloendopeptidase activity, proteolysis; metallopeptidase activity, proteolysis; metallopeptidase activity, proteolysis; peptidase activity, proteolysis; proteolysis, serine-type D-Ala-D-Ala carboxypeptidase activity.

An important finding from this set of secretomics data is the extremely high levels of expression of the various genes encoding the ribosomal proteins of the small subunit (RPSs) and of the ribosomal protein of the large subunit (RPL) that play integral roles in translation. These proteins are among the highest expressed in the ones detected primarily in the beneficial strain. The ribosomal proteins are known to be conserved and direct the protein synthesis in organisms (Makarova et al. 2001). Interestingly, results indicate that rpsA, rpsB, rpsC, rpsE, rpsF, rpsG, rpsI, rpsJ, rpsK, rpsL, rpsS and rplK are expressed at very high levels (7.5 to 10.3 fold change) in the beneficial strain and little to no expression in the control strain of Streptomyces. Other members of the clusters such as rplJ, rpsD, rpsH, rpsM, rpsO, rpsP, rpsQ, and rpsR are expressed 1.4 to 6.7 fold change higher in the beneficial Streptomyces sp. compared to its control counterpart. No rps protein seems to be expressed more in the control relative to the beneficial strain. Surprisingly one member of the rpl cluster of ribosomal encoding gene, rplP is detected to have little to no expression in the beneficial strain relative to the beneficial one (−7.9 fold change) and others such as rpB, rpD, rpM, rplV, rplT are expressed lower in the beneficial strain relative to the control (−0.7 to −3.1).

Comparison of the two in-culture small secreted protein data reveals several striking results in those proteins implicated in response to stress. For instance, the data show the presence of Streptomyces sp. secreted cluster of ter proteins being expressed differentially in the beneficial and control bacterial strain. Four terD proteins are expressed −3.3 to −1.8 fold coverage lower in the beneficial Streptomyces endophyte Strain C compared to Strain B. Another member of the same family of protein, terZ is expressed 2.8 fold higher in Strain C relative to Strain B, while terB is similarly expressed higher in th Strain C (1.2 fold difference). It is noteworthy to state that terA is only expressed in the beneficial Streptomyces sp. and is absent or expressed in extremely low levels in the other strain. The bacterial ter cluster of genes and proteins is well studied and has been reported to play roles in natural resistance to tellurite and other toxic materials, pore-forming colicins and other bacteriophages although how they perform those functions is unclear (Anantharaman et al. 2012). The genes encoding the ter proteins are involved in the production of terpenoid antibiotic-terpentecin (Tp) and ter stands for Tp biosynthetic gene (Hamano et al. 2002). Members included terA, terB, terD and terZ described here. Although the specific roles of the 17 terD-domain-encoding genes in the Streptomyces sp. are unclear, Sanssouci et al. (2012) reported that they are majorly involved in the proper development of the Streptomyces sp. that they worked with.

Small secreted proteins that are involved in carbon and amino acid biosynthesis and metabolism as typified by those involved in the biosynthesis of amino acid such as glycine, serine, lysine and threonine (serA, dapE, thrC), phenylalaline, tyrosine and tryptophan (pheA2), sugar metabolism such as the proteins that play roles in the metabolism of fructose and mannose (manA and manB), pentose, glutathione and glucuronate (xylB, pgd, gnd), starch and sucrose (maZ, glgE, glgX, treX), and other amino acid and sugar metabolism (glmU, nagB, gcvT, eno, murQ) are expressed at very high levels in the beneficial Streptomyces strain relative to the control one. In many cases, these proteins were detected at extremely minimal levels, if not none, in the control bacterium (3 to 9.2 fold difference). Proteins involved in metabolism in Streptomyces sp. have been correlated with the production of antibiotics (Obanye et al 1996) and extensive research has been devoted to studying the carbon and amino acid metabolism with special focus on secondary metabolites in Streptomyces due to their ability to produce the afore-mentioned antibiotics (Tang et al. 1994; Borodina et al. 2005).

Bacterial small secreted proteins found in this study that could be categorized to play important roles in energy generation (i.e. ATP binding functions and nucleotide metabolism) also showed noticeable differences in their expression patterns. For example, the expressions of proteins involved in purine (purL, purM, nudF, allB) and pyrimidine (pyrC) metabolism was markedly higher in the beneficial strain relative to control (3 to 8.1 in fold change difference) and many of the proteins were detected at extremely minimal levels, if at all, in the control bacterium. Interestingly, one protein associated with pyrimidine metabolism, dcd was found to be expressed at a very high level (6.8 fold change) in the beneficial Streptomyces sp. and none in the control strain post-normalization of expression spectra counts). This protein is involved in the production of dCTP deaminase that is instrumental for the synthesis of the nucleotide 2'-deoxyuridine 5'-triphosphate (dUTP) (Weiss and Wang, 1994). In the beneficial Streptomyces strain, proteins that clustered within the ATP binding GO category had substantially high levels of expression (3.5 to 8.4 fold change relative to the control strain). One protein associated with energy and protein folding in this GO category is groES that is a bacterial heat shock protein (HSP). Curiously, this protein expression is only seen in the control Streptomyces strain (−6.8 fold difference relative to the beneficial strain post-normalization of expression spectra counts). The role of groES has been widely investigated in bacteria and initial reports have alluded to its role as a co-chaperonin in Streptomyces sp. cellular metabolism (De León et al. 1997)

The small secreted proteins that play a role in bacterial respiration, specifically aerobic respiration such as coxA was interestingly found to be expressed in abundance in the control Streptomyces sp. (−7.4 fold difference in the beneficial strain relative to the control). The subunit I of cytochrome aa3-type terminal oxidase is encoded by the gene, coxA and catalyzes the reduction of molecular oxygen to water as the final step in the ATP-generating electron transport pathway. In Bradyrhizobium japonicum, the nitrogen fixing bacterial symbiont of soybean, cytochrome aa3 has been reported to be expressed in the free-living aerobic state but not expressed under symbiotic environments (Gabel and Maier, 1990).

Secreted proteins that cluster in the DNA binding and regulation of transcription category was found to be highly expressed in the beneficial strain relative to the control one (3.5 to 7.1 fold change differences). In cases of select proteins namely rsbV, rpoE, regX3, mtrA, hupB and greA, those were found only in the secretome of the beneficial strain. Bacterial transcription elongation factors such as greA play a role in directing the RNAse activity of RNA polymerase and essentially assisting in enzyme read-through (Stepanova et al. 2009). In the model bacterium E. coli, protein HU such as hupB is one of the most abundant DNA-binding protein, and is involved in a host of wide ranging activities like initiation of DNA replication, cell division, DNA binding and partitioning, binding of repressors, and transposition of bacteriophage Mu (Dri et al. 1991). In Mycobacterium smegmatis, regX3 is involved in the regulation of phosphate import (Glover et al. 2007). Proteins like rsvB are majorly associated with sigma factor aB the key transcription factor that regulates response to dynamic environmental conditions in several Gram-positive bacteria like Bacillus sp. (Guldimann et al. 2016).

Several secreted proteins that are encompassed within the hydrolase activity category such as mqnA, mqnD, mqnE and mqnX (4.6, 5.4, 5.7 and 7.3 fold higher, respectively in beneficial relative to control strain) were found to be expressed in relative high levels in the beneficial *Streptomyces* sp. and were extremely low to not expressed at all in the control strain. In *Helicobacter pylori*, the mqn pathway are implicated as being core players in the production of the important prokaryotic respiratory compound menaquinone and are involved in the production of antibiotics (Kim et al. 2014).

Another cluster of proteins that are grouped based on proteolytic activity were observed to be expressed at a high level in both the beneficial 5.1 to 7.4 fold change relative to the control strain) and control *Streptomyces* strains (−5.4 to −9.3 fold change relative to the control strain). The genes for the protein in this category included dacC, dacA and dacA (expressed −2.2 in the beneficial strain relative to the control strain) and have been reported to be encode penicillin-binding proteins (PBPs) with DD-carboxypeptidase activity in *E. coli* (Baquero et al. 1995). In bacteria, PBPs produce and configure peptidoglycan that is an integral structural component of the bacterial cell wall (Denome et al. 1999). In bacteria, members in this group have been reported to play a role in regulated intramembrane proteolysis (Rip) that is implicated in cellular differentiation, lipid metabolism and the cellular response to unfolded proteins by the cleavage of proteins within the membrane (Brown et al. 2000).

In summary, the analysis of the beneficial and control *Streptomyces* sp. secretome have revealed an abundance of differentially expressed small proteins that may play a role in distinguishing the inherent trait of a beneficial bacterial endosymbiont. The presence of molecules outlined above in several biological pathways that are expressed either exclusively or higher in the beneficial strain of *Streptomyces* studied here could provide deeper insights into the adaptation and evolution of the beneficial plant endosymbiont.

Example 4: Coating of Seeds with *Streptomyces* Endophyte Strains

The following protocol was used to coat seeds with bacterial inocula for planting in greenhouse trials. The "sticker" (2% methylcellulose) was autoclaved and aliquoted into 50 mL Falcon tubes. Seeds were pre-weighed and placed into 50 mL Falcon tubes (2 replicate seed aliquots per treatment). *Streptomyces* were prepared by centrifuging cultures (2500×g for 10 minutes), removing supernatant, washing pellets, resuspending in minimal water, diluting to equal OD600 of ~1.3. This was diluted by half with the addition of 1 volume equivalent of 2% methylcellulose. 250 uL of the 2% methylcellulose sticker was pre-mixed with the liquid culture suspension, and this liquid was pipetted onto the pre-weighed seeds. The Falcon tube was closed and shaken to distribute the culture:sticker mixed solution evenly. 150 uL of FloRite flowability polymer was added to the Falcon tube with the coated seeds, and shaken. Seeds were transferred to a labeled envelope and kept at room temperature until sowing. For all treatments, 2 replicate seed treatments were performed and on-seed CFUs were assessed on both replicates.

The following protocol was used to coat seeds with bacterial inocula for planting in field trials. First, 3% Sodium alginate (SA) was prepared and autoclaved in the following manner. Erlenmeyer flasks were filled with the appropriate amount of deionized water and warmed to about 50 degrees C. on a heat plate with agitation using a stirring bar. SA powder was poured slowly into the water until it all dissolved. The solution was autoclaved (121C @15PSI for 30 minutes). Talcum powder was autoclaved in dry cycle (121C @15PSI for 30 minutes) and aliquoted in Ziploc bags or 50 ml falcon tubes at a ratio of 15 g per kg of seed to be treated for formulation controls and 10 g per kg of seed for actual treatments.

The next day, seeds were treated with either powdered or liquid formulations.

For powdered formulations, 10 g per kg of seed is allocated to the seeds to be treated, according to the following procedure. Seeds are placed in large plastic container. 16.6 ml of 2% SA per Kg of seeds to be treated are poured on the seeds. The container is covered and shaken slowly in orbital motion for about 20 seconds to disperse the SA. Endophyte powder is mixed with an equal amount of talcum powder. The mix of endophyte and talc is added on top of the seeds, trying to disperse it evenly. The container is covered and seeds are shaken slowly in orbital motion for about 20 seconds. 13.3 ml of Flo-rite per kg of seed to be treated is poured on the seeds. Seeds are shaken again, slowly and in orbital motion.

For liquid formulations, 8.5 mL per seed was allocated to the seeds to be treated, according to the following procedure. Seeds were placed in large plastic container. 8.3 ml of 2% SA per kg of seed and the same amount of bacterial culture (8.3 ml per kg of seed) were poured on the seeds. The container was covered and shaken slowly in orbital motion for about 20 seconds to disperse the SA. 15 g of talcum powder per kg of seed were added, trying to disperse it evenly. The container was covered and seeds were shaken slowly in orbital motion for about 20 seconds. 13.3 ml of Flo-rite per kg of seed to be treated were poured on the seeds. Seeds were shaken again, slowly and in orbital motion.

Example 5: Seedling Assays

Seeds and Seed Sterilization

Seeds were surface-sterilized with chlorine gas and hydrochloric acid as follows: Seeds were placed in a 250 mL open glass bottle and placed inside a desiccator jar in a fume. The cap of the glass bottle was treated similarly. A beaker containing 100 mL of commercial bleach (8.25% sodium hypochlorite) was placed in the desiccator jar near the bottle containing the seeds. Immediately prior to sealing the jar, 3 mL of concentrated hydrochloric acid (34-37.5%) was carefully added to the bleach and the bottle gently shaken to mix both components. The sterilization was left to proceed for 16 hours. After sterilization, the bottle was closed with its sterilized cap, and reopened in a sterile laminar hood. The opened bottle was left in the sterile hood for a minimum of one hour, with occasional shaking and mixing to air out the seeds and remove chlorine gas leftover. The bottle was then closed and the seeds stored at room temperature in the dark until use.

Seed Coating of Formulation

Coating of seeds with dry or liquid formulation was executed as described in Example 3. All endophytes were grown in UltraYields flasks. Besides non-treated seeds, seeds were also coated with liquid formulation and medium only, to serve as negative controls.

Seed Germination Assay on Water Agar

Sterilized seeds were placed onto water agar plates (1.3% bacto agar) in a biosafety hood using flamed forceps. For each treatment, 4 plates were sowed with 8 seeds each plate. After sowing, plates were sealed with Parafilm, randomized to avoid position effects, and placed in a drawer at room temperature in the dark. Seed germination was monitored every day for 2-4 days. After 3 days, images were taken of each plate and the root length of each seedling is measured using the imaging software ImageJ. The percentage difference between the treated seedlings, the mock-treated seedlings, and non-treated seedlings was then calculated.

Rolling Paper Assay for Evaluating Seed Germination and Seedling Drought Tolerance Sterilized seeds are placed 1-inch apart from each other onto sterilized rolling paper pre-soaked with sterile diH20 in a biosafety hood. The seeds are placed about one inch below the top and about ten inches above the bottom of the rolling paper. After placing the seeds, another layer of pre-soaked rolling paper is covered onto the top and the paper is carefully and slowly rolled up. The paper roll with seeds is placed vertically into autoclaved glass jar and covered with the lid to hold water absorbed in rolling paper. The jars are kept in a growth chamber in the dark, at 22° C., 60% RH for 4 days. At day 4, the lids are open and the jars placed at 22° C., 70% RH, 12 h day light (level 4, –300-350 microE) for 3 more days before scoring.

Drought Tolerance Assay Using Vermiculite

After scoring the germination rate of seeds on water agar, seedlings of similar physiological status (i.e., similar radical and shoot lengths) are transferred onto autoclaved vermiculite loosely packed in test tubes (3-cm in diameter) in their natural position (i.e., root down and shoot up). Before seedling transfer, 1.5 ml of sterile diH20 are added onto the top of the vermiculite. After transfer, the seedlings are gently covered with surrounding vermiculite. Test tubes are covered with lid to keep moisture for seeding to recover from transplanting and incubated in a growth chamber in the dark with the settings described above. The lid is removed the next day and the growth of seedlings was monitored every day for drought tolerance.

Results

As shown in Table 6, both of the tested *Streptomyces* strains Strain C and Strain A promoted wheat root (radical) growth three days after sowing on water agar.

Example 6: Greenhouse Characterization

Setup and Watering Conditions

A sandy loam growth substrate was mixed in the greenhouse and consisting of 60% loam and 40% mortar sand (Northeast Nursery, Peabody, MA). Prior to mixing, loam was sifted through a ⅜" square steel mesh screen to remove larger particles and debris.

For some greenhouse experiments (denoted in tables), half of the nitrogen fertilizer (urea) and all phosphate (monoammonium phosphate, MAP) and potash to be applied during the season were added to the soil mixture prior to sowing. The remaining urea was provided dissolved in irrigation water at the onset of the reproductive stages of development. For soybean the total applied nutrients were 440 lbs/acre of urea, 38 lbs/MAP, and 105 lbs/acre potash. Substrate surface area per pot was calculated based on pot diameter in order to approximate the "acreage" of individual pots. An equivalent volume of fertilized soil was then gently added to each pot in order to minimize compaction of the soil. The substrate was saturated with water 3-4 hours before sowing.

For other greenhouse experiments (unless otherwise denoted), no fertilizer was applied at the start of the drought, as tests of the loam mix demonstrated a complete nutrient profile already existed in the soil.

Commercially available soybean seeds were coated with microbial treatments using the formulation used for field trials and described herein. Treatments included microbial coatings with each of the *Streptomces* strains (Strain C, Strain A, and Strain B) and at least one control (non-treated, or formulation only-treated).

Three seeds were sown evenly spaced at the points of a triangle. Soil was then overlaid atop the seeds (estimated average planting depth at 1.0 to 1.5 inches) and an additional 700 mL water was added to moisten the overlaying substrate. Post-planting, the seeds were watered with 125 mL water per day. Pots were thinned down to 1 best seedling at true leaves stage (approximately 2 weeks).

The transplanting protocol for the seeds was as follows: Transplanting occurred at the time of thinning, to replace pots with no emergence or damaged plants with transplanted healthy plants of the same treatment in new pots. Three liters of the identical soil mix was added to the new pot. One plant was carefully removed from a healthy pot of the same treatment and placed in the new pot. The new pot was filled with soil to 4 L, with gentle packing around the roots. The new pot was watered with 700 mL water immediately after adding soil to each transplant. Transplanted seedlings were monitored for wilt and/or stress symptoms and delayed development. The original pots were retained in case the transplant became unhealthy Drought Stress Testing Plants were provided with water to ~50% capacity of the substrate for the first 14 days after sowing at which point water was withheld from water-stress plants until visible signs of wilting in vegetative tissues (i.e. drooping leaves and petioles, leaf rolling, chlorosis). Water-stressed plants were then irrigated to 50% soil water capacity, after which another drought cycle was initiated. Such drought cycles were continued until plants reached maturity. Throughout the experiment, the greenhouse was maintained on a 14 hour photoperiod where they were provided with at least 800 microE m^-2 s^-1, ~21° C. daytime and ~18° C. nighttime temperatures and a relative humidity of ~20-40%.

The watering regime for the drought-exposed seedlings was conducted as follows: approximately half saturation of soil at first day of emergence, third day of emergence, and 1 week later (day of thinning), full saturation at 5 days after thinning to initiate drought, full saturation to end drought when severe drought symptoms are observed, half saturation of soil maintained evenly (not cycling) until harvest.

Scoring

The first day of emergence and final emergence at the true leaf stage were recorded. As follows: by the soy scale every 7 days; wilt score every other day; early pod count at 45 days post planting (average stage of 2-3 pods per plant) with length of each plant's longest pod providing a better predictive measurement than pod length, which was not found to correlate to yield; leaf count at 45 days post planting (found to correlate strongly to yield), yield as measured by final pod count, seed count, and dry seed weight at harvest, nodule count on roots, final dry biomass of plants (separating stems from roots and washing roots), temperature during greenhouse growth periods.

Seedlings were scored as follows:

Final Emergence: seedlings emerged at 12-13 days post planting, out of 3 seeds planted per pot Pod Count: pods per plant, counted weekly after flowering but before maturity Seed Pre-Count: seeds per plant, counted inside pods weekly before maturity Seed Count, Mature: seeds per plant, harvested, mature Seed Count, Mature+Immature: seeds per plant, harvested, mature and immature Percent of Seeds That Are Mature: calculated from treatment averages, not per plant Seed Weight, Mature: dry grams of seed per plant (dried 3 days at 50 degrees C.; mature only)

Wilt Scores: scored visually on a scale from 0=no wilt to 4=unrecoverable;

Midseason Measurements and Harvest

For soybean, emergence percentage was observed. Further, at various times through the growing season, plants were assessed for pod length, pod number, relative chlorophyll content (SPAD), and total yield as mature seeds produced and seed fresh and dry mass. Soy was harvested at the point of agronomical relevance: senescence of pods.

To compare treated plants to controls, a fully Bayesian robust t-test was performed (Gelman, et al. 2013; Kruschke, 2012). Briefly, R (R Core Team, 2015) was used with the BEST package (Kruschke and Meredith, 2014) and JAGS (Plummer, 2003) to perform a Markov Chain Monte Carlo estimation of the posterior distribution the likely differences between the two experimental groups. A 95% highest density interval (HDI) was overlayed onto this distribution to aid in the interpretation of whether the two biological groups truly differ.

Results

All results are shown in Table 7. Photographs of plants are shown in FIG. 4, FIG. 5, and FIG. 6. All plants grown from seeds treated with any *Streptomyces* strain displayed some improved visual phenotypes under water-limited conditions during at least one point in the plant life cycle.

Plants treated with Strain C displayed the best measurable plant characteristics, including better drought tolerance, increased pod counts, and final harvest yield, as compared to the plants treated with the other *Streptomyces* strains.

Under normal watering (well watered) conditions, Strain C imparted a number of improved agronomic characteristics to soybean plants grown from seeds that were inoculated with the Strain C formulation, vs. controls of isoline plants grown from seeds not inoculated with the bacterial endophyte but additionally comprising the formulation components minus Strain C.

Compared to the formulation control, plants grown from seeds inoculated with the Strain C formulation and grown under normal watering (well-watered) conditions, exhibited an increase in dry weight of mature seeds at harvest, an increase of fresh weight of mature seeds at harvest, increase in number of mature seeds at harvest, increase in number of pods at 77 days post planting, and increase in length of pods at 46 days post planting.

Tissue Collection and Processing for Transcriptomics, Hormone, and Metabolomics Analysis In order to assess the effects of *Streptomyces* seed treatment on plant growth at the transcriptomic, phytohormone, and metabolomic levels, soybean plants were harvested. Three pots from each treatment were selected. Once separated, the tissues (roots, stems, and leaves) from the three pots of each treatment were pooled. For collection, first all loosely attached substrate was removed from the roots by gently tapping and shaking the roots. Any adherent substrate was removed by submerging the roots in water and manually dislodging attached soil and debris. The roots were then blotted dry before being cut from the aerial tissue, followed by separating petioles and leaves from the stem. As tissues were removed from the plant they were immediately bagged and frozen in liquid nitrogen. All harvested tissues were kept in liquid nitrogen or stored at −80° C. until further processing.

To prepare for analyses, the tissues were ground with liquid nitrogen using a pre-chilled mortar and pestle. Approximately 100-200 micrograms of each ground sample pool was transferred to a chilled 1.5 mL microtube for RNA extraction and subsequent transcriptome, phytohormone and metabolite analysis. The remaining ground tissue was then transferred to a chilled 50 mL conical tube and stored in liquid nitrogen or at −80° C. until shipment for further analyses.

Transcriptomics analysis was performed as described in Example 8. Hormone analysis was performed as described in Example 9. Metabolomics was performed as described in Example 10. Community sequencing microbiome profiles were analyzed as described in Example 11.

Example 7: Assessment of Plant Colonization

The establishment of plant-microbe interactions is contingent on close proximity. The microbiome of the host plant consists of microorganisms inside tissues as well as those living on the surface and surrounding rhizosphere. The protocols described in this section allow confirmation of successful colonization of plants by endophytic bacteria, for example by direct recovery of viable colonies from various tissues of the inoculated plant.

Recovery of Viable Colonies

Seeds are surface-sterilized by exposing them to chlorine gas overnight, using the methods described elsewhere. Sterile seeds are then inoculated with submerged in 0.5 OD overnight cultures (Tryptic Soy Broth) of bacteria and allowed to briefly air dry. The seeds are then placed in tubes filled partially with a sterile sand-vermiculite mixture [(1:1 wt:wt)] and covered with 1 inch of the mixture, watered with sterile water, sealed and incubated in a greenhouse for 7 days. After incubation, various tissues of the plants are harvested and used as donors to isolate bacteria by placing tissue section in a homogenizer (TSB 20%) and mechanical mixing. The slurry is then serially diluted in 10-fold steps to 10-3 and dilutions 1 through 10-3 are plated on TSA 20% plates (1.3% agar). Plates are incubated overnight and pictures are taken of the resulting plates as well as colony counts for CFU. Bacteria are identified visually by colony morphotype and molecular methods described herein. Representative colony morphotypes are also used in colony PCR and sequencing for isolate identification via ribosomal gene sequence analysis as described herein. These trials are repeated twice per experiment, with 5 biological samples per treatment.

Culture-Independent Methods to Confirm Colonization of the Plant or Seeds by Bacteria or Fungi One way to detect the presence of endophytes on or within plants or seeds is to use quantitative PCR (qPCR). Internal colonization by the endophyte can be demonstrated by using surface-sterilized plant tissue (including seed) to extract total DNA, and isolate-specific fluorescent MGB probes and amplification primers are used in a qPCR reaction. An increase in the product targeted by the reporter probe at each PCR cycle therefore causes a proportional increase in fluorescence due to the breakdown of the probe and release of the reporter. Fluorescence is measured by a quantitative PCR instrument and compared to a standard curve to estimate the number of fungal or bacterial cells within the plant.

Experimental Description

The design of both species-specific amplification primers, and isolate-specific fluorescent probes are well known in the art. Plant tissues (seeds, stems, leaves, flowers, etc.) are pre-rinsed and surface sterilized using the methods described herein.

Total DNA is extracted using methods known in the art, for example using commercially available Plant-DNA extraction kits, or the following method.

Tissue is placed in a cold-resistant container and 10-50 mL of liquid nitrogen is applied. Tissues are then macerated to a powder.

Genomic DNA is extracted from each tissue preparation, following a chloroform:isoamyl alcohol 24:1 protocol (Sambrook et al., 1989).

Quantitative PCR is performed essentially as described by Gao et al. (2010) with primers and probe(s) specific to the desired isolate using a quantitative PCR instrument, and a standard curve is constructed by using serial dilutions of cloned PCR products corresponding to the specie-specific PCR amplicon produced by the amplification primers. Data are analyzed using instructions from the quantitative PCR instrument's manufacturer software.

As an alternative to qPCR, Terminal Restriction Fragment Length Polymorphism, (TRFLP) can be performed, essentially as described in Johnston-Monje and Raizada (2011). Group specific, fluorescently labelled primers are used to amplify a subset of the microbial population, especially bacteria, especially fungi, especially archaea, especially viruses. This fluorescently labelled PCR product is cut by a restriction enzyme chosen for heterogeneous distribution in the PCR product population. The enzyme cut mixture of fluorescently labelled and unlabeled DNA fragments is then submitted for sequence analysis on a Sanger sequence platform such as the Applied Biosystems 3730 DNA Analyzer.

Immunological Methods to Detect Microbes in Seeds and Vegetative Tissues

A polyclonal antibody is raised against specific bacteria X or fungus Y strains via standard methods. A polyclonal antibody is also raised against specific GUS and GFP proteins via standard methods. Enzyme-linked immunosorbent assay (ELISA) and immunogold labeling is also conducted via standard methods, briefly outlined below.

Immunofluorescence microscopy procedures involve the use of semi-thin sections of seed or seedling or adult plant tissues transferred to glass objective slides and incubated with blocking buffer (20 mM Tris (hydroxymethyl)-aminomethane hydrochloride (TBS) plus 2% bovine serum albumin, pH 7.4) for 30 min at room temperature. Sections are first coated for 30 min with a solution of primary antibodies and then with a solution of secondary antibodies (goat anti-rabbit antibodies) coupled with fluorescein isothiocyanate (FITC) for 30 min at room temperature. Samples are then kept in the dark to eliminate breakdown of the light-sensitive FITC. After two 5-min washings with sterile potassium phosphate buffer (PB) (pH 7.0) and one with double-distilled water, sections are sealed with mounting buffer (100 mL 0.1 M sodium phosphate buffer (pH 7.6) plus 50 mL double-distilled glycerine) and observed under a light microscope equipped with ultraviolet light and a FITC Texas-red filter.

Ultrathin (50- to 70-nm) sections for TEM microscopy are collected on pioloform-coated nickel grids and are labeled with 15-nm gold-labeled goat anti-rabbit antibody. After being washed, the slides are incubated for 1 h in a 1:50 dilution of 5-nm gold-labeled goat anti-rabbit antibody in IGL buffer. The gold labeling is then visualized for light microscopy using a BioCell silver enhancement kit. Toluidine blue (0.01%) is used to lightly counterstain the gold-labeled sections. In parallel with the sections used for immunogold silver enhancement, serial sections are collected on uncoated slides and stained with 1% toluidine blue. The sections for light microscopy are viewed under an optical microscope, and the ultrathin sections are viewed by TEM.

Example 8: Identification of Differentially Regulated Genes (Transcriptomics)

Methods

The first transcriptomics (qualitative) analyses were conducted on SYM57-treated plants and formulation control-treated plants, under both normal watering and water-limited conditions. From this, up- and down-regulated transcripts in plants grown from seeds treated with Strain C compared to those of plants grown from seeds treated with only the formulation control were identified.

Whole RNA was extracted from ground soybean plant tissue (from plants as described in Example 6) over dry ice using the QIAgen Plant RNeasy mini kit (cat. no. 74904) per the manufacturer's instructions with minor modification. DNase treatment was performed on the column with the QIAgen RNase-free DNase kit (cat. no. 79254). The RW1 buffer wash was divided into two washes of half the buffer volume suggested by the manufacturer with the DNase treatment applied in between. After elution, RNA samples were kept on dry ice or at −20° C. until shipping. For transcriptome data acquisition, 1.5 micrograms of whole RNA was sent to Cofactor Genomics (St. Louis, MO). Sequencing was performed using for cDNA samples using the Kapa PolyA Stranded RNA-Seq kit.

To calculate expression values, transcript cDNA sequences were first aligned to the set of identified genes in the soy genome. Sequence read counts for each sample and gene were next normalized to account for differences in the number of reads per sample and differences in gene lengths. More specifically, raw sequence counts per gene were multiplied by a value representing the mean total number of reads aligned to the gene across all samples divided by the total number of aligned reads for a given sample. This value was then divided by the length of the gene it mapped to in order to eliminate gene length biases. The resulting values were considered to be the expression value.

The resulting expression values and their respective transcripts were filtered to reduce the influence of spurious observations. All observations with expression values lower than 10 were removed from downstream analysis. In addition, transcripts that mapped to genes without function information (i.e. 'uncharacterized protein') were not considered further. Fold changes between control and treated samples were calculated for each transcript by dividing the expression value from the treated sample by the expression value from the control sample. Gene ontology terms (functional categories) were determined for each transcript by referencing the Ensembl database (http://ensembl.gramene.org) using their respective genes.

The second transcriptomics (quantitative) analyses were conducted on plants grown from seeds treated with a variety of *Streptomyces* strains, and formulation control-treated plants. From this, up- and down-regulated transcripts in plants grown from seeds treated with the *Streptomyces* strain Strain C were compared with the transcript profiles of plants grown from seeds treated with Strain B and of the plants grown from seeds treated with only the formulation control.

The specific procedures used for the transcriptomics comparison analyses included the following parameters: FastQC v0.10.1 was run to verify quality of sequences (fastqc-o<Output directory>-t 4<Sequence file>). TrimmomaticSE was run to remove TruSeq adapters (TrimmomaticSE-threads 4<Untrimmed filename><Trimmed filename> ILLUMINACLIP:TruSeq3-SE.fa:2:30:10 LEADING:3 TRAILING:3 SLIDINGWINDOW:4:15 MINLEN:36). Quantification of reads mapped to each locus of the reference genome. The *Glycine max* Wm82.a2.vl (Soybean) reference genome was download from Phytozome (phytozome.jgi.doe.gov). Prior to running STAR 2.5.1b_modified, a genome index was generated (STAR—runMode genomeGenerate—runThreadN 8—genomeDir <Output directory>—genomeFastaFiles Gmax_275_v2.0.fa—limitGenomeGenerateRAM 30000000000). Sequences were aligned to the reference genome using STAR 2.5.lb_modified (STAR—genomeDir <Genome index directory>—runThreadN 40—readFilesIn <Trimmed seqs directory>—readFilesCommand zcat—outSAMtype BAM SortedByCoordinate—outFilterIntronMotifs RemoveNoncanonicalUnannotated). The bam file was indexed using Samtools (samtools index <.bam file>). QC was performed on the bam file using the RSeQC bam_stat.py utility (bam_stat.py-i<.bam file>><Output report file>). Reference genome annotation file Gmax_275_Wm82.a2.vl.gene_exons.gff was converted to a.gtf file containing just exon entries with gene_id parameter specifying the locus without specific transcript designation. This results in all reads mapping to the defined range being reported as part of this gene locus. htseq-count 0.6.1p1 was used to quantify the reads (htseq-count -f bam -s reverse <Mapped file from STAR><.gtf file>><counts.txt file>). Quantification of reads mapped to alternatively-spliced transcripts from the reference genome. Salmon 0.6.0 was run in quasi-mapping mode to quantify transcript-specific reads (salmon quant -i transcripts_index -1 SR -r<(gunzip -c<Sequence file>) -o<Quant file>). Differential expression analysis of reads mapped to each locus of the reference genome. Gene locus and transcript counts were run separately. Counts/Quant files for each sample were supplied to DESeq2, which generated log 2Fold-Change values for each comparison between a rep and its formulation. Results with an absolute value of log 2Fold-Change greater than 1.4 and a padj value less than 0.05 were considered high confidence hits.

To compare these results to qualitative results, the reference genome v2.0 gene was cross-referenced (using the Glyma_11_to_Glyma_20_Correspondence_Full.csv file available at Soybase.org) to obtain the reference genome v1.1 gene. If this v1.1 gene was found in the qualitative results output (minus the transcript[.#] specification), the gene was flagged.

Results: Transcriptomics Qualitative Analysis (Soy Normal Watering Conditions)

The transcriptomic analysis of soybean plants inoculated with endophytic bacterial strain Strain C grown under drought watering regimes in the greenhouse revealed several major pathways that are modulated by the endophyte: symbiosis enhancement, resistance against abiotic and biotic stresses and growth promotion. All data are summarized in Table 8A. Plants treated with Strain C exhibited modified (up-regulated and/or down-regulated) gene transcription normal watering (well watered) conditions, as compared to isoline plants not treated with Strain C.

Symbiosis Enhancement

Under normal watering regime, the top induced nitrogen metabolism transcript by Strain C in stems and leaves was asparagine synthetase, an enzyme involved in asparagine metabolism. In most legumes, asparagine is the principal assimilation product of symbiotic nitrogen fixation (Scott et al., 1976). In soybean, high asparagine synthetase transcript level in source leaves is positively correlated with protein concentration of seed (Wan et al., 2006), and in roots, is linked with increased levels of asparagine in xylem sap transported to the shoot (Antunes et al., 2008). The most down-regulated transcripts expressed in roots of soybean plants grown under normal watering regime were: early nodulins (early nodulin-70, -55-1, -93), nodulins (nodulin-16, -24, -26), leghemoglobin C3 and glutamine synthetase. Recent studies revealed that the novel organelle, also termed "symbiosome" (Masalkar et al., 2010) is delimited by the symbiosome membrane (SM)(Day et al., 2001), which controls the transport of all metabolites between the symbiont and the plant host. Biogenesis of the SM is accompanied by the biosynthesis of a variety of nodulin proteins, where they serve transport and regulatory functions in the symbiosis (Fortin et al., 1985). Among these proteins is nod26, a transporter of NH3, which is a major component of the mature symbiosome (Fortin et al., 1987). Nod26 has also been shown to be a site for the interaction of cytosolic nodule glutamine synthetase (GS), which is the critical enzyme for assimilation of environmental ammonia and endogenous ammonia produced metabolically (Masalkar et al., 2010). The binding of GS to nod26 is proposed to promote efficient assimilation of fixed nitrogen and prevent potential ammonia toxicity by localizing the enzyme to the cytosolic side of the symbiosome membrane (Masalkar et al., 2010). Another highly down-regulated transcript in leaves of well-watered plants was malic enzyme, shown to be important for carbon metabolism of bacteroids and free living bacteria by supplying acetyl-CoA for the TCA cycle or providing NADPH and pyruvate for various biosynthetic pathways (Dao et al., 2008a). Soybean plants inoculated with a NAD(+)-dependent malic enzyme mutant formed small root nodules and exhibited significant nitrogen-deficiency symptoms (Dao et al., 2008b).

Resistance Against Abiotic and Biotic Stresses

Plants have evolved multiple strategies to defend themselves against biotic and abiotic stresses.

One of the earliest plant defense responses is the production of reactive oxygen species (ROS) (Bolwell and Daudi, 2009). These oxygen intermediates can serve as signaling molecules that activate plant defense responses (Lamb and Dixon, 1997) or can have direct antimicrobial activity (Peng and Kuc, 1992). However, even though ROS is an important component of signaling during abiotic and biotic stress, the overproduction of ROS leads to oxidative damage to cells and cellular membranes. Plant protection against oxidative damage is regulated through enzymatic and non-enzymatic mechanisms. One of the detoxification enzymes, superoxide dismutase (SOD), catalyses the dismutation of superoxide ($O2-$) to hydrogen peroxide ($H2O2$) that gets reduced to water by peroxidases (POX) (Matamoros et al., 2003).

Transcripts important in protection against oxidative damage that were upregulated in all tissues were: thioredoxin, ferritin and annexin. Thioredoxins are implicated in different aspects of plant life including development and adaptation to environmental changes and stresses. Annexins, a multigene and a multifunctional family of Ca2+-dependent membrane-binding proteins, have been shown to regulate the level and the extent of ROS accumulation and lipid peroxidation during stress responses (Jami et al., 2008). Pectinesterase was another transcript induced by Strain C in roots of plants grown under normal condition that has been implicated in drought resistance (An et al., 2008).

Non-specific lipid transfer proteins (ns-LTPs) are ubiquitous small basic secreted proteins, able to bind to several classes of lipids in vitro (Carvalho and Gomes, 2007). They have been implicated in cutin biosynthesis in pollen development (Zhang et al., 2010), responses to stresses and signaling (Ge et al., 2003). Our data shows that both non-specific lipid transfer protein and Phospholipase D were highly upregulated transcripts in root and stem tissues of plants grown under the normal watering regime. Phospholipase D and its product, phosphatidic acid by functioning in signal transduction cascades and influencing the biophysical state of lipid membranes, have been shown to be implicated in multiple plant stress responses (Bargmann and Munnik, 2006).

S-adenosylmethionine synthase, which catalyzes synthesis of s-adenosylmethionine from methionine and ATP, functions as a primary methyl-group donor and as a precursor for metabolites such as ethylene, polyamines, and vitamin B1 (Hesse et al., 2004). Our data shows that S-adenosylmethionine synthase was upregulated in roots and downregulation in stems of well-watered plants.

Several transcripts that are induced by various biotic stresses and implicated in pathogen defense have been upregulated in plants treated with Strain C: stress-induced protein SAM22, repetitive proline-rich cell wall protein, lipoxygenase, defensing-like protein and phenylalanine ammonia-lyase. Stress-induced protein SAM22 has been shown to be responsive to wounding, salicylic acid, hydrogen peroxide or fungal elicitor (Crowell et al., 1992). Repetitive proline-rich cell wall proteins (PRPs), one of the five families of structural cell wall proteins (Carpita and Gibeaut, 1993) that is associated with early stages of legume root nodule formation (Franssen et al., 1987) and other plant developmental stages, is also contributing to defense reactions against physical damage and pathogen infection (Bradley et al., 1992; Brisson et al., 1994). Lipoxygenases catalyze the dioxygenation of polyunsaturated fatty acids in lipids collectively known as oxylipins. Oxylipins are involved in a number of developmental or stress response processes (Andersson et al., 2006) and they exert protective activities either as signaling molecules in plants during development, wounding, insect and pathogen attack, or direct anti-microbial substances that are toxic to the invader (Yan Y et al., 2013 Plant defensins are small, basic, cysteine rich peptides that inhibit the growth of a broad range of fungi but seem nontoxic to plant cells. Phenylalanine ammonia lyase (PAL) is the first committed enzyme in the phenylpropanoid pathway that leads to biosynthesis of the polyphenol compounds that have multiple functions, such as providing mechanical support (lignins) (Whetten and Sederoff, 1992), protection against abiotic and biotic stress (antioxidants) (Dixon and Paiva, 1995), and signaling with the flavonoid nodulation factors (Weisshaar and Jenkins, 1998).

Together, our data demonstrate that under normal (well watered) growth conditions, Strain C mediates regulation of transcripts involved in protection against abiotic and biotic stress including protection against oxidative stress, defense reactions against physical damage, suppression of inhibition of pollination and fruit setting especially under drought, signaling and induction of local and systemic defense responses against wounding, insect and pathogen attack and production of anti-microbial metabolites.

Growth Promotion

Several groups of transcripts involved in carbon metabolism have been highly upregulated in plants treated with Strain C.

Glucose-1-phosphate adenylyltransferase, a transferase that transfers phosphorous-containing nucleotide groups, is involved in starch and sucrose metabolism (Ghosh and Preiss, 1966). This transcript has been highly upregulated in root tissues grown under normal conditions.

Other transcripts of carbon metabolism induced by Strain C in leaf tissues of plants grown under normal watering condition included genes involved in photosynthesis: Photosystem Q (B) protein, Cytochrome b559 subunit alpha, Cytochrome b6, and ATP synthase subunit b, chloroplastic, and thioredoxins. Major products of photosynthesis, starch and sucrose, provide the carbon sources of all plant compounds and are major plant storage products. Starch metabolism, for example, is important for grain filling. Sucrose plays a pivotal role in plant growth and development. Hydrolysis of sucrose is associated with the respiration required for plant growth and is linked to cell wall synthesis.

The 28 and 31 kDa glycoproteins, also termed pod storage proteins (Zhong et al., 1999), function in nitrogen storage during times of low sink demand for nitrogen because they accumulate in the leaves of soybean plants at anthesis and after depodding, but disappear during pod filling (Wittenbach, 1983). Distribution and accumulation of the 28 and 31 kDa proteins in the stems and leaves of soybean plants are altered when plants are grown from Strain C-treated seeds under well-watered regime.

In summary, the results presented in this section, demonstrate that endophytic bacterium Strain C promotes plant growth and development by enhancing carbon and nitrogen metabolism under normal watering conditions.

Cell Wall Transcripts

The group of cell wall related transcripts upregulated by Strain C in stem and leaf tissues of plants grown under normal watering conditions include: NAC domain protein genes, amine oxidase and auxin-induced protein 15A. NAC domain protein genes are homologous to well-known *Arabidopsis* transcription factors that regulate the differentiation of xylem vessels and fiber cells (Ooka et al., 2003). Amine oxidase generates hydrogen peroxide that is important for lignification of cortical cell wall and xylem tissue under both stress and normal conditions (Angelini et al., 1993). Another group of developmentally regulated genes induced by Strain C in leaf tissues under the normal watering regime included CASP-like proteins that are expressed in floral and root tissues (Roppolo et al., 2014).

Results: Transcriptomics Qualitative Analysis (Soy Water-Limited Conditions)

The transcriptomic analysis of soybean plants inoculated with endophytic bacterial strain Strain C grown under drought watering regimes in the greenhouse revealed three major pathways that are modulated by the endophyte: symbiosis enhancement, resistance against abiotic and biotic stresses and growth promotion (All data are summarized in Table 8A). Plants treated with Strain C exhibited modified (up-regulated and/or down-regulated) gene transcription under water-limited (drought) conditions, as compared to isoline plants not treated with Strain C.

Symbiosis Enhancement

Under drought conditions, Strain C strongly induced a cascade of plant transcripts involved in nodulation and nitrogen fixation—a process known to occur in legumes and stimulated by symbiotic nitrogen-fixing bacteria of the genus *Rhizobium*.

Our data demonstrate that Strain C endophytes contribute to enhancement of symbiosis under drought conditions by altering the transcript levels of several important genes in plants treated with Strain C and exposed to water-limited conditions. In the present experiment, auxin-induced protein 15A was highly upregulated by Strain C in leaf tissues. Additionally, genes involved in nodule development, namely nodulin genes (nodulin-16, -20, -22, -24, -26B, -44, -C51), early nodulin-70, -55-1, -55-2, and -93, and leghemoglobin biosynthesis genes (leghemoglobin -A, -C1, -C2, -C3) were upregulated in roots. Mutualistic symbiosis between legumes and *Rhizobium* species plays an important role in the life of the plants by improving mineral nutrition and water consumption, increasing resistance to pathogenic microorganisms and pests, and improving adaptation to various stresses (Stacey et al., 2006). In return, the plant provides products of photosynthesis and the ecological niche to its microsymbionts. The molecular dialog involves plant signaling molecules, flavonoids and isoflavonoids, and bacterial lipochitooligosaccharidic molecules called Nod factors (Stacey et al., 2006). Consequently, the plant forms a highly specific nitrogen-fixing symbiotic organ called a nodule (Crespi and Frugier, 2008). Nodulin-encoding genes are specifically expressed during the development of symbiotic root nodules (Legocki and Verma, 1980). Upon nodule formation, bacteria differentiate into nitrogen-fixing bacteroids that are beneficial to the plants (Kereszt et al., 2011). Symbiosis promotion can be indirect by activating conditions that aid symbiosis by *Rhizobium* species or direct by producing signals that initiate Nod factor-independent nodulation. Nod factor-independent nodulation is mediated in legumes through control of development of nodule primordium by varying concentrations of plant hormones auxins, cytokinin, and ethylene (Schultze and Kondorosi, 1998).

Several other transcripts related to symbiosis enhancement were upregulated. PUR1 amidophosphoribosyltransferase, chloroplastic, was upregulated in roots. It is the first enzyme in de novo purine biosynthesis (Ito et al., 1994). It is associated with maturation of nodules in soybean and moth-bean (*Vigna aconitifolia*) (Kim et al., 1995).

Chalcone synthases 3, 5, 7 and chalcone—flavonone 1B-2 isomerase are upregulated in root tissues. Chalcone synthase and chalcone-flavonone isomerase are key enzyme of the flavonoid and isoflavonoids biosynthesis pathway (Tohge et al., 2007). Flavonoids are secondary metabolites that have many functions in higher plants, including UV protection, fertility, antifungal defense and the recruitment of nitrogen-fixing bacteria (Dao et al., 2011).

Thus, compositions such as Strain C that modulate gene expression of a plant experiencing stresses, including drought, improve the stressed plant's ability to form and maintain successful symbiotic relationships with *Rhizobium*.

Resistance Against Abiotic and Biotic Stresses

Plants have evolved multiple strategies to defend themselves against biotic and abiotic stresses.

Superoxide dismutase (SOD) and superoxide dismutase (Fe), chloroplastic, were found to be upregulated in stem tissues of Strain C-treated plants grown under drought conditions as compared to untreated control plants grown under the same conditions. One of the earliest plant defense responses is the production of reactive oxygen species (ROS) (Bolwell and Daudi, 2009). However, even though ROS are an important component of signaling during abiotic and biotic stress, the overproduction of ROS leads to oxidative damage to cells and cellular membranes. Plant protection against oxidative damage is regulated through enzymatic and non-enzymatic mechanisms. One of the detoxification enzymes, superoxide dismutase (SOD), catalyses the dismutation of superoxide (O2−) to hydrogen peroxide (H2O2) that gets reduced to water by peroxidases (POX) (Matamoros et al., 2003). Thus, plants treated with compositions such as Strain C may have an improved ability to cope with the stresses associated with water-limited conditions, via upregulation of SOD.

Other transcripts important in protection against oxidative damage that were upregulated in stem tissues in Strain C treated plants were thioredoxin and ferritin, particularly: ferritin, chloroplastic ferritin-2, chloroplastic ferritin-4, and chloroplastic ferritin-1. Thioredoxins are implicated in different aspects of plant life including development and adaptation to environmental changes and stresses. They act as antioxidants by facilitating the reduction of other proteins by cysteine thiol-disulfide exchange (Nordberg and Arner, 2001). Recent reverse genetics studies in *Arabidopsis* revealed that besides their iron storage role, ferritins may be involved in mechanisms of action in oxidative stress pathways (Briat et al., 2010). Thus, plants treated with compositions such as Strain C may have an improved ability to cope with stresses associated with water-limited conditions, via the upgregulation of ferritin and thioredoxin.

In the present experiment, soybeans in Strain C-treated plants expressed annexin at a higher level in leaf tissues of Strain C-treated plants exposed to drought. Annexins, a multigene and a multifunctional family of Ca2+-dependent membrane-binding proteins, have been shown to potentially regulate the level and the extent of ROS accumulation and lipid peroxidation during stress responses (Jami et al., 2008). Thus, plants treated with compositions such as Strain C may have an improved ability to cope with the stresses associated with water-limited conditions, via upregulation of annexin.

In the present experiment, glutathione peroxidase transcripts were down-regulated in roots and leaves of Strain C-treated plants exposed to drought. Plant glutathione peroxidases are ubiquitous enzymes (Yang et al., 2005) that detoxify lipid hydroperoxides and other reactive molecules in a species-, organ- and stress-specific manner (Churin et al., 1999; Ramos et al., 2009). Thus, plants treated with compositions such as Strain C may have an improved ability to cope with the stresses associated with water-limited conditions, via down-regulation of glutathione peroxidase.

Plants exposed to water-limited conditions and treated with Strain C had altered expression levels of additional transcripts implicated in abiotic stress. SAM22 was down-regulated in stems and leaves. The heat-shock proteins are molecular chaperones expressed under various stresses to stabilize proteins (De Maio, 1999). HSP22, a chloroplastic small heat-shock protein, was elevated in stems. S-receptor-like serine/threonine-protein kinase is upregulated in roots and leaves. S-receptor-like serine/threonine protein kinase characterized in *Glycine soja*, has been shown to play a key role as a positive regulator of plant tolerance to salt stress (Sun et al., 2013). In plants, alcohol dehydrogenase, a highly conserved enzyme, is induced by stress conditions, particularly during hypoxic response, to anaerobically supply NAD for metabolism (Chung and Ferl, 1999). Alcohol dehydrogenase 2 was upregulated in roots. Chloroplast translation initiation factor IF-1 (INFA), a factor necessary for initiation of protein biosynthesis in the chloroplast and known to be inducible by salt stress (Omidbakhshfard et al., 2012), was upregulated in stems.

Expression levels of transcripts implicated in biotic stress were altered in plants exposed to water-limited conditions and treated with Strain C. SAM22 was downregulated in stems and leaves. SAM22 has been shown to be involved in mechanisms of wounding, salicylic acid, hydrogen peroxide or fungal elicitor (Crowell et al., 1992). S-adenosylmethionine caffeic acid 3-O-methyltransferase (COMT) was upregulated in stems. S-adenosylmethionine synthase, which catalyzes synthesis of s-adenosylmethionine from methionine and ATP, functions as a primary methyl-group donor for the COMT reaction and as a precursor for metabolites such as ethylene, polyamines, and vitamin B1 (Hesse et al., 2004).

Repetitive proline-rich cell wall protein 3 was upregulated in roots and repetitive proline-rich cell wall protein was downregulated in leaves. Repetitive proline-rich cell wall proteins (PRPs), one of the five families of structural cell wall proteins (Carpita and Gibeaut, 1993) that is associated with early stages of legume root nodule formation (Franssen et al., 1987) and other plant developmental stages, may also contribute to defense reaction mechanisms against physical damage and pathogen infection (Bradley et al., 1992; Brisson et al., 1994).

Lipoxygenase was upregulated in stems. Additional lipoxygenases were upregulated in roots (LOX9, LOX10), stems (LOX7, VLXB) and leaves (LOX7). Lipoxygenases catalyze the dioxygenation of polyunsaturated fatty acids in lipids collectively known as oxylipins. Oxylipins are involved in a number of developmental or stress response processes (Andersson et al., 2006) and they may exert protective activities either as signaling molecules in plants during development, wounding, insect and pathogen attack, or direct anti-microbial substances that are toxic to the invader (Yan Y et al., 2013).

Defensin-like protein was upregulated in leaves and phenylalanine ammonia-lyase was upregulated in stems. Plant defensins are small, basic, cysteine rich peptides that inhibit the growth of a broad range of fungi but seem nontoxic to plant cells. Their antifungal activity may be regulated through specific binding to membrane targets (Thomma et al., 2002). Phenylalanine ammonia lyase (PAL) is the first committed enzyme in the phenyl-propanoid pathway that leads to biosynthesis of the polyphenol compounds that have multiple functions, such as providing mechanical support (lignins) (Whetten and Sederoff, 1992), protection against abiotic and biotic stress (antioxidants) (Dixon and Paiva, 1995), and signaling with the flavonoid nodulation factors (Weisshaar and Jenkins, 1998).

Our data show that genes involved in phytoalexin synthesis in soybean were downregulated in Strain C-treated plants exposed to drought, namely: cytochrome P450 82A2 (roots), cytochrome P450 82A4 (roots), cytochrome P450 93A1 (roots), NAD(P)H-dependent 6'deoxychalcone synthase (roots) and glucan endo-1,3-beta-glucosidase (stems and leaves). Cytochrome P450 93A3 was upregulated in the roots, cytochrome P450 93E1 was upregulated in the stems, and cytochrome P450 76O2 was upregulated in the roots and leaves. The cytochrome P450 93 enzymes are involved in an elicitor-inducible glyceollin biosynthesis in soybean (Schopfer and Ebel, 1998). The CYP76 family is involved in synthesis of indole alkaloids and iridoid monoterpenoids (Hofer et al., 2013), secondary metabolites active in plant-insect interactions (Birkett et al., 2011). Soybean beta-1,3-endoglucanase releases elicitor-active carbohydrates from the cell walls of fungal pathogens initiating phytoalexin accumulation in fungus-infected soybean plants (Takeuchi et al., 1990). Low expression of some of these transcripts in plants that are treated with Strain C may promote the endophyte's systemic colonization of the plant (Reinhold-Hurek and Hurek, 2011). Thus, plants treated with a beneficial *Streptomyces* endophyte composition, for example Strain C, may have an improved ability to cope with the stresses associated with water-limited conditions, via modulation of expression of phytoalexin-associated genes.

Arginine decarboxylase is upregulated in roots and leaves. Arginine decarboxylase is a key enzyme in plant polyamine biosynthesis (Hanfrey et al., 2001). Polyamines have been implicated in a wide range of biological processes including plant growth and development, senescence, environmental stress and they exert an anti-fungal and anti-viral effect (Bais and Ravishankar, 2002).

Thus, plants treated with compositions such as Strain C may have an improved ability to cope with the stresses associated with water-limited conditions, for example via modulation of expression of SAM22, s-adenosylmethionine, defensin-like protein, phenylalanine ammonia-lyase, lipoxygenases, cytochromes, and repetitive proline-rich cell wall protein. Together, our data demonstrate that under drought conditions, Strain C mediates regulation of transcripts involved in protection against abiotic and biotic stresses.

Growth Promotion

Endophytes enable plant growth promotion through different mechanisms that involve nutrient supply to plants or stimulation of plant cell elongation or cell division regulated by phytohormones (Stacey et al., 2006). These mechanisms are modulated through changed rates of carbon metabolism.

Transcripts that were modulated in expression in Strain C-treated plants exposed to water-limiting conditions include: Photosystem Q(B) protein (downregulated in roots) and photosystem I assembly protein Ycf4 (downregulated in roots), cytochrome P450 82A2 (downregulated in roots), cytochrome P450 93A1 (downregulated in roots), cytochrome P450 82A4 (downregulated in roots), cytochrome C oxidase subunit 1 (downregulated in root), ribulose bisphosphate carboxylase small chain (upregulated in stem), fructose-bisphosphate aldolase (upregulated in stem), serine hydroxymethyltransferase (upregulated in leaves) and mitochondrial ATP synthase subunit 9 (downregulated in root). Thus, plants treated with compositions such as Strain C may have an improved ability to cope with the stresses associated with water-limited conditions, via modulation of expression of genes involved in the photosynthetic, carbon fixation and energy transfer pathways.

Sucrose synthase was downregulated in leaf tissues of Strain C treated plants exposed to water-limited conditions. Sucrose is a highly soluble disaccharide that is synthesized in the leaf cytosol from which it diffuses to the rest of the plant (Lunn, 2001). Thus, plants treated with compositions such as Strain C may have an improved ability to cope with the stresses associated with water-limited conditions, via downregulation of expression of sucrose synthase.

Beta-galactosidase, a key enzyme in carbohydrate metabolism was upregulated in roots, stems, and leaves. Beta-amylase (GM-BAMYTKM), a starch-hydrolyzing enzyme (Ishikawa et al., 2007), was upregulated in the roots.

Chlorophyll a-b binding proteins (CABs), protective components of the photosynthetic light harvesting system, were induced in roots (CAB3), stems (CAB2 and LHCB1-7), and leaves (CAB2 and LHCB1-7). Photosystem I subunit F (PSAF) participates in efficiency of electron transfer from plastocyanin to P700 (Haldrup et al., 2000). Photosystem I subunit F was upregulated in roots.

In summary, the results presented in this section, demonstrate that endophytic bacterium Strain C promotes plant growth and development by enhancing carbon metabolism under drought stress watering regimes.

Cell Wall Transcripts

Amine oxidase is upregulated in root, stem and leaf tissues of Strain C-treated plants exposed to water-limited conditions. Amine oxidase generates hydrogen peroxide that is important for lignification of cortical cell wall and xylem tissue under stress conditions (Angelini et al., 1993). Thus, plants treated with compositions such as Strain C may have an improved ability to cope with the stresses associated with water-limited conditions, via upregulation of expression of amine oxidase.

Our data show high levels of transcript expression of auxin-induced protein 15A in stem and leaf tissues, of Strain C treated plants under water-limited growth conditions. One of the mechanisms by which auxin stimulates cell elongation is by stimulating cell wall-loosening factors (Friml, 2003). In addition, increased seed germination, shoot growth and seed production may be accompanied by increased production of auxin-like compounds (Friml, 2003). Thus, plants treated with compositions such as Strain C may have an improved ability to cope with the stresses associated with water-limited conditions, via upregulation of expression of auxin-induced protein 15A.

Pectinesterase is dowregulated in stems of Strain C treated plants that have been subjected to water-limiting conditions. Pectinsterases are thought to be involved in cell-wall remodeling (Imoto et al. (2005) Plant Mol. Biol. 58:177-192). UDP-glucose 6-dehydrogenase, an enzyme that participates in cell wall formation and modification by providing UDP-glucuronate for polysaccharide biosynthesis (Cook et al., 2012), was upregulated in roots, stems, and leaves. Xyloglucan endotransglycosylase (XET1), a key enzyme in cell wall biosynthesis (Bourquin et al., 2002), was upregulated in leaves.

The transcriptomics experiments of the present invention demonstrate upregulation of genes involved in non-specific lipid transfer protein production, in leaf tissues of Strain C-treated plants grown during water-limited conditions. Non-specific lipid transfer proteins (ns-LTPs) are ubiquitous small basic secreted proteins, able to bind to several classes of lipids in vitro (Carvalho and Gomes, 2007). Thus, plants treated with compositions such as Strain C may have an improved ability to cope with the stresses associated with water-limited conditions, via upregulation of expression of non-specific lipid transfer proteins.

Developmental Regulation

Histones are proteins that are primarily involved in DNA packaging into chromatin, and that can affect gene expression. Recent studies show that the developmental transition from a vegetative to a reproductive phase (i.e. flowering) is controlled by chromatin modifications (He, 2009). In addition to histone H2A, which was upregulated in leaves, histone H2B, histone H3, and histone H4 were upregulated in stems and leaves.

A number of other transcripts were altered as a result of treatment with Strain C. Two auxin-induced transcripts, AUX28 (Ainley et al., 1988) and auxin-induced protein 15A were elevated in leaves. Oligopeptide transporter 7 (OPT7) was upregulated in roots. In *Arabidopsis*, oligopeptide transporter 7 is associated with oligopeptide transport in vascular tissue in seedlings and adult plants (Stacey et al., 2006c). Ribonucleoside-diphosphate reductase, responsible for reducing nucleotides to deoxynucleotides prior to DNA synthesis (Guzmin et al., 2002), was upregulated in leaves. The transcription factor PHAN-A, implicated in leaf blade expansion (Eckardt, 2004), was upregulated in leaves. Tubulin beta-1 chain (TUBB1), involved in plant cell growth (Takahashi et al., 1995) and shown to accumulate in roots (Oppenheimer et al., 1988), was upregulated in roots.

Fructose-bisphosphate aldolase is a glycolytic enzyme, induced by the plant hormone gibberellin, that may regulate the vacuolar H-ATPase-mediated control of cell elongation that determines root length (Konishi et al., 2005). Indeed, fructose-bisphosphate aldolase was only induced in roots.

Thus, plants treated with compositions such as Strain C may have an improved ability to cope with the stresses associated with water-limited conditions, for example via upregulation of expression of histones and other genes involved in developmental regulation.

Other

A number of additional transcripts demonstrated modulated expression in Strain C-treated plants grown under water-limited conditions: carbonic anhydrase (downregulated in roots), casparian strip membrane protein 1 (downregulated in roots), isocitrate lyase I (downregulated in roots), 2-hydroxyisoflavanone synthase (downregulated in stems), chloroplastic 50S ribosomal protein L33 (downregulated in leaves), chloroplastic 30S ribosomal protein S18, and serine/threonine protein kinase.

Results: Transcriptomics Quantitative Analysis (Soy Water-Limited Conditions)

Quantitative transcriptomics analyses demonstrated significant conclusions in 6 areas, as described below.

Genes were Quantified as being Significantly Up/Down Regulated in Beneficial Strain c Vs Formulation, that Confirm the Qualitative Analysis (Leaf; Root)

All results are summarized in Table 8B. Descriptions of genes are included in the Qualitative Transcriptomics results section.

Plants treated with Strain C may have an improved ability to cope with the stresses associated with water-limited conditions, primarily by increased uptake of nutrients from soil (e.g. ammonium, sulphur) and symbiotic nitrogen and carbon fixation in root nodules and via increased activity of genes involved in protection against abiotic and biotic factors.

Genes that were Quantified as being Significantly Up/Down Regulated in Beneficial Strain C Vs Formulation, in Leaf; Root)

All results are summarized in Table 8C.

Top up-regulated leaf genes included: Small and basic intrinsic protein 1A; RAD-like 6, 3; Germin-like protein 1; Ammonium transporter 1,2; Protein of unknown function, DUF547; GDSL-like Lipase/Acylhydrolase superfamily protein; N-terminal nucleophile aminohydrolases (Ntn hydrolases) superfamily protein; nodulin MtN21/EamA-like transporter family protein; proline-rich protein 4; Thioredoxin superfamily protein.

Small and basic intrinsic protein 1A belongs to a family of plant aquaporins (Ishikawa et al., 2005). In plants, aquaporins occur as multiple isoforms localized in the plasma membrane, endoplasmic reticulum, vacuoles, plastids and, in some species, in membrane compartments interacting with symbiotic organisms. In addition to water, plant aquaporins can transport various physiological substrates and dissolved gases such as carbon dioxide and ammonia or metalloids such as boron and silicon. Although they play a central role in water relations of roots, leaves, seeds, and flowers, aquaporins have also been linked to plant mineral nutrition, response to light, temperature and carbon and nitrogen fixation (Maurel et al., 2015).

RAD (RADIALIS) is a target gene in a regulatory network responsible for controlling of floral asymmetry in *Antirrhinum*. In *Arabidopsis*, the expression domains of RAD-like genes are often found in growing tissues, suggesting that RAD-like genes may have developmental roles (Baxter et al., 2007).

Germin-like proteins (GLPs) are present ubiquitously in plants (Dunwell and Cupins, 1998). Multiple studies have revealed diverse functions of GLPs in plant development and abiotic and biotic stresses like resistance to *Sclerotinia* stem rot of soybean (Lu et al., 2010) or *Sclerotinia sclerotiorum* (Rietz et al., 2012).

Ammonium transporter proteins are encoded by multigene families in plants with different physiological roles, one of which is ammonium uptake from the soil (Gazzarrini et al., 1999). Recently, in soybean, a novel symbiotic ammonium transporter 1 was described as a putative ammonium ($NH_4^+$) channel localized to the symbiosome membrane of soybean root nodules playing an important role for soybean *rhizobium* symbiosis because loss of activity results in a reduction of nodule fitness and growth (Chiasson et al., 2014).

The DUF547 domain is associated with class IV glutaredoxins, a family of oxidoreductases related to thioredoxins and deeply involved in regulating activity of metabolic enzymes, transcription factors, and stress-related antioxidant enzymes (Rouhier, 2010).

GDSL esterases/lipases are a newly discovered subclass of lipolytic enzymes with multifunctional properties, such as broad substrate specificity and regiospecificity (Brick et al., 1995). They have been reported to be involved in the regulation of plant development, morphogenesis, synthesis of secondary metabolites, and defense response (Chepyshko et al., 2012).

Most Ntn hydrolases catalyze the hydrolysis of amide bonds. Plant asparaginases belong to the superfamily of N-terminal nucleophile (Ntn) hydrolases.

Nodulin-encoding genes are specifically expressed during the development of symbiotic root nodules (Legocki and Verma, 1980). Upon nodule formation bacteria differentiate into nitrogen-fixing bacteroids that are beneficial to the plants (Kereszt et al., 2011). Nodulin proteins serve transport and regulatory functions in symbiosis (Fortin et al., 1985).

Repetitive proline-rich cell wall proteins (PRPs), one of the five families of structural cell wall proteins (Carpita and Gibeaut, 1993) that are associated with early stages of legume root nodule formation (Franssen et al., 1987) and other plant developmental stages, may also contribute to defense reaction mechanisms against physical damage and pathogen infection (Bradley et al., 1992; Brisson et al., 1994).

Thioredoxins are implicated in different aspects of plant life including development and adaptation to environmental changes and stresses. They act as antioxidants by facilitating the reduction of other proteins by cysteine thiol-disulfide exchange (Nordberg and Arner, 2001).

Top upregulated genes in root tissue inclue: Subtilase family protein; Serine carboxypeptidase-like 40; Beta-6 tubulin; 4) Cytochrome P450, family 71, subfamily A, polypeptide 19; Sulfate transporter 2,1; Uridine diphosphate glycosyltransferase 74E2; ATPase E1-E2 type family protein/haloacid dehalogenase-like hydrolase family protein; NAD(P)-binding Rossmann-fold superfamily protein.

Subtilases are a family of subtilisin-like serine proteases expanded in plants by functional diversification—for instance they are involved in development of plants and stress response like resistance to pathogens (Chichkova et al., 2004) or establishment of symbiosis (Takeda et al., 2004).

Serine carboxypeptidase-like (SCPL) proteins have emerged as a new group of acyltransferase enzymes that function in a broad range of biochemical pathways, including secondary metabolite biosynthesis, herbicide conjugation, and germination-associated degradation of seed protein reserves (Lehfeldt et al., 2000). They were demonstrated to be involved in normal plant growth and development, synthesis of compounds that protect plants against pathogens, insects and UV light, and for resistance to natural and manmade xenobiotics (Mugford et al., 2009).

Beta-6 tubulin (TUB6) is a structural constituent of cytoskeleton involved in microtubule-based process, response to salt stress, response to cold and it is expressed in multiple plant structures and growth stages (Oppenheimer et al., 1988).

Cytochromes P450 are involved in the biosynthetic pathway of major phytoalexins—chemicals synthesized by plants to deter microbes or insects (Schuler MA1, Berenbaum MR. 2013). In soybean, Cytochrome P450-dependent enzymes are involved in an elicitor-inducible glyceollin biosynthesis (P450s) (Schopfer and Ebel, 1998).

Plant sulfate transporters of the plant roots cells play a major role in sulphur uptake from the environment, and intracellular and long-distance transport within the plant (Buchner et al., 2004). The sulfate transporter in *Lotus japonicus* was found to be crucial for symbiotic nitrogen fixation root nodules (Krusell et al., 2005).

Applied in transgenic crops for pathogen resistance; produces glucosides and detoxifies microbial products. Uridine diphosphate glycosyltransferases (UGT) are a superfamily of regulatory enzymes that modify the activity, solubility, and transport of plant hormones, secondary metabolites, and xenobiotics, thus participating in plant developmental regulation, biotic stress responses, and detoxification of pollutants and herbicides (Ross et al., 2001; Wang 2009).

The haloacid dehalogenase-like hydrolases (HAD) are a large family of enzymes with diverse activities, all involving cleaving bonds between a carbon and a halogen, or a carbon and a phosphorus-containing group (Caparrós-Martin, 2013). In mustard (*Brassica juncea*), a putative haloacid dehalogenase-like hydrolase was upregulated following cadmium exposure, suggesting a role in abiotic stress responses (Minglin et al., 2005).

A large family, diverse functions—could be involved anywhere in development, regulation, responses. Includes short-chain dehydrogenases/reductases (SDR), already described.

Top down-regulated root genes included: PQ-loop repeat family protein/transmembrane family protein; NAD(P)-binding Rossmann-fold superfamily protein; senescence associated gene 18; Cytidine/deoxycytidylate deaminase family protein; Integrase-type DNA-binding superfamily protein; brassinosteroid-6-oxidase 2; branched-chain amino acid transaminase 2; myb domain protein 62.

PQ-loop repeat family protein/transmembrane family protein is also called a MtN3/saliva domain (Yuan and Wang 2013). Theorized involvement in protein transport and as cargo receptors (Saudek 2012). Diverse processes known so far: "reproductive development, senescence, environmental adaptation, and host-pathogen interaction" (Yuan and Wang 2013) and abiotic stress response (Feng et al. 2015).

NAD(P)-binding Rossmann-fold superfamily protein is a large family, diverse functions—could be involved anywhere in development, regulation, responses. Includes short-chain dehydrogenases/reductases (SDR). Sequence searches in databases revealed that SDR6 encoded a NAD(P)-binding Rossmann-fold superfamily protein, which belongs to the short-chain dehydrogenase/reductase (SDR) family of proteins. By virtue of catalyzing >300 different enzymatic reactions [17], the Rossmann fold is one of the most widely occurring protein folds.

Senescence associated gene 18 is involved in leaf senescence in response to biotic/abiotic stress.

BR hormones promote growth in balance/crosstalk with immune response. This is a synthase of brassinosteroids.

Plants synthesize the amino acids valine, leucine, and isoleucine from the products of branched-chain amino acid (BCAA) metabolism, in which BCAA transaminase plays a key role (Binder, 2010). In *Arabidopsis* and other Brassicaceae, BCAA metabolism also leads to production of glucosinolates, defensive secondary metabolites (Binder, 2010).

MYB proteins are transcription factors present across eukaryotes, involved in growth, metabolism, and stress responses in plants (Li et al., 2015).

Top down-regulated genes in roots included: GAST1 protein homolog 3; oxidative stress 3; S-adenosyl-L-methionine-dependent methyltransferases superfamily protein; Late embryogenesis abundant protein, group 1 protein; Peroxidase superfamily protein; Heavy metal transport/detoxification superfamily protein; alcohol dehydrogenase 1; RING/FYVE/PHD zinc finger superfamily protein; 2-oxoglutarate (2OG) and Fe(II)-dependent oxygenase superfamily protein; seed gene 1.

Gibberellic acid-stimulated transcript (GAST) proteins in tomato and their homologs in *Arabidopsis*, rice, and other plant species regulate growth and development in relation to gibberellin signaling, including the development of roots and reproductive structures (Herzog et al., 1995; Ben-Nissan and Weiss, 1996; Furukawa et al., 2006).

The Oxidative Stress 3 (OXS3) protein improves tolerance to heavy metals and oxidative stress, possibly by acting as a chromatin remodeling factor to coordinate stress responses (Blanvillain et al., 2008).

S-adenosylmethionine synthase, which catalyzes synthesis of s-adenosylmethionine from methionine and ATP, functions as a primary methyl-group donor and as a precursor for metabolites such as ethylene, polyamines, and vitamin B1 (Hesse et al., 2004).

Late embryogenesis abundant proteins (LEA) provide desiccation tolerance by changing their folding during drying, possibly creating a water shell under drought and stabilizing cellular components in the absence of water under full desiccation (Shih et al., 2008). The LEA gene HVA1 was successfully transferred from barley into rice to provide water deficit and salt stress tolerance (Xu et al., 1996).

In plants, peroxidases are involved in cell wall lignification, usually associated with pathogen resistance (Bruce and West, 1989), abiotic stress (Huttovi et al., 2006; Quiroga et al., 2001), or cell wall modification during growth (Arnaldos et al., 2002; G Martinez Pastur, 2001; Van Hoof and Gaspar, 1976; Kukavica et al., 2012).

In plants, alcohol dehydrogenase, a highly conserved enzyme, is induced by stress conditions, particularly during hypoxic response, to anaerobically supply NAD+ for metabolism (Chung and Ferl, 1999).

Plant homeodomain (PHD) finger domains read chromatin modifications during development and in response to stress, including distinguishing between mono-, di-, and tri-methylated states. This family is present with similar activities across eukaryotes.

Seed gene 1 is involved in lipid storage in seeds. A highly conserved calcium-binding domain located in *Arabidopsis thaliana* Seed Gene 1 (ATSG1) classifies this gene in the caleosin family. Caleosins are oleosin-like proteins, highly expressed in *A. thaliana* mature seeds, where they are largely associated with storage of lipids.

Q3 Up/Down Regulated Genes that are Unique to Strain C Treated Plants (Leaf; Root) as Compared to Plants Grown-from Seeds Treated with the Formulation Control, that are not Found Significantly Up- or Down-Regulated in Plants Grown from Seeds Treated with Strain A or Strain B All results are summarized in Table 8D.

The top upregulated genes in leaf tissue included: Pathogenesis-related thaumatin superfamily protein; Protein of unknown function, DUF547; PEBP (phosphatidylethanolamine-binding protein) family protein; CLAVATA3/ESR-RELATED 17; cytokinin oxidase/dehydrogenase 6.

The pathogenesis-related thaumatin-like proteins (PR-5) are inducible proteins that regulate plant-microbe interactions (Velazhahan et al., 1999). In soybean, a specific gene encoding a thaumatin-like protein in pathogenesis-related family 5 was discovered to regulate which bacterial species would be accepted in nodule formation (Hayashi et al., 2014).

The DUF547 domain is associated with class IV glutaredoxins, a family of oxidoreductases related to thioredoxins and deeply involved in regulating activity of metabolic enzymes, transcription factors, and stress-related antioxidant enzymes (Rouhier, 2010).

In plants, phosphatidylethanolamine-binding proteins (PEBP) are known to initiate and regulate flowering through interactions with the hormone giberellin and several transcription factors (Harig et al., 2012).

The CLAVATA3/ESR-related genes are essential to regulating growth, development, and meristem maintenance in the shoot and root apical meristems (Miwa et al., 2008).

Cytokinin oxidase/dehydrogenase (CKX) enzymes participate in developmental regulation by inactivating the hormone cytokinin (Schmulling et al., 2003). Cytokinin oxidase has been linked directly to grain yield in rice, as the accumulation of cytokinin leads to the development of increased numbers of fruiting structures (Ashikari et al., 2005).

The top upregulated genes in root included: Subtilase family protein; sulfate transporter 2,1; Uridine diphosphate glycosyltransferase 74E2; ATPase E1-E2 type family protein/haloacid dehalogenase-like hydrolase family protein; early nodulin-like protein 15.

Subtilases are a family of subtilisin-like serine proteases expanded in plants by functional diversification—for instance they are involved in development of plants and stress response like resistance to pathogens (Chichkova et al., 2004) or establishment of symbiosis (Takeda et al., 2004).

Sulfate transporters in the roots are responsible for uptake of the micronutrient sulfate (Takahashi et al., 1997). In legumes, nodule-specific sulfate transporters provide sulfate from the plant host to the *rhizobia*, where sulfate is necessary for synthesis of the nitrogen-fixing enzyme nitrogenase, among other proteins (Krusell et al., 2005).

Uridine diphosphate glycosyltransferases (UGT) are a superfamily of regulatory enzymes that modify the activity, solubility, and transport of plant hormones, secondary metabolites, and xenobiotics, thus participating in plant developmental regulation, biotic stress responses, and detoxification of pollutants and herbicides (Ross et al., 2001; Wang 2009).

The haloacid dehalogenase-like hydrolases (HAD) are a large family of enzymes with diverse activities, all involving cleaving bonds between a carbon and a halogen, or a carbon and a phosphorus-containing group (Caparrós-Martin, 2013). In mustard (*Brassica juncea*), a putative haloacid dehalogenase-like hydrolase was upregulated following cadmium exposure, suggesting a role in abiotic stress responses (Minglin et al., 2005).

Nodulin-encoding genes are specifically expressed during the development of symbiotic root nodules (Legocki and Verma, 1980). Upon nodule formation bacteria differentiate into nitrogen-fixing bacteroids that are beneficial to the plants (Kereszt et al., 2011). Nodulin proteins serve transport and regulatory functions in symbiosis (Fortin et al., 1985).

The following genes were downregulated in leaf: branched-chain amino acid transaminase 2; myb domain protein 62; Protein of unknown function (DUF506); Regulator of chromosome condensation (RCC1) family protein; Dynein light chain type 1 family protein; Acyl-CoA N-acyltransferases (NAT) superfamily protein.

Plants synthesize the amino acids valine, leucine, and isoleucine from the products of branched-chain amino acid (BCAA) metabolism, in which BCAA transaminase plays a key role (Binder, 2010). In *Arabidopsis* and other Brassicaceae, BCAA metabolism also leads to production of glucosinolates, defensive secondary metabolites (Binder, 2010).

MYB proteins are transcription factors present across eukaryotes, involved in growth, metabolism, and stress responses in plants (Li et al., 2015).

The DUF506 family is believed to belong to the PD-(D/E)XK nuclease superfamily, involved in DNA repair and recombination (Jorgensen and Dorantes-Acosta, 2012), which is essential in preventing genotoxic stress during abiotic stress and pathogen attack (Dona et al., 2013).

The regulator of chromosome condensation (RCC) family are essential regulatory proteins in the cell cycle, responsible for ensuring mitosis does not begin before DNA replication is completed (Dasso, 1993). DNA maintenance is essential in preventing genotoxic stress during abiotic stress and pathogen attack (Dona et al., 2013).

Dynein is an essential molecule for intracellular transport, physically moving proteins, vesicles, and small organelles along a network of microtubules (Lo et al., 2001).

Acyl-CoA acyltransferases are a group of enzymes involved in synthesizing triacylglycerol, which accumulates in the seed, permitting normal seed embryo development (Zhang et al., 2009) and providing the main component of soybean oil (Wang et al., 2006).

The top downregulated genes in root tissue included: GAST1 protein homolog 3; oxidative stress 3; S-adenosyl-L-methionine-dependent methyltransferases superfamily protein; Late embryogenesis abundant protein, group 1 protein; Peroxidase superfamily protein.

Gibberellic acid-stimulated transcript (GAST) proteins in tomato and their homologs in *Arabidopsis*, rice, and other plant species regulate growth and development in relation to gibberellin signaling, including the development of roots and reproductive structures (Herzog et al., 1995; Ben-Nissan and Weiss, 1996; Furukawa et al., 2006).

The Oxidative Stress 3 (OXS3) protein improves tolerance to heavy metals and oxidative stress, possibly by acting as a chromatin remodeling factor to coordinate stress responses (Blanvillain et al., 2008).

S-adenosylmethionine synthase, which catalyzes synthesis of s-adenosylmethionine from methionine and ATP, functions as a primary methyl-group donor and as a precursor for metabolites such as ethylene, polyamines, and vitamin B1 (Hesse et al., 2004).

Late embryogenesis abundant proteins (LEA) provide desiccation tolerance by changing their folding during drying, possibly creating a water shell under drought and stabilizing cellular components in the absence of water under full desiccation (Shih et al., 2008). The LEA gene HVA1 was successfully transferred from barley into rice to provide water deficit and salt stress tolerance (Xu et al., 1996).

In plants, peroxidases are involved in cell wall lignification, usually associated with pathogen resistance (Bruce and West, 1989), abiotic stress (Huttovi et al., 2006; Quiroga et al., 2001), or cell wall modification during growth (Arnaldos et al., 2002; G Martinez Pastur, 2001; Van Hoof and Gaspar, 1976; Kukavica et al., 2012).

Up/Down Regulated Genes that are Significantly Represented in Plants Grown from Seeds Treated with Strain C Versus Plants Grown from Seeds Treated with Strain a or Strain B All results are summarized in Table 8E.

In case of Streptomycetes Strain C-top upregulated genes or transcripts are expressed at much higher levels than in semi-beneficial strain Strain B compared to control Strain A suggesting presence of genes or transcripts that will lead to drought protection and subsequently yield increase.

The top upregulated genes in leaf included: PQ-loop repeat family protein/transmembrane family protein; NAD (P)-binding Rossmann-fold superfamily protein; Senescence associated gene 18; Integrase-type DNA-binding superfamily protein; Small and basic intrinsic protein 1A.

PQ-loop repeat family proteins are composed of seven predicted transmembrane domains (TMs) and serve functions in amino acid transport (Xuan et al., 2013). In soybean, PQ-loop repeat genes were found to be upregulated in the tolerant genotype 15 days post-infestation by aphids, suggesting their implication in plant tolerance to biotic stress (Prochaska et al., 2015).

NAD(P)-binding Rossmann-fold superfamily protein is involved in oxidoreductase activity, binding, and catalytic activity (Hanukoglu, 2015).

Genes with increased expression during senescence, identified in multiple plant species, are often referred to as SAGs or senescence-upregulated genes (Buchanan-Wollaston, 1997). Senescence associated gene 18 (SAG18) encodes a novel protein (Weaver et al., 1998) and was found to be induced by ozone (Miller et al., 1999). While the initiation of leaf senescence is developmentally regulated, external factors such as nutrient deficiency, pathogenic attack, drought, light limitation, and temperature can induce premature senescence (Smart, 1994).

Integrase-type DNA-binding superfamily protein is a member of the DREB subfamily A-2 of ERF/AP2 transcription factor family that have important functions in the transcriptional regulation of a variety of biological processes related to growth and development, as well as various responses to environmental stimuli like drought (Nakano et al., 2006; Ding et al., 2013).

Small and basic intrinsic protein 1A belongs to a family of plant aquaporins (Ishikawa et al., 2005). In plants, aquaporins occur as multiple isoforms localized in the plasma membrane, endoplasmic reticulum, vacuoles, plastids and, in some species, in membrane compartments interacting with symbiotic organisms. In addition to water, plant aquaporins can transport various physiological substrates and dissolved gases such as carbon dioxide and ammonia or metalloids such as boron and silicon. Although they play a central role in water relations of roots, leaves, seeds, and flowers, aquaporins have also been linked to plant mineral nutrition, response to light, temperature and carbon and nitrogen fixation (Maurel et al., 2015).

Top upregulated genes in root included: Subtilase family protein; Beta-6 tubulin; Cytochrome P450, family 71, subfamily A, polypeptide 19; Serine carboxypeptidase-like 40; Nuclear factor Y, subunit C4.

Subtilases are a family of subtilisin-like serine proteases expanded in plants by functional diversification—for instance they are involved in development of plants and stress response like resistance to pathogens (Chichkova et al., 2004) or establishment of symbiosis (Takeda et al., 2004).

Beta-6 tubulin (TUB6) is a structural constituent of cytoskeleton involved in microtubule-based process, response to salt stress, response to cold and it is expressed in multiple plant structures and growth stages (Oppenheimer et al., 1988).

Cytochromes P450 are involved in the biosynthetic pathway of major phytoalexins—chemicals synthesized by plants to deter microbes or insects (Schuler MA1, Berenbaum MR. 2013). In soybean, Cytochrome P450-dependent enzymes are involved in an elicitor-inducible glyceollin biosynthesis (P450s) (Schopfer and Ebel, 1998).

Serine carboxypeptidase-like (SCPL) proteins have emerged as a new group of acyltransferase enzymes that function in a broad range of biochemical pathways, including secondary metabolite biosynthesis, herbicide conjugation, and germination-associated degradation of seed protein reserves (Lehfeldt et al., 2000). They were demonstrated to be involved in normal plant growth and development, synthesis of compounds that protect plants against pathogens, insects and UV light, and for resistance to natural and manmade xenobiotics (Mugford et al., 2009).

Nuclear factor Ys (NF-Ys) are heterotrimeric transcription factors evolutionary conserved in yeast, mammals and plants composed of three subunits: NF-YA, NF-YB, and NF-YC, which bind with high affinity and specificity to the CCAAT box, cis elements present in many eukaryotic promoters, activating or repressing transcription of the downstream genes (Ceribelli et al., 2008). More recently, plant NF-Y genes have gained major interest due to their roles in many biological processes in plant development or adaptation to environmental conditions, particularly in the root nodule symbiosis established between legume plants and nitrogen fixing bacteria (Riojas et al., 2015).

The top down-regulated genes in leaf included: Pathogenesis-related thaumatin superfamily protein; Vacuolar iron transporter (VIT) family protein; PLAT/LH2 domain-containing lipoxygenase family protein; Disease resistance protein (TIR-NBS-LRR class), putative; Protein of unknown function, DUF547.

The pathogenesis-related thaumatin-like proteins (PR-5) are inducible proteins that regulate plant-microbe interactions (Velazhahan et al., 1999). In soybean, a specific gene encoding a thaumatin-like protein in pathogenesis-related family 5 was discovered to regulate which bacterial species would be accepted in nodule formation (Hayashi et al., 2014).

The majority of disease resistance genes (R genes) in plants encode nucleotide-binding site leucine-rich repeat (NBS-LRR) proteins. This large family is encoded by hundreds of diverse genes per genome and can be subdivided into the functionally distinct TIR-domain-containing (TNL) and CC-domain-containing (CNL) subfamilies. Genetically, the LRRs of plant R proteins are determinants of response specificity, and their action can lead to plant cell death in the form of the familiar hypersensitive response (HR).

The DUF547 domain is associated with class IV glutaredoxins, a family of oxidoreductases related to thioredoxins and deeply involved in regulating activity of metabolic enzymes, transcription factors, and stress-related antioxidant enzymes (Rouhier, 2010).

The top down-regulated genes in root included: Cytochrome P450, family 71, subfamily B, polypeptide 35; Major facilitator superfamily protein; Ammonium transporter; Protein kinase superfamily protein; ABC-2 type transporter family protein.

Cytochromes P450 are involved in the biosynthetic pathway of major phytoalexins—chemicals synthesized by plants to deter microbes or insects (Schuler MA1, Berenbaum MR. 2013). In soybean, Cytochrome P450-dependent enzymes are involved in an elicitor-inducible glyceollin biosynthesis (P450s) (Schopfer and Ebel, 1998).

The major facilitator superfamily (MFS) is a class of membrane transport proteins that facilitate import/export of small solutes (drugs, metabolites, oligosaccharides, amino acids and oxyanions) across cell membranes in response to chemiosmotic gradients (Marger and Saier, 1993). In plants, MFS transporters play critical roles in withstanding harmful stresses, for example, which are involved in the transport of sugar, phosphates and nitrate, but also in plant defense against various toxin stresses by exporting toxin outside the cell (Peng et al., 2011).

Ammonium transporter proteins are encoded by multi-gene families in plants with different physiological roles, one of which is ammonium uptake from the soil (Gazzarrini et al., 1999). Recently, in soybean, a novel symbiotic ammonium transporter 1 was described as a putative ammonium (NH4+) channel localized to the symbiosome membrane of soybean root nodules playing an important role for soybean *rhizobium* symbiosis because loss of activity results in a reduction of nodule fitness and growth (Chiasson et al., 2014).

Eukaryotic protein kinase superfamily constitutes enzymes that catalyze the reversible transfer of the gamma-phosphate from ATP to amino acid side chains of proteins. In plants, protein phosphorylation has been implicated in responses to many signals, including light, pathogen invasion, hormones, temperature stress, and nutrient deprivation (Laurie and Halford, 2001).

ABC transporters, driven by ATP hydrolysis, constitute one of the largest protein families found in all living organisms (Jones and George, 2004). ABC transporters were originally identified as transporters involved in detoxification processes, that have been later shown to be required for organ growth, plant nutrition, plant development, response to abiotic stresses, pathogen resistance and the interaction of the plant with its environment (Kang et al., 2011).

Up/Down Regulated Transcripts that are Significantly Represented in Strain C Treated Plants Vs. The *Streptomyces* Strains Strain B and Strain a All results are summarized in Table 8F.

Compared to plants grown from seeds treated with Strain B or Strain A, there were significantly increased (>=5x) or decreased (<=5x) transcripts in plants grown from seeds treated with the beneficial endophyte *Streptomyces* Strain C. Plants grown from seeds treated with Strain C displayed the best phenotypes under drought conditions, and best final harvest yield and plant scores.

Expression Patterns in Putative Sugar Transporter Genes in *Streptomyces*

A total of 16 genes annotated with sugar transporter domains (PF00083, PF04142, PF07690) were upregulated in roots or leaves of soybeans treated with *Streptomyces* Strain B and Strain C relative to roots of untreated controls, and downregulated in roots and leaves of soybeans treated with *Streptomyces* Strain A. These genes are annotated as components of membranes having transmembrane transporter activity. The soybean gene Glyma.06G313500 was found to be down regulated in both leaf and root tissue in Strain A treated soybean and upregulated in both leaf and root tissue in Strain B and Strain C. Glyma.06G313500 is a homolog of the *Arabidopsis thaliana* gene zinc induced facilitator-like 1 (ZIFL1) which is involved in the directional transport of the plant hormone auxin between cells (Remy, Baster, Friml, & Duque, 2013). Results are shown in Table 9.

The inventors particularly point out the correlation between the upregulation of transcription of sugar transporter genes in plant tissues of plants grown from seeds treated with a beneficial *Streptomyces* strain Strain B or Strain C as compared to Strain A, and the increased numbers of arabinose transporter genes of beneficial *Streptomyces* strains Strain B or Strain C as compared to the genome of Strain A (as described in Example 2). Increases in sugar transport for both the microbe and the plant were an important feature of a beneficial *Streptomyces* endophyte-plant relationship.

Example 9: Identification of Differentially Regulated Hormones

Methods

For hormone analysis, 100±10 mg tissue was measured into microtubes (chilled with liquid nitrogen), and sent on dry ice to the lab of Dr. Michael Kolomiets in the Department of Plant Pathology and Microbiology at Texas A&M University. Plant hormone analysis was performed per Christiansen et al. (2014) with slight modification. Briefly, hormones were extracted from 100±10 mg of frozen tissue and tissue weights were recorded for quantification. A mixture containing 10 microliters of 2.5 microMolar internal standards and 500 microliters of extraction buffer [1–propanol/H2O/concentrated HCl (2:1:0.002, vol/vol/vol) was added to each sample and vortexed until thawed. Samples were agitated for 30 min at 4° C., then 500 microliters of dichloromethane (CH2Cl2) were added. Samples were agitated again for 30 min at 4° C., and then centrifuged at 13,000×g for 5 min. in darkness. The lower organic layer was removed into a glass vial and the solvent was evaporated by drying samples for 30-40 min under a N2 stream. Samples were re-solubilized in 150 microliters of MeOH, shaken for 1 min and centrifuged at 14,000×g for 2 min. A supernatant of 90 microliters was transferred into the autosampler vial and hormones were analyzed by ultraperformance liquid chromatography, coupled to mass spectrometry (UPLC-MS/MS). Ascentis Express C-18 Column (3 cm×2.1 mm, 2.7 cm) connected to an API 3200 using electrospray ionization-tandem mass spectrometry (MS/MS) with scheduled multiple reaction monitoring (SMRM). The injection volume was 5 microliters and had a 300 microliters/min mobile phase consisting of Solution A (0.05% acetic acid in water) and Solution B (0.05% acetic acid in acetonitrile) with a gradient consisting of (time—% B): 0.3-1%, 2-45%, 5-100%, 8-100%, 9-1%, 11—stop. Quantitation was carried out with Analyst software (AB Sciex), using the internal standards as a reference for extraction recovery. Leaf and root tissue was saved in −62° C. and saved for subsequent gene expression analysis.

Mass spectra of 8 plant hormones were obtained: jasmonic acid (JA), jasmonic acid-isoleucine (JA-Ile), salicylic acid (SA), abscisic acid (ABA), 12-oxo-phytodienoic acid (OPDA), 10-oxo-11 phytoenoic acid (OPEA), traumatic acid (TA) and cinnaminic acid (CA). Fold changes between control and treated samples were calculated by dividing the mass spectrum value from the treated sample by the value from the control sample.

Results

Normal Watering Conditions

All results are summarized in Table 10A.

The plant hormone analysis of soybean plants inoculated with endophytic bacterial strain Strain C grown under a normal (well watered) watering regime in the greenhouse revealed that Strain C augmented and modified hormone levels in different tissue types in planta.

Plant phytohormone ABA is involved in regulation of developmental processes such as seed maturation and dormancy (Baker et al., 1988), responses to environmental stresses (Shinozaki and Yamaguchi-Shinozaki, 2000) including stomatal closure (McAinsh, 1990) and expression of stress-related genes (Urao et al., 1993). Data show that ABA levels were highly upregulated in roots of Strain C-treated plants grown under normal watering condition.

Salicylic acid (SA) is considered one of the key endogenous component involved in local and systemic defense responses in plants (Shah and Klessig, 1999). SA is synthesized through phenylpropanoid pathway from cinnamic acid (CA) via two possible pathways (Klambt, 1962; el-Basyouni et al., 1964). Cinnamic acid is a precursor for biosynthesis of the polyphenol compounds (Lee et al., 1995) that have multiple functions, such as providing mechanical support (lignins) (Whetten and Sederoff, 1992), protection against abiotic and biotic stress (antioxidants) (Dixon and Paiva, 1995), and signaling with the flavonoid nodulation factors (Weisshaar and Jenkins, 1998). Our data show that pattern of expression of SA and CA is very similar to ABA.

Lipoxygenases catalyze the dioxygenation of polyunsaturated fatty acids in lipids collectively known as oxylipins. Oxylipins are involved in a number of developmental or stress response processes (Andersson et al., 2006) and they exert protective activities either as signaling molecules in plants during development, wounding, insect and pathogen attack, or direct anti-microbial substances that are toxic to the invader (Yan Y et al., 2013). Particularly well studied examples of the plant oxylipins are jasmonates (JAs) that are formed by the enzymatic action of 13-LOX on linolenic acid that enables production of 12-oxo-phytodienoic acid (OPDA) and its downstream products such as free JA, MeJA, cis-jasmone and JA-Ile (Göbel and Feussner, 2009). Down-regulation is observed in root tissues of well-watered plants. Our results are in line with evidence showing that depending on particular stress, JA can act both synergistically and antagonistically with salicylic acid (Beckers and Spoel, 2006) and abscisic acid (ABA) (Anderson et al., 2004) in plant-pathogen or -insect interactions. In addition, our data demonstrates that the levels of JA and JA-Ile were upregulated in leaves of well-watered plants.

Depending on the source of the enzyme, lipoxygenase activity on linolenic acid will yield either 9- or 13-hydroperoxides which are further metabolized into diverse oxylipins (Andersson et al., 2006; Göbel and Feussner, 2009). Hydroperoxide lyase can then catalyze the breakdown of 13-hydroperoxylinolenic acid to C12 and C6 moieties that are further metabolized to traumatic acid (TA) and the various C6 aldehydes and alcohols (Croft et al., 1993). Traumatic acid, which is produced from both linoleic acid and linolenic acids, is a plant wound hormone associated with cell proliferation in plants (Vick and Zimmerman, 1987) and causes abscission in cotton buds (Strong and Kruitwagen, 1967). Data show that TA is upregulated in all tissues of metabolically active well-watered plants.

A parallel pathway involving 9-LOX activity on linoleic acid leads to the production of 10-oxo-11-phytoenoic acid (OPEA). Despite structural similarity to jasmonates, physiological roles for OPEA is not well understood. This hormone is highly induced at the site of pathogen infection and it can suppress the growth of mycotoxigenic fungi suggesting more specialized roles in local defense reactions (Christensen et al., 2015). Even though OPDA and OPEA may have slightly different biological functions, they belong to the same pathway and show similar pattern of expression in our experiments: down-regulated under normal condition (except OPDA, stem tissue).

Water-Limited (Drought) Conditions

All results are summarized in Table 10B.

The plant hormone analysis of soybean plants inoculated with endophytic bacterial strain Strain C grown under drought watering regime in the greenhouse revealed that Strain C augmented and modified hormone levels in different tissue types and growth conditions in planta (Table 7).

Our data shows that the levels of the plant hormone abscisic acid (ABA) levels were decreased in Strain C-treated plants in all three tissue types in plants exposed to drought, compared to plants grown from seed treated with formulation only and exposed to drought. ABA is involved in regulation of developmental processes such as seed maturation and dormancy (Baker et al., 1988), responses to environmental stresses (Shinozaki and Yamaguchi-Shinozaki, 2000) including stomatal closure (McAinsh, 1990) and expression of stress-related genes (Urao et al., 1993). ABA negatively affects root nodule formation (Phillips, 1971; Bano and Harper, 2002). Thus, plants treated with compositions such as Strain C may have an improved ability to cope with the stresses associated with water-limited conditions, via decreased expression of ABA.

Our data shows that the pattern of expression of salicylic acid (SA) and cinnamic acid (CA) is very similar to ABA, with slightly upregulated levels of SA and CA in leaf tissues. SA is an endogenous component involved in local and systemic defense responses in plants (Shah and Klessig, 1999). At the infection site, the plant triggers localized programmed cell death, a phenomenon known as the hypersensitive response (Caplan et al., 2008), followed by accumulation of SA, and an induction of pathogenesis-related proteins in distal tissues to protect plants from secondary infections. This type of protection is called systemic acquired resistance (SAR) and it provides broad-spectrum resistance against pathogenic fungi, oomycetes, bacteria and viruses (Shah and Klessig, 1999). The protective effect of SAR can last for months, and possibly even throughout the whole growing season (Kuc, 1987). SA is synthesized through phenylpropanoid pathway from cinnamic acid (CA) via two possible pathways (Klambt, 1962; el-Basyouni et al., 1964). Cinnamic acid is a precursor for biosynthesis of the polyphenol compounds (Lee et al., 1995) that have multiple functions, such as providing mechanical support (lignins) (Whetten and Sederoff, 1992), protection against abiotic and biotic stress (antioxidants) (Dixon and Paiva, 1995), and signaling with the flavonoid nodulation factors (Weisshaar and Jenkins, 1998). Thus, plants treated with compositions such as Strain C may have an improved ability to cope with the stresses associated with water-limited conditions, via modulation of expression of SA and/or CA.

Jasmonic acid (JA) and its derivative jasmonic acid isoleucine (JA-Ile) are down-regulated in Strain C-treated plants grown under water-limited conditions, in all tissues. Jasmonates (JAs) are formed by the enzymatic action of 13-LOX on linolenic acid that enables production of 12-oxo-phytodienoic acid (OPDA) and its downstream products such as free JA, MeJA, cis-jasmone and JA-Ile (Göbel and Feussner, 2009). JAs are a type of oxylipins, which are involved in a number of developmental or stress response processes (Andersson et al., 2006) and they exert protective activities either as signaling molecules in plants during development, wounding, insect and pathogen attack, or direct anti-microbial substances that are toxic to the invader (Yan Y et al., 2013). Oxylipins are formed by the dioxygenation of polyunsaturated fatty acids in lipids, a reaction catalyzed by lipoxygenases. Thus, plants treated with compositions such as Strain C may have an improved ability to cope with the stresses associated with water-limited conditions, via decreased expression of JA and/or JA-Ile.

Levels of traumatic acid (TA) are down-regulated in all tissues of Strain C-treated plants grown under water-limited conditions. TA, which is produced from both linoleic acid and linolenic acid, is a plant wound hormone associated with cell proliferation in plants (Vick and Zimmerman, 1987) and causes abscission in cotton buds (Strong and Kruitwagen, 1967). Thus, plants treated with compositions such as Strain C may have an improved ability to cope with the stresses associated with water-limited conditions, via decreased expression of TA.

In Strain C-treated plants grown under water-limited conditions, OPDA levels were slightly but not significantly decreased in root tissues, and significantly increased in both stem and leaf tissues. OPEA levels were increased in all tissues of Strain C-treated plants grown under water-limited conditions. Despite structural similarity to jasmonates, physiological roles for OPEA is not well understood. This hormone is highly induced at the site of pathogen infection and it can suppress the growth of mycotoxigenic fungi suggesting more specialized roles in local defense reactions (Christensen et al., 2015). Thus, plants treated with compositions such as Strain C may have an improved ability to cope with the stresses associated with water-limited conditions, via modulation of expression of OPEA and/or OPDA.

Example 10: Identification of Differentially Regulated Metabolites (Metabolomics)

Methods

For metabolite analysis, 150±10 mg of each sample was transferred into 1.5 mL microtubes (chilled in liquid nitrogen) and sent on dry ice to the Proteomics and Metabolomics Facility at Colorado State University. Metabolomics data acquisition was performed per the following methods provided by Dr. Corey Broeckling at CSU. To prepare the samples for analysis, phytohormones were extracted from ground plant material using a biphasic protocol. One mL of a methyl tert-butyl ether (MTBE): methanol:water mixture (6:3:1) was added to each sample then shaken for 1 hour. Next, 250 microliters cold water and a mix of internal standards was added to each sample to promote phase separation. Samples were shaken again for 5 minutes. Samples were then centrifuged at 2,095×g at 4° C. for 15 minutes. The organic top phase was removed for hormone analysis, dried under an inert nitrogen environment, then re-suspended in 400 microliters of 50% acetonitrile. Extracts were then directly analyzed by LC-MS.

For GC-MS, the polar (lower phase) extract was dried using a speedvac, resuspended in 50 microliters of pyridine containing 50 mg/mL of methoxyamine hydrochloride, incubated at 60° C. for 45 min, sonicated for 10 min, and incubated for an additional 45 min at 60° C. Next, 25 microliters of N-methyl-N-trimethylsilyltrifluoroacetamide with 1% trimethylchlorosilane (MSTFA+1% TMCS, Thermo Scientific) was added and samples were incubated at 60° C. for 30 min, centrifuged at 3000×g for 5 min, cooled to room temperature, and 80 microliters of the supernatant was transferred to a 150 microliters glass insert in a GC-MS autosampler vial. Metabolites were detected using a Trace GC Ultra coupled to a Thermo ISQ mass spectrometer (Thermo Scientific). Samples were injected in a 1:10 split ratio twice in discrete randomized blocks. Separation occurred using a 30 m TG-5MS column (Thermo Scientific, 0.25 mm i.d., 0.25 micrometer film thickness) with a 1.2 mL/min helium gas flow rate, and the program consisted of 80° C. for 30 sec, a ramp of 15° C. per min to 330° C., and an 8 min hold. Masses between 50-650 m/z were scanned at 5 scans/sec after electron impact ionization. The ionization source was cleaned and retuned and the injection liner replaced between injection replicates. Analysis for plant hormones was performed by UPLC-MS/MS as follows.

Over 1250 metabolites were detected and mass spectra annotated by comparing to libraries of known spectra including an in-house database of ~1200 compounds at CSU (LC-MS only), the National Institute of Standards and Technology databases, Massbank MS database, and the Golm Metabolite Database. Initial annotation was automated, followed by manual validation of annotations. Following annotation, approximately 160 compounds were identified. After removal of technical artifacts (e.g. siloxane), and ambiguous or vague annotations (e.g. carbohydrate or saccharide), 145 identified compounds remained for analysis. These compounds were assessed for fold change over control plants. Metabolites were grouped by pathways (e.g. carbohydrate metabolism or alkaloid biosynthesis) and the KEGG database and literature were manually referenced to identify pertinent shifts in metabolic patterns in plants treated with microbes. Any compound without an appreciable shift compared to that observed in control plants was removed from further analysis.

Results

Normal Watering Conditions

All results are summarized in Table 11A.

An important metabolic system in plants involves the production of phenylpropanoid compounds. SYM treatments show modulation of phenylpropanoid production under well-watered conditions, often in a tissue-specific manner, as well as causing alterations in the levels of aromatic amino acid precursors (phenylalanine, tyrosine, tryptophan) that feed into these pathways. Lignin, for example, is an important structural component in plants, second in abundance only to cellulose. Strain C-treatment under well-watered conditions stimulates relative increases in a variety of lignin precursors in stem tissue (caffeic acid) and leaf tissue (sinapic acid, ferulic acid).

Another diverse group of plant metabolites, the alkaloids, may be constitutively synthesized in the plant or may be produced de novo. Although alkaloids can be synthesized in response to stresses such as wounding, they are also transiently produced in early stages of plant development (Cheong et al., 2002). Strain C treatments elicit a variety of alterations in alkaloid biosynthetic pathways under well-watered conditions. An increase in pipecolic acid is observed in root tissues of Strain C-treated plants under normal watering regimes. Strain C also appears to have a positive effect on the transportation of tryptophan, an important alkaloid precursor, as evinced by its accumulation in stem tissues of plants under normal watering regime.

Flavonoid and isoflavonoids compounds are exuded by plant roots into the rhizosphere in response to nutrient stress in order to recruit compatible nitrogen-fixing bacteria. These signals are perceived by N-fixing *rhizobia*, which then begin production of nodulation factors that stimulate the development of nodules in the roots of the host plant (Gibson et al., 2008).

A variety of other metabolites appear to be modulated by Strain C treatments. For instance, a direct precursor to brassinosteroid production, campesterol, is increased relative to control in well-watered leaf tissue treated with Strain C. Lumichrome has the ability to affect plant root respiration, transpiration rates, as well as stomatal conductance in a variety agrinomically relevant plants (Phillips et al., 1999, Matiru and Dakora, 2005). In addition to production by members of the *Rhizobia*, it has been shown that soil microbes such as *Pseudomonas* can degrade riboflavin to lumichrome in rhizosphere systems (Yanagita and Foster, 1956). Well-watered plants present with decreased amounts of lumichrome in plants grown from Strain C treated seeds.

In addition to the specific compounds and pathways above, SYM treatments cause significant modulation in the levels of free amino acids and nitrogenous compounds. Allantoin, a product of urea metabolism, can constitute a large percentage of the soluble nitrogen in plant sap and may be integral in nitrogen transport in nodulated soybean plants (Reinbothe and Mothes, 1962; McClure and Israel, 1979Strain C-treatment modulates allantoin accumulation in various tissues. Well-watered plants accumulate allantoin in both stem and leaf tissue, perhaps denoting an increase in nitrogen transport and metabolism, or an increase in N-assimilation. Strain C treatment causes an increase in the levels of several amino acids in stem tissue of well-watered plants.

The metabolism of carbohydrates and lipids also shift under SYM treatment. Carbohydrates and lipids are utilized in a wide range of functions, whether for energy storage, as signaling molecules, or the composition of structural material. Treatment by Strain C modulates the levels of a variety of carbohydrate and lipid metabolites including galactose, which is increased in stem and leaf tissue of well-watered plant). Fatty acids may serve as precursors to lipid-based hormones such as the jasmonates. Strain C appears to affect lipid metabolism as shown by the modulation in levels of a variety of fatty acids (hexadecanoic acid) as well as other precursors to lipid biosynthesis (ethanolamine, sphingosine).

Water-Limited (Drought) Conditions

All results are summarized in Table 11B.

An important metabolic system in plants involves the production of phenylpropanoid compounds. The production of a wide variety of phenylpropanoids may be influenced by stress conditions and important plant signaling molecules. The shikimic acid pathway sits atop many of these mechanisms as it produces the cyclic amino acids that constitute the raw materials for many defense compounds. Strain C treatments show modulation of phenylpropanoid production under drought conditions, often in a tissue-specific manner, as well as causing alterations in the levels of aromatic amino acid precursors (phenylalanine, tyrosine, tryptophan) that feed into these pathways. All tested phenylpropanoid compounds (phenylalanine, shikimic acid, tyrosine, quinic acid, sinapic acid, ferulic acid, caffeic acid) displayed reduced production under water-limited conditions in leaf tissues; all but phenylalanine and shikimic acid displayed reduced production in root tissues; ferulic acid alone demonstrated increased production in stem tissues. Thus, plants treated with compositions such as Strain C may have an improved ability to cope with the stresses associated with water-limited conditions, via modulation of production of phenylpropanoids.

Another diverse group of plant metabolites, the alkaloids, may be constitutively synthesized in the plant or may be produced de novo. Although alkaloids can be synthesized in response to stresses such as wounding, they are also transiently produced in early stages of plant development (Cheong et al., 2002). Strain C treatments elicited a variety of alterations in alkaloid biosynthetic pathways under drought conditions. For instance, 2-piperidinecarboxylic acid (pipecolic acid), which accumulates in plants in response to pathogen attack and has been shown to accumulate in halotolerant species (Navarova et al., 2012, Moulin et al., 2006). Pipecolic acid, a non-protein amino acid and degradation product of the amino acid lysine, is an intermediary of tropane alkaloid biosynthesis. A relative increase in pipecolic acid was observed in root tissues of Strain C-treated plants. Strain C also appears to have a positive effect on the transportation of tryptophan, an important alkaloid precursor, as evidenced by its accumulation in stem tissues of plants. In addition to these, the following compounds involved in alkaloid biosynthetic pathways were altered in Strain C-treated plants grown under water-limited conditions: phenylalanine (decreased production in leaf), tyrosine (decreased production in leaf and root), tryptamine (decreased production in leaf), benzoic acid (decreased production in root and leaf), nicotinic acid (decreased production in root and leaf). Thus, plants treated with compositions such as Strain C may have an improved ability to cope with the stresses associated with water-limited conditions, via modulation of production of alkaloids.

Flavonoid and isoflavonoids compounds are exuded by plant roots into the rhizosphere in response to nutrient stress in order to recruit compatible nitrogen-fixing bacteria. These signals are perceived by N-fixing *rhizobia*, which then begin production of nodulation factors that stimulate the development of nodules in the roots of the host plant (Gibson et al., 2008). Indeed, one study showed that *Rhizobium legumi-nosarum* cells pretreated with plant-produced hesperetin stimulate increased nodulation in the host compared to bacteria that are not pretreated (Begum et al., 2001). Hesperetin levels showed a relative increase in stem tissue of drought plants treated with Strain C and a decrease in leaf tissue. In addition to playing a role in symbiosis development, these compounds may also function in pathogen response. Daidzein, which was decreased in roots and leaves of Strain C-treated plants, accumulates in soybean plants in response to invasion by pathogenic *Pseudomonas* (Osman and Fett, 1982). In altering the accumulation of two distinct (iso)-flavonoid compounds Strain C may be influencing both stress response and the recruitment and colonization of beneficial N-fixing symbionts. In addition to hesperetin and diadzein, the following compounds were evaluated in Strain C-treated plants grown under water-limited conditions: quinic acid (decreased production in root and leaf tissues) and shikimic acid (decreased in leaf tissues). Thus, plants treated with compositions such as Strain C may have an improved ability to cope with the stresses associated with water-limited conditions, via modulation of production of flavonoids and/or isoflavonoids.

A variety of other compounds, such as those involved in lipid and/or fatty alcohol metabolism, appear to be modulated by Strain C treatments. The following compounds were evaluated in Strain C-treated plants grown under water-limited conditions: ethanoliamine (increased in stem tissues and decreased in leaf tissues), ethanolaminephosphate (decreased in leaf tissues), sphingosine (decreased in both stem and leaf tissues), glycerol (increased in stem tissues), hexadecanoic acid (increased in both root and stem tissues), octadecadienoic acid (decreased in leaf tissues), octadecanoic acid (increased in both root and stem tissues and decreased in leaves), dodecanol (decreased in both root and leaf tissues), and campesterol (decreased in leaf tissues). Thus, plants treated with compositions such as Strain C may have an improved ability to cope with the stresses associated with water-limited conditions, via modulation of production of compounds involved in lipid and/or fatty alcohol metabolism.

In addition to the specific compounds and pathways above, SYM treatments cause significant modulation in the levels of free amino acids and nitrogenous compounds. Allantoin, a product of urea metabolism, can constitute a large percentage of the soluble nitrogen in plant sap and may be integral in nitrogen transport in nodulated soybean plants (Reinbothe and Mothes, 1962; McClure and Israel, 1979). Interestingly, Strain C-treatment modulates allantoin accumulation in various tissues. Strain C appears to cause a general depression in free-amino acids in leaf and root tissues under drought stress, with decreases in both leaf and root tissues observed for the following compounds: alanine, allantoin, glutamic acid, glutamine, histidine, leucine, methionine, proline, threonine, tryptophan, tyrosine, and valine. Additionally, decreases in root tissue alone were seen for: asparagine and aspartic acid. Decreases in leaf tissue alone were seen for: beta-alanine, isoleucine, phenylalanine, and serine. For stem tissues, any modulation of concentration was always an increase, and seen for the following compounds: glutamine, histidine, leucine, tryptophan, and valine. Thus, plants treated with compositions such as Strain C may have an improved ability to cope with the stresses associated with water-limited conditions, via modulation of production of free amino acids and/or nitrogen metabolism.

The metabolism of carbohydrates and lipids also shift under Strain C treatment. Carbohydrates and lipids are utilized in a wide range of functions, whether for energy storage, as signaling molecules, or the composition of structural material. Treatment by Strain C modulates the levels of a variety of compounds, including increases in stem tissues and decreases in root tissues seen for D-glucopyranose, and decreases in leaf tissues for each of the following: galactose, lyxose, threose, and trehalose. Thus, plants treated with compositions such as Strain C may have an improved ability to cope with the stresses associated with water-limited conditions, via modulation of production of carbohydrates.

Finally, other compounds were found to have modulated levels of production in Strain C-treated plants grown under water-limited conditions. For example, leaf tissue of plants treated with Strain C accumulates higher levels of lumichrome than control plants under water-limiting conditions. Lumichrome has the ability to affect plant root respiration, transpiration rates, as well as stomatal conductance in a variety agrinomically relevant plants (Phillips et al., 1999, Matiru and Dakora, 2005). In addition to production by members of the *Rhizobia*, it has been shown that soil microbes such as *Pseudomonas* can degrade riboflavin to lumichrome in rhizosphere systems (Yanagita and Foster, 1956). Further, lumichrome can promote plant growth, perhaps through its ability to stimulate increases in photosynthetic rates (Matiru and Dakora, 2005; Khan et al., 2008). Other compounds whose levels are altered as a result of treatment with Strain C included: salicylic acid (decreased in root and leaf tissues, increased in stem tissues), pyrogallol (decreased in root tissues), vanillic acid (increased in stem tissues and decreased in leaf tissues), gallic acid (decreased in leaf tissues), beta-tocopherol (decreased in root tissues), and galacturonic acid (decreased in root tissues). Thus, plants treated with compositions such as Strain C may have an improved ability to cope with the stresses associated with water-limited conditions, via modulation of production of any of the preceeding compounds.

Example 11: Microbial Community Sequencing of Plants

Methods
Cultivation-independent analysis of microbial taxa based on marker gene high-throughput sequencing was performed as follows.

Leaf and root tissue was obtained from soybean plants grown from seeds treated with active and mock microbial compositions grown under water-stressed conditions (seed treatment and growth conditions described above). Whole leaves and roots were collected from 4 biological replicates per treatment. For each treatment and tissue, the biological replicates were processed independently. The roots were cleaned in successive water baths, with manual disaggregation and removal of larger pieces of material. Tissues were flash frozen in liquid nitrogen, then ground using a mortar and pestle treated with 95% ethanol and RNAse Away (Life Technologies, Inc., Grand Island, NY) to remove contaminant RNA and DNA. DNA was extracted from the ground tissues using the DNeasy DNA extraction kit (Qiagen, Hilden, Germany) according to the manufacturer's instructions.

Marker genes were amplified and sequenced from the extracted DNA. For the bacterial and archaeal analyses, the V4 hypervariable region of the 16S rRNA gene was targeted (primers 515f, 806r), and for fungi, the second internal transcribed spacer (ITS2) region of the rRNA operon (primers fITS7, ITS4) was targeted. The two marker genes were PCR amplified separately using 35 cycles, and staggered 9-bp barcoded primers specific to each sample were used to facilitate combining of samples. To reduce the amplification of chloroplast and mitochondrial DNA, PNA clamps specific to the rRNA genes in these organelles were used. PCR reactions to amplify 16S rRNA and ITS regions followed the protocol of Kozich et al. (2013) (Kozich, Westcott, Baxter, Highlander, & Schloss, 2013). PCR products were cleaned with Agencourt AMPure XP beads at a 0.7:1 bead-to-library ratio (Beckman Coulter), quantified using the PicoGreen assay (Life Technologies, Inc., Grand Island, NY) and pooled in equimolar concentrations. The final library was quantified by qPCR using the KAPA Library quantification kit (KAPA Biosystems) and diluted to 4 nM. In preparation for cluster generation and sequencing, pooled libraries were denatured with NaOH, diluted with hybridization buffer, and then heat denatured before MiSeq sequencing (Illumina). Each run included a minimum of 2.5% PhiX to serve as an internal control.

OTU Assignment
For both 16S rRNA and ITS2 sequences, the raw sequence data were reassigned to distinct samples based on barcode sequences introduced during library prep, and quality filtering and OTU (i.e. operational taxonomic unit) clustering was conducted using the UPARSE pipeline (Edgar 2013). Each endophyte was assigned to an Operational Taxonomic Unit (OTU). OTU clustering (Rideout et al, 2014) was performed using a cascading approach, comparing the sequences against the Greengenes (McDonald et al., 2012) and SILVA (Quast et al., 2013) and UNITE (Abarenkov et al., 2010) reference databases, which are provided with full-length clustering at various widths. Bacterial sequences were compared to the combined Greengenes 99% OTU representative sequences and SILVA non-redundant sequences. Sequences without a 99% match to the combined reference 99% OTUs but having a 97% match were assigned to 97% OTUs with the best match representative sequence from the 99% reference sequences. Fungal sequences were compared to the UNITE Dynamic OTU representative sequences, where dynamic represents values between 97% and 99% depending on the OTU. Sequences that did not match the UNITE Dynamic OTUs at the appropriate clustering level, but did have a 97% match were assigned to 97% OTUs with best match representative sequence from the Dynamic OTUs. The remaining sequences that did not match any of the three reference databases, Greengenes. SILVA, or UNITE, but were present at a level of at least 10 reads across the samples, were de novo clustered using UPARSE (independently for the bacterial and fungal sequences). Sequences that did not match a reference sequence were mapped to the de novo OTUs at 97%. Remaining sequences that did not match either a reference or de novo OTU were removed from this analysis.

Identification of Differences Between Treatments
Only samples having at least 1000 reads after quality filtering were retained, and only OTUs with a mean relative abundance of 0.1% within a tissue/treatment were included in this analysis. Community differences at the genus and family level were computed by summing the relative abundance of OTUs by their taxonomic assignments at the genus and family levels across all biological replicates of the tissue/treatment using the phyloseq package in R (McMurdie and Holmes (2013)) (Figures CSGen1-4 and Figures CSFam1-4). For each tissue, we identified OTUs found in all biological replicates of beneficial microbial treatment and not in microbial treatments with negative or neutral affects or in untreated controls (Tables CSUOTU1-3). OTUs with significant differences in abundance between treatments/tissues were identified using the R package DESeq2 (Love et al. 2014). Raw read counts per OTU for biological replicates of different microbial treatments and untreated controls were used as inputs to DESeq2, the log 2 fold change and adjusted p-value of each contrast are included in Tables CSDE1-2 as are the average, normalized abundance of each OTU (as counts per million) in each treatment.

Results
All results are summarized in FIGS. 7-10, Table 12, and Table 13.

In all treatments, Enterobacteriaceae was the most abundant family of bacteria in soybean leaves and *Escherichia-Shigella* the most abundant bacterial genera. Seeds treated with *Streptomyces* sp. reduced the average abundance of members of the Enterobacteriaceae family and the *Escherichia-Shigella* genera. The biggest decreases were seen in plants treated with Strain C whose mean abundance decreased 37% relative to untreated controls.

Treatment with Strain C increased the abundance of the arbuscular mycorrhizal (AM) fungi in roots of treated plants. Fungal communities of Strain C treated soybean roots are enriched in Glomeraceae, showing an increase in average abundance of 140% relative to untreated controls and 92% relative to Strain B. Glomeraceae contains several genera of AM fungi including *Rhizophagus* and *Glomus*. The *Glomus* genus of arbuscular mycorrhizal are more abundant in Strain C treated samples relative to controls, and the *Glomus* OTU F1.0|SYM97_ITS2|1707 and F1.0|SYM97_ITS2|1548 are found in all replicates of the Strain C treatment and not in Strain B or untreated samples. Additionally, the *Glomus* OTU F1.01SYM97_ITS21594 is significantly differentially abundant in Strain C treated samples relative to untreated samples.

The communities of both Strain C treated samples are enriched in OTU belonging to the genus *Rhizophagus*, compared to co-generic treatments or untreated controls. Fungal communities of Strain C treated soybean roots are enriched in *Rhizophagus*, showing an increase in average abundance of 88% relative to untreated controls and 106% relative to Strain B. The *Rhizophagus* OTUs F1.0ISYM97_ITS2|1548 and F1.0ISYM97_ITS2|1707 are found in all biological replicates of Strain C treated soybean roots but not in Strain B or untreated controls.

Example 12: Field Trials

Seeds from soybean were treated with Strain C as well as the formulation control as described in Example 4. Seeds were sown in at least two different growing regions for efficacy testing. Trials consisted of ten replicate plots for each treatment and control respectively arranged in a spatially balanced randomized complete block design (Van Es et al. 2007). The plot area was well-maintained and kept weed-, insect- and disease-free In addition to measuring total yield, metrics such as seedling emergence, normalized difference vegetation index (NDVI) and time to flowering were assessed. Trials were conducted during non-irrigated conditions.

All results are shown in Table 14.

Soybean trials under were conducted at three different locations using two soybean varieties in the Midwest region of the United States during 2015. Field conditions during the trial were particularly wet: field conditions did not constitute drought or water-limited conditions even though they were non-irrigated. No negative impacts on any measured variable was seen for plants grown from seeds treated with Strain C as compared to plants grown from seeds treated with the formulation control only. Parity was achieved for yield (bushels per acre), percent moisture (% per plot), and seed weight (pounds per bushel).

Maize trials were conducted at three different locations using four soybean varieties in the Midwest region of the United States during 2015. Field conditions during the trial were particularly wet: field conditions did not constitute drought or water-limited conditions even though they were non-irrigated. No negative impacts on any measured variable was seen for plants grown from seeds treated with Strain C as compared to plants grown from seeds treated with the formulation control only. Parity was achieved for yield (bushels per acre), percent moisture (% per plot), and seed weight (pounds per bushel). Two varieties of maize demonstrated improvements in yield for plants grown from seeds treated with Strain C as compared to plants grown from seeds treated with the formulation control only.

Example 13: Gene Enrichment Analysis

Gene set enrichment analysis (GSEA) was used to identify molecular functions, biological processes and cellular components that are enriched in the set of genes which are differentially expressed between water stressed soybean plants treated with beneficial *Streptomyces* and untreated water stressed soybean plants. Soybean genes whose expression had absolute value of log 2 fold change differences greater than two between plants treatment with a beneficial *Streptomyces* and untreated plants, the "query", were submitted to GSEA tool AgriGO (http://bioinfo.cau.edu.en/agriGO/). Singular enrichment analysis was run using Fishers exact test and multi-test adjustment using the method of Benjamini & Yekutieli (Benjamini, Y. & Yekutieli, D. (2001) The Annals of Statistics, 29(4): 1165-1188).

Results are given in Table 15.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated herein by reference. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Lengthy table referenced here

US11819027-20231121-T00001

Please refer to the end of the specification for access instructions.

Lengthy table referenced here

US11819027-20231121-T00002

Please refer to the end of the specification for access instructions.

Lengthy table referenced here

US11819027-20231121-T00003

Please refer to the end of the specification for access instructions.

Lengthy table referenced here

US11819027-20231121-T00004

Please refer to the end of the specification for access instructions.

Lengthy table referenced here

US11819027-20231121-T00005

Please refer to the end of the specification for access instructions.

Lengthy table referenced here

US11819027-20231121-T00006

Please refer to the end of the specification for access instructions.

Lengthy table referenced here
US11819027-20231121-T00007
Please refer to the end of the specification for access instructions.

Lengthy table referenced here
US11819027-20231121-T00008
Please refer to the end of the specification for access instructions.

Lengthy table referenced here
US11819027-20231121-T00009
Please refer to the end of the specification for access instructions.

Lengthy table referenced here
US11819027-20231121-T00010
Please refer to the end of the specification for access instructions.

Lengthy table referenced here
US11819027-20231121-T00011
Please refer to the end of the specification for access instructions.

Lengthy table referenced here
US11819027-20231121-T00012
Please refer to the end of the specification for access instructions.

Lengthy table referenced here
US11819027-20231121-T00013
Please refer to the end of the specification for access instructions.

Lengthy table referenced here
US11819027-20231121-T00014
Please refer to the end of the specification for access instructions.

Lengthy table referenced here
US11819027-20231121-T00015
Please refer to the end of the specification for access instructions.

Lengthy table referenced here
US11819027-20231121-T00016
Please refer to the end of the specification for access instructions.

Lengthy table referenced here
US11819027-20231121-T00017
Please refer to the end of the specification for access instructions.

Lengthy table referenced here
US11819027-20231121-T00018
Please refer to the end of the specification for access instructions.

Lengthy table referenced here
US11819027-20231121-T00019
Please refer to the end of the specification for access instructions.

Lengthy table referenced here
US11819027-20231121-T00020
Please refer to the end of the specification for access instructions.

Lengthy table referenced here
US11819027-20231121-T00021
Please refer to the end of the specification for access instructions.

Lengthy table referenced here
US11819027-20231121-T00022
Please refer to the end of the specification for access instructions.

Lengthy table referenced here
US11819027-20231121-T00023
Please refer to the end of the specification for access instructions.

Lengthy table referenced here
US11819027-20231121-T00024
Please refer to the end of the specification for access instructions.

Lengthy table referenced here
US11819027-20231121-T00025
Please refer to the end of the specification for access instructions.

Lengthy table referenced here
US11819027-20231121-T00026
Please refer to the end of the specification for access instructions.

Lengthy table referenced here
US11819027-20231121-T00027
Please refer to the end of the specification for access instructions.

Lengthy table referenced here
US11819027-20231121-T00028
Please refer to the end of the specification for access instructions.

Lengthy table referenced here
US11819027-20231121-T00029
Please refer to the end of the specification for access instructions.

Lengthy table referenced here
US11819027-20231121-T00030
Please refer to the end of the specification for access instructions.

Lengthy table referenced here
US11819027-20231121-T00031
Please refer to the end of the specification for access instructions.

Lengthy table referenced here
US11819027-20231121-T00032
Please refer to the end of the specification for access instructions.

Lengthy table referenced here
US11819027-20231121-T00033
Please refer to the end of the specification for access instructions.

Lengthy table referenced here
US11819027-20231121-T00034
Please refer to the end of the specification for access instructions.

Lengthy table referenced here
US11819027-20231121-T00035
Please refer to the end of the specification for access instructions.

Lengthy table referenced here
US11819027-20231121-T00036
Please refer to the end of the specification for access instructions.

Lengthy table referenced here
US11819027-20231121-T00037
Please refer to the end of the specification for access instructions.

Lengthy table referenced here
US11819027-20231121-T00038
Please refer to the end of the specification for access instructions.

Lengthy table referenced here
US11819027-20231121-T00039
Please refer to the end of the specification for access instructions.

REFERENCES

Abarenkov, K., Henrik Nilsson, R., Larsson, K.-H., Alexander, I. J., Eberhardt, U., Erland, S., . . . Koljalg, U. (2010, April). The UNITE database for molecular identification of fungi—recent updates and future perspectives. The New Phytologist. England.

Ainley, W. M., Walker, J. C., Nagao, R. T., and Key, J. L. (1988). Sequence and characterization of two auxin-regulated genes from soybean. J. Biol. Chem. 263, 10658-10666.

Amann et al. (2001) Current Opinion in Biotechnology 12:231-236 Anantharaman, V., Iyer, L. M. and Aravind, L., 2012. Ter-dependent stress response systems: novel pathways related to metal sensing, production of a nucleoside-like metabolite, and DNA-processing. Molecular bioSystems, 8(12), pp. 3142-3165.

Andersson, M. X., Hamberg, M., Kourtchenko, O., Brunnstrom, A., McPhail, K. L., Gerwick, W. H., Göbel, C., Feussner, I., and Ellerstrom, M. (2006). Oxylipin profiling of the hypersensitive response in *Arabidopsis thaliana*.

Formation of a novel oxo-phytodienoic acid-containing galactolipid, arabidopside E. J. Biol. Chem. 281, 31528-31537.

Angelini, R., Bragaloni, M., Federico, R., Infantino, A., and Porta-Pugua, A. (1993). Involvement of Polyamines, Diamine Oxidase and Peroxidase in Resistance of Chickpea to *Ascochyta rabiei*. J. Plant Physiol. 142, 704-709.

Arnaldos, T. L., Ferrer, M. A., Garcia, A. A. C., and Munoz, R. (2002). Changes in peroxidase activity and isoperoxidase pattern during strawberry (*Fragaria* x *ananassa*) callus development. J. Plant Physiol. 159, 429-435.

Bais, H. P., and Ravishankar, G. A. (2002). Role of polyamines in the ontogeny of plants and their biotechnological applications. Plant Cell Tissue Organ Cult. 69, 1-34.

Baker, J., dennSteele, C. V., and Iii, L. D. (1988). Sequence and characterization of 6 Lea proteins and their genes from cotton. Plant Mol. Biol. 11, 277-291.

Baquero, M. R., Bouzon, M., Quintela, J. C., Ayala, J A. and Moreno, F., 1996. dacD, an *Escherichia coli* gene encoding a novel penicillin-binding protein (PBP6b) with DD-carboxypeptidase activity. Journal of bacteriology, 178 (24), pp. 7106-7111.

Barka et al. 2006, Appl. Environ. Microbiol. 72:7246-7252

Baxter CE, Costa M M, Coen E S. 2007. Diversification and co-option of RAD-like genes in the evolution of floral asymmetry. Plant J. 2007 52(1):105-13.

Begum, A. A., Leibovitch, S., Migner, P., and Zhang, F. 2001. Specific flavonoids induced nod gene expression and pre-activated nod genes of *Rhizobium leguminosarum* increased pea (*Pisum sativum* L.) and lentil (*Lens culinaris* L.) nodulation in controlled growth chamber environments. J. Exp. Bot. 52, (360) 1537-1543.

Binder S. (2010) Branched-Chain Amino Acid Metabolism in *Arabidopsis thaliana*. The *Arabidopsis* Book 8:e0137. doi:10.1199/tab.0137

Birkett, M. A., Hassanali, A., Hoglund, S., Pettersson, J., and Pickett, J. A. (2011). Repellent activity of catmint, *Nepeta cataria*, and iridoid nepetalactone isomers against Afrotropical mosquitoes, ixodid ticks and red poultry mites. Phytochemistry 72, 109-114.

Blanvillain R, Kim J H, Wu S, Lima A, Ow D W. 2008. OXIDATIVE STRESS 3 is a chromatin-associated factor involved in tolerance to heavy metals and oxidative stress. The Plant Journal. 57(4):654-65.

Bolwell, G. P., and Daudi, A. (2009). Reactive Oxygen Species in Plant-Pathogen Interactions. In Reactive Oxygen Species in Plant Signaling, L. A. Rio, and A. Puppo, eds. (Springer Berlin Heidelberg), pp. 113-133.

Borodina, I., Krabben, P. and Nielsen, J., 2005. Genome-scale analysis of *Streptomyces coelicolor* A3 (2) metabolism. Genome research, 15(6), pp. 820-829.

Bourquin, V., Nishikubo, N., Abe, H., Brumer, H., Denman, S., Eklund, M., Christiemin, M., Teen, T. T., Sundberg, B., and Mellerowicz, E. J. (2002). Xyloglucan Endotransglycosylases Have a Function during the Formation of Secondary Cell Walls of Vascular Tissues. Plant Cell 14, 3073-3088.

Bradley, D. J., Kjellbom, P., and Lamb, C. J. (1992). Elicitor- and wound-induced oxidative cross-linking of a proline-rich plant cell wall protein: a novel, rapid defense response. Cell 70, 21-30.

Briat, J.-F., Ravet, K., Amaud, N., Duc, C., Boucherez, J., Touraine, B., Cellier, F., and Gaymard, F. (2010). New insights into ferritin synthesis and function highlight a link between iron homeostasis and oxidative stress in plants. Ann. Bot. 105, 811-822.

Brick D J, Brumlik M J, Buckley J T, Cao J-X, Davies P C, Misra S, Tranbarger T J, Upton C A. 1995. New family of lipolytic plant enzymes with members in rice, *Arabidopsis* and maize. FEBS Lett. 377 (3): 475-480.

Brisson, L. F., Tenhaken, R., and Lamb, C. (1994). Function of Oxidative Cross-Linking of Cell Wall Structural Proteins in Plant Disease Resistance. Plant Cell 6, 1703-1712.

Brown, M. S., Ye, J., Rawson, R. B. and Goldstein, J. L., 2000. Regulated intramembrane proteolysis: a control mechanism conserved from bacteria to humans. Cell, 100(4), pp. 391-398.

Bruce, R. J., and West, C. A. (1989). Elicitation of Lignin Biosynthesis and Isoperoxidase Activity by Pectic Fragments in Suspension Cultures of Castor Bean. Plant Physiol. 91, 889-897.

Buchanan-Wollaston V. 1997. The molecular biology of leaf senescence. J Exp Bot 48: 181-199

Burd et al. 2000, Can. J. Microbiol. 46:237-245

Caplan, J., Padmanabhan, M., and Dinesh-Kumar, S. P. (2008). Plant NB-LRR Immune Receptors: From Recognition to Transcriptional Reprogramming. Cell Host Microbe 3, 126-135.

Carpita, N. C., and Gibeaut, D. M. (1993). Structural models of primary cell walls in flowering plants: consistency of molecular structure with the physical properties of the walls during growth. Plant J. Cell Mol. Biol. 3, 1-30.

Carvalho, A. de O., and Gomes, V. M. (2007). Role of plant lipid transfer proteins in plant cell physiology—A concise review. Peptides 28, 1144-1153.

Ceribelli, M., Dolfini, D., Merico, D., Gatta, R., Vigano, A. M., Pavesi, G., et al. (2008). The histone-like NF-Y is a bifunctional transcription factor. Mol. Cell. Biol. 28, 2047-2058.

Cheong, Y. H., Chang, H., Gupta, R., Wang, X., Zhu, T., Luan, S. 2002. Transcriptional profiling reveals novel interactions between wounding, pathogen, abiotic stress, and hormonal responses in *Arabidopsis*. Plant Physiol. 129, 661-677.

Chepyshko H, Lai C H, Huang L M, Liu J H, Shaw J F. 2012. Multifunctionality and diversity of GDSL esterase/lipase gene family in rice (*Oryza sativa* L. *japonica*) genome: new insights from bioinformatics analysis. BMC Genomics 2012 13:309.

Chichkova N V, Kim S H, Titova E S, Kalkum M, Morozov V S, Rubtsov Y P, Kalinina N O, Taliansky M E, Vartapetian A B. 2004. A plant-caspase-like protease activated during hypersensitive response. Plant Cell. 16:157-171.

Choi et al. 2001, Planta 213:45-50

Christensen, S., Kaplan, F., Huffaker, A., Sims, J., Doehlemann, G., Teal, P., and Schmelz, E. (2015). The maize death acids, 10-oxo-11-phytoenoic acid and derivatives, demonstrate specificity in jasmonate-related signaling and defense. In 57th Annual Maize Genetics Conference, (Pheasant Run, St. Charles, Illinois), Christensen, Shawn A., et al. "The novel monocot-specific 9-lipoxygenase ZmLOX12 is required to mount an effective jasmonate-mediated defense against *Fusarium verticillioides* in Maize." Molecular Plant-Microbe Interactions 27.11 (2014): 1263-1276.

Chung, H.-J., and Ferl, R. J. (1999). *Arabidopsis* Alcohol Dehydrogenase Expression in Both Shoots and Roots Is Conditioned by Root Growth Environment. Plant Physiol. 121, 429-436.

Churin, Y., Schilling, S., and Borner, T. (1999). A gene family encoding glutathione peroxidase homologues in *Hordeum vulgare* (barley)1. FEBS Lett. 459, 33-38.

Claus Lehfeldt, Amber M. Shirley, Knut Meyer, Max 0. Ruegger, Joanne C. Cusumano, Paul V. Viitanen, Dieter Strack, and Clint Chapple. 2000. Cloning of the SNG1Gene of *Arabidopsis* Reveals a Role for a Serine Carboxypeptidase-like Protein as an Acyltransferase in Secondary Metabolism. The Plant Cell, Vol. 12, 1295-1306.

Conesa A, Gotz S, Garcia-Gomez J M, Terol J, Talon M, Robles M. 2005. Blast2GO: a universal tool for annotation, visualization and analysis in functional genomics research. Bioinformatics 21:3674-3676.

Cook, Charis M., et al. "Transcriptional changes related to secondary wall formation in xylem of transgenic lines of tobacco altered for lignin or xylan content which show improved saccharification." Phytochemistry 74 (2012): 79-89.

Crespi, M., and Frugier, F. (2008). De Novo Organ Formation from Differentiated Cells: Root Nodule Organogenesis. Sci. Signal. 1, re11-re11.

Crowell, D. N., John, M. E., Russell, D., and Amasino, R. M. (1992). Characterization of a stress-induced, developmentally regulated gene family from soybean. Plant Mol. Biol. 18, 459-466.

D. Xu, X. Duan, B. Wang, B. Hong, T H D. Ho and R. Wu. 1996. Expression of a Late Embryogenesis Abundant Protein Gene, HVA1, from Barley Confers Tolerance to Water Deficit and Salt Stress in Transgenic Rice. Plant Physiology. 110(1):249-57.

Daniels et al., (2006). PNAS 103: 14965-14970

Dao, T. T. H., Linthorst, H. J. M., and Verpoorte, R. (2011). Chalcone synthase and its functions in plant resistance. Phytochem. Rev. 10, 397-412.

Dasso, Mary. 1993. RCC1 in the cell cycle: the regulator of chromosome condensation takes on new roles. Trends in Biochemical Sciences. 18(3):96-101.

David M. Chiasson, Patrick C. Loughlin, Danielle Mazurkiewicz, Manijeh Mohammadidehcheshmeh, Elena E. Fedorova, Mamoru Okamoto, Elizabeth McLean, Anthony D. M. Glass, Sally E. Smith, Ton Bisseling, Stephen D. Tyerman, David A. Day, and Brent N. Kaiser. 2014. Soybean S AT1 (Symbiotic Ammonium Transporter 1) encodes a bHLH transcription factor involved in nodule growth and NH4+ transport. Proc Natl Acad Sci USA; 111(13):4814-4819.

De León, P., Marco, S., Isiegas, C., Marina, A., Carrascosa, J. L. and Mellado, R. P., 1997. *Streptomyces* lividans groES, groEL1 and groEL2 genes. Microbiology, 143 (11), pp. 3563-3571.

Denome, S A., Elf, P. K., Henderson, T. A., Nelson, D. E. and Young, K. D., 1999. *Escherichia coli* mutants lacking all possible combinations of eight penicillin binding proteins: viability, characteristics, and implications for peptidoglycan synthesis. Journal of bacteriology, 181(13), pp. 3981-3993.

Ding Y, Liu N, Virlouvet L, Riethoven J, Fromm M and Avramova Z. Four distinct types of dehydration stress memory genes in *Arabidopsis thaliana*. 2013. BMC Plant Biology 13: 229.

Dixon, R. A., and Paiva, N. L. (1995). Stress-Induced Phenylpropanoid Metabolism. Plant Cell 7, 1085-1097.

Doná, M., Macovei, A., Fae, M., Carbonera, D., and Balestrazzi, A. (2013). Plant hormone signaling and modulation of DNA repair under stressful conditions. Plant Cell Rep. 32, 1043-1052.

Dri, A. M., Rouviere-Yaniv, J. and Moreau, P. L., 1991. Inhibition of cell division in hupA hupB mutant bacteria lacking HU protein. Journal of bacteriology, 173(9), pp. 2852-2863.

Dunwell J M: Cupins. 1998. A new superfamilly of functionally diverse proteins that include germins and plant storage proteins. Biotechnology & Genetic Engineering Reviews. 15: 1-32.

Eberhard et al., (1981). Biochemistry 20 (9): 2444-2449

Eckardt, N. A. (2004). The Role of PHANTASTICA in Leaf Development. Plant Cell 16, 1073-1075. Edgar (2010) Nature methods 10:996-8 el-Basyouni, S. Z., Chen, D., Ibrahim, R. K., Neish, A. C., and Towers, G. H. N. (1964). The biosynthesis of hydroxybenzoic acids in higher plants. Phytochemistry 3, 485-492.

Fiehn et al., (2000) Nature Biotechnol., 18, 1157-1161

Fischer S, Brunk B P, Chen F, Gao X, Harb O S, Iodice J B, Shanmugam D, Roos D S, Stoeckert C J, Jr. 2011. Using OrthoMCL to assign proteins to OrthoMCL-DB groups or to cluster proteomes into new ortholog groups. Curr Protoc Bioinformatics Chapter 6: Unit 6 12 11-19.

Fortin, M. G., Zelechowska, M., and Verma, D. P. S. (1985). Specific targeting of membrane nodulins to the bacteroid-enclosing compartment in soybean nodules. EMBO J. 4, 3041-3046.

Franssen, H. J., Nap, J. P., Gloudemans, T., Stiekema, W., Van Dam, H., Govers, F., Louwerse, J., Van Kammen, A., and Bisseling, T. (1987). Characterization of cDNA for nodulin-75 of soybean: A gene product involved in early stages of root nodule development. Proc. Natl. Acad. Sci. U.S.A 84, 4495-4499.

Friml, J. (2003). Auxin transport—shaping the plant. Curr. Opin. Plant Biol. 6, 7-12.

G Martinez Pastur, D. Z. (2001). CHANGES IN ISOPEROXIDASE PATTERNS DURING THE IN VITRO ROOTING OF NOTHOFAGUS ANTARCTICA. Bulg. J. Plant Physiol. 27, 43-53.

Gabel, C. and Maier, R. J., 1990. Nucleotide sequence of the coxA gene encoding subunit I of cytochrome aa3 of *Bradyrhizobium japonicum*. Nucleic acids research, 18(20), pp. 6143-6143.

Gao, Zhan, et al. "Quantitation of major human cutaneous bacterial and fungal populations." Journal of clinical microbiology 48.10 (2010): 3575-3581.

Gelman, A.; Carlin, J. B.; Stem, H. S. & Dunson, D. B. Bayesian Data Analysis CRC Press, 2013

Gibson, K. E., Kobayashi, H., and Walker, G. 2008. Molecular determinants of a symbiotic chronic infection. Annu. Rev. Genet. 42, 413-41.

Gili Ben-Nissan, David Weiss. 1996. The *petunia* homologue of tomato gast1: transcript accumulation coincides with gibberellin-induced corolla cell elongation. Plant Molec Biol. 32(6):1067-74.

Gilmour et al. (2000) Plant Physiol. 124: 1854-1865

Glover, R. T., Kriakov, J., Garforth, S. J., Baughn, A. D. and Jacobs, W. R., 2007. The two-component regulatory system senX3-regX3 regulates phosphate-dependent gene expression in *Mycobacterium smegmatis*. Journal of bacteriology, 189(15), pp. 5495-5503.

Göbel, C., and Feussner, I. (2009). Methods for the analysis of oxylipins in plants. Phytochemistry 70, 1485-1503.

Guldimann, C., Boor, K. J., Wiedmann, M. and Guariglia-Oropeza, V., 2016. Resilience in the face of uncertainty: sigma B fine-tunes gene expression to support homeostasis in Gram-positive bacteria. Applied and environmental microbiology, pp. AEM-00714.

Guzmán, E. C., Caballero, J. L., and Jiménez-Sánchez, A. (2002). Ribonucleoside diphosphate reductase is a component of the replication hyperstructure in *Escherichia coli*. Mol. Microbiol. 43, 487-495.

Haake et al. (2002) Plant Physiol. 130: 639-648

Haldrup, A., Simpson, D. J., and Scheller, H. V. (2000). Down-regulation of the PSI-F Subunit of Photosystem I (PSI) in *Arabidopsis thaliana* THE PSI-F SUBUNIT IS ESSENTIAL FOR PHOTOAUTOTROPHIC GROWTH AND CONTRIBUTES TO ANTENNA FUNCTION. J. Biol. Chem. 275, 31211-31218.

Hallman, J., et al., (1997) Canadian Journal of Microbiology. 43(10): 895-914

Hamano, Y., Dairi, T., Yamamoto, M., Kuzuyama, T., Itoh, N. and Seto, H., 2002. Growth-phase dependent expression of the mevalonate pathway in a terpenoid antibiotic-producing *Streptomyces* strain. Bioscience, biotechnology, and biochemistry, 66(4), pp. 808-819.

Hanfrey, C., Sommer, S., Mayer, M. J., Burtin, D., and Michael, A. J. (2001). *Arabidopsis* polyamine biosynthesis: absence of ornithine decarboxylase and the mechanism of arginine decarboxylase activity. Plant J. 27, 551-560.

Hanukoglu L. 2015. Proteopedia: Rossmann fold: A beta-alpha-beta fold at dinucleotide binding sites. Biochem Mol Biol 43 (3): 206-9.

Harig, L., Beinecke, F. A., Oltmanns, J., Muth, J., Müller, O., Rüping, B., Twyman, R. M., Fischer, R., Prüfer, D. and Noll, G. A. 2012. Proteins from the FLOWERING LOCUS T-like subclade of the PEBP family act antagonistically to regulate floral initiation in tobacco. The Plant Journal, 72: 908-921.

Hesse, H., Kreft, O., Maimann, S., Zeh, M., and Hoefgen, R. (2004). Current understanding of the regulation of methionine biosynthesis in plants. J. Exp. Bot. 55, 1799-1808.

Hesse, H., Kreft, O., Maimann, S., Zeh, M., and Hoefgen, R. (2004). Current understanding of the regulation of methionine biosynthesis in plants. J. Exp. Bot. 55, 1799-1808.

Hideki Takahashi, Mami Yamazaki, Noriko Sasakura, Akiko Watanabe, Thomas Leustek, Janice de Almeida Engler, Gilbert Engler, Marc Van Montagu, and Kazuki Saito. 1997. Regulation of sulfur assimilation in higher plants: A sulfate transporter induced in sulfate-starved roots plays a central role in *Arabidopsis thaliana*. Proc Nat Acad Sci. 94(20):11102-07.

Hiroki Miwa, Atsuko Kinoshita, Hiroo Fukuda, Shinichiro Sawa. 2008. Plant meristems: CLAVATA3/ESR-related signaling in the shoot apical meristem and the root apical meristem. J of Plant Res. 122(1):31-39.

Höfer, R., Dong, L., Andre, F., Ginglinger, J.-F., Lugan, R., Gavira, C., Grec, S., Lang, G., Memelink, J., Van Der Krol, S., et al. (2013). Geraniol hydroxylase and hydroxygeraniol oxidase activities of the CYP76 family of cytochrome P450 enzymes and potential for engineering the early steps of the (seco)iridoid pathway. Metab. Eng. 20, 221-232.

Hua Peng, Sufen Han, Mao Luo, Jian Gao, Xuan Liu, and Maojun Zhao. 2011. Roles of Multidrug Transporters of MFS in Plant Stress Responses. International Journal of Bioscience, Biochemistry and Bioinformatics, Vol. 1, No. 2, July 2011.

Huang da W, Sherman B T, Lempicki R A. 2009. Bioinformatics enrichment tools: paths toward the comprehensive functional analysis of large gene lists. Nucleic Acids Res 37:1-13.

Hui-Wen Wang, Jin-Song Zhang, Jun-Yi Gai, Shou-Yi Chen. 2006. Cloning and comparative analysis of the gene encoding diacylglycerol acyltransferase from wild type and cultivated soybean. Theoretical and Applied Genetics. 112(6):1086-97.

Huttová, J., Mistrík, I., Olle-Simonovicova, M., and Tamás, L. (2006). Cadmium induced changes in cell wall peroxidase isozyme pattern in barley root tips. Plant Soil Environ. 52, 250.

Ishikawa, Fumiyoshi, Suga, Shinobu, Uemura, Tomohiro, Sato, Masa H, Maeshima, Masayoshi. 2005. Novel type aquaporin SIPs are mainly localized to the ER membrane and show cell-specific expression in *Arabidopsis thaliana*. FEBS LETTERS 579: 5814-2

Ishikawa, K., Nakatani, H., Katsuya, Y., and Fukazawa, C. (2007). Kinetic and Structural Analysis of Enzyme Sliding on a Substrate: Multiple Attack in beta-Amylase. Biochemistry (Mosc.) 46, 792-798.

Ito, T., Shiraishi, H., Okada, K., and Shimura, Y. (1994). Two amidophosphoribosyltransferase genes of *Arabidopsis thaliana* expressed in different organs. Plant Mol. Biol. 26, 529-533.

Jami, S. K., Clark, G. B., Turlapati, S. A., Handley, C., Roux, S. J., and Kirti, P. B. (2008). Ectopic expression of an annexin from *Brassica juncea* confers tolerance to abiotic and biotic stress treatments in transgenic tobacco. Plant Physiol. Biochem. 46, 1019-1030.

Joe Ross, Yi Li, Eng-Kiat Lim and Dianna J Bowles. 2001. Higher plant glycosyltransferases. Genome Biol. 2(2): reviews 3004.1-3004.6.

Johnston-Monje, David, and Manish N. Raizada. "Conservation and diversity of seed associated endophytes in *Zea* across boundaries of evolution, ethnography and ecology." PLoS One 6.6 (2011): e20396.

Jones P M, George A M. 2004. The ABC transporter structure and mechanism: perspectives on recent research". Cellular and Molecular Life Sciences 61 (6): 682-99.

Joohyun Kang, Jiyoung Park, Hyunju Choi, Bo Burla, Tobias Kretzschmar, Youngsook Lee, and Enrico Martinoia. 2011. Plant ABC Transporters. *Arabidopsis* Book. 2011; 9: e0153.

José A. Caparrós-Martin, Iva McCarthy-Suárez, Francisco A. Culiáñez-Macià. 2013. HAD hydrolase function unveiled by substrate screening: enzymatic characterization of *Arabidopsis thaliana* subclass I phosphosugar phosphatase AtSgpp. Planta. 237(4):943-54.

Kereszt, A., Mergaert, P., and Kondorosi, E. (2011). Bacteroid Development in Legume Nodules: Evolution of Mutual Benefit or of Sacrificial Victims? Mol. Plant. Microbe Interact. 24, 1300-1309.

Kereszt, A., Mergaert, P., and Kondorosi, E. (2011). Bacteroid Development in Legume Nodules: Evolution of Mutual Benefit or of Sacrificial Victims? Mol. Plant. Microbe Interact. 24, 1300-1309.

Kevin W.-H. Lo, Scott Naisbitt, Jing-Song Fan, Morgan Sheng and Mingjie Zhang. 2001. The 8-kDa Dynein Light Chain Binds to Its Targets via a Conserved (K/R)XTQT Motif. The Journal of Biological Chemistry. 276:14059-66.

Khan, W., Balakrishnan, P., and Smith, D. L. 2008. Nod factor [Nod Bj V (C18:1, MeFuc)] and lumichrome enhance photosynthesis and growth of corn and soybean.

Kidd et al. 2007, Chemosphere 66:1458-1467

Kim, R. Q., Offen, W A, Davies, G. J. and Stubbs, K A, 2014. Structural enzymology of *Helicobacter pylori* methylthioadenosine nucleosidase in the futalosine pathway. Acta Crystallographica Section D: Biological Crystallography, 70(1), pp. 177-185.

Klambt, H. D. (1962). Conversion in plants of benzoic acid to salicylic acid and its [beta]d-glucoside. Nature 196, 491.

Konishi, H., Yamane, H., Maeshima, M., and Komatsu, S. (2004). Characterization of fructose-bisphosphate aldolase regulated by gibberellin in roots of rice seedling. Plant Mol. Biol. 56, 839-848.

Kozich, J. J., Westcott, S. L., Baxter, N. T., Highlander, S. K., & Schloss, P. D. (2013). Development of a dual-index sequencing strategy and curation pipeline for analyzing amplicon sequence data on the miseq illumina sequencing platform. Applied and Environmental Microbiology, 79(17), 5112-5120.

Kruschke, J. K. Bayesian Estimation Supersedes the t Test. Journal of Experimental Psychology: General, 2012

Kruschke, John K and Mike Meredith, BEST: Bayesian Estimation Supersedes the t-Test, R package version 0.2.2, http://CRAN.R-project.org/package=BESTKuc, J. (1987). Translocated Signals for Plant Immunization. Ann. N. Y. Acad. Sci. 494, 221-223.

Krusell L1, Krause K, Ott T, Desbrosses G, Kramer U, Sato S, Nakamura Y, Tabata S, James E K, Sandal N, Stougaard J, Kawaguchi M, Miyamoto A, Suganuma N, Udvardi M K. 2005. The sulfate transporter SST1 is crucial for symbiotic nitrogen fixation in Lotus japonicus root nodules. Plant Cell. 2005 17(5):1625-36.

Kuc, J. (1987). Translocated Signals for Plant Immunization. Ann. N. Y. Acad. Sci. 494, 221-223.

Kukavica, B. M., Veljović-Jovanovicć, S. D., Menckhoff, L., and Lüthje, S. (2012). Cell wall-bound cationic and anionic class III isoperoxidases of pea root: biochemical characterization and function in root growth. J. Exp. Bot.

Kumar et al. 1995, Environ. Sci. Technol. 29:1232-1238

Lang Minglin, Zhang Yuxiu, Chai Tuanyao. 2005. Identification of genes up-regulated in response to Cd exposure in Brassica juncea L. Gene. 363:151-58.

Laurie S, Halford N G. 2001. The role of protein kinases in the regulation of plant growth and development. Plant Growth Regulation 34: 253-265.

Leah McHale, Xiaoping Tan, Patrice Koehl and Richard W Michel. 2006. Plant NBS-LRR proteins: adaptable guards. Genome Biology 7:212.

Lee, H. I., León, J., and Raskin, I. (1995). Biosynthesis and metabolism of salicylic acid. Proc. Natl. Acad. Sci. 92, 4076-4079.

Legocki, R. P., and Verma, D. P. S. (1980). Identification of "nodule-specific" host proteins (nodulins) involved in the development of Rhizobium-Legume symbiosis. Cell 20, 153-163.

Legocki, R. P., and Verma, D. P. S. (1980). Identification of "nodule-specific" host proteins (nodulins) involved in the development of Rhizobium-Legume symbiosis. Cell 20, 153-163.

Lene Krusella, Katja Krausea, Thomas Otta, Guilhem Desbrossesa, Ute Kramera, Shusei Satob, Yasukazu Nakamurab, Satoshi Tabatab, Euan K. Jamesc, Niels Sandald, Jens Stougaardd, Masayoshi Kawaguchie, Ai Miyamotof, Norio Suganumaf and Michael K. Udvardia. 2005. The Sulfate Transporter SST1 Is Crucial for Symbiotic Nitrogen Fixation in Lotus japonicus Root Nodules. The Plant Cell. 17(5):1625-36.

Li et al., (2004) Mycologia 96: 526-536

Li, C., Ng, C. K.-Y., and Fan, L.-M. (2015). MYB transcription factors, active players in abiotic stress signaling. Environ. Exp. Bot. 114, 80-91.

Lunn, J. E. (2001). Sucrose Metabolism. In eLS, (John Wiley & Sons, Ltd).

Makarova, K. S., Ponomarev, V. A. and Koonin, E. V., 2001. Two C or not two C: recurrent disruption of Zn-ribbons, gene duplication, lineage-specific gene loss, and horizontal gene transfer in evolution of bacterial ribosomal proteins. Genome Biol, 2(9), p. 0033.

Marger M D, Saier M H. A major superfamily of transmembrane facilitators that catalyze uniport, symport and antiport. 1993. Trends in Biochemical Sciences 18 (1): 13-20.

Masaki Hayashi, Sokichi Shiro, Hiroyuki Kanamori, Satomi Mori-Hosokawa, Harumi Sasaki-Yamagata, Takashi Sayama, Miki Nishioka, Masakazu Takahashi, Masao Ishimoto, Yuichi Katayose, Akito Kaga, Kyuya Harada, Hiroshi Kouchi, Yuichi Saeki and Yosuke Umehara. 2014. A Thaumatin-Like Protein, Rj4, Controls Nodule Symbiotic Specificity in Soybean. Plant & Cell Phys. 55(9): 1679-89.

Matamoros, M. A., Dalton, D. A., Ramos, J., Clemente, M. R., Rubio, M. C., and Becana, M. (2003). Biochemistry and Molecular Biology of Antioxidants in the Rhizobia-Legume Symbiosis. Plant Physiol. 133, 499-509.

Matiru, V. N. and Dakora, F. D. 2005. Xylem transport and shoot accumulation of lumichrome, a newly recognized rhizobial signal, alters root respiration, stomatal conductance, leaf transpiration and photosynthetic rates in legumes and cereals. New Phytologist. 165, 847-855.

Maurel C, Boursiac Y, Luu D T, Santoni V, Shahzad Z, Verdoucq L. 2015. Aquaporins in Plants. Physiol Rev. 2015 95(4):1321-58.

McAinsh, M. R. (1990). Abscisic acid-induced elevation of guard cell cytosolic $Ca_2+$ precedes stomatal closure. Nature 343, 186-188.

McClure, P. R. and Israel, D. W. 1979. Transport of nitrogen in the xylem of soybean plants. Plant Physiol. 64, 411-416.

McDonald et al. (2012), ISME journal 6:610-8 McDonald, D., Price, M. N., Goodrich, J., Nawrocki, E. P., DeSantis, T. Z., Probst, A., . . . Hugenholtz, P. (2012). An improved Greengenes taxonomy with explicit ranks for ecological and evolutionary analyses of bacteria and archaea. The ISME Journal, 6(3), 610-8.

McDonald, D., Price, M. N., Goodrich, J., Nawrocki, E. P., DeSantis, T. Z., Probst, A., . . . Hugenholtz, P. (2012). An improved Greengenes taxonomy with explicit ranks for ecological and evolutionary analyses of bacteria and archaea. The ISME Journal, 6(3), 610-8.

Meng Zhang, Jilian Fan, David C. Taylor and John B. Ohlrogge. 2009. DGAT1 and PDAT1 Acyltransferases Have Overlapping Functions in Arabidopsis Triacylglycerol Biosynthesis and Are Essential for Normal Pollen and Seed Development. The Plant Cell. 21(12):3885-3901.

Michel Herzog, Anne-Marie Dorne, Frangoise Grellet. 1995. GASA, a gibberellin-regulated gene family from Arabidopsis thaliana related to the tomato GAST1 gene. Plant Molec Biol. 27(4):743-52.

Miller J D, Arteca R N, Pell E J. 1999. Senescence-associated gene expression during ozone-induced leaf senescence in Arabidopsis. Plant Physiol 120:1015-1024.

Ming-Der Shih, Folkert A. Hoekstra, Yue-Ie C. Hsing. 2008. Late Embryogenesis Abundant Proteins. Advances in Botanical Research. 48:211-55.

Mo Lu, Ying-Peng Han, Ji-Guo Gao, Xiang-Jing Wang, and Wen-Bin Li. 2010. Identification and analysis of the germin-like gene family in soybean. BMC Genomics, 11: 620.

Mortvedt 1996, Fertilizer Res. 43:55-61

Motoyuki Ashikari, Hitoshi Sakakibara, Shaoyang Lin, Toshio Yamamoto, Tomonori Takashi, Asuka Nishimura, Enrique R. Angeles, Qian Qian, Hidemi Kitano, Makoto Matsuoka. 2005. Cytokinin Oxidase Regulates Rice Grain Production. Science. 309(5735):741-45.

Moulin, M., Deleu, C., Larher, F., Bouchereau, A. 2006. The lysine-ketoglutarate reductase-saccharopine dehydrogenase is involved in the osmo-induced synthesis of pipecolid acid in rapeseed leaf tissues. Plant Physiol. and Biochem. 44, 474-482.

Mugford Sam T, Xiaoquan Qi, Saleha Bakht, Lionel Hill, Eva Wegel, Richard K. Hughes, Kalliopi Papadopoulou, Rachel Melton, Mark Philo, Frank Sainsbury, George P. Lomonossoff, Abhijeet Deb Roy, Rebecca J. M. Goss, and Anne Osbourn. 2009. A Serine Carboxypeptidase-Like Acyltransferase Is Required for Synthesis of Antimicrobial Compounds and Disease Resistance in Oats. The Plant Cell, Vol. 21: 2473-2484.

Naoya Takeda, Kristina Haage, Shusei Sato, Satoshi Tabata, and Martin Parniske. 2004. Activation of a *Lotus japonicus* Subtilase Gene During Arbuscular Mycorrhiza Is Dependent on the Common Symbiosis Genes and Two cis-Active Promoter Regions. Molecular Plant-Microbe Interactions 24: 662-670

Navarova, H., Bernsdorff, F., Doring, A., and Zeier, J. 2012. Pipecolic acid, an endogenous mediator of defense amplification and priming, is a critical regulator of inducible plant immunity. The Plant Cell. 24, 5123-5141.

Nordberg, J., and Arnér, E. S. J. (2001). Reactive oxygen species, antioxidants, and the mammalian thioredoxin system1. Free Radic. Biol. Med. 31, 1287-1312.

Obanye, A. I. C., Hobbs, G., Gardner, D. C. J. and Oliver, S. G., 1996. Correlation between carbon flux through the pentose phosphate pathway and production of the antibiotic methylenomycin in Streptomycescoelicolor A3 (2). Microbiology, 142(1), pp. 133-137.

Omidbakhshfard, M. A., Omranian, N., Ahmadi, F. S., Nikoloski, Z., and Mueller-Roeber, B. (2012). Effect of salt stress on genes encoding translation-associated proteins in *Arabidopsis thaliana*. Plant Signal. Behav. 7, 1095-1102.

Oppenheimer, D. G., Haas, N., Silflow, C. D., and Snustad, D. P. (1988). The beta-tubulin gene family of *Arabidopsis thaliana*: preferential accumulation of the beta1 transcript in roots. Gene 63, 87-102.

Oppenheimer, D. G., Haas, N., Silflow, C. D., and Snustad, D. P. (1988). The β-tubulin gene family of *Arabidopsis thaliana*: preferential accumulation of the β1 transcript in roots. Gene 63, 87-102.

Oppenheimer, D. G., Haas, N., Silflow, C. D., and Snustad, D. P. (1988). The β-tubulin gene family of *Arabidopsis thaliana*: preferential accumulation of the β1 transcript in roots. Gene 63, 87-102.

Osman, S. F. and Felt, W. F. 1982. Isoflavone glucoside stress metabolites of soybean leaves. Phytochem. 22, 1921-1923.

Pearson, Methods Enzymol. 183:63-98 (1990).

Perez-Miranda et al. (2007), J Microbiol Methods 70: 127-131

Peter Buchner, Hideki Takahashi, Malcolm J. Hawkesford. 2004. Plant sulphate transporters: co-ordination of uptake, intracellular and long-distance transport. Journal of Experimental Botany 55: 1765-1773.

Phalip et al., (1994) J Basic Microbiol 34: 277-280

Phillips, D. A., Joseph, C. M., Yang, G., Martinez-Romero, E., Sanborn, J. R., and Volpin, H. 1999. Identification of lumichrome as a *Sinorhizobium* enhancer of alfalfa root respiration and shoot growth. PNAS. 96, (22) 12275-12280.

Plummer, M. et al., JAGS: A program for analysis of Bayesian graphical models using Gibbs sampling Proceedings of the 3rd international workshop on distributed statistical computing, 2003, 124, 125

Pohland B and Owen B (2009). TAS technical bulletin. Biolog. 1, 1-3.

Quadt-Hallmann et al., (1997) Can. J. Microbiol., 43: 577-582

Quast, C., Pruesse, E., Yilmaz, P., Gerken, J., Schweer, T., Glo, F. O., & Yarza, P. (2013). The SILVA ribosomal RNA gene database project: improved data processing and web-based tools. Nucleic Acids Research, 41(November 2012), 590-596.

Quiroga, M., de Forchetti, S. M., Taleisnik, E., and Tigier, H. A. (2001). Tomato root peroxidase isoenzymes: kinetic studies of the coniferyl alcohol peroxidase activity, immunological properties and role in response to salt stress. J. Plant Physiol. 158, 1007-1013.

R Core Team, 2015, A Language and Environment for Statistical Computing, R Foundation for Statistical Computing, Vienna, Austria, 2015, http://www.R-project.org/

Rajkumar et al. 2009, Chemosphere 77:153-160

Ramos, J., Matamoros, M. A., Naya, L., James, E. K., Rouhier, N., Sato, S., Tabata, S., and Becana, M. (2009). The glutathione peroxidase gene family of *Lotus japonicus*: characterization of genomic clones, expression analyses and immunolocalization in legumes. New Phytol. 181, 103-114.

Reinbothe, H. and Mothes, K. 1962. Urea, ureides and guanidine in plants. Annu. Rev. Plant Physiol. 13, 129-149.

Reinhold-Hurek, B., and Hurek, T. (2011). Living inside plants: bacterial endophytes. Curr. Opin. Plant Biol. 14, 435-443.

Richard A. Jorgensen and Ana E. Dorantes-Acosta. 2012. Conserved peptide upstream open reading frames are associated with regulatory genes in angiosperms. Frontiers in Plant Science. 3:1-11.

Rietz Steffen, Friederike E. M. Bernsdorff, and Daguang Cai. 2012. Members of the germin-like protein family in *Brassica napus* are candidates for the initiation of an oxidative burst that impedes pathogenesis of *Sclerotinia sclerotiorum*. J Exp Bot. 63(15): 5507-5519.

Rípodas C, Castaingts M, Clúa J, Blanco F, Zanetti M E. 2015. Annotation, phylogeny and expression analysis of the nuclear factor Y gene families in common bean (*Phaseolus vulgaris*). Front Plant Sci. 14; 5:761

Roessner et al., (2001) Plant Cell, 13, 11-29

Rouhier N. 2010. Plant glutaredoxins: pivotal players in redox biology and iron-sulphur centre assembly. New Phytol. 186(2):365-72.

S. Gazzarrini, L. Lejay, A. Gojon, O. Ninnemann, W. B. Frommer, N. von Wirén. 1999. Plant Cell, 11 (1999), pp. 937-947

S. Pérez-Miranda, Journal of Microbiological Methods, Volume 70, Issue 1, Pages 127-131 (2007)

Sambrook, J., E. F. Fritsch, and T. Maniatis. "Molecular cloning: A laboratory manual. Sambrook 1989." (1989).

Sanssouci, É., Lerat, S., Daigle, F., Grondin, G., Shareck, F. and Beaulieu, C., 2012. Deletion of TerD-domain-encoding genes: effect on Streptomycescoelicolor development. Canadian journal of microbiology, 58(10), pp. 1221-1229.

Schmieder and Edwards (2011) Bioinformatics. 2011; 27:863-864

Schmülling Thomas, Tomis Werner, Michael Riefler, Eva Krupkovi, Isabel Bartrina y Manns. 2003. Structure and function of cytokinin oxidase/dehydrogenase genes of maize, rice, *Arabidopsis* and other species. J of Plant Res. 116(3):241-52.

Schuler MA1, Berenbaum MR. 2013. Structure and function of cytochrome P450S in insect adaptation to natural and synthetic toxins: insights gained from molecular modeling. J Chem Ecol. 39(9):1232-45.

Schultze, M., and Kondorosi, A. (1998). Regulation of Symbiotic Root Nodule Development. Annu. Rev. Genet. 32, 33-57.

Shah, J., and Klessig, D. (1999). Chapter 23 Salicylic acid: signal perception and transduction. In New Comprehensive Biochemistry, M. A. H. and K. R. L. P. J. J. Hooykaas, ed. (Elsevier), pp. 513-541.

Shinozaki, K., and Yamaguchi-Shinozaki, K. (2000). Molecular responses to dehydration and low temperature: differences and cross-talk between two stress signaling pathways. Curr. Opin. Plant Biol. 3, 217-223.

Smart C M (1994) Gene expression during leaf senescence. New Phytol 126: 419-448

Soares et al. (1999). Revista de Microbiolgia 30(4): 299-303

Stacey, G., Libault, M., Brechenmacher, L., Wan, J., and May, G. D. (2006a). Genetics and functional genomics of legume nodulation. Curr. Opin. Plant Biol. 9, 110-121.

Stacey, G., McAlvin, C. B., Kim, S.-Y., Olivares, J., and Soto, M. J. (2006b). Effects of endogenous salicylic acid on nodulation in the model legumes *Lotus japonicus* and *Medicago truncatula*. Plant Physiol. 141, 1473-1481.

Stacey, M. G., Osawa, H., Patel, A., Gassmann, W., and Stacey, G. (2006c). Expression analyses of *Arabidopsis* oligopeptide transporters during seed germination, vegetative growth and reproduction. Planta 223, 291-305.

Stepanova, E., Wang, M., Severinov, K. and Borukhov, S., 2009. Early transcriptional arrest at *Escherichia coli* rplN and ompX promoters. Journal of Biological Chemistry, 284(51), pp. 35702-35713.

Strong, F. E., and Kruitwagen, E. (1967). Traumatic Acid: an Accelerator of Abscission in Cotton Explants. Nature 215, 1380-1381.

Subramanian A, Tamayo P, Mootha V K, Mukherjee S, Ebert B L, Gillette M A, Paulovich A, Pomeroy S L, Golub T R, Lander E S, Mesirov J P. 2005. Gene set enrichment analysis: a knowledge-based approach for interpreting genome-wide expression profiles. Proc Natl Acad Sci USA 102:15545-15550.

Sun, X.-L., Yu, Q.-Y., Tang, L.-L., Ji, W., Bai, X., Cai, H., Liu, X.-F., Ding, X.-D., and Zhu, Y.-M. (2013). GsSRK, a G-type lectin S-receptor-like serine/threonine protein kinase, is a positive regulator of plant tolerance to salt stress. J. Plant Physiol. 170, 505-515.

Suto et al., (2002) J Biosci Bioeng. 93:88-90

T. J. Prochaska, T. Donze-Reiner, L. Marchi-Werle, N. A. Palmer, T. E. Hunt, G. Sarath, T. Heng-Moss. 2015. Transcriptional responses of tolerant and susceptible soybeans to soybean aphid (*Aphis glycines* Matsumura) herbivory. Arthropod-Plant Interactions 9:347-359.

Takahashi, T., Gasch, A., Nishizawa, N., and Chua, N. H. (1995). The DIMINUTO gene of *Arabidopsis* is involved in regulating cell elongation. Genes Dev. 9, 97-107.

Takeuchi, Y., Yoshikawa, M., Takeba, G., Tanaka, K., Shibata, D., and Horino, O. (1990). Molecular Cloning and Ethylene Induction of mRNA Encoding a Phytoalexin Elicitor-Releasing Factor, beta-1,3-Endoglucanase, in Soybean. Plant Physiol. 93, 673-682.

Tang, L., Zhang, Y. X. and Hutchinson, C. R., 1994. Amino acid catabolism and antibiotic synthesis: valine is a source of precursors for macrolide biosynthesis in *Streptomyces ambofaciens* and *Streptomyces fradiae*. Journal of bacteriology, 176(19), pp. 6107-6119.

Thomashow (2001) Plant Physiol. 125: 89-93

Thomma, B. P. H. J., Cammue, B. P. A., and Thevissen, K. (2002). Plant defensins. Planta 216, 193-202.

Tohge, T., Yonekura-Sakakibara, K., Niida, R., Watanabe-Takahashi, A., and Saito, K. (2007). Phytochemical genomics in *Arabidopsis thaliana*: A case study for functional identification of flavonoid biosynthesis genes. Pure Appl. Chem. 79, 811-823.

Tomoyuki Furukawa, Norihiro Sakaguchi, Hiroaki Shimada. 2006. Two OsGASR genes, rice GAST homologue genes that are abundant in proliferating tissues, show different expression patterns in developing panicles. Genes & Genetic Systems. 81(3):171-80.

Toshitsugu Nakano, Kaoru Suzuki, Tatsuhito Fujimura, and Hideaki Shinshi. 2006. Genome-wide analysis of the ERF gene family in *Arabidopsis* and rice. Plant Physiol, 140 (2): p. 411-32.

Urao, T., Yamaguchi-Shinozaki, K., Urao, S., and Shinozaki, K. (1993). An *Arabidopsis* myb homolog is induced by dehydration stress and its gene product binds to the conserved MYB recognition sequence. Plant Cell 5, 1529-1539.

Usadel & Ferie, (2013). Front Plant Sci. 4:48

Van Hoof, P., and Gaspar, T. (1976). Peroxidase and isoperoxidase changes in relation to root initiation of Asparagus cultured in vitro. Sci. Hortic. 4, 27-31.

Velazhahan R, Datta S K, Muthukrishnan S (1999) The PR-5 family: thaumatin-like proteins in plants. In: Datta S K, Muthukrishnan S (eds) Pathogenesis-related proteins in plants. CRC Press, Boca Raton, pp 107-129

Vick, B., and Zimmerman, D. (1987). Oxidative systems for modification of fatty acids: the lipoxygenase pathway. In Lipids: Structure and Function. The Biochemistry of Plants, (New York), pp. 53-90.

Vining et al., (2013) BMC Plant Biol. 13:92

Wang et al., (2007) Applied and environmental microbiology 73:5261-7

Weaver L M, Gan S, Quirino B, Amasino R M. 1998. A comparison of the expression patterns of several senescence-associated genes in response to stress and hormone treatment. Plant Mol Biol 37:455-469.

Weiss, B. and Wang, L., 1994. De novo synthesis of thymidylate via deoxycytidine in dcd (dCTP deaminase) mutants of *Escherichia coli*. Journal of bacteriology, 176(8), pp. 2194-2199.

Weisshaar, B., and Jenkins, G. I. (1998). Phenylpropanoid biosynthesis and its regulation. Curr. Opin. Plant Biol. 1, 251-257.

Whetten, R. W., and Sederoff, R. R. (1992). Phenylalanine ammonia-lyase from loblolly pine: purification of the enzyme and isolation of complementary DNA clones. Plant Physiol. 98, 380-386.

Xiaoqiang Wang. 2009. Structure, mechanism and engineering of plant natural product glycosyltransferases. FEBS Letters. 583(20):3303-09.

Xuan Y H, Hu Y B, Chen L-Q, Sosso D, Ducat D C, Hou B-H, et al. 2013. Functional role of oligomerization for bacterial and plant SWEET sugar transporter family. Proc Natl Acad Sci USA. 110(39):E3685-94.

Yan Y, Borrego E, and Kolomiets M V (2013). Jasmonate Biosynthesis, Perception and Function in Plant Development and Stress Responses. In Lipid Metabolism, (Intech), pp. 393-442.

Yanagita, T. and Foster, J. W. 1956. A bacterial riboflavin hydrolase. J. Biol. Chem. 221, 593-607.

Yang, X.-D., Li, W.-J., and Liu, J.-Y. (2005). Isolation and characterization of a novel PHGPx gene in *Raphanus sativus*. Biochim. Biophys. Acta BBA—Gene Struct. Expr. 1728, 199-205.

Yu G, Wang L G, Han Y, He Q Y. 2012. clusterProfiler: an R package for comparing biological themes among gene clusters. OMICS 16:284-287.

LENGTHY TABLES

The patent contains a lengthy table section. A copy of the table is available in electronic form from the USPTO web site (https://seqdata.uspto.gov/?pageRequest=docDetail&DocID=US11819027B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US11819027B2). An electronic copy of the sequence listing will also be available from the USPTO upon request and payment of the fee set forth in 37 CFR 1.19(b)(3).

We claim:

1. A method of enhancing symbiosis in a plant grown from a plant reproductive element, comprising treating the plant reproductive element with a formulation comprising an effective amount of a *Streptomyces* endophyte that is heterologous to the plant reproductive element, wherein the *Streptomyces* endophyte comprises a 16S polynucleotide sequence having at least 97% identity to SEQ ID NO 2; and at least 3 polynucleotides that encode an arabinose transporter protein;

wherein the effective amount is effective to increase expression of one or more genes encoding a sugar transporter domain in a plant grown from the treated plant reproductive element, as compared to an isoline plant grown from a plant reproductive element not treated with the *Streptomyces* endophyte.

2. The method of claim 1, wherein the plant is soybean.

3. The method of claim 1, wherein the plant reproductive element is a seed.

4. The method of claim 3, wherein the seed is a transgenic seed.

5. The method of claim 1, wherein the formulation comprises a purified population of the *Streptomyces* endophyte at a concentration of at least about $10^2$ CFU/ml in a liquid formulation or about $10^2$ CFU/gm in a non-liquid formulation.

6. The method of claim 1, wherein the formulation further comprises one or more of the following: stabilizer, preservative, carrier, surfactant, anticomplex agent, fungicide, nematicide, bactericide, insecticide, herbicide, or any combination thereof.

7. The method of claim 1, wherein the treating comprises coating the plant reproductive element with the formulation, spraying the formulation onto the plant reproductive element, or introducing the formulation onto a soil comprising the plant reproductive element.

8. A method of decreasing abundance of one or more bacteria of the genus *Escherichia-Shigella* in leaves of a plant under water-stressed conditions, comprising treating a plant reproductive element with a formulation comprising an effective amount of a *Streptomyces* endophyte that is heterologous to the plant reproductive element, wherein the *Streptomyces* endophyte comprises a 16S polynucleotide sequence having at least 97% identity to SEQ ID NO: 2 and at least 3 polynucleotides that encode an arabinose transporter protein, wherein the effective amount is effective to decrease abundance of one or more bacteria of the genus *Escherichia-Shigella* in leaves of a plant grown from the treated reproductive element under water-stressed conditions, as compared to an isoline plant grown from a plant reproductive element not treated with the *Streptomyces* endophyte.

9. The method of claim 8, wherein the plant is soybean.

10. The method of claim 8, wherein the plant reproductive element is a seed.

11. The method of claim 10, wherein the seed is a transgenic seed.

12. The method of claim 8, wherein the formulation comprises a purified population of the *Streptomyces* endophyte at a concentration of at least about $10^2$ CFU/ml in a liquid formulation or about $10^2$ CFU/gm in a non-liquid formulation.

13. The method of claim 8, wherein the formulation further comprises one or more of the following: stabilizer, preservative, carrier, surfactant, anticomplex agent, fungicide, nematicide, bactericide, insecticide, herbicide, or any combination thereof.

14. The method of claim 8, wherein the treating comprises coating the plant reproductive element with the formulation, spraying the formulation onto the plant reproductive element, or introducing the formulation onto a soil comprising the plant reproductive element.

15. A synthetic composition comprising a plant reproductive element with a formulation comprising a purified *Streptomyces* endophyte population applied thereon, wherein the *Streptomyces* endophyte is heterologous to the plant reproductive element and comprises a 16S polynucleotide sequence having at least 97% identity to SEQ ID NO: 2; and at least 3 polynucleotides that encode an arabinose transporter protein;

wherein the endophyte is present in the synthetic composition in an amount capable of conferring to a plant at least one plant trait selected from: increased expression of one or more genes encoding a sugar transporter domain, and decreased abundance of one or more bacteria of the genus *Escherichia-Shigella* in leaves of the plant under water-stressed conditions; as compared to an isoline plant grown from a plant reproductive element not treated with the *Streptomyces* endophyte.

16. The composition of claim 15, wherein the plant is soybean.

17. The composition of claim 15, wherein the plant reproductive element is a seed.

18. The composition of claim 17, wherein the seed is a transgenic seed.

19. The composition of claim 15, wherein the formulation comprises a purified population of the *Streptomyces* endophyte at a concentration of at least about 10^2 CFU/ml in a liquid formulation or about 10^2 CFU/gm in a non-liquid formulation.

20. The composition of claim 15, wherein the formulation further comprises one or more of the following: stabilizer, preservative, carrier, surfactant, anticomplex agent, fungicide, nematicide, bactericide, insecticide, herbicide, or any combination thereof.

21. The composition of claim 15, wherein the 16S polynucleotide sequence has least 98% identity to SEQ ID NO: 2.

22. The composition of claim 15, wherein the 16S polynucleotide sequence has least 99% identity to SEQ ID NO: 2.

23. The composition of claim 15, wherein the 16S polynucleotide sequence comprises the sequence set forth in SEQ ID NO: 2.

24. The method of claim 8, wherein the 16S polynucleotide sequence has least 98% identity to SEQ ID NO: 2.

25. The method of claim 8, wherein the 16S polynucleotide sequence has least 99% identity to SEQ ID NO: 2.

26. The method of claim 8, wherein the 16S polynucleotide sequence comprises the sequence set forth in SEQ ID NO: 2.

* * * * *